(12) United States Patent
Briles et al.

(10) Patent No.: US 6,592,876 B1
(45) Date of Patent: *Jul. 15, 2003

(54) PNEUMOCOCCAL GENES, PORTIONS THEREOF, EXPRESSION PRODUCTS THEREFROM, AND USES OF SUCH GENES, PORTIONS AND PRODUCTS

(75) Inventors: David E. Briles, Birmingham, AL (US); Larry S. McDaniel, Ridgland, MS (US); Edwin Swiatlo, Birmingham, AL (US); Janet Yother, Birmingham, AL (US); Alexis Brooks-Walter, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 160 days.

This patent is subject to a terminal disclaimer.

(21) Appl. No.: 08/529,055

(22) Filed: Sep. 15, 1995

Related U.S. Application Data

(63) Continuation-in-part of application No. 08/465,746, filed on Jun. 6, 1995, now Pat. No. 5,679,768, which is a continuation of application No. 08/048,896, filed on Apr. 20, 1993, now abandoned.

(51) Int. Cl.[7] ............... A61K 39/09; G01N 33/569; C07K 1/00; C07H 21/04
(52) U.S. Cl. ............... 424/244.1; 424/165.1; 424/184.1; 424/93.44; 424/237.1; 435/6; 435/7.34; 530/350; 536/23.7
(58) Field of Search ............... 424/184.1, 244.1, 424/165.1, 237.1, 93.44; 435/6, 7.34; 530/350; 536/23.7

(56) References Cited

U.S. PATENT DOCUMENTS

| | | | | |
|---|---|---|---|---|
| 4,152,413 A | * | 5/1979 | Goodnow | 424/16 |
| 4,748,019 A | * | 5/1988 | Lysons | 424/92 |
| 5,364,774 A | * | 11/1994 | Huir et al. | 435/69.3 |
| 5,698,394 A | * | 12/1997 | Duhamel et al. | 435/6 |

FOREIGN PATENT DOCUMENTS

| | | | | |
|---|---|---|---|---|
| WO | WO 92/14488 | | 9/1992 | A61K/39/12 |
| WO | 93/24000 | * | 12/1993 | A01N/37/18 |

OTHER PUBLICATIONS

McDaniel et al Infection & Immunity 59 222–228, 1991.*
Crain et al Infection & Immunity 58:3293 3299, 1990.*
Talkington Microbial Pathogenesis 13:343–355, 1992.*
McDaniel Microbial Pathogenesis 17:323–337, 1994.*
Lysons et al, Clin. & Molecular Aspects of Anaeroles, 1990, vol. 25, p 147–151.*
Tart et al. "Truncated *Streptococcus pneumoniae* PspA Molecules Elicit Cross–Protective Immunity Against Pneumococcal Challenge in Mice," *J. Infectious Disease*, 173:380–386 (1996).
McDaniel et al., "A Pneumococcal Surface Protein (PspB) That Exhibits the Same Protease Sensitivity as Strepococcal R Antigen," *Infection and Immunity*, 56(11):3001–3003 (1988).
Hollingshead et al., "Diversity of PspA: Mosaic Genes and Evidence for Past Recombination in *Streptococcus pneumoniae*," *Infection and Immunity*, 68(10):5889–5900 (2000).
Briles et al., "Immunization of Humans with Recominant Pneumococcal Surface Protein A (rPspA) Elicts Antibodies That Passively Protect Mice from Fatal Infection with *Streptococcus pneumoniae* Bearing Heterologous PspA," *J. Infectious Disease*, 182:1694–1701 (2000).
Briles et al., "The Potential for Using Protein Vaccines to Protect Against Otitis Media Caused by *Streptococcus pneumoniae*," *Vaccine*, 19:S87–S95 (2001).
McDaniel et al., Molecular Localization of Variable and Conserved Regions of pspA and Identification of Additional pspA Homologous Sequences in *Streptococcus pneumoniae*, *Microbial Pathogenesis*, 13:261–269 (1992).
Swiatlo et al., "Genetic Analysis of Pneumococcal Surface Protein A (PspA) Using Southern Blot Hybridization with Oligonucleotide Probes," 93rd General Meeting of the American Society for Microbiology, D–70, p. 107 (1993) (abstract).
Crain et al., "Simultaneous Expression of Two Apparent PspA Molecules by Some Capsular Group 6 Isolates of *Streptococcus pneumoniae*," 93rd General Meeting of the American Society for Microbiology, D–71, p. 107 (1993) (abstract).

* cited by examiner

*Primary Examiner*—Rodney P Swartz
(74) *Attorney, Agent, or Firm*—Nixon Peabody LLP

(57) ABSTRACT

PspAs, portions thereof, DNA therefor, and immunological compositions, primers and probes based thereon are disclosed claimed.

3 Claims, 32 Drawing Sheets

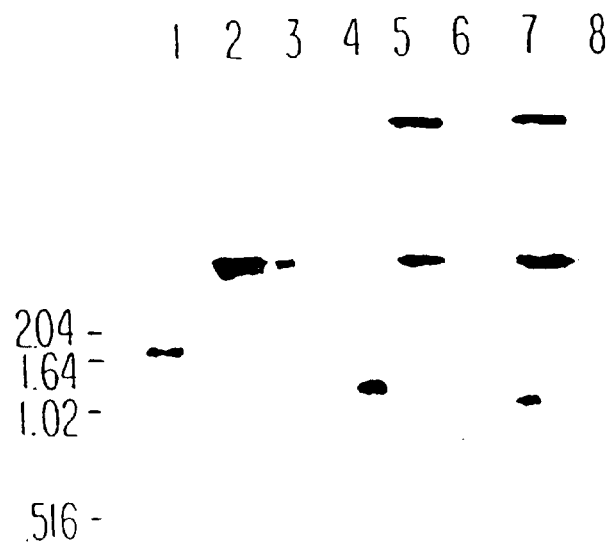
FIG. IA
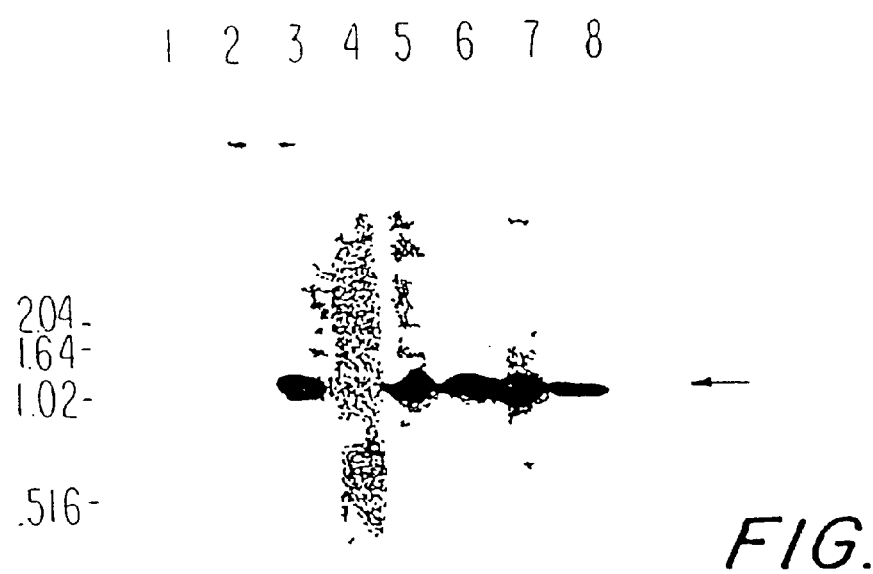
FIG. IB

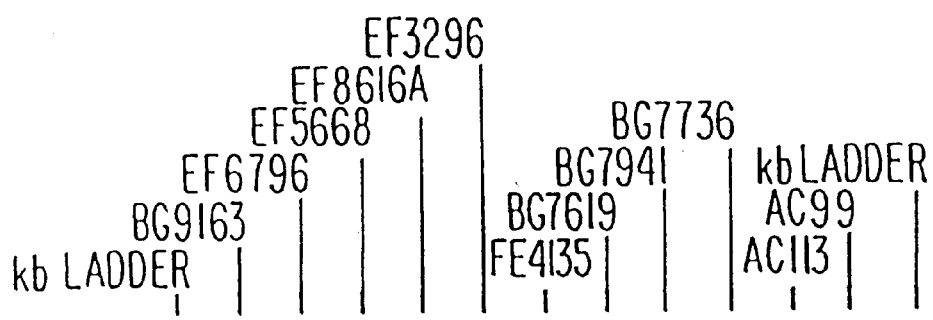
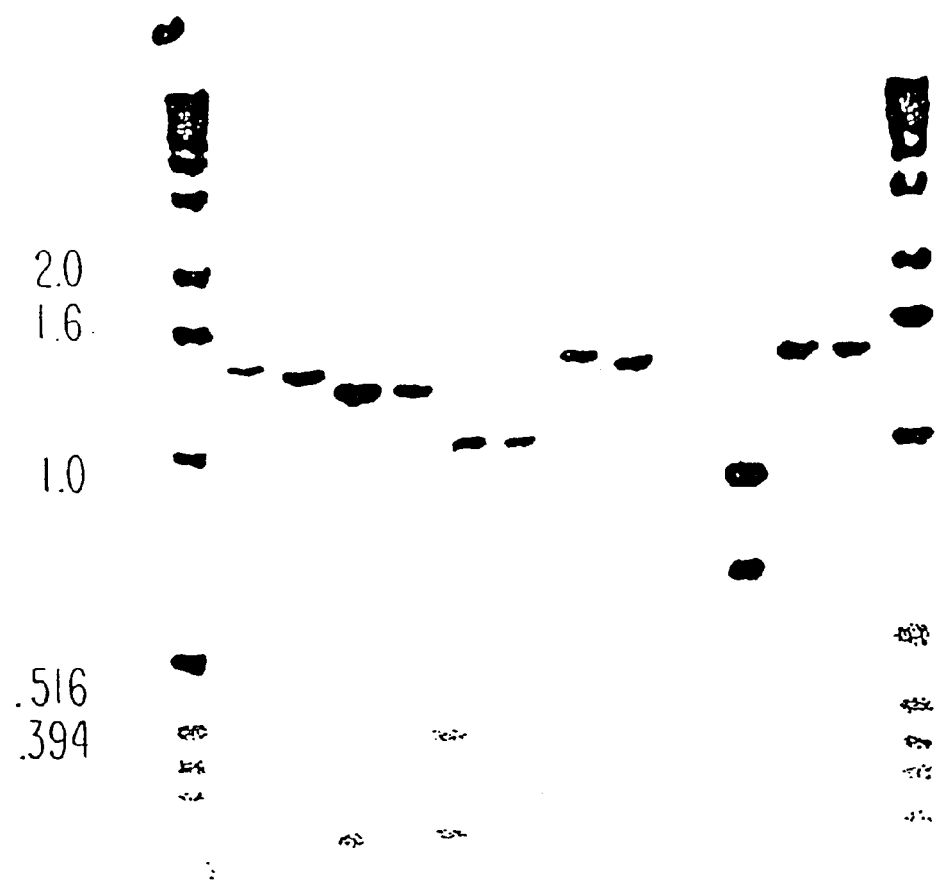
FIG. 12

AMINO ACID SEQUENCES IN THE NH2-TERMINAL END OF DIFFERENT PSPA GENES.
Gap inserted to maximize alignment with related PspA sequences).

```
AtCC6303    ..........  MNKKKMILTS  LASVAILGTG  FVASPPTLVR  AEESPQVVEK  SSLEKKYEEA
            KAKADTAKKD  YETAKK...K  AEDAQKKYDE  DQKKTEDKAK  A.VKKVDEER
            QKAILAVQKA  YVEY....RE  AKDKASAEKQ  IAEAKRKT..  ..........
            ..........  ..........  ..........  ..........  ..........

Ac94....    ..........  MNKKKMILTS  LASVAILGAG  LVTAQPTLVR  AEEAP.VASQ  SKAEKDYDTA
            KRDAENAKKA  LEEAKR....  ..AQKKYED   DQKKTEEKAK  E.EKQASEAE
            QKANLQYQLK  LREYIQ..KT  GDRSKIQTEM  EEAEKKHKTA  KAEFDKVRGT
            VIPSAARV..  ..........  ..........  ..........  ..........

Bg11703pro  ..........  MNKKKMILTS  LASVAILGAG  LVTSQPTLVR  AEEAP.VASQ  SKAEKDYDAA
            VKKSEAAKKA  YEEAKK...K  AEDAQKKYDE  DQKKTEEKA.  ENEKKAAADL
            TEATEVHQKA  YVRYSGSNEQ  KIKNFKILAI  ..........  ..........
            ..........  ..........  ..........  ..........  ..........

Bg7322pro   ..........  MXKKKMILTS  LASVAILGAG  XVASQPTXVR  AEDAP.VANQ  SQAEKDYXAA
            XXKSEAAKKX  YXXAKKVLAE  AEAAQKXXED  XQKKPEEKA.  EKAKAASEEI
            VKATEEVQXA  A.........  ..........  ..........  ..........
            ..........  ..........  ..........  ..........  ..........
```

FIG. 13A

```
Bg7561pro  MNKKKMILTS LASVAILGAG LVTSQPTLVR AEEAP.GASQ SKAEKDYXAA
           XKKSEAAKKA YEEAAKK...K AEDAQKKYDE GQKKTEEKA. RKAEEASKEL
           AKATSEVQNA YVKYQGVQRN SRLNEKERKK QLAEIDEEIN KAKQIWNEKN
           EDFKKVREEV IPEPTELAKD QRKAEEEAKAE EKVAKRKYDY ATLKVALAKS
           YVEAEEAXL. .......... .......... .......... ..........

Bg8090pro  MNKKKMILTS LASVAILGAG LVTSQPTFVR AEEAP.VASQ PKAEKDYDPA
           GKKSEAATKA YEDAKP...T AEDAQKKYDE AQKKPDAER. ..........
           .......... .......... .......... .......... ..........

Bg8743pro  MNKKKMILTS LASVAILGAG LVASQPTVVR AEEAP.VAKQ SQAERDYDAA
           MKKSEAAKKE YEEAKKDLEE AKAAQKKYGG DPKKTGEETK LVPK.ADGER
           PKANVAVPKA YLKLREAQEQ LNQSPNNKKN SAQQKLKDAL AHIDEVTLNQ
           KEAEA..... .......... .......... .......... ..........

Bg8838pro  MNKKKMILTS LASVAILGAG LVTSQPTVVR AEESP.VASQ SKAEKDYDAA
           VKNATAAKKA AEDAHRALDE AKAAQKNYDE DQKKPEEKAK EVPKAPAEE.
           .......... .......... .......... .......... ..........
```

*FIG. 13B*

```
Bg9163pro    MNKKKMILTS LASVAILGAG LVASQPTLVR AEDAP.VANQ SQAEKDYDAA
             MKKSEAAKKE YEDAKKVLAE AEAAQKKYED DQKKTEEKA. ENANAASEEI
             AKATEEVH.. .......... .......... .......... ..........

Bg9739pro    .......... LASVAILGAG LVASSPTVVR AEEAP.VASQ SKAEKDYDTA
             KRDAENAKKA LEEEAKR... ..AQEKYAD YQRRIEEKAA K.ETQASLEQ
             QEANKDYQLK LKKYLDGRNL SNSSVLKKEM EEAEKKDKEN QAEFNKIRRE
             IVVPNPQELE MARRKSEVVK ATESGLVTRV EEAEKNVTDA RQKLVLKCNE
             VVLQAXXAEL ESGGHKLEPK .......... .......... ..........

Db11pro      MNKKKMILTS LASXAILGAG LVASQPTVVR AEEAP.VASQ SKAEKDYDAA
             KRDAENAKKA LEEEAKR... ..AQKXXED DQKKTEEKAK X.DXQASEAE
             QKANLXYQLL LQKYVSESDG KKKKKEXEXXA DAAKKEIELK XADLXKIXQE Db15pro      .......... LASVAILGAG LVASQPTVVR AEEAP.VASQ SKAEKDYDAA
             MKKSKAAEED LE..... E AEAAQRKYDE DQKKSEENEK E.TEEASERQ
             QAATLKYHLE SXEFLNYFQD NHR....... .......... ..........

Db16aapro    MNKKKMILTS LASVAILGAG LVASPPTVVR AEEAP.VASQ SKAEKDYDTA
             KRDAENAKKA LEEEAKR... ..AQEKYAD YQRRIEEKAA K.ETHASLEQ
             QEANKDYQLK LKKYLDGRNL SNSSVLKKEM EEAEKKDKEK PAEFNKIRRE
             IVVPNPQELE MARRKSEVAK TKESGLVKRV EEAEKKVTEA RPKLDAERAK
             EVVLQAQIA. .......... .......... .......... ..........
```

FIG. 13C

```
Db16apro    MNKKKMILTS LASVAILGAG LVASPPTVVR AEEAP.VASQ SKAEKDYDTA
            KRDAENAKKA LEEAKR.... ...AQEKYAD YQRRIEEKAA K.ETHASLEQ
            QEANKDYQLK LKKYLDGRNL SNSSVLKKEM EEAEKKDKEK QAGL......
            .......... .......... .......... .......... ..........

Ef10197pro  MNKKKMILTS LASVAILGAG LVTSQPTLVR AEESP.VASQ SKAEKDYDAA
            KRDAENAKKA LEEAKR.... ...AQEKYAD YQRRIEEKAA K.EQQASLEQ
            QEANKDYQLK LKKYLDGRNL SNSSVLKKEM EEAEKKDKEK QAEFNKIRRE
            IVVPNPQELE MARRKSEVVK AKESGLVKRV EEAEKKVTEA RQKLDAERAK
            EVVLQPTR*V ENEVHKLXQK .......... .......... ..........

Ef3296pro   MNKKKMILTS LASVAILGAG LVTSQPTFVR AEESPQVVEK SSLEKKYEEA
            KAKADTAKKD YETAKK...K AEDAQKKYED DQKRTEEKAR K.EAEASQKL
            IDVALVVQNA YKEY....RE VQNQRSKYKS DADYQKKLTE VDSKIEKARK
            EQQDLQNNFN EVRAVVAPDP TCVGXDXR.. .......... ..........

Ef6796pro   .......... LASVAILGAG XVTSQPTXVR AEEAPQVVEK SSLEKKYEEA
            MNKKKMILTS KAKYDAAKKD YDEAKK...K AAEAQKKYEE DQKKTEEKAE K.AKAASEEI
            AKATEEVQKA VLDYITAIRN HNDSGKTSAE EAENKAKERD YCCAGKKFDP
            IQTPFVASLT QMIL...... .......... .......... ..........

L81905pro   MNKKKMILTS LASVAILGAG LVASSPTVVR AEEAP.VASQ SKAEKDYDTA
            KRDAENAKKA LEEAKR.... ...AQEKYAD YQRRIEEKAA K.ETQASLEQ
            QEANKDYQLK LKKYLDGRNL SNSSVLKKEM EEAEKKDKEN QAEFNKIRRE
            IVVPNPQELE MA........ .......... .......... ..........
```

FIG. 13D

```
Rx1pro      MNKKKMILTS  LASVAILGAG  FVASQPTVVR  AEESP.VASQ  SKAEKDYDAA
            KKDAKNAKKA  VEDAQKALDD  AKAAQKKYDE  DQKKTEEKA.  ALEKAASEEM
            DKAVAAVQQA  YLAYQQATDK  AAKDAADKMI  DEAKKREEEA  KTKFNTVRAM
            VVPEPEQLAE  TKKKSEEAKQ  KAPELTKKLE  EAKAKLEEAE  KKATEAKQKV
            DA........  ..........  ..........  ..........  ..........

Wu2pro      MNKKKMILTS  LASVAILGAG  LVASQPTLVR  AEESP.VASQ  SKAEKDYDAA
            VKKSEAAKKA  YEEAKKALEE  AKVAQKKYED  DQKKTEEKA.  ELEKEASEAI
            AKATEEVQQA  YLAYQRASNK  A..EAAKMIE  EAQRRENEAR  AKFTTIRTTM
            VVPEPEQLAE  TKKKAEEAKA  KEPKLAKKAA  EAKAKLEEAE  KKATEANPQV
            DA........  ..........  ..........  ..........  ..........

Ef5668pro   MNKKKMILTS  LASVAILGAG  FVASSPTFVR  AEEAP.VANQ  SKAEKDYDAA
            VKKSEAAKKD  YETAKK...K  AEDAQKKYDE  DQKKTEAKAE  K.ERKASEKI
            AEATKEVQQA  YLAYLQASNE  SQRKEADKKI  KEATHAKMRR  TCNLTIEFEQ
            QLYFLNQVSY  LRLRKKQKRQ  QKKQKYLRKN  LKRQLKRYKY  RKIKYLNKML
            KTKRKL....  ..........  ..........  ..........  ..........

Bg6692pro   MNKKKLIVTS  LASVAILGAD  SVTSPPALVR  ADEASLIASQ  SKAEKDYDAA
            KKDAKNAKKA  VEDAQKALDD  AKAAQKKYDE  DQKKTEKKAA  AV.KKIDEEH
            QAANLKSQQA  LVEFLAAQRE  GNPKKKKAAQ  ATLEEAENAE  KETK......
```

FIG. 13E

```
Ac122pro     MNKKKMIKTS LASAAIFGAX SETSQPTRVR PVEAPE.ARH PKVDKYYDAE
             ADEY...... .......... .......... .......... ..........
             .......... .......... .......... .......... ..........
             .......... .......... .......... .......... ..........
             .......... ..........
A66pro       MNKKKMILTS LASVAILGAG FGCVSAYSCK SRRISRS*SA *SSQRL....
             .......... .......... .......... .......... ..........
             .......... .......... .......... .......... ..........
             .......... .......... .......... .......... ..........
             .......... ..........
L82013pro    MNKKKMILKS LASAAISGAX LVXPQPTLVR AEESP.AASQ SHPEQDYDXX
             XXLCXXLXHQ PSXGRTLLXX XXSXPXSPTP XXXXXXPXSX LTXLXPLXXX
             LKPFPLPXSX PXPPXPPXSP PSPPPRPXLY XXPPXPXPXL SLXLIPFLLL
             XLPPPXXXLP HLXSPPXPXL PPSPTPX... .......... ..........
             .......... ..........
```

*FIG. 13F*

SEQUENCES IN THE CENTRAL REGION - (Includes Carboxy-terminus of alpha-helix region and some of the proline-rich region. Gaps are inserted to maximize alignment related PspA sequences.)

```
30 336      ......L  .......  KEIDESDSED  YLKEGLRAPL  ...........  QSKLDTKKAK  LSKLEELSDK
0922134c    IDELDAEIAK  LEVQLKDAEG  NNNVE.....  A.YFKEGLEK  TTAEKKAELE
            KAEADLKKAV  DEPETPAPA.  ......PQPA  PAPEKPAE..  .........K
            PAPAPAP...  EKPAPAPE..  ....K.PAEK  PAEKPAEEPA  EKPAPAPEK.
            ..........  ....PAPTPE  .KPAPTPETP  KTGWKQENGM

Atcc6303c   ..........  KT....PKDL  EDSGLGLEKV  LATLDPGGET  .........V  LDXTIAEGKA  GIAAXPPNID
            VSDLENQVSE  LDREVTRLPS  DLKDTEGNNV  GDYVKGGLEK  ALTDEKVGLN
            NTPKALDTAP  KALDTALNEL  G.PDGDEEET  PAPAPKPE..  ......QPA
            EQP.....K.  ..........  ......PAPK  PAPAPK  PEKTDDQQAE  EDYARRSEEE
            YNRLPQQQPP  KAEK..PAPA  PKPEQPVPAP Ac122c      DRLAARQAEL  AQKQTELGKL  LDSLDPEGKT  QDELDKEAGE  ......GGW  SWR*ILLARP
            ADGLPNKVSD  LEKEISNLEI  LLGGADSEDD  T....AALPN  .AELDKK
            KTQKELDAAL  NELG......  ..PDGDEEET  PAPAPQPE..  KLATKKAELE
            PAPAPKPEQ.  ..........  ...PTPAPK  PEQPTPAPKP  EQ..PAP...  .......Q
            ......AP  KPEQ..PAPA  PKPEQPAPAP  KP.EQPTPGP  KIE.......
```

```
Bg8743c   ..........  .L........  .KEIDESDSED  YIKEGLRAPL  .QSKLDAKKAK  .LSKLDELSDK
          IDELDAEIAK  LEKDVGDFPN  SDGEQ.....  AGQYLVAAEK  DLDAKEAELG
          NTGADLKKAV  DEPETPAPA.  ....PAPK..  PAPAPT....  .........P
          EAPAPA....  PKPAPAPK..  ....PAPAPK  PAPAPKPAPA  PKPAPAPK..
          ..........  ..PAPAPKPE  RT........  ..........  ..........

Bg9163c   ..........  GVQRTRKRAP  KRIMSLSQKV  XLKXVCRAPL  .QSKLDAQKAE  .LLKLEELSGK
          IEELDAEIAE  LEVQLKDAEG  NNNVE.....  A.YFKEGLEK  TTAEKKAELE
          XAXADLKKAV  DEPETPAPA.  ....PAPA..  PAP.......  .........A
          PAPAPA....  PAPAPK....  ....PAPAPK  PAPAPAPAPA  PKPAPAPK..
          ..........  ..PAPAPAPA  PKPEKPAEKP  APAPKPETXX  TYG.......  .....END

Bg9739c   ..........  .L........  .KEIDESDSED  YVREGFRAPL  .QSELDAKQAK  .LSKLEELSDK
          IDELDAEIAK  LEKDVEDFQN  SDGEQ.....  AGQYLAAAGE  DLIAKKAELE
          KAEADLKKAV  DEPETPAPA.  ....PA....  PAPAPT....  .........P
          EAPAPAPAPA  PKPAPAPK..  ....PAPAPK  PAPAPKPAPA  PKPAPAPK..
          ..........  ..PAPAPAPA  PKPEKPAEKP  APAPKPE...  ..........
```

FIG. 13I

```
Ef1019c   ........L  KEIDESDSED  YVKEGFRAPL  .QSELDAKQAK  .LSKLEELSDK
          IDELDAEIAK  LEDQLKAAEE  NNNVE.....  ..DYFKEGLEK  TIAAKKAELE
          KTEADLKKAV  NEPEKPAEEP  SQPEKPAEEA  PAPEQPTEPT  QPEKPAEQPQ
          PAPAPQPEKP  AEETPAPKPE  K...PAEQPK  AEKPADQQAE  EDYARRSEEE
          YNRLTQQQPP  KAEKPAPA..  PKTK......  ..........  ..........

Ef3296c   ........GGS  ALDQEAAAPP  HQVADLEKQI  TGPEIFLGGA  DPEADIAARP
          NELAAKQAEL  AQKPTGLEKL  LDSLDPGGKT  QDELDKEAGE  ...AELDKK
          ADELPNKVAD  LEKEISNLEI  LLGGADSEDD  T....AALPN  KLAXKXAELE
          KTQKELDAAP  NELG......  ..PDGDEET  PAPAPQPE..  .........Q
          PAPAPKPEQ.  ........  .PAPAPK  PEQPAPAPKP  EQ..PAP...
          .......AP  KPEQ..PAPA  PKPEQPAKPE  KPAEEPTQPE  KPATPKT...

Ef6796xc  ..........  ..........  ..........  ..........  ........R
          VRAL..KVAE  FGVQLRDAGG  SNNVG.....  A.YFKEGLEE  TTAEXEAGLG
          KAEADLKKAV  DEPET.....  ..........  PAP.......  .........A
          PAPAPA....  PAPAPAPK..  ...PAPAPK  PAPAPAPAPA  PKPAPAPK..
          ..........  .PAPAPAPA  PKPEKPAEKP  APAPKPETPK  T.........
```

FIG. 13J

```
Db15c    ..........  .L KDIDESDSED YAKEGLRAPL QSELDTKKAK ..LLKLEELSGK
         IEELDAEIXE LEVQLKDAEG NNNVE..... A.YFKEGLEK TTAEKKAELE
         KAEADLKKAV DEPETPAPA. ....PAPA PAPAPTPE.. ...........A
         PAPAPA.... PKPAPAPK.. ....PAPAPK PAPAPKPAPA PKPAPAPKPA
         PAPAPAPAPK PAPAPAPAPA PKPEKPAEKP APAPKPETPK TGWKQENGM.

L81905c  ..........  .L KEIDESDSED YVKEGFRAPL QSELDAKQAK ..LSKLEEXSDK
         XDELDAEIAK LEKDVEDFKN SDGEQ..... AGQYLAAAEE DLIAKKAXLE
         KAEADLKKAV DEPETPAPA. ......PA PAPAPT.... ...........P
         EAPAPA.... .....PAPAPK PAPAPKPAPA PAPAPT.... ...........
         ..........  PAPAPAPA PKPEKPAA.. PAPAPKPAPA PKPAPAPK...

Rct115c  ..........  LKEIDESDVE VKKAELELVK EEAKEPRNEE KVKQAKAEVE
         SKKAEATRLE KIKTDRKKAE EAKRKAAEED KVKEK..... ..........
         ..PAPKPEN. ...........  ...PAEQPK AEKPADQQAE EDYARRSEEE
         YXRLTQQPP KTEKPAQPST PKT....... .......... ..........
```

*FIG. 13K*

```
Rct121c  ..........  ..........  ..........  ..........  ..........  ..........
         SKKXEATRLE  KIKTDRKKAE  ..........  ........K   GEARESRXEE  ..........
         PAPAPKPEN.  EAXRKAAEED  KVKEKPAEQP  KVNQPKXEVE
         YNRLTQQQPP  KTEKPAQPST  ....PAEQPK  AEKPADQQAE  QPAPAPQPEK
         ..........  XK........  ..........  ..........  EDYARRSEEE
                                                         .

Rct123c  ..........  ..........  ..........  ..........  ..........  ..........
         .......I    KEXDESXSED  YLKEGLRAPL  QSKLDTKKAK  LSKLEELSDK
         IDELDAEIAK  LEVQLKDAEG  NNNVE.....  A.YFKEGLEK  TTAEKKAELE
         KAEADLKKAV  DEPETPAPA.  ...PQPA     PAPEKPAE..  ........K.
         PAPAPAP...  .....PAPTPE  .KPAPTPETP  PAPEKPAE.   EKPAPAPEK.
         ATGWLQNNGS  WYYLNSNGAM  ATGWHQNNGS  KTGWKQENGM  WYFYNTDGSM
                                  WYYLNS

Rct129c  ..........  ..........  ..........  ..........  ..........  ..........
         .......L    KEIDESDSED  YLKEGLRAPL  QSKLDTKKAK  LSKLEELSDK
         IDELDAEIAK  LEVQLKDAEG  NNNVE.....  A.YFKEGLEK  TTAEKKAELE
         KAEADLKKAV  DEPDTPAPA.  ...PQPA     PAPEKPAE..  ........K.
         PAPAPAP...  EKPAPAPE.   ..K.PAPA    PEKPAP..AP  EKPAPAPEK.
         .........   .....PAPAPE  .KPAPAPEKP  APAPKPETPE  TRLETRKRY.
```

FIG. 13L

```
Rct135c  ..........L  KEIDESDSED  YLKEGLRAPL  QSKLDTKKAK  LSKLEELSDK
         IDELDAEIAK   LEVQLKDAEG  NNNVE.....  A.YFKEGLEK  TTAEKKAELE
         KAEADLKKAV   DEPETPAPA.  ....PQPA    PAPEKPAE..  .......K
         ..PAPAP...   EKPAPAPE.   ...K.PAPA   P........   EKPAPAPEK.
         ..........   .....PAPAPE .KPAPTPETP  KTGWKQENGM  ..........

RX1c     ..........L  KEIDESESED  YAKEGFRAPL  QSKLDAKKAK  LSKLEELSDK
         IDELDAEIAK   LEDQLKAAEE  NNNVE.....  .DYFKEGLEK  TIAAKKAELE
         KTEADLKKAV   NEPEKPA...  ....PAPET   PAPEAPAE..  ......QPK
         PAPAPQP...   .APAPKPE    K...PAEQPK  PEKTDDQQAE  EDYARRSEEE
         YNRLTQQQPP   KAEKPAPA.   PKTGWKQENG  MWYFYNTDGS  M.........

Bg6692c  ..........   ..........  ..........  .GQYRAAAEG  DLAAKQAELE
         KTEADLKKAV   NEPEK..PA.  ....GEQA..  .PAPET      PAPEAPAE..
         PAPAPQP...   .APAPKPE    K...PAEQPK  AEKTDDQQAE  EDYARRSEEE
         YNRLTQQQPP   KAEKPAPA.   PKPEQPAPA.  ..........  ..........
```

*FIG. 13M*

```
Bg8838c                                          ..........PK  NSKGEQA....  .EQYRSAAGG  DLAAKQVELE
          KTEADLKKAV  NEPEK..PA.  .PAPET  PAPEAPAE..  .QPK
          PAPAPQP...  .APAPKPE..  K..PAEQPK  AEKPADQQAE  EDYDRRSEEE
          YNRLTQQQPP  KAEKPAPA..  PQPEQPAPAP  KS........  ..........

Db16ac    ..........  ........L  KEIDESDSED  YVKEGFRAPL  QSELDAKQAK  LSKLEELSDK
          IDELDAEIAK  .LEKDVEDFK  XSDGEQA...  .GQYLAAAEE  DLIAKKAELE
          QTEADLKKAV  NEPGKPAPA.  ....PAPET  PAPEAPAE..  ...QPK
          PAPET.P...  .APAPKPE..  K..PAEQPK  PEKPADQQAE  EDYARRSEEE
          YNRLTQQQPA  PAQKPEQP..  AKPEKPAEEP  TQPEK.....  ..........

Db11c     ..........  ..........  ..........  ..........  ..........
          ...DAEIAK  .LEKNVEYFK  KTDAEQT...  .EQYLAAAEK  DLADKKAELE
          KTEADLKKAV  NEPEKPAEE.  ...TPAPA  PKPEQPAE..  .QPK
          PAPAPQP...  .APAPKPE..  K..APAPKP.  .EKTDDQQAE  EDYARRSEEE
          YNRLPQQQPP  KAEKPAPA..  PKPEQPVP..  ..........  ..........
```

FIG. 13N

```
L820131c                                          ..........  ..........  ..........  ..........  ..........
                                                  ..........  ..........  ..........  ..........  ..........
         PAXAPQPLKP  EEPAEQPKPE  KPEEPAGQPE  .A  EXPENPAP..  ..........
         YNRFPQQQPP  KAEKPAPA..  PKPEQPVPAP  PEKPDDQQAG  EDYARRSGGE
                                              KT........  .......APK

Bg11703c                                          ..........  ..........  ..........  ..........  ..........
         ...TKKAELEPEL  EKAEAELENL  LSTLDPEGKT  ....LLKKA  KLAGAKSKAA
         VEALPNQVSE  LEEELSKLED  NLKDAETNNV  QDELDKEAAE  ...AELNKK
         KT.....P   KELDAALNEL   G.PDGDEEET  EDYIKEGLEE  AIATKQAELE
         PEK.PAEET.  ..........   PPPEAPAE..  ..........  ....QPK
         YNRLTQQQPP  KAEKPAPAPA  ...PAPAPK   PEKSADQQAE  EDYARRSEEE
                                  PKPEQPAPAP  KSR.......

Bg7817c                                           ..........  ..........  ..........  ..........  ..........
         ...LKKLGLEPGL  EKAGAGLGNL  LSTLDPEGKT  ..GLATKKKL  NLAEARIELL
         VEALPNQVAE  LEEELSKLED  NLKDAETNHV  QDELDKEAAE  ...AELNKK
         KT.....P   KELDAALNEL   G.PDGDEEET  EDYIKEGLEE  AIATKQAELE
         PEK.PAEET.  ..........   PAPEAPAE..  ..........  ....QPK
         YNRLTQQQPP  KAEKPAPAPA  ...PAPAPK   PEKSADQQAE  EDYARRSEEE
                                  PKPEQPAPAP  K.........
```

FIG. 130

```
Bg7561c  ..........  ..........  ..........  ..........  ..........
         VEALPNPVXE  KKQKVNLENL  LSTLDPGGKT  QDELDKGAAE  ....AELNKK
         ET......P   QEVDAALNDL  NLKDAETNHV  EDYIKEGLEE  AIATKQAELE
         PAPAPNAEQ.  ..........  V.PDGGEEET  PAPAPQPD..  ......EPA
         YNRLTQQQPP  KAEKPAPAPA  .PAPAPK     PEKSADQQAE  EDYARRSEGE
         ..........  ..........  PKPEQPAPAP  N.........  ..........

Ef5668c  ..........  ..........  ..........  ..........  ..........
         ....KEIAR   LQSDLKDAEE  NNVEDYIKEG  LEQAITNKKA  ELATTQQNID
         KT...QKDL   EDAELELEKV  LATLDPEGKT  QDELDKEAAE  ....AELNEK
         VEALQNQVAE  LEEELSKLED  NLKDAETNNV  EDYIKEGLEE  AIATKKAELE
         KT......Q   KELDAALNEL  G.PDGDEEET  PAPAPQPE..  ......KPA
         EEP.....EN  ..........  .PAPAPK     PEKSADQQAE  EDYARRSEEE
         YNRLTQQQPP  KAEK..PAPA  PQPEQPAPAP  KIE.......  ..........

Wu2c     ..........  ..........  ..........  ..........  ..........
         ....L       KEIDESESED  YAKEGFRAPL  HSKLDAKKAK  LSKLEELSDK
         IDELDAEIAK  LEDQLKAVEE  NNNVE.....  .DYSTEGLEK  TIAAKKTELE
         KTEADLKKAV  NEPEKSAEEP  SQPEKPAEEA  PAPEQPTEPT  ..........
         ...QPEKP    AEETPAPKPE  K...PAEQPN  AEKTDDQQAE  EDYARRSEEE
         YNRLTQQQPP  KAEKPAPA..  PQPEQTSSLH  ..........  ..........
```

FIG. 13P

Complete sequence for EF5668 pspA
Sequence Range: 1 to 1453

```
         10         20         30         40         50         60         70
          *          *          *          *          *          *          *
TTGACAAATA TTTACGGAGG AGGCTTATGC TTAATATAAG AAATGATTAT CAGAAAGAG
         80         90        100        110        120        130
          *          *          *          *          *          *
GTAAATTTAG ATG AAT AAG AAA AAA ATG ATT TTA ACA AGC CTA GCC AGC GTC GCT ATC TTA GGG>
         140 M   N   K   K   K   M   I   L   T   S   L   A   S   V   A   I   L   G>
          *         150                   160                   170                   180                   190
                     *                     *                     *                     *                     *
GCT GGT TTT GTT GCG TCT TCG CCT ACT TTT GTA AGA GCA GAA GCT GAA GAA GCT GAA GCT AAC>
 A   G   F   V   A   S   S   P   T   F   V   R   A   E   A   E   E   A   E   A   N>
        200                   210                   220                   230                   240                   250
          *                     *                     *                     *                     *                     *
CAG TCT AAA GCT GAG ACG GCT AAA GAA AAA GAC TAT GAT GCA GAA GAC GTG AAA GCT GTA AAA>
 Q   S   K   A   E   T   A   K   E   K   D   Y   D   A   E   D   V   K   A   V   K>
        260                   270                   280                   290                   300                   310
          *                     *                     *                     *                     *                     *
GAT TAC GAA ACG GCT AAA GCT GAG AAA AAG AAA GCA GAA GCA AAA TCT GAA GCT GAA AAG AAA>
 D   Y   E   T   A   K   A   E   K   K   K   A   E   A   K   S   E   A   E   K   K>
        320                   330                   340                   350                   360                   370
          *                     *                     *                     *                     *                     *
AAG AAA ACT GAG GCA AAA GCG GAA AAA GAA AGA AAA GAA AAA GCT TCT GAA AAG ATA GCT GAG GAT CAG>
 K   K   T   E   A   K   A   E   K   E   R   K   E   K   A   S   E   K   I   A   E   D   Q>
        380                   390                   400                   410                   420                   430
          *                     *                     *                     *                     *                     *
                                                                                          GCA>
                                                                                           A>
```

FIG. 13Q

```
ACA AAA GAA GTT CAA CAA GCG TAC CTA GCT TAT CTA CAA GCT AGC AAC GAA AGT CAG AGA
 T   K   E   V   Q   Q   A   Y   L   A   Y   L   Q   A   S   N   E   S   Q   R>
440         450         460         470         480         490
 *           *           *           *           *           *
AAA GAG GCA GAT AAG AAG ATA AAA GAA GCT GCT ACG CAC GCA AAG ATG AGG CGG ACG TGC AAT
 K   E   A   D   K   K   I   K   E   A   A   T   H   A   K   M   R   R   T   C   N>
500         510         520         530         540         550
 *           *           *           *           *           *
TTG ACT ATC GAA TTC GAA CAA CAA TTG TAC TTC CTG TAC AAC CAA AAG CAA GTG AGT TAC CTG AGA CTA
 L   T   I   E   F   E   Q   Q   L   Y   F   L   Y   N   Q   K   Q   V   S   Y   L   R   L>
560         570         580         590         600         610
 *           *           *           *           *           *
AGA AAG CAG AGG CAA AGG TAT AAG AAG AAG CAG CAA AAA ATA AAC CTG AAA AGG
 R   K   Q   R   Q   R   Y   K   K   K   Q   Q   K   I   N   L   K   R>
620         630         640         650         660         670
 *           *           *           *           *           *
CAG CTA AAG AGG TAT AAG TAT AGA AAA ATA AAA TAC TTG AAC AAG ATG CTG AAA ACG AAA
 Q   L   K   R   Y   K   Y   R   K   I   K   Y   L   N   K   M   L   K   T   K>
680         690         700         710         720         730
 *           *           *           *           *           *
AGA AAA TTG ACG TAC TTC AAA ACA AAG TCG CTG ATT TAT AAA AAG GAA TTG CTC TCC ATC
 R   K   L   T   Y   F   K   T   K   S   L   I   Y   K   K   E   L   L   S   I>
740         750         760         770         780         790
 *           *           *           *           *           *
AAA ACA GTC GCT GAA TTA AAT AAA GAA ATT GCT AGA CTT CAA AGC GAT TTA AAA GAT GCT
 K   T   V   A   E   L   N   K   E   I   A   R   L   Q   S   D   L   K   D   A>
800         810         820         830         840         850
 *           *           *           *           *           *
```

FIG. 13R

```
GAA GAA AAT AAT GTA GAA GAC TAC ATT AAA GAA GGT TTA GAG CAA GCT ATC ACT AAT AAA
 E   E   N   N   V   E   D   Y   I   K   E   G   L   E   Q   A   I   T   N   K>
        860             870             880             890             900             910

AAA GCT GAA TTA GAA GCT ACA ACT CAA CAA AAC ATA GAT AAA GAT TTA GAG GAT
 K   A   E   L   A   T   T   Q   Q   N   I   D   K   D   L   E   D>
        920             930             940             950             960             970

GCT GAA TTA GAA CTT GAA AAA GAA GTA TTA GCT ACA TTA GAC CCT GAA AAA ACT CAA GAT
 A   E   L   E   L   E   K   E   V   L   A   T   L   D   P   E   K   T   Q   D>
        980             990             1000            1010            1020            1030

GAA TTA GAT AAA GAA GCT GCT GAA AAA GAG TTG AAT GAA AAA GTT GAA GCT CTT CAA AAC
 E   L   D   K   E   A   A   E   K   E   L   N   E   K   V   E   A   L   Q   N>
        1040            1050            1060            1070            1080            1090

CAA GTT GCT GAA GAA GAA TTA GAA GAA CTT TCA AAA CTT GAA GAT AAT CTT AAA GAT GCT GAA
 Q   V   A   E   E   E   L   E   E   L   S   K   L   E   D   N   L   K   D   A   E>
        1100            1110            1120            1130            1140            1150
```

*FIG. 13S*

```
ACA AAC AAC GTT GAA GAC TAC ATT AAA GAA GGT TTA GAA GAA GCT ATC GCG ACT AAA AAA
 T   N   N   V   E   D   Y   I   K   E   G   L   E   E   A   I   A   T   K   K>
1160            1170            1180            1190            1200            1210
  *               *               *               *               *               *
GCT GAA TTG GAA AAA ACT CAA AAA GAA GAA TTA GAT GCA GCT CTT AAT GAG TTA GGC CCT GAT
 A   E   L   E   K   T   Q   K   E   E   L   D   A   A   L   N   E   L   G   P   D>
1220            1230            1240            1250            1260            1270
  *               *               *               *               *               *
GGA GAT GAA GAA GAA GAG ACT CCA GCG CCG CCT CAA GCT CCT CAA GAA CCA CAA GAA GAG CCT
 G   D   E   E   E   E   T   P   A   P   P   Q   A   P   Q   E   P   Q   E   E   P>
1280            1290            1300            1310            1320            1330
  *               *               *               *               *               *
GAG AAT CCA GCT CGA GCA GCA CCA GCG GCT AAG TCA ACC CAA GAT CAA CAA GCT GAA GAA GAC
 E   N   P   A   R   A   A   P   A   A   K   S   T   Q   D   Q   Q   A   E   E   D>
1340            1350            1360            1370            1380            1390
  *               *               *               *               *               *
TAT GCT CGT AGA TCA GAA GAA TAT AAT CGC TTG ACC CAA CAA CAG CAA CCG CCA AAA GCA
 Y   A   R   R   S   E   E   Y   N   R   L   T   Q   Q   Q   Q   P   P   K   A>
1400            1410            1420            1430            1440            1450
  *               *               *               *               *               *
GAA AAA CCA GCT CCT GCA CCA CCA CAA CAA CCA GAG CAA CCA CCA GCA CCA AAA ATA GAG GC
 E   K   P   A   P   A   P   P   Q   Q   P   E   Q   P   P   A   P   K   I   E   A>
```

*FIG. 13T*

SEQUENCE LISTING (1) GENERAL INFORMATION:

(iii) NUMBER OF SEQUENCES: 73

(2) INFORMATION FOR SEQ ID NO:1:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

CCGGATCCAG CTCCTGCACC AAAAAC    26

(2) INFORMATION FOR SEQ ID NO:2:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

GCGCGTCGAC GGCTTAAACC CATTCACCAT TGG    33

(2) INFORMATION FOR SEQ ID NO:3:

(i) SEQUENCE CHARACTERISTICS:

(A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CCGGATCCTG AGCCAGAGCA GTTGGCTG                    28

(2) INFORMATION FOR SEQ ID NO:4:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CCGGATCCGG CTCAAAGAGA TTGATGAGTC TG                32

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GCGGATCCCG TAGCCAGTCA GTCTAAAGCT G                 31

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CTGAGTCGAC TGGAGTTTCT GGAGCTGGAG C                 31

(2) INFORMATION FOR SEQ ID NO:7:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CCGGATCCAG CTCCAGCTCC AGCTCCAGAA ACTCCAG          37

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear

```
        (ii) MOLECULE TYPE: DNA (genomic)

(xi) SEQUENCE DESCRIPTION: SEQ ID NO:8:

GCGGATCCTT GACCAATATT TACGGAGGAG GC                                      32

(2) INFORMATION FOR SEQ ID NO:9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

GTTTTTGGTG CAGGAGCTGG                                                    20

(2) INFORMATION FOR SEQ ID NO:10:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:10:

GCTATGGCTA CAGGTTG                                                       17

(2) INFORMATION FOR SEQ ID NO:11:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

CCACCTGTAG CCATAGC                                                       17

(2) INFORMATION FOR SEQ ID NO:12:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

CCGGATCCAG CGTCGCTATC TTAGGGGCTG GTT                                     33

(2) INFORMATION FOR SEQ ID NO:13:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:
```

```
GCAAGCTTAT GATATAGAAA TTTGTAAC                                                28
```

(2) INFORMATION FOR SEQ ID NO:14:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
GGAAGGCCAT ATGCTCAAAG AGATTGATGA GTCT                                         34
```

(2) INFORMATION FOR SEQ ID NO:15:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
CCAAGGATGC CTTAAACCCA TTCACCATTG GC                                           32
```

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
CCACATACCG TTTTCTTGTT TCCAGCC                                                 27
```

(2) INFORMATION FOR SEQ ID NO:17:

(i) SEQUENCE CHARACTERISTICS:
        (A) LENGTH: 130 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Met Asn Lys Lys Met Ile Leu Thr Ser Leu Ala Ser Val Ala Ile
 1               5                  10                  15

Leu Gly Thr Gly Phe Val Ala Ser Pro Pro Thr Leu Val Arg Ala Glu
                20                  25                  30

Glu Ser Pro Gln Val Val Glu Lys Ser Ser Leu Glu Lys Lys Tyr Glu
                35                  40                  45

Glu Ala Lys Ala Lys Ala Asp Thr Ala Lys Lys Asp Tyr Glu Thr Ala
            50                  55                  60

Lys Lys Lys Ala Glu Asp Ala Gln Lys Lys Tyr Asp Glu Asp Gln Lys
65                  70                  75                  80

Lys Thr Glu Asp Lys Ala Lys Ala Val Lys Val Asp Glu Glu Arg
                85                  90                  95
```

```
Gln Lys Ala Ile Leu Ala Val Gln Lys Ala Tyr Val Glu Tyr Arg Glu
            100                 105                 110

Ala Lys Asp Lys Ala Ser Ala Glu Lys Gln Ile Ala Glu Ala Lys Arg
        115                 120                 125

Lys Thr
    130

(2) INFORMATION FOR SEQ ID NO:18:

(i) SEQUENCE CHARACTERISTICS:
        (A) LENGTH: 147 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Met Asn Lys Lys Lys Met Ile Leu Thr Ser Leu Ala Ser Val Ala Ile
1               5                   10                  15

Leu Gly Ala Gly Leu Val Thr Ala Gln Pro Thr Leu Val Arg Ala Glu
            20                  25                  30

Glu Ala Pro Val Ala Ser Gln Ser Lys Ala Glu Lys Asp Tyr Asp Thr
        35                  40                  45

Ala Lys Arg Asp Ala Glu Asn Ala Lys Lys Ala Leu Glu Glu Ala Lys
    50                  55                  60

Arg Ala Gln Lys Lys Tyr Glu Asp Asp Gln Lys Lys Thr Glu Glu Lys
65                  70                  75                  80

Ala Lys Glu Glu Lys Gln Ala Ser Glu Ala Glu Gln Lys Ala Asn Leu
            85                  90                  95

Gln Tyr Gln Leu Lys Leu Arg Glu Tyr Ile Gln Lys Thr Gly Asp Arg
            100                 105                 110

Ser Lys Ile Gln Thr Glu Met Glu Glu Ala Glu Lys Lys His Lys Thr
        115                 120                 125

Ala Lys Ala Glu Phe Asp Lys Val Arg Gly Thr Val Ile Pro Ser Ala
    130                 135                 140

Ala Arg Val
145

(2) INFORMATION FOR SEQ ID NO:19:

(i) SEQUENCE CHARACTERISTICS:
        (A) LENGTH: 125 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Met Asn Lys Lys Lys Met Ile Leu Thr Ser Leu Ala Ser Val Ala Ile
1               5                   10                  15

Leu Gly Ala Gly Leu Val Thr Ser Gln Pro Thr Leu Val Arg Ala Glu
            20                  25                  30

Glu Ala Pro Val Ala Ser Gln Ser Lys Ala Glu Lys Asp Tyr Asp Ala
        35                  40                  45

Ala Val Lys Lys Ser Glu Ala Ala Lys Lys Ala Tyr Glu Glu Ala Lys
    50                  55                  60

Lys Lys Ala Glu Asp Ala Gln Lys Lys Tyr Glu Asp Gln Lys Lys
65                  70                  75                  80
```

```
Thr Glu Glu Lys Ala Glu Asn Glu Lys Lys Ala Ala Ala Asp Leu Thr
                85                  90                  95

Glu Ala Thr Glu Val His Gln Lys Ala Tyr Val Arg Tyr Ser Gly Ser
            100                 105                 110

Asn Glu Gln Lys Ile Lys Asn Phe Lys Ile Leu Ala Ile
        115                 120                 125
```

(2) INFORMATION FOR SEQ ID NO:20:

(i) SEQUENCE CHARACTERISTICS:
        (A) LENGTH: 109 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Met Xaa Lys Lys Met Ile Leu Thr Ser Leu Ala Ser Val Ala Ile
1               5                   10                  15

Leu Gly Ala Gly Xaa Val Ala Ser Gln Pro Thr Xaa Val Arg Ala Glu
                20                  25                  30

Asp Ala Pro Val Ala Asn Gln Ser Gln Ala Glu Lys Asp Tyr Xaa Ala
            35                  40                  45

Ala Xaa Xaa Lys Ser Glu Ala Ala Lys Lys Xaa Tyr Xaa Xaa Ala Lys
        50                  55                  60

Lys Val Leu Ala Glu Ala Glu Ala Ala Gln Lys Xaa Xaa Glu Asp Xaa
65                  70                  75                  80

Gln Lys Lys Pro Glu Glu Lys Ala Glu Lys Ala Lys Ala Ala Ser Glu
                85                  90                  95

Glu Ile Val Lys Ala Thr Glu Glu Val Gln Xaa Ala Ala
                100                 105
```

(2) INFORMATION FOR SEQ ID NO:21:

(i) SEQUENCE CHARACTERISTICS:
        (A) LENGTH: 204 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Met Asn Lys Lys Met Ile Leu Thr Ser Leu Ala Ser Val Ala Ile
1               5                   10                  15

Leu Gly Ala Gly Leu Val Thr Ser Gln Pro Thr Leu Val Arg Ala Glu
                20                  25                  30

Glu Ala Pro Gly Ala Ser Gln Ser Lys Ala Glu Lys Asp Tyr Xaa Ala
            35                  40                  45

Ala Xaa Lys Lys Ser Glu Ala Ala Lys Lys Ala Tyr Glu Glu Ala Lys
        50                  55                  60

Lys Lys Ala Glu Asp Ala Gln Lys Lys Tyr Asp Glu Gly Gln Lys Lys
65                  70                  75                  80

Thr Glu Glu Lys Ala Arg Lys Ala Glu Glu Ala Ser Lys Glu Leu Ala
                85                  90                  95

Lys Ala Thr Ser Glu Val Gln Asn Ala Tyr Val Lys Tyr Gln Gly Val
            100                 105                 110

Gln Arg Asn Ser Arg Leu Asn Glu Lys Glu Arg Lys Lys Gln Leu Ala
```

```
             115                 120                 125
Glu Ile Asp Glu Glu Ile Asn Lys Ala Lys Gln Ile Trp Asn Glu Lys
    130                 135                 140

Asn Glu Asp Phe Lys Lys Val Arg Glu Glu Val Ile Pro Glu Pro Thr
145                 150                 155                 160

Glu Leu Ala Lys Asp Gln Arg Lys Ala Glu Ala Lys Ala Glu Glu
                165                 170                 175

Lys Val Ala Lys Arg Lys Tyr Asp Tyr Ala Thr Leu Lys Val Ala Leu
                180                 185                 190

Ala Lys Ser Tyr Val Glu Ala Glu Ala Xaa Leu
                195                 200
```

(2) INFORMATION FOR SEQ ID NO:22:

(i) SEQUENCE CHARACTERISTICS:
        (A) LENGTH: 85 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Met Asn Lys Lys Lys Met Ile Leu Thr Ser Leu Ala Ser Val Ala Ile
1               5                   10                  15

Leu Gly Ala Gly Leu Val Thr Ser Gln Pro Thr Phe Val Arg Ala Glu
                20                  25                  30

Glu Ala Pro Val Ala Ser Gln Pro Lys Ala Glu Lys Asp Tyr Asp Pro
                35                  40                  45

Ala Gly Lys Lys Ser Glu Ala Ala Thr Lys Ala Tyr Glu Asp Ala Lys
            50                  55                  60

Pro Thr Ala Glu Asp Ala Gln Lys Lys Tyr Asp Glu Ala Gln Lys Lys
65                  70                  75                  80

Pro Asp Ala Glu Arg
                85
```

(2) INFORMATION FOR SEQ ID NO:23:

(i) SEQUENCE CHARACTERISTICS:
        (A) LENGTH: 153 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Met Asn Lys Lys Lys Met Ile Leu Thr Ser Leu Ala Ser Val Ala Ile
1               5                   10                  15

Leu Gly Ala Gly Leu Val Ala Ser Gln Pro Thr Val Val Arg Ala Glu
                20                  25                  30

Glu Ala Pro Val Ala Lys Gln Ser Gln Ala Glu Arg Asp Tyr Asp Ala
                35                  40                  45

Ala Met Lys Lys Ser Glu Ala Ala Lys Lys Glu Tyr Glu Glu Ala Lys
            50                  55                  60

Lys Asp Leu Glu Glu Ala Lys Ala Ala Gln Lys Lys Tyr Gly Gly Asp
65                  70                  75                  80

Pro Lys Lys Thr Gly Glu Glu Thr Lys Leu Val Pro Lys Ala Asp Gly
                85                  90                  95
```

```
Glu Arg Pro Lys Ala Asn Val Ala Val Pro Lys Ala Tyr Leu Lys Leu
            100                 105                 110

Arg Glu Ala Gln Glu Gln Leu Asn Gln Ser Pro Asn Asn Lys Lys Asn
            115                 120                 125

Ser Ala Gln Gln Lys Leu Lys Asp Ala Leu Ala His Ile Asp Glu Val
            130                 135                 140

Thr Leu Asn Gln Lys Glu Ala Glu Ala
145                 150
```

(2) INFORMATION FOR SEQ ID NO:24:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
Met Asn Lys Lys Met Ile Leu Thr Ser Leu Ala Ser Val Ala Ile
1               5                   10                  15

Leu Gly Ala Gly Leu Val Thr Ser Gln Pro Thr Val Val Arg Ala Glu
            20                  25                  30

Glu Ser Pro Val Ala Ser Gln Ser Lys Ala Glu Lys Asp Tyr Asp Ala
            35                  40                  45

Ala Val Lys Asn Ala Thr Ala Lys Lys Ala Ala Glu Asp Ala His
            50                  55                  60

Arg Ala Leu Asp Glu Ala Lys Ala Ala Gln Lys Asn Tyr Asp Glu Asp
65                  70                  75                  80

Gln Lys Lys Pro Glu Glu Lys Ala Lys Glu Val Pro Lys Ala Pro Ala
                    85                  90                  95

Glu Glu
```

(2) INFORMATION FOR SEQ ID NO:25:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Met Asn Lys Lys Met Ile Leu Thr Ser Leu Ala Ser Val Ala Ile
1               5                   10                  15

Leu Gly Ala Gly Leu Val Ala Ser Gln Pro Thr Leu Val Arg Ala Glu
            20                  25                  30

Asp Ala Pro Val Ala Asn Gln Ser Gln Ala Glu Lys Asp Tyr Asp Ala
            35                  40                  45

Ala Met Lys Lys Ser Glu Ala Lys Lys Glu Tyr Glu Asp Ala Lys
            50                  55                  60

Lys Val Leu Ala Glu Ala Glu Ala Gln Lys Lys Tyr Glu Asp Asp
65                  70                  75                  80

Gln Lys Lys Thr Glu Glu Lys Ala Glu Asn Ala Asn Ala Ser Glu
                    85                  90                  95

Glu Ile Ala Lys Ala Thr Glu Glu Val His
            100                 105
```

(2) INFORMATION FOR SEQ ID NO:26:

(i) SEQUENCE CHARACTERISTICS:
        (A) LENGTH: 211 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

```
Met Asn Lys Lys Lys Met Ile Leu Thr Ser Leu Ala Ser Val Ala Ile
 1               5                  10                  15

Leu Gly Ala Gly Leu Val Ala Ser Ser Pro Thr Val Val Arg Ala Glu
             20                  25                  30

Glu Ala Pro Val Ala Ser Gln Ser Lys Ala Glu Lys Asp Tyr Asp Thr
             35                  40                  45

Ala Lys Arg Asp Ala Glu Asn Ala Lys Lys Ala Leu Glu Glu Ala Lys
 50                  55                  60

Arg Ala Gln Glu Lys Tyr Ala Asp Tyr Gln Arg Arg Ile Glu Glu Lys
 65                  70                  75                  80

Ala Ala Lys Glu Thr Gln Ala Ser Leu Glu Gln Gln Glu Ala Asn Lys
                 85                  90                  95

Asp Tyr Gln Leu Lys Leu Lys Lys Tyr Leu Asp Gly Arg Asn Leu Ser
                100                 105                 110

Asn Ser Ser Val Leu Lys Lys Glu Met Glu Glu Ala Glu Lys Lys Asp
            115                 120                 125

Lys Glu Asn Gln Ala Glu Phe Asn Lys Ile Arg Arg Glu Ile Val Val
130                 135                 140

Pro Asn Pro Gln Glu Leu Glu Met Ala Arg Arg Lys Ser Glu Val Val
145                 150                 155                 160

Lys Ala Thr Glu Ser Gly Leu Val Thr Arg Val Glu Glu Ala Glu Lys
                165                 170                 175

Asn Val Thr Asp Ala Arg Gln Lys Leu Val Leu Lys Cys Asn Glu Val
            180                 185                 190

Val Leu Gln Ala Xaa Xaa Ala Glu Leu Glu Ser Gly Gly His Lys Leu
            195                 200                 205

Glu Pro Lys
    210
```

(2) INFORMATION FOR SEQ ID NO:27:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

```
Met Asn Lys Lys Lys Met Ile Leu Thr Ser Leu Ala Ser Xaa Ala Ile
 1               5                  10                  15

Leu Gly Ala Gly Leu Val Ala Ser Gln Pro Thr Val Val Arg Ala Glu
             20                  25                  30

Glu Ala Pro Val Ala Ser Gln Ser Lys Ala Glu Lys Asp Tyr Asp Ala
             35                  40                  45

Ala Lys Arg Asp Ala Glu Asn Ala Lys Lys Ala Leu Glu Glu Ala Lys
 50                  55                  60
```

```
Arg Ala Gln Lys Xaa Xaa Glu Asp Asp Gln Lys Lys Thr Glu Glu Lys
 65                  70                  75                  80

Ala Lys Xaa Asp Xaa Gln Ala Ser Glu Ala Glu Gln Lys Ala Asn Leu
                 85                  90                  95

Xaa Tyr Gln Leu Leu Leu Gln Lys Tyr Val Ser Glu Ser Asp Gly Lys
             100                 105                 110

Lys Lys Lys Glu Xaa Glu Xaa Xaa Ala Asp Ala Ala Lys Lys Glu Ile
             115                 120                 125

Glu Leu Lys Xaa Ala Asp Leu Xaa Lys Ile Xaa Gln Glu
130                 135                 140
```

(2) INFORMATION FOR SEQ ID NO:28:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

```
Met Asn Lys Lys Lys Met Ile Leu Thr Ser Leu Ala Ser Val Ala Ile
  1               5                  10                  15

Leu Gly Ala Gly Leu Val Ala Ser Gln Pro Thr Val Val Arg Ala Glu
                 20                  25                  30

Glu Ala Pro Val Ala Ser Gln Ser Lys Ala Glu Lys Asp Tyr Asp Ala
             35                  40                  45

Ala Val Glu Lys Ser Lys Ala Ala Glu Glu Asp Leu Glu Glu Ala Glu
 50                  55                  60

Ala Ala Gln Arg Lys Tyr Asp Glu Asp Gln Lys Lys Ser Glu Glu Asn
 65                  70                  75                  80

Glu Lys Glu Thr Glu Glu Ala Ser Glu Arg Gln Gln Ala Ala Thr Leu
                 85                  90                  95

Lys Tyr His Leu Glu Ser Xaa Glu Phe Leu Asn Tyr Phe Gln Asp Asn
             100                 105                 110

His Arg
```

(2) INFORMATION FOR SEQ ID NO:29:

(i) SEQUENCE CHARACTERISTICS:
        (A) LENGTH: 200 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

```
Met Asn Lys Lys Lys Met Ile Leu Thr Ser Leu Ala Ser Val Ala Ile
  1               5                  10                  15

Leu Gly Ala Gly Leu Val Ala Ser Pro Pro Thr Val Val Arg Ala Glu
                 20                  25                  30

Glu Ala Pro Val Ala Ser Gln Ser Lys Ala Glu Lys Asp Tyr Asp Thr
             35                  40                  45

Ala Lys Arg Asp Ala Glu Asn Ala Lys Lys Ala Leu Glu Glu Ala Lys
 50                  55                  60

Arg Ala Gln Glu Lys Tyr Ala Asp Tyr Gln Arg Arg Ile Glu Glu Lys
 65                  70                  75                  80
```

```
Ala Ala Lys Glu Thr His Ala Ser Leu Glu Gln Gln Glu Ala Asn Lys
                85                  90                  95

Asp Tyr Gln Leu Lys Leu Lys Lys Tyr Leu Asp Gly Arg Asn Leu Ser
            100                 105                 110

Asn Ser Ser Val Leu Lys Lys Glu Met Glu Glu Ala Glu Lys Lys Asp
            115                 120                 125

Lys Glu Lys Pro Ala Glu Phe Asn Lys Ile Arg Arg Glu Ile Val Val
        130                 135                 140

Pro Asn Pro Gln Glu Leu Glu Met Ala Arg Arg Lys Ser Glu Val Ala
145                 150                 155                 160

Lys Thr Lys Glu Ser Gly Leu Val Lys Arg Val Glu Glu Ala Glu Lys
                165                 170                 175

Lys Val Thr Glu Ala Arg Pro Lys Leu Asp Ala Glu Arg Ala Lys Glu
            180                 185                 190

Val Val Leu Gln Ala Gln Ile Ala
        195                 200
```

(2) INFORMATION FOR SEQ ID NO:30:

(i) SEQUENCE CHARACTERISTICS:
        (A) LENGTH: 135 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

```
Met Asn Lys Lys Lys Met Ile Leu Thr Ser Leu Ala Ser Val Ala Ile
1               5                   10                  15

Leu Gly Ala Gly Leu Val Ala Ser Pro Pro Thr Val Val Arg Ala Glu
                20                  25                  30

Glu Ala Pro Val Ala Ser Gln Ser Lys Ala Glu Lys Asp Tyr Asp Thr
            35                  40                  45

Ala Lys Arg Asp Ala Glu Asn Ala Lys Lys Ala Leu Glu Glu Ala Lys
        50                  55                  60

Arg Ala Gln Glu Lys Tyr Ala Asp Tyr Gln Arg Arg Ile Glu Glu Lys
65                  70                  75                  80

Ala Ala Lys Glu Thr His Ala Ser Leu Glu Gln Gln Glu Ala Asn Lys
                85                  90                  95

Asp Tyr Gln Leu Lys Leu Lys Lys Tyr Leu Asp Gly Arg Asn Leu Ser
            100                 105                 110

Asn Ser Ser Val Leu Lys Lys Glu Met Glu Glu Ala Glu Lys Lys Asp
            115                 120                 125

Lys Glu Lys Gln Ala Gly Leu
        130                 135
```

(2) INFORMATION FOR SEQ ID NO:31:

(i) SEQUENCE CHARACTERISTICS:
        (A) LENGTH: 210 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

Met Asn Lys Lys Lys Met Ile Leu Thr Ser Leu Ala Ser Val Ala Ile

```
 1               5                    10                   15
Leu Gly Ala Gly Leu Val Thr Ser Gln Pro Thr Leu Val Arg Ala Glu
                20                  25                  30

Glu Ser Pro Val Ala Ser Gln Ser Lys Ala Glu Lys Asp Tyr Asp Ala
        35                  40                  45

Ala Lys Arg Asp Ala Glu Asn Ala Lys Lys Ala Leu Glu Glu Ala Lys
    50                  55                  60

Arg Ala Gln Glu Lys Tyr Ala Asp Tyr Gln Arg Arg Ile Glu Glu Lys
65                  70                  75                  80

Ala Ala Lys Glu Gln Gln Ala Ser Leu Glu Gln Gln Glu Ala Asn Lys
                85                  90                  95

Asp Tyr Gln Leu Lys Leu Lys Lys Tyr Leu Asp Gly Arg Asn Leu Ser
                100                 105                 110

Asn Ser Ser Val Leu Lys Lys Glu Met Glu Glu Ala Glu Lys Lys Asp
            115                 120                 125

Lys Glu Lys Gln Ala Glu Phe Asn Lys Ile Arg Arg Glu Ile Val Val
        130                 135                 140

Pro Asn Pro Gln Glu Leu Glu Met Ala Arg Arg Lys Ser Glu Val Val
145                 150                 155                 160

Lys Ala Lys Glu Ser Gly Leu Val Lys Arg Val Glu Ala Glu Lys
                165                 170                 175

Lys Val Thr Glu Ala Arg Gln Lys Leu Asp Ala Glu Arg Ala Lys Glu
                180                 185                 190

Val Val Leu Gln Pro Thr Arg Val Glu Asn Glu Val His Lys Leu Xaa
                195                 200                 205

Gln Lys
    210

(2) INFORMATION FOR SEQ ID NO:32:

(i) SEQUENCE CHARACTERISTICS:
         (A) LENGTH: 170 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:32:

Met Asn Lys Lys Lys Met Ile Leu Thr Ser Leu Ala Ser Val Ala Ile
1               5                   10                  15

Leu Gly Ala Gly Leu Val Thr Ser Gln Pro Thr Phe Val Arg Ala Glu
                20                  25                  30

Glu Ser Pro Gln Val Val Glu Lys Ser Ser Leu Glu Lys Lys Tyr Glu
        35                  40                  45

Glu Ala Lys Ala Lys Ala Asp Thr Ala Lys Lys Asp Tyr Glu Thr Ala
    50                  55                  60

Lys Lys Lys Ala Glu Asp Ala Gln Lys Lys Tyr Glu Asp Asp Gln Lys
65                  70                  75                  80

Arg Thr Glu Glu Lys Ala Arg Lys Glu Ala Glu Ala Ser Gln Lys Leu
                85                  90                  95

Ile Asp Val Ala Leu Val Val Gln Asn Ala Tyr Lys Glu Tyr Arg Glu
            100                 105                 110

Val Gln Asn Gln Arg Ser Lys Tyr Lys Ser Asp Ala Asp Tyr Gln Lys
        115                 120                 125

Lys Leu Thr Glu Val Asp Ser Lys Ile Glu Lys Ala Arg Lys Glu Gln
```

```
              130                 135                 140
Gln Asp Leu Gln Asn Asn Phe Asn Glu Val Arg Ala Val Val Ala Pro
145                 150                 155                 160

Asp Pro Thr Cys Val Gly Xaa Asp Xaa Arg
                165                 170
```

(2) INFORMATION FOR SEQ ID NO:33:

(i) SEQUENCE CHARACTERISTICS:
        (A) LENGTH: 160 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

```
Met Asn Lys Lys Lys Met Ile Leu Thr Ser Leu Ala Ser Val Ala Ile
1               5                   10                  15

Leu Gly Ala Gly Xaa Val Thr Ser Gln Pro Thr Xaa Val Arg Ala Glu
                20                  25                  30

Glu Ala Pro Gln Val Val Glu Lys Ser Ser Leu Glu Lys Lys Tyr Glu
                35                  40                  45

Glu Ala Lys Ala Lys Tyr Asp Ala Ala Lys Lys Asp Tyr Asp Glu Ala
            50                  55                  60

Lys Lys Lys Ala Ala Glu Ala Gln Lys Lys Tyr Glu Asp Gln Lys
65                  70                  75                  80

Lys Thr Glu Glu Lys Ala Glu Lys Ala Lys Ala Ala Ser Glu Ile
                85                  90                  95

Ala Lys Ala Thr Glu Glu Val Gln Lys Ala Val Leu Asp Tyr Ile Thr
                100                 105                 110

Ala Ile Arg Asn His Asn Asp Ser Gly Lys Thr Ser Ala Glu Ala
            115                 120                 125

Glu Asn Lys Ala Lys Glu Arg Asp Tyr Cys Cys Ala Gly Lys Lys Phe
130                 135                 140

Asp Pro Ile Gln Thr Pro Phe Val Ala Ser Leu Thr Gln Met Ile Leu
145                 150                 155                 160
```

(2) INFORMATION FOR SEQ ID NO:34:

(i) SEQUENCE CHARACTERISTICS:
        (A) LENGTH: 153 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

```
Met Asn Lys Lys Lys Met Ile Leu Thr Ser Leu Ala Ser Val Ala Ile
1               5                   10                  15

Leu Gly Ala Gly Leu Val Ala Ser Ser Pro Thr Val Val Arg Ala Glu
                20                  25                  30

Glu Ala Pro Val Ala Ser Gln Ser Lys Ala Glu Lys Asp Tyr Asp Thr
                35                  40                  45

Ala Lys Arg Asp Ala Glu Asn Ala Lys Lys Ala Leu Glu Glu Ala Lys
            50                  55                  60

Arg Ala Gln Glu Lys Tyr Ala Asp Tyr Gln Arg Arg Ile Glu Glu Lys
65                  70                  75                  80
```

```
Ala Ala Lys Glu Thr Gln Ala Ser Leu Glu Gln Gln Glu Ala Asn Lys
                85                  90                  95

Asp Tyr Gln Leu Lys Leu Lys Lys Tyr Leu Asp Gly Arg Asn Leu Ser
               100                 105                 110

Asn Ser Ser Val Leu Lys Lys Glu Met Glu Glu Ala Glu Lys Lys Asp
           115                 120                 125

Lys Glu Asn Gln Ala Glu Phe Asn Lys Ile Arg Arg Glu Ile Val Val
130                 135                 140

Pro Asn Pro Gln Glu Leu Glu Met Ala
145                 150
```

(2) INFORMATION FOR SEQ ID NO:35:

(i) SEQUENCE CHARACTERISTICS:
        (A) LENGTH: 200 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

```
Met Asn Lys Lys Lys Met Ile Leu Thr Ser Leu Ala Ser Val Ala Ile
1               5                  10                  15

Leu Gly Ala Gly Phe Val Ala Ser Gln Pro Thr Val Val Arg Ala Glu
               20                  25                  30

Glu Ser Pro Val Ala Ser Gln Ser Lys Ala Glu Lys Asp Tyr Asp Ala
           35                  40                  45

Ala Lys Lys Asp Ala Lys Asn Ala Lys Lys Ala Val Glu Asp Ala Gln
50                  55                  60

Lys Ala Leu Asp Asp Ala Lys Ala Ala Gln Lys Lys Tyr Asp Glu Asp
65                  70                  75                  80

Gln Lys Lys Thr Glu Glu Lys Ala Ala Leu Glu Lys Ala Ala Ser Glu
                85                  90                  95

Glu Met Asp Lys Ala Val Ala Ala Val Gln Gln Ala Tyr Leu Ala Tyr
               100                 105                 110

Gln Gln Ala Thr Asp Lys Ala Ala Lys Asp Ala Ala Asp Lys Met Ile
           115                 120                 125

Asp Glu Ala Lys Lys Arg Glu Glu Glu Ala Lys Thr Lys Phe Asn Thr
130                 135                 140

Val Arg Ala Met Val Val Pro Glu Pro Glu Gln Leu Ala Glu Thr Lys
145                 150                 155                 160

Lys Lys Ser Glu Glu Ala Lys Gln Lys Ala Pro Glu Leu Thr Lys Lys
               165                 170                 175

Leu Glu Glu Ala Lys Ala Lys Leu Glu Glu Ala Glu Lys Lys Ala Thr
           180                 185                 190

Glu Ala Lys Gln Lys Val Asp Ala
           195                 200
```

(2) INFORMATION FOR SEQ ID NO:36:

(i) SEQUENCE CHARACTERISTICS:
        (A) LENGTH: 198 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

```
Met Asn Lys Lys Lys Met Ile Leu Thr Ser Leu Ala Ser Val Ala Ile
1               5                   10                  15

Leu Gly Ala Gly Leu Val Ala Ser Gln Pro Thr Leu Val Arg Ala Glu
            20                  25                  30

Glu Ser Pro Val Ala Ser Gln Ser Lys Ala Glu Lys Asp Tyr Asp Ala
        35                  40                  45

Ala Val Lys Lys Ser Glu Ala Ala Lys Lys Ala Tyr Glu Glu Ala Lys
    50                  55                  60

Lys Ala Leu Glu Glu Ala Lys Val Ala Gln Lys Lys Tyr Glu Asp Asp
65              70                  75                  80

Gln Lys Lys Thr Glu Glu Lys Ala Glu Leu Glu Lys Glu Ala Ser Glu
            85                  90                  95

Ala Ile Ala Lys Ala Thr Glu Glu Val Gln Gln Ala Tyr Leu Ala Tyr
            100                 105                 110

Gln Arg Ala Ser Asn Lys Ala Glu Ala Ala Lys Met Ile Glu Glu Ala
            115                 120                 125

Gln Arg Arg Glu Asn Glu Ala Arg Ala Lys Phe Thr Thr Ile Arg Thr
            130                 135                 140

Thr Met Val Val Pro Glu Pro Glu Gln Leu Ala Glu Thr Lys Lys Lys
145                 150                 155                 160

Ala Glu Glu Ala Lys Ala Lys Glu Pro Lys Leu Ala Lys Lys Ala Ala
                165                 170                 175

Glu Ala Lys Ala Lys Leu Glu Glu Ala Glu Lys Lys Ala Thr Glu Ala
                180                 185                 190

Asn Pro Gln Val Asp Ala
            195
```

(2) INFORMATION FOR SEQ ID NO:37:

(i) SEQUENCE CHARACTERISTICS:
        (A) LENGTH: 201 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

```
Met Asn Lys Lys Lys Met Ile Leu Thr Ser Leu Ala Ser Val Ala Ile
1               5                   10                  15

Leu Gly Ala Gly Phe Val Ala Ser Ser Pro Thr Phe Val Arg Ala Glu
            20                  25                  30

Glu Ala Pro Val Ala Asn Gln Ser Lys Ala Glu Lys Asp Tyr Asp Ala
        35                  40                  45

Ala Val Lys Lys Ser Glu Ala Ala Lys Lys Asp Tyr Glu Thr Ala Lys
    50                  55                  60

Lys Lys Ala Glu Asp Ala Gln Lys Lys Tyr Asp Glu Asp Gln Lys Lys
65              70                  75                  80

Thr Glu Ala Lys Ala Glu Lys Glu Arg Lys Ala Ser Glu Lys Ile Ala
            85                  90                  95

Glu Ala Thr Lys Glu Val Gln Gln Ala Tyr Leu Ala Tyr Leu Gln Ala
            100                 105                 110

Ser Asn Glu Ser Gln Arg Lys Glu Ala Asp Lys Lys Ile Lys Glu Ala
            115                 120                 125

Thr His Ala Lys Met Arg Arg Thr Cys Asn Leu Thr Ile Glu Phe Glu
            130                 135                 140
```

```
Gln Gln Leu Tyr Phe Leu Asn Gln Val Ser Tyr Leu Arg Leu Arg Lys
145                 150                 155                 160

Lys Gln Lys Arg Gln Gln Lys Lys Gln Lys Tyr Leu Arg Lys Asn Leu
                165                 170                 175

Lys Arg Gln Leu Lys Arg Tyr Lys Tyr Arg Lys Ile Lys Tyr Leu Asn
                180                 185                 190

Lys Met Leu Lys Thr Lys Arg Lys Leu
                195                 200
```

(2) INFORMATION FOR SEQ ID NO:38:

(i) SEQUENCE CHARACTERISTICS:
        (A) LENGTH: 143 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

```
Met Asn Lys Lys Lys Leu Ile Val Thr Ser Leu Ala Ser Val Ala Ile
1               5                   10                  15

Leu Gly Ala Asp Ser Val Thr Ser Pro Ala Leu Val Arg Ala Asp
                20                  25                  30

Glu Ala Ser Leu Ile Ala Ser Gln Ser Lys Ala Glu Lys Asp Tyr Asp
                35                  40                  45

Ala Ala Lys Lys Asp Ala Lys Asn Ala Lys Lys Ala Val Glu Asp Ala
                50                  55                  60

Gln Lys Ala Leu Asp Asp Ala Lys Ala Ala Gln Lys Lys Tyr Asp Glu
65                  70                  75                  80

Asp Gln Lys Lys Thr Glu Lys Lys Ala Ala Val Lys Lys Ile Asp
                85                  90                  95

Glu Glu His Gln Ala Ala Asn Leu Lys Ser Gln Gln Ala Leu Val Glu
                100                 105                 110

Phe Leu Ala Ala Gln Arg Glu Gly Asn Pro Lys Lys Lys Ala Ala
                115                 120                 125

Gln Ala Thr Leu Glu Glu Ala Glu Asn Ala Glu Lys Glu Thr Lys
                130                 135                 140
```

(2) INFORMATION FOR SEQ ID NO:39:

(i) SEQUENCE CHARACTERISTICS:
        (A) LENGTH: 53 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

```
Met Asn Lys Lys Lys Met Ile Lys Thr Ser Leu Ala Ser Ala Ala Ile
1               5                   10                  15

Phe Gly Ala Xaa Ser Glu Thr Ser Gln Pro Thr Arg Val Arg Pro Val
                20                  25                  30

Glu Ala Pro Glu Ala Arg His Pro Lys Val Asp Lys Tyr Tyr Asp Ala
                35                  40                  45

Glu Ala Asp Glu Tyr
            50
```

(2) INFORMATION FOR SEQ ID NO:40:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:40:

Met Asn Lys Lys Lys Met Ile Leu Thr Ser Leu Ala Ser Val Ala Ile
1               5                   10                  15

Leu Gly Ala Gly Phe Gly Cys Val Ser Ala Tyr Ser Cys Lys Ser Arg
                20                  25                  30

Arg Ile Ser Arg Ser Ser Ala Ser Ser Gln Arg Leu
            35                  40

(2) INFORMATION FOR SEQ ID NO:41:

(i) SEQUENCE CHARACTERISTICS:
        (A) LENGTH: 176 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:41:

Met Asn Lys Lys Lys Met Ile Leu Lys Ser Leu Ala Ser Ala Ala Ile
1               5                   10                  15

Ser Gly Ala Xaa Leu Val Xaa Pro Gln Pro Thr Leu Val Arg Ala Glu
                20                  25                  30

Glu Ser Pro Ala Ala Ser Gln Ser His Pro Glu Gln Asp Tyr Asp Xaa
                35                  40                  45

Xaa Xaa Xaa Leu Cys Xaa Xaa Leu Xaa His Gln Pro Ser Xaa Gly Arg
            50                  55                  60

Thr Leu Leu Xaa Xaa Xaa Xaa Ser Xaa Pro Xaa Ser Pro Thr Pro Xaa
65                  70                  75                  80

Xaa Xaa Xaa Xaa Xaa Pro Xaa Ser Xaa Leu Thr Xaa Leu Xaa Pro Leu
                85                  90                  95

Xaa Xaa Xaa Leu Lys Pro Phe Pro Leu Pro Xaa Ser Xaa Pro Xaa Pro
                100                 105                 110

Pro Xaa Pro Pro Xaa Ser Pro Xaa Pro Pro Arg Pro Xaa Leu
            115                 120                 125

Tyr Xaa Xaa Pro Pro Xaa Pro Xaa Pro Xaa Leu Ser Leu Xaa Leu Ile
    130                 135                 140

Pro Phe Leu Leu Leu Xaa Leu Pro Pro Xaa Xaa Xaa Leu Pro His
145                 150                 155                 160

Leu Xaa Ser Pro Pro Xaa Pro Xaa Leu Pro Pro Ser Pro Thr Pro Xaa
                165                 170                 175

(2) INFORMATION FOR SEQ ID NO:42:

(i) SEQUENCE CHARACTERISTICS:
        (A) LENGTH: 181 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:42:

```
Leu Lys Glu Ile Asp Glu Ser Asp Ser Glu Asp Tyr Leu Lys Glu Gly
  1               5                  10                  15

Leu Arg Ala Pro Leu Gln Ser Lys Leu Asp Thr Lys Lys Ala Lys Leu
                 20                  25                  30

Ser Lys Leu Glu Glu Leu Ser Asp Lys Ile Asp Glu Leu Asp Ala Glu
             35                  40                  45

Ile Ala Lys Leu Glu Val Gln Leu Lys Asp Ala Glu Gly Asn Asn Asn
         50                  55                  60

Val Glu Ala Tyr Phe Lys Glu Gly Leu Glu Lys Thr Thr Ala Glu Lys
 65                  70                  75                  80

Lys Ala Glu Leu Glu Lys Ala Glu Ala Asp Leu Lys Lys Ala Val Asp
                 85                  90                  95

Glu Pro Glu Thr Pro Ala Pro Ala Pro Gln Pro Ala Pro Ala Pro Glu
                100                 105                 110

Lys Pro Ala Glu Lys Pro Ala Pro Ala Pro Ala Pro Glu Lys Pro Ala
            115                  120                 125

Pro Ala Pro Glu Lys Pro Ala Glu Lys Pro Ala Glu Lys Pro Ala Glu
130                 135                 140

Glu Pro Ala Glu Lys Pro Ala Pro Ala Pro Glu Lys Pro Ala Pro Thr
145                 150                 155                 160

Pro Glu Lys Pro Ala Pro Thr Pro Glu Thr Pro Lys Thr Gly Trp Lys
                165                 170                 175

Gln Glu Asn Gly Met
                180

(2) INFORMATION FOR SEQ ID NO:43:

(i) SEQUENCE CHARACTERISTICS:
        (A) LENGTH: 215 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:43:

Val Leu Asp Xaa Thr Ile Ala Glu Gly Lys Ala Gly Ile Ala Ala Xaa
  1               5                  10                  15

Pro Pro Asn Ile Asp Lys Thr Pro Lys Asp Leu Glu Asp Ser Gly Leu
                 20                  25                  30

Gly Leu Glu Lys Val Leu Ala Thr Leu Asp Pro Gly Gly Glu Thr Pro
             35                  40                  45

Asp Gly Leu Asp Lys Glu Ala Ser Glu Asp Ser Asn Ile Gly Ala Leu
         50                  55                  60

Pro Asn Gln Val Ser Asp Leu Glu Asn Gln Val Ser Glu Leu Asp Arg
 65                  70                  75                  80

Glu Val Thr Arg Leu Pro Ser Asp Leu Lys Asp Thr Glu Gly Asn Asn
                 85                  90                  95

Val Gly Asp Tyr Val Lys Gly Gly Leu Glu Lys Ala Leu Thr Asp Glu
                100                 105                 110

Lys Val Gly Leu Asn Asn Thr Pro Lys Ala Leu Asp Thr Ala Pro Lys
            115                  120                 125

Ala Leu Asp Thr Ala Leu Asn Glu Leu Gly Pro Asp Gly Asp Glu Glu
            130                  135                 140

Glu Thr Pro Ala Pro Ala Pro Lys Pro Glu Gln Pro Ala Glu Gln Pro
145                 150                 155                 160
```

```
Lys Pro Ala Pro Ala Pro Lys Pro Glu Lys Thr Asp Asp Gln Gln Ala
                165                 170                 175

Glu Glu Asp Tyr Ala Arg Arg Ser Glu Glu Tyr Asn Arg Leu Pro
            180                 185                 190

Gln Gln Gln Pro Pro Lys Ala Glu Lys Pro Ala Pro Ala Pro Lys Pro
        195                 200                 205

Glu Gln Pro Val Pro Ala Pro
    210                 215
```

(2) INFORMATION FOR SEQ ID NO:44:

(i) SEQUENCE CHARACTERISTICS:
        (A) LENGTH: 197 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:44:

```
Gly Gly Trp Ser Trp Arg Ile Leu Leu Ala Arg Pro Asp Arg Leu Ala
1               5                   10                  15

Ala Arg Gln Ala Glu Leu Ala Gln Lys Gln Thr Glu Leu Gly Lys Leu
            20                  25                  30

Leu Asp Ser Leu Asp Pro Glu Gly Lys Thr Gln Asp Glu Leu Asp Lys
        35                  40                  45

Glu Ala Gly Glu Ala Glu Leu Asp Lys Lys Ala Asp Gly Leu Pro Asn
50                  55                  60

Lys Val Ser Asp Leu Glu Lys Glu Ile Ser Asn Leu Glu Ile Leu Leu
65                  70                  75                  80

Gly Gly Ala Asp Ser Glu Asp Asp Thr Ala Ala Leu Pro Asn Lys Leu
                85                  90                  95

Ala Thr Lys Lys Ala Glu Leu Glu Lys Thr Gln Lys Glu Leu Asp Ala
                100                 105                 110

Ala Leu Asn Glu Leu Gly Pro Asp Gly Asp Glu Glu Thr Pro Ala
                115                 120                 125

Pro Ala Pro Gln Pro Glu Gln Pro Ala Pro Ala Pro Lys Pro Glu Gln
                130                 135                 140

Pro Thr Pro Ala Pro Lys Pro Glu Gln Pro Thr Pro Ala Pro Lys Pro
145                 150                 155                 160

Glu Gln Pro Ala Pro Ala Pro Lys Pro Glu Gln Pro Ala Pro Ala Pro
                165                 170                 175

Lys Pro Glu Gln Pro Ala Pro Ala Pro Lys Pro Glu Gln Pro Thr Pro
                180                 185                 190

Gly Pro Lys Ile Glu
        195
```

(2) INFORMATION FOR SEQ ID NO:45:

(i) SEQUENCE CHARACTERISTICS:
        (A) LENGTH: 122 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:45:

```
Glu Leu Leu Leu Leu Glu Lys Ala Gly Leu Gly Lys Ala Gly Ala Asp
```

```
1               5                   10                  15
Leu Lys Glu Ala Val Asn Glu Pro Gly Glu Ser Ala Gly Glu Pro Ser
                    20                  25                  30
Gln Pro Glu Glu Pro Ala Glu Ala Pro Ala Pro Glu Gln Pro Thr
            35                  40                  45
Glu Pro Thr Gln Pro Glu Glu Pro Ala Gly Glu Thr Pro Ala Pro Lys
        50                  55                  60
Pro Glu Lys Pro Ala Gly Gln Pro Lys Ala Glu Lys Thr Asp Asp Gln
65                  70                  75                  80
Gln Ala Glu Glu Asp Tyr Ala Arg Arg Ser Glu Glu Tyr Asn Arg
                85                  90                  95
Leu Thr Gln Gln Gln Pro Pro Lys Ala Glu Lys Pro Ala Pro Ala Pro
            100                 105                 110
Gln Pro Glu Gln Pro Ala Pro Ala Pro Lys
        115                 120
```

(2) INFORMATION FOR SEQ ID NO:46:

(i) SEQUENCE CHARACTERISTICS:
        (A) LENGTH: 185 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:46:

```
Leu Lys Glu Ile Asp Glu Ser Asp Ser Glu Asp Tyr Val Lys Glu Gly
1               5                   10                  15
Leu Arg Val Pro Leu Gln Ser Glu Leu Asp Val Lys Gln Ala Lys Leu
                20                  25                  30
Leu Lys Leu Glu Glu Leu Ser Asp Lys Ile Asp Glu Leu Asp Ala Glu
            35                  40                  45
Ile Ala Lys Asn Leu Lys Lys Asp Val Glu Asp Phe Gln Asn Ser Gly
        50                  55                  60
Gly Gly Tyr Ser Ala Leu Tyr Leu Glu Ala Ala Glu Lys Asp Leu Val
65                  70                  75                  80
Ala Lys Lys Ala Glu Leu Glu Lys Thr Glu Ala Asp Leu Lys Lys Ala
                85                  90                  95
Val Asn Glu Pro Glu Lys Pro Ala Glu Glu Pro Glu Asn Pro Ala Pro
            100                 105                 110
Ala Pro Lys Pro Ala Pro Ala Pro Gln Pro Glu Lys Pro Ala Pro Ala
        115                 120                 125
Pro Ala Pro Lys Pro Glu Lys Ser Ala Asp Gln Gln Ala Glu Glu Asp
    130                 135                 140
Tyr Ala Arg Arg Ser Glu Glu Tyr Asn Arg Leu Thr Gln Gln Gln
145                 150                 155                 160
Pro Pro Lys Ala Glu Lys Pro Ala Pro Ala Pro Val Pro Lys Pro Glu
                165                 170                 175
Gln Pro Ala Pro Ala Pro Lys Ser Arg
            180                 185
```

(2) INFORMATION FOR SEQ ID NO:47:

(i) SEQUENCE CHARACTERISTICS:
        (A) LENGTH: 213 amino acids
        (B) TYPE: amino acid
        (C) STRANDEDNESS: single -continued (D) TOPOLOGY: linear (ii) MOLECULE TYPE: peptide (xi) SEQUENCE DESCRIPTION: SEQ ID NO:47:

```
Val Xaa Leu Asp Arg Gly Pro Ala Glu Ala Val Lys Glu Gln Val
1               5                  10                  15

Asp Ser Pro Pro Gln Gln Leu Ala Asp Val Lys Glu Ile Ser Thr Arg
                20                  25                  30

Gly Lys Phe Leu Gly Gly Ala Ala Thr Glu Asp Glu Thr Ser Ala Leu
            35                  40                  45

Pro Asn Lys Ile Thr Ala Lys Gln Ala Glu Leu Ala Lys Lys Gln Thr
    50                  55                  60

Glu Leu Glu Lys Leu Leu Asp Asn Leu Asp Pro Glu Gly Lys Thr Gln
65                  70                  75                  80

Asp Glu Leu Asp Lys Glu Ala Ala Glu Ala Glu Leu Asp Lys Lys Ala
                85                  90                  95

Asp Glu Leu Pro Asn Lys Val Ala Asp Leu Glu Lys Glu Ile Ser Asn
                100                 105                 110

Leu Glu Ile Leu Leu Gly Gly Ala Asp Pro Glu Asp Thr Ala Ala
            115                 120                 125

Leu Pro Asn Lys Leu Ala Thr Lys Lys Ala Glu Phe Glu Lys Thr Pro
    130                 135                 140

Lys Glu Leu Asp Ala Ala Leu Asn Glu Leu Gly Pro Asp Gly Asp Glu
145                 150                 155                 160

Glu Glu Thr Pro Ala Pro Ala Pro Lys Pro Glu Gln Pro Ala
                165                 170                 175

Pro Ala Pro Ala Pro Lys Pro Glu Gln Pro Ala Pro Ala Pro Ala Pro
                180                 185                 190

Lys Pro Glu Gln Pro Ala Pro Ala Pro Lys Pro Glu Gln Pro
                195                 200                 205

Thr Pro Ala Pro Lys
    210
```

(2) INFORMATION FOR SEQ ID NO:48:

(i) SEQUENCE CHARACTERISTICS:
        (A) LENGTH: 166 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:48:

```
Leu Lys Glu Ile Asp Glu Ser Asp Ser Glu Asp Tyr Ile Lys Glu Gly
1               5                  10                  15

Leu Arg Ala Pro Leu Gln Ser Lys Leu Asp Ala Lys Lys Ala Lys Leu
                20                  25                  30

Ser Lys Leu Asp Glu Leu Ser Asp Lys Ile Asp Glu Leu Asp Ala Glu
            35                  40                  45

Ile Ala Lys Leu Glu Lys Asp Val Gly Asp Phe Pro Asn Ser Asp Gly
    50                  55                  60

Glu Gln Ala Gly Gln Tyr Leu Val Ala Ala Glu Lys Asp Leu Asp Ala
65                  70                  75                  80

Lys Glu Ala Glu Leu Gly Asn Thr Gly Ala Asp Leu Lys Lys Ala Val
                85                  90                  95
```

```
Asp Glu Pro Glu Thr Pro Ala Pro Ala Pro Lys Pro Ala Pro
            100                 105                 110

Ala Pro Ala Pro Thr Pro Glu Ala Pro Ala Pro Lys Pro Ala
            115                 120                 125

Pro Ala Pro Lys Pro Ala Pro Ala Pro Lys Pro Ala Pro Lys
            130                 135                 140

Pro Ala Pro Ala Pro Lys Pro Ala Pro Lys Pro Ala Pro Ala
145                 150                 155                 160

Pro Lys Pro Glu Arg Thr
            165
```

(2) INFORMATION FOR SEQ ID NO:49:

(i) SEQUENCE CHARACTERISTICS:
        (A) LENGTH: 193 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:49:

```
Glu Asn Asp Gly Val Gln Arg Thr Arg Lys Arg Ala Pro Lys Arg Ile
1               5                   10                  15

Met Ser Leu Ser Gln Lys Val Xaa Leu Lys Xaa Val Cys Arg Ala Pro
            20                  25                  30

Leu Gln Ser Lys Leu Asp Ala Gln Lys Ala Glu Leu Leu Lys Leu Glu
            35                  40                  45

Glu Leu Ser Gly Lys Ile Glu Glu Leu Asp Ala Glu Ile Ala Glu Leu
50                  55                  60

Glu Val Gln Leu Lys Asp Ala Glu Gly Asn Asn Asn Val Glu Ala Tyr
65                  70                  75                  80

Phe Lys Glu Gly Leu Glu Lys Thr Thr Ala Glu Lys Lys Ala Glu Leu
            85                  90                  95

Glu Xaa Ala Xaa Ala Asp Leu Lys Lys Ala Val Asp Glu Pro Glu Thr
            100                 105                 110

Pro Ala Pro Ala Pro Ala Pro Ala Pro Ala Pro Ala Pro Ala Pro Ala
            115                 120                 125

Pro Ala Pro Ala Pro Ala Pro Ala Pro Lys Pro Ala Pro Ala Pro Lys
            130                 135                 140

Pro Ala Pro Ala Pro Ala Pro Ala Pro Lys Pro Ala Pro Ala Pro Ala
145                 150                 155                 160

Pro Lys Pro Ala Pro Ala Pro Ala Pro Lys Pro Glu Lys Pro
            165                 170                 175

Ala Glu Lys Pro Ala Pro Ala Pro Lys Pro Glu Thr Xaa Lys Thr Tyr
            180                 185                 190

Gly
```

(2) INFORMATION FOR SEQ ID NO:50:

(i) SEQUENCE CHARACTERISTICS:
        (A) LENGTH: 183 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:50:

-continued

```
Leu Lys Glu Ile Asp Glu Ser Asp Ser Glu Asp Tyr Val Arg Glu Gly
1               5                   10                  15

Phe Arg Ala Pro Leu Gln Ser Glu Leu Asp Ala Lys Gln Ala Lys Leu
            20                  25                  30

Ser Lys Leu Glu Glu Leu Ser Asp Lys Ile Asp Glu Leu Asp Ala Glu
        35                  40                  45

Ile Ala Lys Leu Glu Lys Asp Val Glu Asp Phe Gln Asn Ser Asp Gly
50                  55                  60

Glu Gln Ala Gly Gln Tyr Leu Ala Ala Gly Glu Asp Leu Ile Ala
65                  70                  75                  80

Lys Lys Ala Glu Leu Glu Lys Ala Glu Ala Asp Leu Lys Lys Ala Val
            85                  90                  95

Asp Glu Pro Glu Thr Pro Ala Pro Ala Pro Ala Pro Ala Pro Ala Pro
            100                 105                 110

Ala Pro Thr Pro Glu Ala Pro Ala Pro Ala Pro Ala Pro Ala Pro Lys
            115                 120                 125

Pro Ala Pro Ala Pro Lys Pro Ala Pro Ala Pro Lys Pro Ala Pro Ala
            130                 135                 140

Pro Lys Pro Ala Pro Ala Pro Lys Pro Ala Pro Ala Pro Lys Pro Ala
145                 150                 155                 160

Pro Ala Pro Ala Pro Ala Pro Lys Pro Glu Lys Pro Ala Glu Lys Pro
            165                 170                 175

Ala Pro Ala Pro Lys Pro Glu
            180
```

(2) INFORMATION FOR SEQ ID NO:51:

(i) SEQUENCE CHARACTERISTICS:
        (A) LENGTH: 204 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:51:

```
Leu Lys Glu Ile Asp Glu Ser Asp Ser Glu Asp Tyr Val Lys Glu Gly
1               5                   10                  15

Phe Arg Ala Pro Leu Gln Ser Glu Leu Asp Ala Lys Gln Ala Lys Leu
            20                  25                  30

Ser Lys Leu Glu Glu Leu Ser Asp Lys Ile Asp Glu Leu Asp Ala Glu
        35                  40                  45

Ile Ala Lys Leu Glu Asp Gln Leu Lys Ala Ala Glu Glu Asn Asn Asn
50                  55                  60

Val Glu Asp Tyr Phe Lys Glu Gly Leu Glu Lys Thr Ile Ala Ala Lys
65                  70                  75                  80

Lys Ala Glu Leu Glu Lys Thr Glu Ala Asp Leu Lys Lys Ala Val Asn
            85                  90                  95

Glu Pro Glu Lys Pro Ala Glu Pro Ser Gln Pro Glu Lys Pro Ala
            100                 105                 110

Glu Glu Ala Pro Ala Pro Glu Gln Pro Thr Glu Pro Thr Gln Pro Glu
            115                 120                 125

Lys Pro Ala Glu Gln Pro Gln Pro Ala Pro Gln Pro Glu Lys
            130                 135                 140

Pro Ala Glu Glu Thr Pro Ala Pro Lys Pro Glu Lys Pro Ala Glu Gln
145                 150                 155                 160
```

```
Pro Lys Ala Glu Lys Pro Ala Asp Gln Gln Ala Glu Asp Tyr Ala
                165                 170                 175

Arg Arg Ser Glu Glu Glu Tyr Asn Arg Leu Thr Gln Gln Pro Pro
                180                 185                 190

Lys Ala Glu Lys Pro Ala Pro Ala Pro Lys Thr Lys
                195                 200
```

(2) INFORMATION FOR SEQ ID NO:52:

(i) SEQUENCE CHARACTERISTICS:
        (A) LENGTH: 233 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:52:

```
Gly Gly Ser Ala Leu Asp Gln Glu Ala Ala Pro Pro His Gln Val
 1               5                  10                  15

Ala Asp Leu Glu Lys Gln Ile Thr Gly Pro Glu Ile Phe Leu Gly Gly
                20                  25                  30

Ala Asp Pro Glu Ala Asp Ile Ala Ala Arg Pro Asn Glu Leu Ala Ala
                35                  40                  45

Lys Gln Ala Glu Leu Ala Gln Lys Pro Thr Gly Leu Glu Lys Leu Leu
 50                 55                  60

Asp Ser Leu Asp Pro Gly Gly Lys Thr Gln Asp Glu Leu Asp Lys Glu
 65                 70                  75                  80

Ala Gly Glu Ala Glu Leu Asp Lys Lys Ala Asp Glu Leu Pro Asn Lys
                85                  90                  95

Val Ala Asp Leu Glu Lys Glu Ile Ser Asn Leu Glu Ile Leu Leu Gly
                100                 105                 110

Gly Ala Asp Ser Glu Asp Asp Thr Ala Ala Leu Pro Asn Lys Leu Ala
                115                 120                 125

Xaa Lys Xaa Ala Glu Leu Glu Lys Thr Gln Lys Glu Leu Asp Ala Ala
                130                 135                 140

Pro Asn Glu Leu Gly Pro Asp Gly Asp Glu Glu Thr Pro Ala Pro
145                 150                 155                 160

Ala Pro Gln Pro Glu Gln Pro Ala Pro Lys Pro Glu Gln Pro
                165                 170                 175

Ala Pro Ala Pro Lys Pro Glu Gln Pro Ala Pro Lys Pro Glu
                180                 185                 190

Gln Pro Ala Pro Ala Pro Lys Pro Glu Gln Pro Ala Pro Lys
                195                 200                 205

Pro Glu Gln Pro Ala Lys Pro Glu Lys Pro Ala Glu Glu Pro Thr Gln
                210                 215                 220

Pro Glu Lys Pro Ala Thr Pro Lys Thr
225                 230
```

(2) INFORMATION FOR SEQ ID NO:53:

(i) SEQUENCE CHARACTERISTICS:
        (A) LENGTH: 129 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:53:

```
Arg Val Arg Ala Leu Lys Val Ala Glu Phe Gly Val Gln Leu Arg Asp
1               5                   10                  15

Ala Gly Gly Ser Asn Asn Val Gly Ala Tyr Phe Lys Glu Gly Leu Glu
            20                  25                  30

Glu Thr Thr Ala Glu Xaa Glu Ala Gly Leu Gly Lys Ala Glu Ala Asp
                35                  40                  45

Leu Lys Lys Ala Val Asp Glu Pro Glu Thr Pro Ala Pro Ala Pro Ala
        50                  55                  60

Pro Ala Pro Ala Pro Ala Pro Ala Pro Lys Pro Ala Pro Ala
65                  70                  75                  80

Pro Lys Pro Ala Pro Ala Pro Ala Pro Ala Pro Lys Pro Ala
                85                  90                  95

Pro Ala Pro Lys Pro Ala Pro Ala Pro Ala Pro Ala Pro Lys Pro Glu
            100                 105                 110

Lys Pro Ala Glu Lys Pro Ala Pro Ala Pro Lys Pro Glu Thr Pro Lys
        115                 120                 125

Thr
```

(2) INFORMATION FOR SEQ ID NO:54:

(i) SEQUENCE CHARACTERISTICS:
        (A) LENGTH: 206 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:54:

```
Leu Lys Asp Ile Asp Glu Ser Asp Ser Glu Asp Tyr Ala Lys Glu Gly
1               5                   10                  15

Leu Arg Ala Pro Leu Gln Ser Glu Leu Asp Thr Lys Lys Ala Lys Leu
            20                  25                  30

Leu Lys Leu Glu Glu Leu Ser Gly Lys Ile Glu Glu Leu Asp Ala Glu
        35                  40                  45

Ile Xaa Glu Leu Glu Val Gln Leu Lys Asp Ala Glu Gly Asn Asn Asn
    50                  55                  60

Val Glu Ala Tyr Phe Lys Gly Leu Glu Lys Thr Thr Ala Glu Lys
65                  70                  75                  80

Lys Ala Glu Leu Gly Lys Ala Gly Ala Asp Leu Lys Lys Ala Val Asp
            85                  90                  95

Glu Pro Glu Thr Pro Ala Pro Ala Pro Ala Pro Ala Pro Ala
            100                 105                 110

Pro Thr Pro Glu Ala Pro Ala Pro Ala Pro Lys Pro Ala Pro
    115                 120                 125

Ala Pro Lys Pro Ala Pro Ala Pro Lys Pro Ala Pro Ala Pro Lys Pro
    130                 135                 140

Ala Pro Ala Pro Lys Pro Ala Pro Ala Pro Lys Pro Ala Pro Ala Pro
145                 150                 155                 160

Ala Pro Ala Pro Ala Pro Lys Pro Ala Pro Ala Pro Ala Pro
            165                 170                 175

Ala Pro Lys Pro Glu Lys Pro Ala Glu Lys Pro Ala Pro Ala Pro Lys
            180                 185                 190

Pro Glu Thr Pro Lys Thr Gly Trp Lys Gln Glu Asn Gly Met
        195                 200                 205
```

(2) INFORMATION FOR SEQ ID NO:55:

(i) SEQUENCE CHARACTERISTICS:
        (A) LENGTH: 168 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:55:

```
Leu Lys Glu Ile Asp Glu Ser Asp Ser Glu Asp Tyr Val Lys Glu Gly
1               5                   10                  15

Phe Arg Ala Pro Leu Gln Ser Glu Leu Asp Ala Lys Gln Ala Lys Leu
            20                  25                  30

Ser Lys Leu Glu Glu Xaa Ser Asp Lys Xaa Asp Glu Leu Asp Ala Glu
        35                  40                  45

Ile Ala Lys Leu Glu Lys Asp Val Glu Asp Phe Lys Asn Ser Asp Gly
50                  55                  60

Glu Gln Ala Gly Gln Tyr Leu Ala Ala Ala Glu Asp Leu Ile Ala
65                  70                  75                  80

Lys Lys Ala Xaa Leu Glu Lys Ala Glu Ala Asp Leu Lys Lys Ala Val
            85                  90                  95

Asp Glu Pro Glu Thr Pro Ala Pro Ala Pro Ala Pro Ala Pro Ala Pro
            100                 105                 110

Ala Pro Thr Pro Glu Ala Pro Ala Pro Ala Pro Ala Pro Ala Pro Lys
            115                 120                 125

Pro Ala Pro Ala Pro Lys Pro Ala Pro Ala Pro Lys Pro Ala Pro Ala
130                 135                 140

Pro Lys Pro Ala Pro Ala Pro Lys Pro Ala Pro Ala Pro Ala Pro Ala
145                 150                 155                 160

Pro Lys Pro Glu Lys Pro Ala Ala
            165
```

(2) INFORMATION FOR SEQ ID NO:56:

(i) SEQUENCE CHARACTERISTICS:
        (A) LENGTH: 131 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:56:

```
Leu Lys Glu Ile Asp Glu Ser Asp Val Glu Val Lys Lys Ala Glu Leu
1               5                   10                  15

Glu Leu Val Lys Glu Glu Ala Lys Glu Pro Arg Asn Glu Glu Lys Val
            20                  25                  30

Lys Gln Ala Lys Ala Glu Val Glu Ser Lys Lys Ala Glu Ala Thr Arg
        35                  40                  45

Leu Glu Lys Ile Lys Thr Asp Arg Lys Lys Ala Glu Ala Lys Arg
50                  55                  60

Lys Ala Ala Glu Glu Asp Lys Val Lys Glu Lys Pro Ala Pro Lys Pro
65                  70                  75                  80

Glu Asn Pro Ala Glu Gln Pro Lys Ala Glu Lys Pro Ala Asp Gln Gln
            85                  90                  95

Ala Glu Glu Asp Tyr Ala Arg Arg Ser Glu Glu Glu Tyr Xaa Arg Leu
            100                 105                 110
```

Thr Gln Gln Gln Pro Pro Lys Thr Glu Lys Pro Ala Gln Pro Ser Thr
        115                 120                 125

Pro Lys Thr
    130

(2) INFORMATION FOR SEQ ID NO:57:

(i) SEQUENCE CHARACTERISTICS:
        (A) LENGTH: 128 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:57:

Lys Gly Glu Ala Arg Glu Ser Arg Xaa Glu Glu Lys Val Asn Gln Pro
1                5                  10                  15

Lys Xaa Glu Val Glu Ser Lys Lys Xaa Glu Ala Thr Arg Leu Glu Lys
         20                  25                  30

Ile Lys Thr Asp Arg Lys Lys Ala Glu Glu Ala Xaa Arg Lys Ala Ala
         35                  40                  45

Glu Glu Asp Lys Val Lys Glu Lys Pro Ala Glu Gln Pro Gln Pro Ala
 50                  55                  60

Pro Ala Pro Gln Pro Glu Lys Pro Ala Pro Lys Pro Glu Asn
65                   70                  75                  80

Pro Ala Glu Gln Pro Lys Ala Glu Lys Pro Ala Asp Gln Gln Ala Glu
                 85                  90                  95

Glu Asp Tyr Ala Arg Arg Ser Glu Glu Glu Tyr Asn Arg Leu Thr Gln
            100                 105                 110

Gln Gln Pro Pro Lys Thr Glu Lys Pro Ala Gln Pro Ser Thr Xaa Lys
        115                 120                 125

(2) INFORMATION FOR SEQ ID NO:58:

(i) SEQUENCE CHARACTERISTICS:
        (A) LENGTH: 204 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:58:

Ile Lys Glu Xaa Asp Glu Ser Xaa Ser Glu Asp Tyr Leu Lys Glu Gly
1                5                   10                  15

Leu Arg Ala Pro Leu Gln Ser Lys Leu Asp Thr Lys Lys Ala Lys Leu
             20                  25                  30

Ser Lys Leu Glu Glu Leu Ser Asp Lys Ile Asp Glu Leu Asp Ala Glu
         35                  40                  45

Ile Ala Lys Leu Glu Val Gln Leu Lys Asp Ala Glu Gly Asn Asn Asn
 50                  55                  60

Val Glu Ala Tyr Phe Lys Gly Leu Glu Lys Thr Thr Ala Glu Lys
65                   70                  75                  80

Lys Ala Glu Leu Glu Lys Ala Glu Ala Asp Leu Lys Lys Ala Val Asp
                 85                  90                  95

Glu Pro Glu Thr Pro Ala Pro Ala Pro Gln Pro Ala Pro Ala Pro Glu
            100                 105                 110

Lys Pro Ala Glu Lys Pro Ala Pro Ala Pro Ala Pro Glu Lys Pro Ala

-continued

```
                115                 120                 125
Pro Ala Pro Glu Lys Pro Ala Pro Thr Pro Glu Lys Pro Ala Pro Thr
        130                 135                 140

Pro Glu Thr Pro Lys Thr Gly Trp Lys Gln Glu Asn Gly Met Trp Tyr
145                 150                 155                 160

Phe Tyr Asn Thr Asp Gly Ser Met Ala Thr Gly Trp Leu Gln Asn Asn
                165                 170                 175

Gly Ser Trp Tyr Tyr Leu Asn Ser Asn Gly Ala Met Ala Thr Gly Trp
                180                 185                 190

His Gln Asn Asn Gly Ser Trp Tyr Tyr Leu Asn Ser
        195                 200
```

(2) INFORMATION FOR SEQ ID NO:59:

(i) SEQUENCE CHARACTERISTICS:
        (A) LENGTH: 188 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:59:

```
Leu Lys Glu Ile Asp Glu Ser Asp Ser Glu Asp Tyr Leu Lys Glu Gly
1               5                   10                  15

Leu Arg Ala Pro Leu Gln Ser Lys Leu Asp Thr Lys Lys Ala Lys Leu
                20                  25                  30

Ser Lys Leu Glu Glu Leu Ser Asp Lys Ile Asp Glu Leu Asp Ala Glu
            35                  40                  45

Ile Ala Lys Leu Glu Val Gln Leu Lys Asp Ala Glu Gly Asn Asn Asn
    50                  55                  60

Val Glu Ala Tyr Phe Lys Glu Gly Leu Glu Lys Thr Thr Ala Glu Lys
65                  70                  75                  80

Lys Ala Glu Leu Glu Lys Ala Glu Ala Asp Leu Lys Lys Ala Val Asp
                85                  90                  95

Glu Pro Asp Thr Pro Ala Pro Ala Pro Gln Pro Ala Pro Ala Pro Glu
                100                 105                 110

Lys Pro Ala Glu Lys Pro Ala Pro Ala Pro Glu Lys Pro Ala
            115                 120                 125

Pro Ala Pro Glu Lys Pro Ala Pro Glu Lys Pro Ala Pro Ala
        130                 135                 140

Pro Glu Lys Pro Ala Pro Ala Pro Glu Lys Pro Ala Pro Ala Pro Glu
145                 150                 155                 160

Lys Pro Ala Pro Ala Pro Glu Lys Pro Ala Pro Ala Pro Lys Pro Glu
                165                 170                 175

Thr Pro Glu Thr Arg Leu Glu Thr Arg Lys Arg Tyr
            180                 185
```

(2) INFORMATION FOR SEQ ID NO:60:

(i) SEQUENCE CHARACTERISTICS:
        (A) LENGTH: 170 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:60:

-continued

```
Leu Lys Glu Ile Asp Glu Ser Asp Ser Glu Asp Tyr Leu Lys Glu Gly
  1               5                  10                  15

Leu Arg Ala Pro Leu Gln Ser Lys Leu Asp Thr Lys Lys Ala Lys Leu
             20                  25                  30

Ser Lys Leu Glu Glu Leu Ser Asp Lys Ile Asp Glu Leu Asp Ala Glu
         35                  40                  45

Ile Ala Lys Leu Glu Val Gln Leu Lys Asp Ala Glu Gly Asn Asn Asn
     50                  55                  60

Val Glu Ala Tyr Phe Lys Glu Gly Leu Glu Lys Thr Thr Ala Glu Lys
 65                  70                  75                  80

Lys Ala Glu Leu Glu Lys Ala Glu Ala Asp Leu Lys Lys Ala Val Asp
                 85                  90                  95

Glu Pro Glu Thr Pro Ala Pro Ala Pro Gln Pro Ala Pro Ala Pro Glu
                100                 105                 110

Lys Pro Ala Glu Lys Pro Ala Pro Ala Pro Glu Lys Pro Ala Pro Ala
             115                 120                 125

Pro Glu Lys Pro Ala Pro Ala Pro Glu Lys Pro Ala Pro Ala Pro Glu
         130                 135                 140

Lys Pro Ala Pro Ala Pro Glu Lys Pro Ala Pro Thr Pro Glu Thr Pro
145                 150                 155                 160

Lys Thr Gly Trp Lys Gln Glu Asn Gly Met
                165                 170
```

(2) INFORMATION FOR SEQ ID NO:61:

(i) SEQUENCE CHARACTERISTICS:
(A) LENGTH: 198 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:61:

```
Leu Lys Glu Ile Asp Glu Ser Glu Ser Glu Asp Tyr Ala Lys Glu Gly
  1               5                  10                  15

Phe Arg Ala Pro Leu Gln Ser Lys Leu Asp Ala Lys Lys Ala Lys Leu
             20                  25                  30

Ser Lys Leu Glu Glu Leu Ser Asp Lys Ile Asp Glu Leu Asp Ala Glu
         35                  40                  45

Ile Ala Lys Leu Glu Asp Gln Leu Lys Ala Ala Glu Glu Asn Asn Asn
     50                  55                  60

Val Glu Asp Tyr Phe Lys Glu Gly Leu Glu Lys Thr Ile Ala Ala Lys
 65                  70                  75                  80

Lys Ala Glu Leu Glu Lys Thr Glu Ala Asp Leu Lys Lys Ala Val Asn
                 85                  90                  95

Glu Pro Glu Lys Pro Ala Pro Ala Pro Glu Thr Pro Ala Pro Glu Ala
                100                 105                 110

Pro Ala Glu Gln Pro Lys Pro Ala Pro Ala Pro Gln Pro Ala Pro Ala
             115                 120                 125

Pro Lys Pro Glu Lys Pro Ala Glu Gln Pro Lys Pro Glu Lys Thr Asp
         130                 135                 140

Asp Gln Gln Ala Glu Glu Asp Tyr Ala Arg Arg Ser Glu Glu Glu Tyr
145                 150                 155                 160

Asn Arg Leu Thr Gln Gln Gln Pro Pro Lys Ala Glu Lys Pro Ala Pro
                165                 170                 175
```

```
Ala Pro Lys Thr Gly Trp Lys Gln Glu Asn Gly Met Trp Tyr Phe Tyr
            180                 185                 190

Asn Thr Asp Gly Ser Met
        195

(2) INFORMATION FOR SEQ ID NO:62:

(i) SEQUENCE CHARACTERISTICS:
        (A) LENGTH: 124 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:62:

Gly Glu Gln Ala Gly Gln Tyr Arg Ala Ala Glu Gly Asp Leu Ala
1               5                   10                  15

Ala Lys Gln Ala Glu Leu Glu Lys Thr Glu Ala Asp Leu Lys Lys Ala
                20                  25                  30

Val Asn Glu Pro Glu Lys Pro Ala Pro Ala Pro Glu Thr Pro Ala Pro
            35                  40                  45

Glu Ala Pro Ala Glu Gln Pro Lys Pro Ala Pro Ala Pro Gln Pro Ala
        50                  55                  60

Pro Ala Pro Lys Pro Glu Lys Pro Ala Glu Gln Pro Lys Ala Glu Lys
65                  70                  75                  80

Thr Asp Asp Gln Gln Ala Glu Glu Asp Tyr Ala Arg Arg Ser Glu Glu
                85                  90                  95

Glu Tyr Asn Arg Leu Thr Gln Gln Pro Pro Lys Ala Glu Lys Pro
            100                 105                 110

Ala Pro Ala Pro Lys Pro Glu Gln Pro Ala Pro Ala
        115                 120

(2) INFORMATION FOR SEQ ID NO:63:

(i) SEQUENCE CHARACTERISTICS:
        (A) LENGTH: 132 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:63:

Pro Lys Asn Ser Lys Gly Glu Gln Ala Glu Gln Tyr Arg Ser Ala Ala
1               5                   10                  15

Gly Gly Asp Leu Ala Ala Lys Gln Val Glu Leu Glu Lys Thr Glu Ala
            20                  25                  30

Asp Leu Lys Lys Ala Val Asn Glu Pro Glu Lys Pro Ala Pro Ala Pro
            35                  40                  45

Glu Thr Pro Ala Pro Glu Ala Pro Ala Glu Gln Pro Lys Pro Ala Pro
        50                  55                  60

Ala Pro Gln Pro Ala Pro Ala Pro Lys Pro Lys Pro Ala Glu Gln
65                  70                  75                  80

Pro Lys Ala Glu Lys Pro Ala Asp Gln Gln Ala Glu Glu Asp Tyr Asp
                85                  90                  95

Arg Arg Ser Glu Glu Glu Tyr Asn Arg Leu Thr Gln Gln Pro Pro
            100                 105                 110

Lys Ala Glu Lys Pro Ala Pro Ala Pro Gln Pro Glu Gln Pro Ala Pro
        115                 120                 125
```

```
Ala Pro Lys Ser
    130
```

(2) INFORMATION FOR SEQ ID NO:64:

(i) SEQUENCE CHARACTERISTICS:
        (A) LENGTH: 194 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:64:

```
Leu Lys Glu Ile Asp Glu Ser Asp Ser Glu Asp Tyr Val Lys Glu Gly
1               5                   10                  15

Phe Arg Ala Pro Leu Gln Ser Glu Leu Asp Ala Lys Gln Ala Lys Leu
            20                  25                  30

Ser Lys Leu Glu Glu Leu Ser Asp Lys Ile Asp Glu Leu Asp Ala Glu
        35                  40                  45

Ile Ala Lys Leu Glu Lys Asp Val Glu Asp Phe Lys Xaa Ser Asp Gly
50                  55                  60

Glu Gln Ala Gly Gln Tyr Leu Ala Ala Glu Glu Asp Leu Ile Ala
65                  70                  75                  80

Lys Lys Ala Glu Leu Glu Gln Thr Glu Ala Asp Leu Lys Lys Ala Val
                85                  90                  95

Asn Glu Pro Gly Lys Pro Ala Pro Ala Pro Glu Thr Pro Ala
            100                 105                 110

Pro Glu Ala Pro Ala Gln Pro Lys Pro Ala Pro Glu Thr Pro Ala
        115                 120                 125

Pro Ala Pro Lys Pro Glu Lys Pro Ala Glu Gln Pro Lys Pro Glu Lys
        130                 135                 140

Pro Ala Asp Gln Gln Ala Glu Glu Asp Tyr Ala Arg Arg Ser Glu Glu
145                 150                 155                 160

Glu Tyr Asn Arg Leu Thr Gln Gln Gln Pro Ala Pro Ala Gln Lys Pro
                165                 170                 175

Glu Gln Pro Ala Lys Pro Glu Lys Pro Ala Glu Glu Pro Thr Gln Pro
            180                 185                 190

Glu Lys
```

(2) INFORMATION FOR SEQ ID NO:65:

(i) SEQUENCE CHARACTERISTICS:
        (A) LENGTH: 134 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:65:

```
Asp Ala Glu Ile Ala Lys Leu Glu Lys Asn Val Glu Tyr Phe Lys Lys
1               5                   10                  15

Thr Asp Ala Glu Gln Thr Glu Gln Tyr Leu Ala Ala Glu Lys Asp
            20                  25                  30

Leu Ala Asp Lys Lys Ala Glu Leu Glu Lys Thr Glu Ala Asp Leu Lys
        35                  40                  45

Lys Ala Val Asn Glu Pro Glu Lys Pro Ala Glu Glu Thr Pro Ala Pro
50                  55                  60
```

```
Ala Pro Lys Pro Glu Gln Pro Ala Glu Gln Pro Lys Pro Ala Pro Ala
65                  70                  75                  80

Pro Gln Pro Ala Pro Ala Pro Lys Pro Glu Lys Thr Asp Asp Gln Gln
                85                  90                  95

Ala Glu Glu Asp Tyr Ala Arg Arg Ser Glu Glu Tyr Asn Arg Leu
            100                 105                 110

Pro Gln Gln Pro Pro Lys Ala Glu Lys Pro Ala Pro Ala Pro Lys
        115                 120                 125

Pro Glu Gln Pro Val Pro
    130
```

(2) INFORMATION FOR SEQ ID NO:66:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:66:

```
Ala Glu Xaa Pro Glu Asn Pro Ala Pro Ala Pro Lys Pro Ala Xaa Ala
1               5                   10                  15

Pro Gln Pro Leu Lys Pro Glu Glu Pro Ala Glu Gln Pro Lys Pro Glu
                20                  25                  30

Lys Pro Glu Glu Pro Ala Gly Gln Pro Glu Pro Glu Lys Pro Asp Asp
            35                  40                  45

Gln Gln Ala Gly Glu Asp Tyr Ala Arg Arg Ser Gly Gly Glu Tyr Asn
50                  55                  60

Arg Phe Pro Gln Gln Pro Pro Lys Ala Glu Lys Pro Ala Pro Ala
65                  70                  75                  80

Pro Lys Pro Glu Gln Pro Val Pro Ala Pro Lys Thr
                85                  90
```

(2) INFORMATION FOR SEQ ID NO:67:

(i) SEQUENCE CHARACTERISTICS:
        (A) LENGTH: 211 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:67:

```
Leu Leu Lys Lys Ala Lys Leu Ala Gly Ala Lys Ser Lys Ala Ala Thr
1               5                   10                  15

Lys Lys Ala Glu Leu Glu Pro Glu Leu Glu Lys Ala Glu Ala Glu Leu
                20                  25                  30

Glu Asn Leu Leu Ser Thr Leu Asp Pro Glu Gly Lys Thr Gln Asp Glu
            35                  40                  45

Leu Asp Lys Glu Ala Ala Glu Ala Glu Leu Asn Lys Lys Val Glu Ala
50                  55                  60

Leu Pro Asn Gln Val Ser Glu Leu Glu Glu Leu Ser Lys Leu Glu
65                  70                  75                  80

Asp Asn Leu Lys Asp Ala Glu Thr Asn Asn Val Glu Asp Tyr Ile Lys
                85                  90                  95

Glu Gly Leu Glu Glu Ala Ile Ala Thr Lys Gln Ala Glu Leu Glu Lys
```

```
                100              105              110
Thr Pro Lys Glu Leu Asp Ala Ala Leu Asn Glu Leu Gly Pro Asp Gly
        115                 120                 125

Asp Glu Glu Thr Pro Pro Glu Ala Pro Ala Glu Gln Pro Lys
130                 135                 140

Pro Glu Lys Pro Ala Glu Thr Pro Ala Pro Ala Pro Lys Pro Glu
145                 150                 155                 160

Lys Ser Ala Asp Gln Gln Ala Glu Glu Asp Tyr Ala Arg Arg Ser Glu
            165                 170                 175

Glu Glu Tyr Asn Arg Leu Thr Gln Gln Gln Pro Pro Lys Ala Glu Lys
            180                 185                 190

Pro Ala Pro Ala Pro Ala Pro Lys Pro Glu Gln Pro Ala Pro Ala Pro
            195                 200                 205

Lys Ser Arg
    210

(2) INFORMATION FOR SEQ ID NO:68:

(i) SEQUENCE CHARACTERISTICS:
        (A) LENGTH: 212 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:68:

Gly Leu Ala Thr Lys Lys Leu Asn Leu Ala Glu Ala Arg Ile Glu
1               5                   10                  15

Leu Leu Leu Lys Lys Leu Gly Leu Glu Pro Gly Leu Glu Lys Ala Gly
            20                  25                  30

Ala Gly Leu Gly Asn Leu Leu Ser Thr Leu Asp Pro Glu Gly Lys Thr
            35                  40                  45

Gln Asp Glu Leu Asp Lys Glu Ala Ala Glu Ala Glu Leu Asn Lys Lys
        50                  55                  60

Val Glu Ala Leu Pro Asn Gln Val Ala Glu Leu Glu Glu Leu Ser
65                  70                  75                  80

Lys Leu Glu Asp Asn Leu Lys Asp Ala Glu Thr Asn His Val Glu Asp
                85                  90                  95

Tyr Ile Lys Glu Gly Leu Glu Glu Ala Ile Ala Thr Lys Gln Ala Glu
                100                 105                 110

Leu Glu Lys Thr Pro Lys Glu Leu Asp Ala Ala Leu Asn Glu Leu Gly
            115                 120                 125

Pro Asp Gly Asp Glu Glu Thr Pro Ala Pro Glu Ala Pro Ala Glu
            130                 135                 140

Gln Pro Lys Pro Glu Lys Pro Ala Glu Thr Pro Ala Pro Ala Pro
145                 150                 155                 160

Lys Pro Glu Lys Ser Ala Asp Gln Gln Ala Glu Glu Asp Tyr Ala Arg
                165                 170                 175

Arg Ser Glu Glu Glu Tyr Asn Arg Leu Thr Gln Gln Gln Pro Pro Lys
            180                 185                 190

Ala Glu Lys Pro Ala Pro Ala Pro Ala Pro Lys Pro Glu Gln Pro Ala
            195                 200                 205

Pro Ala Pro Lys
    210
```

(2) INFORMATION FOR SEQ ID NO:69:

(i) SEQUENCE CHARACTERISTICS:
        (A) LENGTH: 185 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:69:

```
Lys Lys Gln Lys Val Asn Leu Glu Asn Leu Leu Ser Thr Leu Asp Pro
1               5                  10                  15

Gly Gly Lys Thr Gln Asp Glu Leu Asp Lys Gly Ala Ala Glu Ala Glu
                20                  25                  30

Leu Asn Lys Lys Val Glu Ala Leu Pro Asn Pro Val Xaa Glu Leu Glu
                35                  40                  45

Glu Glu Leu Ser Pro Pro Glu Asp Asn Leu Lys Asp Ala Glu Thr Asn
50                  55                  60

His Val Glu Asp Tyr Ile Lys Glu Gly Leu Glu Glu Ala Ile Ala Thr
65                  70                  75                  80

Lys Gln Ala Glu Leu Glu Thr Pro Gln Glu Val Asp Ala Ala Leu
                85                  90                  95

Asn Asp Leu Val Pro Asp Gly Gly Glu Glu Glu Thr Pro Ala Pro Ala
                100                 105                 110

Pro Gln Pro Asp Glu Pro Ala Pro Ala Pro Asn Ala Glu Gln
                115                 120                 125

Pro Ala Pro Ala Pro Lys Pro Glu Lys Ser Ala Asp Gln Gln Ala Glu
130                 135                 140

Glu Asp Tyr Ala Arg Arg Ser Glu Gly Glu Tyr Asn Arg Leu Thr Gln
145                 150                 155                 160

Gln Gln Pro Pro Lys Ala Glu Lys Pro Ala Pro Ala Pro Ala Pro Lys
                165                 170                 175

Pro Glu Gln Pro Ala Pro Ala Pro Asn
                180                 185
```

(2) INFORMATION FOR SEQ ID NO:70:

(i) SEQUENCE CHARACTERISTICS:
        (A) LENGTH: 232 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:70:

```
Lys Glu Ile Ala Arg Leu Gln Ser Asp Leu Lys Asp Ala Glu Glu Asn
1               5                   10                  15

Asn Val Glu Asp Tyr Ile Lys Glu Gly Leu Glu Gln Ala Ile Thr Asn
                20                  25                  30

Lys Lys Ala Glu Leu Ala Thr Thr Gln Gln Asn Ile Asp Lys Thr Gln
                35                  40                  45

Lys Asp Leu Glu Asp Ala Glu Leu Glu Leu Lys Val Leu Ala Thr
50                  55                  60

Leu Asp Pro Glu Gly Lys Thr Gln Asp Glu Leu Asp Lys Glu Ala Ala
65                  70                  75                  80

Glu Ala Glu Leu Asn Glu Lys Val Glu Ala Leu Gln Asn Gln Val Ala
                85                  90                  95
```

-continued

```
Glu Leu Glu Glu Glu Leu Ser Lys Leu Glu Asp Asn Leu Lys Asp Ala
            100                 105                 110

Glu Thr Asn Asn Val Glu Asp Tyr Ile Lys Glu Gly Leu Glu Glu Ala
            115                 120                 125

Ile Ala Thr Lys Lys Ala Glu Leu Glu Lys Thr Gln Lys Glu Leu Asp
            130                 135                 140

Ala Ala Leu Asn Glu Leu Gly Pro Asp Gly Asp Glu Glu Glu Thr Pro
145                 150                 155                 160

Ala Pro Ala Pro Gln Pro Glu Lys Pro Ala Glu Glu Pro Glu Asn Pro
            165                 170                 175

Ala Pro Ala Pro Lys Pro Glu Lys Ser Ala Asp Gln Ala Glu Glu
            180                 185                 190

Asp Tyr Ala Arg Arg Ser Glu Glu Tyr Asn Arg Leu Thr Gln Gln
            195                 200                 205

Gln Pro Pro Lys Ala Glu Lys Pro Ala Pro Ala Pro Gln Pro Glu Gln
            210                 215                 220

Pro Ala Pro Ala Pro Lys Ile Glu
225                 230
```

(2) INFORMATION FOR SEQ ID NO:71:

(i) SEQUENCE CHARACTERISTICS:
        (A) LENGTH: 195 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:71:

```
Leu Lys Glu Ile Asp Glu Ser Glu Ser Glu Asp Tyr Ala Lys Glu Gly
1                   5                   10                  15

Phe Arg Ala Pro Leu His Ser Lys Leu Asp Ala Lys Lys Ala Lys Leu
            20                  25                  30

Ser Lys Leu Glu Glu Leu Ser Asp Lys Ile Asp Glu Leu Asp Ala Glu
            35                  40                  45

Ile Ala Lys Leu Glu Asp Gln Leu Lys Ala Val Glu Glu Asn Asn Asn
50                  55                  60

Val Glu Asp Tyr Ser Thr Glu Gly Leu Glu Lys Thr Ile Ala Ala Lys
65                  70                  75                  80

Lys Thr Glu Leu Glu Lys Thr Glu Ala Asp Leu Lys Lys Ala Val Asn
            85                  90                  95

Glu Pro Glu Lys Ser Ala Glu Glu Pro Ser Gln Pro Glu Lys Pro Ala
            100                 105                 110

Glu Glu Ala Pro Ala Pro Glu Gln Pro Thr Glu Pro Thr Gln Pro Glu
            115                 120                 125

Lys Pro Ala Glu Glu Thr Pro Ala Pro Lys Pro Glu Lys Pro Ala Glu
            130                 135                 140

Gln Pro Asn Ala Glu Lys Thr Asp Asp Gln Gln Ala Glu Glu Asp Tyr
145                 150                 155                 160

Ala Arg Arg Ser Glu Glu Glu Tyr Asn Arg Leu Thr Gln Gln Gln Pro
            165                 170                 175

Pro Lys Ala Glu Lys Pro Ala Pro Ala Pro Gln Pro Glu Gln Thr Ser
            180                 185                 190

Ser Leu His
        195
```

(2) INFORMATION FOR SEQ ID NO:72:

(i) SEQUENCE CHARACTERISTICS:
        (A) LENGTH: 1453 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:72:

```
TTGACAAATA TTTACGGAGG AGGCTTATGC TTAATATAAG TATAGGCTAA AAATGATTAT    60

CAGAAAAGAG GTAAATTTAG ATGAATAAGA AAAAAATGAT TTTAACAAGC CTAGCCAGCG   120

TCGCTATCTT AGGGGCTGGT TTTGTTGCGT CTTCGCCTAC TTTTGTAAGA GCAGAAGAAG   180

CTCCTGTAGC TAACCAGTCT AAAGCTGAGA AAGACTATGA TGCAGCAGTG AAAAAATCTG   240

AAGCTGCTAA GAAAGATTAC GAAACGGCTA AAAAGAAAGC AGAAGACGCT CAGAAGAAAT   300

ATGATGAGGA TCAGAAGAAA ACTGAGGCAA AAGCGGAAAA AGAAAGAAAA GCTTCTGAAA   360

AGATAGCTGA GGCAACAAAA GAAGTTCAAC AAGCGTACCT AGCTTATCTA CAAGCTAGCA   420

ACGAAAGTCA GAGAAAAGAG GCAGATAAGA AGATAAAAGA AGCTACGCAC GCAAAGATGA   480

GGCGGACGTG CAATTTGACT ATCGAATTCG AACAACAATT GTACTTCCTG AACCAAGTGA   540

GTTACCTGAG ACTAAGAAAA AGCAGAAGA GGCAACAAAA GAAGCAGAAG TATCTAAGAA   600

AAAATCTGAA GAGGCAGCTA AGAGGTATA AGTATAGAAA AATAAAATAC TTGAACAAGA   660

TGCTGAAAAC GAAAAGAAAA TTGACGTACT TCAAACAAA GTCGCTGATT TATAAAAAGG   720

AATTGCTCTC CATCAAAACA GTCGCTGAAT TAAATAAAGA AATTGCTAGA CTTCAAAGCG   780

ATTTAAAAGA TGCTGAAGAA ATAATGTAG AAGACTACAT TAAAGAAGGT TTAGAGCAAG   840

CTATCACTAA TAAAAAAGCT GAATTAGCTA CAACTCAACA AAACATAGAT AAAACTCAAA   900

AAGATTTAGA GGATGCTGAA TTAGAACTTG AAAAAGTATT AGCTACATTA GACCCTGAAG   960

GTAAAACTCA AGATGAATTA GATAAAGAAG CTGCTGAAGC TGAGTTGAAT GAAAAAGTTG  1020

AAGCTCTTCA AAACCAAGTT GCTGAATTAG AAGAAGAACT TTCAAAACTT GAAGATAATC  1080

TTAAAGATGC TGAAACAAAC AACGTTGAAG ACTACATTAA AGAAGGTTTA GAAGAAGCTA  1140

TCGCGACTAA AAAAGCTGAA TTGGAAAAAA CTCAAAAAGA ATTAGATGCA GCTCTTAATG  1200

AGTTAGGCCC TGATGGAGAT GAAGAAGAGA CTCCAGCGCC GGCTCCTCAA CCAGAAAAAC  1260

CAGCTGAAGA GCCTGAGAAT CCAGCTCCAG CACCAAAACC AGAGAAGTCA GCAGATCAAC  1320

AAGCTGAAGA AGACTATGCT CGTAGATCAG AAGAAGAATA TAATCGCTTG ACCCAACAGC  1380

AACCGCCAAA AGCAGAAAAA CCAGCTCCTG CACCACAACC AGAGCAACCA GCTCCTGCAC  1440

CAAAAATAGA GGC                                                    1453
```

(2) INFORMATION FOR SEQ ID NO:73:

(i) SEQUENCE CHARACTERISTICS:
        (A) LENGTH: 458 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:73:

```
Met Asn Lys Lys Lys Met Ile Leu Thr Ser Leu Ala Ser Val Ala Ile
1               5                   10                  15
```

```
Leu Gly Ala Gly Phe Val Ala Ser Ser Pro Thr Phe Val Arg Ala Glu
            20                  25                  30

Glu Ala Pro Val Ala Asn Gln Ser Lys Ala Glu Lys Asp Tyr Asp Ala
            35                  40                  45

Ala Val Lys Lys Ser Glu Ala Lys Lys Asp Tyr Glu Thr Ala Lys
            50                  55                  60

Lys Lys Ala Glu Asp Ala Gln Lys Lys Tyr Asp Glu Asp Gln Lys Lys
 65                  70                  75                  80

Thr Glu Ala Lys Ala Glu Lys Glu Arg Lys Ala Ser Glu Lys Ile Ala
                85                  90                  95

Glu Ala Thr Lys Glu Val Gln Gln Ala Tyr Leu Ala Tyr Leu Gln Ala
            100                 105                 110

Ser Asn Glu Ser Gln Arg Lys Glu Ala Asp Lys Lys Ile Lys Glu Ala
            115                 120                 125

Thr His Ala Lys Met Arg Arg Thr Cys Asn Leu Thr Ile Glu Phe Glu
            130                 135                 140

Gln Gln Leu Tyr Phe Leu Asn Gln Val Ser Tyr Leu Arg Leu Arg Lys
145                 150                 155                 160

Lys Gln Lys Arg Gln Gln Lys Lys Gln Lys Tyr Leu Arg Lys Asn Leu
                165                 170                 175

Lys Arg Gln Leu Lys Arg Tyr Lys Tyr Arg Lys Ile Lys Tyr Leu Asn
            180                 185                 190

Lys Met Leu Lys Thr Lys Arg Lys Leu Thr Tyr Phe Lys Thr Lys Ser
            195                 200                 205

Leu Ile Tyr Lys Lys Glu Leu Leu Ser Ile Lys Thr Val Ala Glu Leu
            210                 215                 220

Asn Lys Glu Ile Ala Arg Leu Gln Ser Asp Leu Lys Asp Ala Glu Glu
225                 230                 235                 240

Asn Asn Val Glu Asp Tyr Ile Lys Glu Gly Leu Glu Gln Ala Ile Thr
                245                 250                 255

Asn Lys Lys Ala Glu Leu Ala Thr Thr Gln Gln Asn Ile Asp Lys Thr
            260                 265                 270

Gln Lys Asp Leu Glu Asp Ala Glu Leu Glu Leu Glu Lys Val Leu Ala
            275                 280                 285

Thr Leu Asp Pro Glu Gly Lys Thr Gln Asp Glu Leu Asp Lys Glu Ala
            290                 295                 300

Ala Glu Ala Glu Leu Asn Glu Lys Val Glu Ala Leu Gln Asn Gln Val
305                 310                 315                 320

Ala Glu Leu Glu Glu Glu Leu Ser Lys Leu Glu Asp Asn Leu Lys Asp
                325                 330                 335

Ala Glu Thr Asn Asn Val Glu Asp Tyr Ile Lys Glu Gly Leu Glu Glu
            340                 345                 350

Ala Ile Ala Thr Lys Lys Ala Glu Leu Glu Lys Thr Gln Lys Glu Leu
            355                 360                 365

Asp Ala Ala Leu Asn Glu Leu Gly Pro Asp Gly Asp Glu Glu Glu Thr
            370                 375                 380

Pro Ala Pro Ala Pro Gln Pro Glu Lys Pro Ala Glu Glu Pro Glu Asn
385                 390                 395                 400

Pro Ala Pro Ala Pro Lys Pro Glu Lys Ser Ala Asp Gln Gln Ala Glu
                405                 410                 415

Glu Asp Tyr Ala Arg Arg Ser Glu Glu Glu Tyr Asn Arg Leu Thr Gln
            420                 425                 430
```

```
Gln Gln Pro Pro Lys Ala Glu Lys Pro Ala Pro Ala Pro Gln Pro Glu
        435                 440                 445

Gln Pro Ala Pro Ala Pro Lys Ile Glu Ala
    450                 455
```

PNEUMOCOCCAL GENES, PORTIONS THEREOF, EXPRESSION PRODUCTS THEREFROM, AND USES OF SUCH GENES, PORTIONS AND PRODUCTS

RELATED APPLICATIONS

This application is a continuation-in-part ("CIP"): of application Ser. No. 08/456,746, filed Jun. 6, 1995, now U.S. Pat. No. 5,679,768, which is a continuation of application Ser. No. 08/048,896, filed Apr. 20, 1993, now abandoned. Reference is made to application Ser. No.07/889,918, filed May 29, 1992 and PCT/US93/05191, filed May 28, 1993; of application Ser. No. 08/482,981, filed Jun. 7, 1995; of application Ser. No. 08/458,399, filed Jun. 2, 1995; of application Ser. No. 08/446,201, filed May 19, 1995 (as a CIP of U.S. Ser. No. 08/246,636); of application Ser. No. 08/246,636, filed May 20, 1994 (as a CIP of U.S. Ser. No. 68/048,896, filed Apr. 20, 1993 as a CIP of U.S. Ser. No. 07/835,698, filed Feb. 12, 1992 as a CIP of U.S. Ser. No. 07/656,773); of application Ser. 08/319,795, filed Oct. 7, 1994 (as a CIP of U.S. Ser. No. 08/246,636); of application Ser. No. 08/072,070, filed Jun. 3, 1993; of application Ser. No. 07/656,773, filed Feb. 15, 1991 (U.S. Ser. No. 656,773 and 835,698 corresponding to Int'l application WO 92/1448); and, each of these applications, as well as each application, document or reference cited in these applications, is hereby incorporated herein by reference. Documents or references are also cited in the following text, either in a Reference List appended to certain Examples, or before the claims, or in the text itself; and, each of these documents or references is hereby expressly incorporated herein by reference.

FIELD OF THE INVENTION

This invention relates to pneumococcal genes, portions thereof, expression products therefrom and uses of such genes, portions and products; especially to genes of *Streptococcus pneumoniae*, e.g., the gene encoding pneumococcal surface protein A (PspA) (said gene being "pspA"), pspA-like genes, portions of such genes, expression products therefrom, and the uses of such genes, portions thereof and expression products therefrom. Such uses include uses of the genes and portions thereof for obtaining expression products by recombinant techniques, as well as for detecting the presence of *Streptococcus pneumoniae* or strains thereof by detecting DNA thereof by hybridization or amplification (e.g., PCR) and hybridization techniques (e.g., obtaining DNA-containing sample, contacting same with genes or fragment under PCR, amplification and/or hybridization conditions, and detecting presence of or isolating hybrid or amplified product). The expression product uses include use in preparing antigenic, immunological or vaccine compositions, for eliciting antibodies, an immunological response (other than or additional to antibodies) or a protective response (including antibody or other immunological response by administering composition to a suitable host); or, the expression product can be for use in detecting the presence of *Streptococcus pneumoniae* by detecting antibodies to *Streptococcus pneumoniae* protein(s) or antibodies to a portion thereof in a host, e.g., by obtaining an antibody-containing sample from a relevant host, contacting the sample with expression product and detecting binding (for instance by having the product labeled); and, the antibodies generated by the aforementioned compositions are useful in diagnostic or detection kits or assays. Thus, the invention relates to varied compositions of matter and methods for use thereof.

BACKGROUND OF THE INVENTION

*Streptococcus pneumoniae* is an important cause of otitis media, meningitis, bacteremia and pneumonia. Despite the use of antibiotics and vaccines, the prevalence of pneumococcal infections has declined little over the last twenty-five years.

It is generally accepted that immunity to *Streptococcus pneumoniae* can be mediated by specific antibodies against the polysaccharide capsule of the pneumococcus. However, neonates and young children fail to make an immune response against polysaccharide antigens and can have repeated infections involving the same capsular serotype.

One approach to immunizing infants against a number of encapsulated bacteria is to conjugate the capsular polysaccharide antigens to protein to make them immunogenic. This approach has been successful, for example, with *Haemophilus influenzae* b (see U.S. Pat. No. 4,496,538 to Gordon and U.S. Pat. No. 4,673,574 to Anderson). However, there are over eighty known capsular serotypes of *S. pneumoniae* of which twenty-three account for most of the disease. For a pneumococcal polysaccharide-protein conjugate to be successful, the capsular types responsible for most pneumococcal infections would have to be made adequately immunogenic. This approach may be difficult, because the twenty-three polysaccharides included in the presently-available vaccine are not all adequately immunogenic, even in adults.

An alternative approach for protecting children, and also the elderly, from pneumococcal infection would be to identify protein antigens that could elicit protective immune responses. Such proteins may serve as a vaccine by themselves, may be used in conjunction with successful polysaccharide-protein conjugates, or as carriers for polysaccharides.

McDaniel et al. (I), J. Exp. Med. 160:386–397, 1984, relates to the production of hybridoma antibodies that recognize cell surface polypeptide(s) on *S. pneumoniae* and protection of mice from infection with certain strains of encapsulated pneumococci by such antibodies. This surface protein antigen has been termed "pneumococcal surface protein A" or PspA for short.

McDaniel et al. (II), Microbial Pathogenesis 1:519–531, 1986, relates to studies on the characterization of the PspA. Considerable diversity in the PspA molecule in different strains was found, as were differences in the epitopes recognized by different antibodies.

McDaniel et al. (III), J. Exp. Med. 165:381–394, 1987, relates to immunization of X-linked immunodeficient (XID) mice with non-encapsulated pneumococci expressing PspA, but not isogenic pneumococci lacking PspA, protects mice from subsequent fatal infection with pneumococci.

McDaniel et al. (IV), Infect. Immun., 59:222–228, 1991, relates to immunization of mice with a recombinant full length fragment of PspA that is able to elicit protection against pneumococcal strains of capsular types 6A and 3.

Crain et al, Infect.Immun., 56:3293–3299, 1990, relates to a rabbit antiserum that detects PspA in 100% (n =95) of clinical and laboratory isolates of strains of *S. pneumoniae*. When reacted with seven monoclonal antibodies to PspA, fifty-seven *S. pneumoniae* isolates exhibited thirty-one different patterns of reactivity.

The PspA protein type is independent of capsular type. It would seem that genetic mutation or exchange in the environment has allowed for the development of a large pool of strains which are highly diverse with respect to capsule, PspA, and possibly other molecules with variable structures.

Variability of PspA's from different strains also is evident in their molecular weights, which range from 67 to 99 kD. The observed differences are stably inherited and are not the result of protein degradation.

Immunization with a partially purified PspA from a recombinant X gt11 clone, elicited protection against challenge with several *S. pneumoniae* strains representing different capsular and PspA types, as described in McDaniel et al. (IV), Infect. Immun. 59:222–228, 1991. Although clones expressing PspA were constructed according to that paper, the product was insoluble and isolation from cell fragments following lysis was not possible.

While the protein is variable in structure between different pneumococcal strains, numerous cross-reactions exist between all PspA's, suggesting that sufficient common epitopes may be present to allow a single PspA or at least a small number of PspA's to elicit protection against a large number of *S. pneumoniae* strains.

In addition to the published literature specifically referred to above, the inventors, in conjunction with co-workers, have published further details concerning PspA's, as follows:
1. Abstracts of 89th Annual Meeting of the American Society for Microbiology, p. 125, item D-257, May 1989;
2. Abstracts of 90th Annual Meeting of the American Society for Microbiology, p. 98, item D-106, May 1990;
3. Abstracts of 3rd International ASM Conference on Streptococcal Genetics, p. 11, item 12, June 1990;
4. Talkington et al, Infect. Immun. 59:1285–1289, 1991;
5. Yother et al (I), J. Bacteriol. 174:601–609, 1992;
6. Yother et al (II), J. Bacteriol. 174:610–618, 1992; and
7. McDaniel et al (V), Microbiol. Pathogenesis, 13:261–268.

It would be useful to provide PspA or fragments thereof in compositions, including PspA's or fragments from varying strains in such compositions, to provide antigenic, immunological or vaccine compositions; and, it is even further useful to show that the various strains can be grouped or typed, thereby providing a basis for cross-reactivities of PspA's or fragments thereof, and thus providing a means for determining which strains to represent in such compositions (as well as how to test for, detect or diagnose one strain from another). Further, it would be advantageous to provide evidence of a pspA—like gene or second pspA gene in certain strains, as well as primers (oligonucleotides) for identification of such a gene, as well as of conserved regions in that gene and in pspA; for instance, for detecting, determining, isolating, or diagnosing strains of *S. pneumonia*. These uses and advantages, it is believed, have not heretofore been provided in the art.

SUMMARY OF THE INVENTION

The invention provides an isolated amino acid molecule comprising of residues 1 to 115, 1 to 260, 192 to 588, 192 to 299, or residues 192 to 260 of pneumococcal surface protein A of *Streptococcus pneumoniae*.

The invention further provides an isolated DNA molecule comprising of a fragment of a pneumococcal surface protein A gene of *Streptococcus pneumoniae* encoding the isolated amino acid molecule.

The invention also provides PCR primer or hybridization probe comprising the isolated DNA molecule.

The invention additionally provides an antigenic, vaccine or immunological composition comprising the amino acid molecule.

The invention includes an isolated DNA molecule comprising nucleotides 1 to 26, 1967 to 1990, 161 to 187, 1093 to 1117, or 1312 to 1331 or 1333 to 1335 of a pneumococcal surface protein A gene of *Streptococcus pneumoniae*. The DNA molecule can be used as a PCR primer or hybridization probe; and therefore the invention comprehends a PCR primer or hybridization probe comprising of the isolated DNA molecule.

The invention also includes an isolated DNA molecule comprising a fragment having homology with a portion of a pneumococcal surface protein A gene of *Streptococcus pneumoniae*. The DNA preferably is comprising a nucleotide sequence (5' to 3') selected from the following (which include the portion having homology and restriction sits) [selection of other restriction sites or consequences for such DNA is within the ambit of the skilled artisan from this disclosure]:

SEQ ID NO 1 CCGGATCCAGCTCGCACCAAAAAC;
SEQ ID NO 2 GCGCGTCGACGGCCTTAAACCCAT-TCACCATTGG;
SEQ ID NO 3 CCGGATCCTGAGCCAGAGCAGTTG-GCTG;
SEQ ID NO 4 CCGGATCCGCTCAAAGAGATTGAT-GAGTCTG;
SEQ ID NO 5 GCGGATCCCGTAGCCAGT-CAGTCTAAAGCTG;
SEQ ID NO 6 CTGAGTCGACTGGAGTTTCTG-GAGCTGGAGC;
SEQ ID NO 7 CCGGATCCAGCTCCAGCTCCA-GAAACTCCAG;
SEQ ID NO 8 GCGGATCCTTGACCAATATTTACG-GAGGC;
SEQ ID NO 9 GTTTTTGGTGCAGGAGCTGG;
SEQ ID NO 10 GCTATGGCTACAGGTTG;
SEQ ID NO 11 CCACCTGTAGCCATAGC;
SEQ ID NO 12 CCGGATCCAGCGTGCCTATCT-TAGGGGCTGGTT; and
SEQ ID NO 13 GCAAGCTTATGATATAGAAATTTG-TAAC.

Thus, the invention broadly comprehends DNA homologous to portions of pspA; preferably further including restriction sequences.

These DNA molecules can be used as PCR primers or probes; and thus, the invention comprehends a primer or probe comprising any of these molecules.

The invention further still provides PCR probe(s) which distinguishes between pspA and pspA-like nucleotide sequences, as well as PCR probe(s) which hybridizes to both pspA and pspA-like nucleotide sequences.

Additionally, the invention includes a PspA extract prepared by a process comprising: growing pneumococci in a first medium containing choline chloride, eluting live pneumococci with a choline chloride containing salt solution, and growing the pneumococci in a second medium containing an alkanolamine and substantially no choline; as well as a PspA extract prepared by that process and further comprising purifying PspA by isolation on a choline-Sepharose affinity column. These processes are also included in the invention.

An immunological composition comprising these extracts is comprehended by the invention, as well as an immunological composition comprising full-length PspA.

A method for enhancing immunogenicity of a PspA-containing immunological composition comprising including in said composition the C-terminal portion of PspA, is additionally comprehended, as well as an immunological composition comprising at least two PspAs. The latter immunological composition can have the PspAs from different groups or families; the groups or families can be based on RFLP or sequence studies (see, e.g., FIG. 13).

These and other embodiments are disclosed or are obvious from the following detailed description.

BRIEF DESCRIPTION OF THE FIGURES

FIGS. 1A and 1B show: Evaluation of digested plasmid constructs. FIG. 1A: 1% agarose gel electrophoresis of plasmids isolated from transformed E. coli BL21(DE3) strains stained with ethidium bromide. Lane 1: 1 kb DNA ladder (sizes noted in kb), lane 2: pRCT125, lane 3: pRC105, lane 4: DBL5 pspA insert, lane 5: pRCT113, lane 6: BG9739 pspA insert, lane 7: pRCT117, and lane 8: L81905 pspA insert. FIG. 1B: Corresponding Southern blot of gel in FIG. 1A probed with full-length Rx1 pspA and hybridization detected as described in Example 1. The arrow indicates the 1.2 kb pspA digested inserts from plasmid constructs and the PCR-amplified pspA fragments from the pneumococcal donor strains used in cloning.

FIG. 12 shows: RFLP pattern of two isolates from six families (using products from amplification with SKH2 and LSM13).

FIG. 13 shows: Sequence primarily in the N-terminal half of PspA, Central Region, and Complete Sequence EF5668.

DETAILED DESCRIPTION

Figure 2:
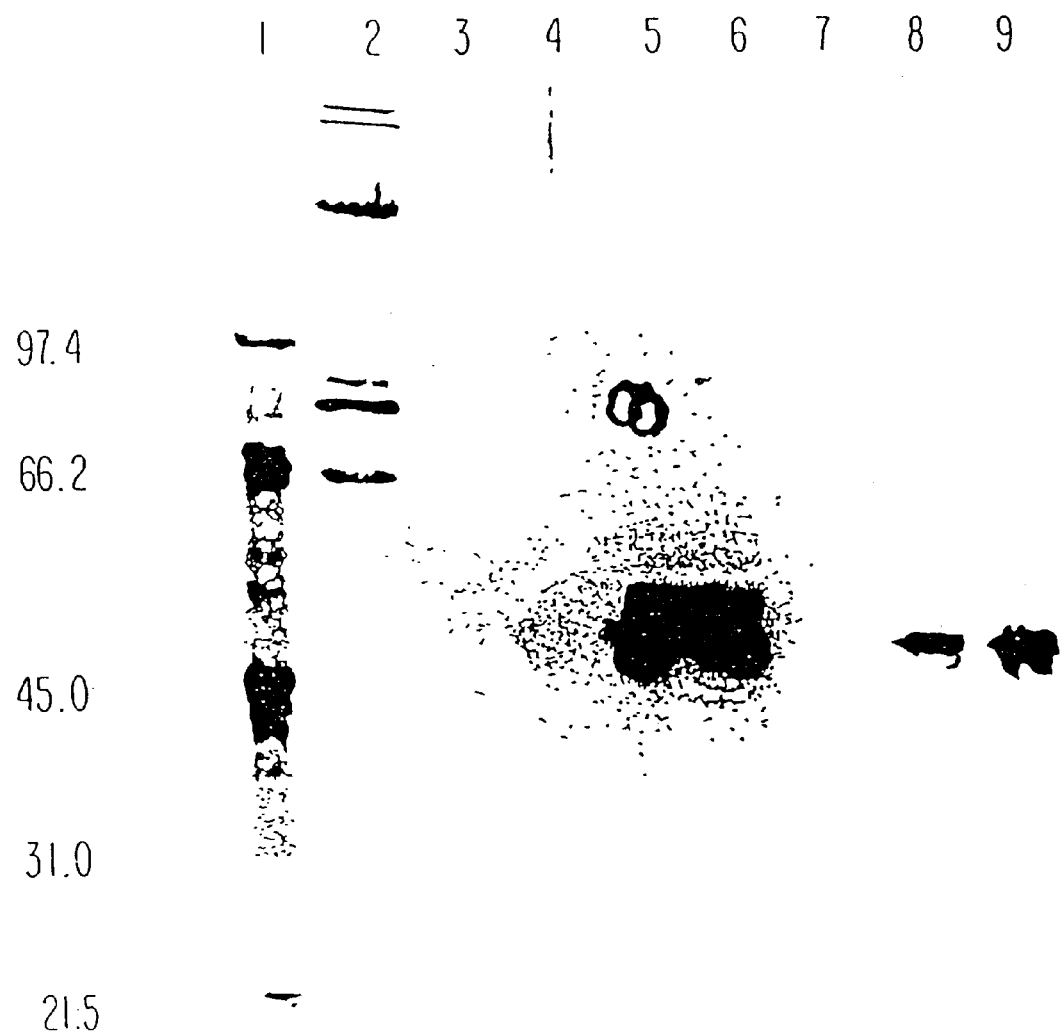
FIG. 2 shows: Evaluation of strain RCT105 cell fractions containing truncated DBL5 PspA. Proteins from E. coli cell fractions were resolved by 10% SDS-PAGE, transferred to NC, and probed with MAb XiR278. Lane 1: molecular weight markers (noted in kDa), lane 2: full-length, native DBL5 PspA, lane 3: uninduced cells, lanes 4–6: induced cells; 1 hr, 2 hr, and 3 hr of IPTG induction respectively, lane 7: periplasmic proteins, lane 8: cytoplasmic proteins, and lane 9: insoluble cell wall/membrane material.

Knowledge of and familiarity with the applications incorporated herein by reference is assumed; and, those applications disclose the sequence of pspA as well as certain portions thereof, and PspA and compositions containing PspA.

As discussed above and in the following Examples, the invention relates to truncated PspA, e.g., PspA C-terminal to position 192 such as a.a. 192–588 ("BC100") 192–299 and 192–260 of PspA eliciting cross-protection, as well as to DNA encoding such truncated PspA (which amplify the coding for these amino acid regions homologous to most PspAs). The invention further relates to the pspA-like gene, or a second pspA gene and portions thereof (e.g., probes, primers) which can hybridize thereto and/or amplify that gene, as well as to DNA molecules which hybridize to pspA, so that one can by hybridization assay and/or amplification ascertain the presence of a particular pneumococcal strain; and, the invention provides that a second PspA can be produced by the pspA-like sequence (which second PspA can be used like PspA).

Indeed, the invention further relates to oligonucleotide probes and/or primers which react with pspA of many, if not all, strains, so as to permit identification, detection or diagnosis of any pneumococcal strain, as well as to expression products of such probes and/or primers, which can provide cross-reactive epitopes.

The repeat region of pspA is highly conserved such that the present invention provides oligonucleotide probes or primers to this region reactive with most is not all strains, thereby providing diagnostic assays and a means for identifying epitopes. The invention demonstrates that the pspA-like gene is homologous to the pspA gene in the leader sequence, first portion of the proline-rich region and in the repeat region; but, these genes differ in the second portion of their proline-rich regions and at the very 3' end of the gene encoding the 17 amino acid tail of PspA. The product of the pspA-like gene is expected to lack a C-terminal tail, suggesting different anchoring than PspA. Drug interference with functions such as surface binding of the coding for repeat regions of pspA and the pspA-like genes, or with the repeat regions of the expression products, is therefore a target for intervention of pneumococcal infection. Further still, the invention provides evidence of additional pspA homologous sequences, in addition to pspA and the pspA-like sequence. The invention, as mentioned above, includes oligonucleotide probes or primers which distinguish between pspA and the pspA-like sequence, e.g., LSM1 and LSM2, useful for diagnostic detecting, or isolating purposes; and LSM1 and LSM10 or LSM1 and LSM7 which amplify a portion of the pspA-like gene, particularly the portion of that gene which encodes an antigenic, immunological or protective protein.

The invention further relates to a method for the isolation of native PspA by growth of pneumococci medium containing high concentrates (about 0.9% to about 1.4%, preferably 1.2%) choline chloride, elation of live pneumococci with a salt solution containing choline chloride, e.g., about 1% about 3%, preferably 2% choline chloride, and growth of pneumococci in medium in which the choline in the medium has been almost or substantially completely replaced with a lower alkanolamine, e.g., $C_1$–$C_6$, preferably $C_2$ alkanolamine, i.e., preferably $C_2$ alkanolamine, i.e., preferably ethanolamine (e.g. 0.0000005% to 0.0000015%, preferably 0.000001% choline chloride plus 0.02% to 0.04% alkanolamine (ethanolamine), preferably 0.03%). PspA from such pneumococci is then preferably isolated from a choline-sephanrose affinity column, thereby providing highly purified PspA. Such isolated and/or purified PspA is highly immunogenic and is useful in antigenic, immunological or vaccine composition. Indeed, the growth media of the pneumococci grown in the presence of the alkanolamine (rather than choline) contains PspA and is itself highly immunogenic and therefore useful as an antigenic, immunological or vaccine composition; and, is rather inexpensive to produce. Per microgram of PspA, the PspA in the alkanolamine medium is much more protective than PspA isolated by other means, e.g., from extracts. Perhaps, without wishing to necessarily be bound by any one particular theory, there is a synergistic effect upon PspA by the other components present prior to isolation, or simply PspA is more protective (more antigenic) prior to isolation and/or purification (implying a possibility of some loss of activity from the step of isolation and/or purification).

The invention further relates to the N-terminal 115 amino acids of PspA, which is useful for antigenic, immunological or vaccine compositions, as well as the DNA coding therefor, which is useful in preparing these N-terminal amino acids by recombination, or for use as probes and/or primers for hybridization and/or amplification for identification, detection or diagnosis purposes.

The invention further demonstrates that there is a grouping among the pspA RFLP families. This provides a method of identifying families of different PspAs based on RFLP pattern of PspAs, as well as a means for obtaining diversity of PspAs in an antigenic, immunological or vaccine composition; and, a method of characterizing clonotypes of PspA based on RFLP patterns of PspA. And, the invention thus provides oligonucleotides which permit amplification of most, e.g., a majority, if not all of *S. pneumoniae* and thereby permit RFLP analysis of a majority, if not all, *S. pneumoniae*.

Further, the invention demonstrates that more than one serologically complementary PspA molecule can be in an antigenic, immunological or vaccine composition, so as to elicit better response, e.g., protection, for instance, against a variety of strains of pneumococci; and, the invention provides a system of selecting PspAs for a multivalent composition which includes cross-protection evaluation so as to provide a maximally efficacious composition.

The determination of the amount of antigen, e.g., PspA or truncated portion thereof and optional adjuvant in the inventive compositions and the preparation of those compositions can be in accordance with standard techniques well known to those skilled in the pharmaceutical or veterinary arts. In particular, the amount of antigen and adjuvant in the inventive compositions and the dosages administered are determined by techniques well known to those skilled in the medical or veterinary arts taking into consideration such factors as the particular antigen, the adjuvant (if present), the age, sex, weight, species and condition of the particular patient, and the route of administration. For instance, dosages of particular PspA antigens for suitable hosts in which an immunological response is desired, can be readily ascertained by those skilled in the art from this disclosure (see, e.g., the Examples), as is the amount of any adjuvant typically administered therewith. Thus, the skilled artisan can readily determine the amount of antigen and optional adjuvant in compositions and to be administered in methods of the invention. Typically, an adjuvant is commonly used as 0.001 to 50 wt % solution in phosphate buffered saline, and the antigen is present on the order of micrograms to milligrams, such as about 0.0001 to about 5 wt %, preferably about 0.0001 to about 1 wt %, most preferably about 0.0001 to about 0.05 wt % (see, e.g., Examples below or in applications cited herein).

Typically, however, the antigen is present in an amount on the order of micrograms to milligrams, or, about 0.001 to about 20 wt %, preferably about 0.01 to about 10 wt %, and most preferably about 0.05 to about 5 wt % (see, e.g., Examples below).

Of course, for any composition to be administered to an animal or human, including the components thereof, and for any particular method of administration, it is preferred to determine therefor: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable immunological response, such as by titrations of sera and analysis thereof for antibodies or antigens, e.g., by ELISA and/or RFFIT analysis. Such determinations do not require undue experimentation from the knowledge of the skilled artisan, this disclosure and the documents cited herein. And, the time for sequential administrations can be ascertained without undue experimentation.

Examples of compositions of the invention include liquid preparations for orifice, e.g., oral, nasal, anal, vaginal, peroral, intragastric, mucosal (e.g., perlingual, alveolar, gingival, olfactory or respiratory mucosa) etc., administration such as suspensions, syrups or elixirs; and, preparations for parenteral, subcutaneous, intradermal, intramuscular or intravenous administration (e.g., injectable administration), such as sterile suspensions or emulsions. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention, are conveniently provided as liquid preparations, e.g., isotonic aqueous solutions, suspensions, emulsions or viscous compositions which may be buffered to a selected pH. If digestive tract absorption is preferred, compositions of the invention can be in the "solid" form of pills, tablets, capsules, caplets and the like, including "solid" preparations which are time-released or which have a liquid filling, e.g., gelatin covered liquid, whereby the gelatin is dissolved in the stomach for delivery to the gut. If nasal or respiratory (mucosal) administration is desired, compositions may be in a form and dispensed by a squeeze spray dispenser, pump dispenser or aerosol dispenser. Aerosols are usually under pressure by means of a hydrocarbon. Pump dispensers can preferably dispense a metered dose or, a dose having a particular particle size.

Compositions of the invention can contain pharmaceutically acceptable flavors and/or colors for rendering them more appealing, especially if they are administered orally. The viscous compositions may be in the form of gels, lotions, ointments, creams and the like and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer. However, above that range, the compositions can approach solid or gelatin forms which are then easily administered as a swallowed pill for oral ingestion.

Liquid preparations are normally easier to prepare than gels, other viscous compositions, and solid compositions. Additionally, liquid compositions are somewhat more convenient to administer, especially by injection or orally, to animals, children, particularly small children, and others who may have difficulty swallowing a pill, tablet, capsule or the like, or in multi-dose situations. Viscous compositions, on the other hand, can be formulated within the appropriate viscosity range to provide longer contact periods with mucosa, such as the lining of the stomach or nasal nucosa.

Obviously, the choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels, normally contain a major amount of water (preferably purified water) in addition to the antigen, lipoprotein and optional adjuvant. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions can be isotonic, i.e., it can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions must be selected to be chemically inert with respect to the PspA antigen and optional adjuvant. This will present no problem to those skilled in chemical and pharmaceutical principles, or problems can be readily avoided by reference to standard texts or by simple experiments (not involving undue experimentation), from this disclosure and the documents cited herein.

The immunologically effective compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity. Generally the pH may be from about 3 to 7.5. Compositions can be administered in dosages and by techniques well known to those skilled in the medical and veterinary arts taking into consideration such factors as the age, sex, weight, and condition of the particular patient or animal, and the composition form used for administration (e.g., solid vs. liquid). Dosages for humans or other mammals can be determined without undue experimentation by the skilled artisan, from this disclosure, the documents cited herein, the Examples below (e.g., from the Examples involving mice).

Suitable regimes for initial administration and booster doses or for sequential administrations also are variable, may include an initial administration followed by subsequent administrations; but nonetheless, may be ascertained by the skilled artisan, from this disclosure, the documents cited herein, and the Examples below.

PCR techniques for amplifying sample DNA for diagnostic detection or assay methods are known from the art cited herein and the documents cited herein (see Examples), as are hybridization techniques for such methods. And, without undue experimentation, the skilled artisan can use gene products and antibodies therefrom in diagnostic, detection or assay methods by procedures known in the art.

The following Examples are provided for illustration and are not to be considered a limitation of the invention.

EXAMPLES

Example 1

Truncated Streptococcus Pneumoniae PspA Molecules Elicit Cross-Protective Immunity Against Pneumococcal Challenge Since the isolation of *S. pneumoniae* from human saliva in 1881 and its subsequent connection with lobar pneumonia two years later, human disease resulting from pneumococcal infection has been associated with a significant degree of morbidity and mortality [1]. A recent survey of urgently needed vaccines in the developing and developed world places an improved pneumococcal vaccine among the top three vaccine priorities of industrialized countries [2]. The currently licensed vaccine is a 23-valent composition of pneumococcal capsular polysaccharides that is only about 60% effective in the elderly and due to poor efficacy is not recommended for use in children below two years of age [3]. Furthermore the growing frequency of multi-drug resistant strains of *S. pneumoniae* being isolated accentuates the need for a more effective vaccine to prevent pneumococcal infections.

The immunogenic nature of proteins makes them prime targets for new vaccine strategies. Pneumococcal molecules being investigated as potential protein vaccine candidates include pneumolysis (4), neuraminidase (5), autolysin [5], PspA [6], and PspA [7]. All of these proteins are capable of eliciting immunity in mice resulting in extension of life and protection against death with challenge doses near the $LD_{50}$ (5,8,9]. PspA is unique among these macromolecules in that it can elicit antibodies in animals that protect against inoculums 100-fold greater than the $LD_{50}$ [10]

PspA is a surface-exposed protein with an apparent molecular weight of 60–99 kDa [11] that is expressed by all clinically relevant S. pneumoniae strains examined to date [12]. Though PspAs from different pneumococcal strains are serologically variable, many PspA antibodies exhibit cross-reactivities with PspAs from unrelated strains [12]. Upon active immunization with PspA, mice generate PspA antibodies that protect against subsequent challenge with diverse strains of S. pneumoniae [10, 7]. The immunogenic and protection-eliciting properties of PspA suggest that it may be a good candidate molecule for a protein-based pneumococcal vaccine.

Four distinct domains of PspA have been identified based on DNA sequence. They include a N-terminal highly charged a-helical region, a proline-rich amino acid stretch, a C-terminal repeat segment comprised of app. ten app. 20-amino acid repeat sequences, and a 17-amino acid tail [13]. A panel of MAbs to Rx1 PspA have been produced [14,12,15] and the binding sites of nine of these Mabs were recently localized within the Rx1pspA sequence in the a-helical region (15). Five of the Rx1 Mabs were protective in mice infected with a virulent pneumococcal strain, WU2. Four of these five protective antibodies were mapped to the distal third (amino acids 192–260) of the α-helical domain of Rx1PspA [15].

Truncated PspAs containing amino acids 192–588 or 192–299, from pneumococcal strain Rx1 were cloned and the recombinant proteins expressed and evaluated for their ability to elicit protection against subsequent challenge with S. pneumoniae WU2 [15]. As with full-length Rx1 PspA[7], both truncated PspAs containing the distal a-helical region protected mice against fatal WU2 pneumococcal infection [15]. However, the recombinant PspA fragment extending from amino acid 192 to 588 was more immunogenic than the smaller fragment, probably due to its larger size. In addition, the protection elicited by the amino acid fragment 192–588 of Rx1 was comparable to that elicited by full-length Rx1 PspA [15]. Therefore, cross-protective epitopes of other PspAs were also sought in the C-terminal two-thirds of the molecule. As discussed below, PspAs homologous to amino acids 192–588 of strain Rx1 were amplified by PCR, cloned, and expressed in E. coli. Then three recombinant PspAs, from capsule type 4 and 5 strains, were evaluated for their ability to confer cross-protection against challenge strains of variant capsular types. The data demonstrate that the truncated PspAs from capsular type 4 and 5 strains collectively protect against or early death caused by challenge with capsular type 4 and 5 parental strains as well as type 3, 6A, and 6B S. pneumoniae.

Bacterial Strains and Culture Conditions.

All pneumococci were from the culture collection of this laboratory and have been previously described [16, 17, 18, 19] with the exception of clinical isolates TJO893, 0922134, and BG8740. Pneumococcal strains TJO893 and 0922134 were recovered from the blood of a 43-year old male and an elderly female, respectively. S. pneumoniae BG8743 is a blood isolate from an 8-month old infant. Strains employed in this study included capsular type 3 (A66.3, EF10197, WU2), type 4 (BG9739, EF3296, EF5668, L81905), type 5 (DBL5), type 6A (DBL6A, EF6796), type 6B (BG7322, BG9163, DBLI), type 14 (TJO893), type 19 (BG8090), and type 23 (0922134, BG8743). In addition strain WG44.1 [10], which expresses no detectable PspA, was employed in PspA-specific antibody analysis. All chemicals were purchased from Fisher Scientific, Fair Lawn, N.J. unless indicated otherwise.

S. pneumoniae were grown in Todd Hewitt broth (Difco, Detroit, Mich.) supplemented with 5% yeast extract (Difco). Mid-exponential phase cultures were used for seeding inocula in Lactated Ringer's (Abbott laboratories, North Chicago, Ill.) for challenge studies. The $LD_{50s}$ were previously determined [16, 20]. For pneumococcal strains used in challenge studies, inocula ranged from 2.8 to 3.8 $\log_{10}$ CFU (verified by dilution plating on blood agar). Plates were incubated overnight in a candle jar at 37° C.

E. coli DH1 and BL21(DE3) were cultured in LB medium (1% Bactotryptone (Difco), 0.5% Bacto Yeast (Difco), 0.5% NaCl, 0.1% dextrose). For the preparation of cell lysates, recombinant E. coli were grown in minimal E medium [21] supplemented with 0.05 M thiamine, 0.2% glucose, 0.1% casamino acids (Difco), and 50 mg/ml kanamycin. Permanent bacterial stocks were stored at −80° C. in growth medium containing 10% glycerol.

Construction of Plasmid-based Strains.

pET-9a (Novagen, Madison, Wis.) was used for cloning truncated pspA genes from fourteen S. pneumoniae strains: DBL5, DBL6A, WU2, BG9739, EF5668, L81905, 0922134, BG8090, BG8743, BG9163, DBL1, EF3296, EF6796, and EF10197 (Table 1). pspA gene fragments, from fifteen strains, were amplified by PCR using two primers provided by Connaught Laboratories, Swiftwater, Pa. Primer N192 (Sequence ID No. 14)-5'GGAAGGCCATATGCTCAAAGAGATTGAT-GAGTCT3' and primer C588 (Sequence ID No. 15)-5'CCAAGGATCCTTAAACCCATTCACCATTGGC3' were engineered with NdeI and BamHI restriction endonuclease sites, respectively. PCR-amplified gene products were digested with BamHI and NdeI, and ligated to linearized pET-9a digested likewise and further treated with bacterial alkaline phosphatase United States Biochemical Corporation, Cleveland, Ohio) to prevent recirculization of the cut plasmid. Clones were first established in E. coli BL21(DE3) which contains a chromosomal copy of the T7 RNA polymerase gene under the control of an inducible lacUV5 promoter [22].

E. coli DH1 cells were transformed by the method of Hanahan [23]. Stable transformants were identified by screening on LB-kanamycin plates. Plasmid constructs, isolated from each of these strains, were electroporated (Electro Cell Manipulator 600, BTX Electroporation System, San Diego, Calif.) into E. coli BL21(DE3) and their respective strain designations are listed in Table 1. The pET-9a vector alone was introduced into E. coli BL21(DES) by electroporation to yield strain RCT125 (Table 2). All plasmid constructs and PCR-amplified pspA gene fragments were evaluated by agarose gel electrophoresis (with 1 kb DNA ladder, Gibco BRL, Gaithersburg, Md.). Next, Southern analysis was performed using LmpspA1, a previously described full-length pspA probe [18] random primed labeled with digoxigenin-11-dUTP (Genius System, Boehringer Mannheim, Indianapolis, Ind.). Hybridization was detected with chemiluminescent sheets as per manufacturer's instructions (Schleicher & Schuell, Keene, N.H.).

Cell Fractionation of Recombinant E. coli Strains.

Multiple cell fractions from transformed E. coli were evaluated for the expression of truncated PspA molecules. Single colonies were inoculated into 3 ml LB cultures containing kanamycin and grown overnight at 37° C. Next, an 80 ml LB culture, inoculated with 1:100 dilution of the overnight culture, was grown at 37° C. to mid-exponential phase ($A_{600}$ of ca. 0.5) and a 1 ml sample was harvested and resuspended (uninduced cells) prior to induction with isopropylthiogalactoside (IPTG, 0.3 mM final concentration). Following 1, 2, and 3 hr of induction, 0.5 ml of cells were centrifuges, resuspended, and labeled induced cells. The remaining culture was divided into two aliquots, centrifuged (4000×g, 10 min, DuPont Sorvall RC 5B Plus), and the supernatant discarded. One pellet was resuspended in 5 ml of 20 mM Tris-HCl ph 7.4 200 Mm NaCl, 1 Mm (ethylenedinitrilo)tetraacetic acid disodium salt (EDTA) and frozen at −20° C. overnight. Cells were thawed at 65° C. for 30 min, placed on ice, and sonicated for vive 10-sec pulses (0.4 relative output, Fisher Sonic Dismembrator, Dynatech Laboratories, Inc. Chantilly, Va.). Next, the material was centrifuged (9000×g, 20 min) and the supernatant was designed the crude extract-cytoplasmic fraction. The pellet was resuspended in Tris-NaCl-EDTA buffer and labeled the insoluble cell well and membrane fraction. The other pellet, from the divided induced culture, was resuspended in 10 ml of 30 mM Tris-HCl pH 8.0 containing 20% sucrose and 1 mM EDTA and incubated at room temperature for 10 min with agitation. Cells were then centrifuged, the supernatant removed, and the pellet resuspended in 5 mM $MgSO_4$ (10 Ml, 10 min, shaking 4° C. bath). This material was centrifuged and the supernatant was designated osmotic shock-periplasmic fraction. Cell fractions were evaluated by SDS-PAGE and immunoblot analysis.

MAbs to PsPA.

PspA-specific monoclonal antibodies (MAbs) XiR278 and 1A4 were previously described [12]. MAb P50–92D9 was produced by immunization with DBL5 PspA (kindly provided by Dr. Robert Becker, Connaught Laboratories, Swiftwater, Pa.). The PspA-specificity of MAb P50–92D9 was confirmed by Western Analysis by its reactivity with native PspAs from S. pneumoniae DBL5, BG9739, EF5668, and L81095 and its failure to recognize the PspA-control strain WG44.1.

SDS-PAGE and Immunoblot Analysis.

E. coli cell fractions containing recombinant PspA proteins and biotinylated molecular weight markers (low range, Bio-Rad, Richmond, Calif.) were separated by sodium dodecyl sulfate-polyacrylamide (10%; Bethesda Research Laboratories, Gaithersburg, Md.) gel electrophoresis (SDS-PAGE) by the method of Laemmli [24]. Samples were first boiled for 5 min in sample buffer containing 60 mM Tris pH 6.8, 1% 2-Bmercaptoethanol (Sigma, St. Louis, Mo.), 1% SDS, 10% glycerol, and 0.01% bromophenol blue. Gels were subsequently transferred (1 hr, 100 volts) to nitrocellulose (0.45 mM pores, Millipore, Bedford, Mass.) as per the method of Towbin et al. [25]. Blots were blocked with 3% casein, 0.05% Tween 20 in 10 mM Tris, 0.1 M NaCl, pH 7.4 for 30 min prior to incubating with PspA-specific monoclonal antibodies diluted in PBST for 1 hr at 25° C. Next, the blot was washed 3 times with PBST before incubating with alkaline phosphatase-labeled goat anti-mouse immunoglobulin (Southern Biotechnology Associates, Inc., Birmingham, Ala.) for 1 hr at 25° C. Washes were performed as before and blots was developed with 0.5 mg/ml 5-bromo-4-chloro-3-indolyl phosphate and 0.01% nitro blue tetrazolium (Sigma) first dissolved in 150 μl of dimethyl sulfoxide and then diluted in 1.5 M Tris-HCl pH 8.8. Dot blots were analyzed similarly: Lysate samples (2 μl) were spotted on nitrocellulose filters (Millipore), allowed to dry, blocked, and detected as just described.

Preparation of Cell Lysates Containing Recombinant PsDA Proteins.

Transformed E. coli strains RCT105, RCT113, RCT117, and RCT125 (Table 2) were grown in mid-exponential phase in minimal E medium before IPTG induction (2 mM final concentration, 2 hours, 37° C.). Cultures were harvested by centrifugation (10 min at 9000×g), resuspended in Trisacetate pH 6.9, and frozen at −80° C. overnight. Samples were thawed at 65° C. for 30 min, cooled on ice, sonicated as previously described. Next the samples were treated with 0.2 mM AEBSF (Calbiochem, La Jolla, Calif.) at 37° C. for 30 min and finally centrifuged to remove cell wall and membrane components. Dot blot analysis was performed using PspA-specific MAbs to validate the presence of recombinant, truncated PspA molecules in the lysates prior to their use as immunogens in mice. Unused lysate material was stored at −20° C. until subsequent immunizations were performed.

Mouse Immunization and Challenge.

CBA/CAHN-XID/J mice (Jackson Laboratories, Bar Harbor, Me.), 6–12 weeks old, were employed for protection studies. These mice carry a X-linked immunodeficiency that prevents them from generating antibody to polysaccharide components, thus making them extremely susceptible to pneumococcal infection [26, 27]. Animals were immunized subcutaneously with cell lysates from E coli recombinant strains RCT105, RCT113, RCT117, and RCT125 (Table 2) in complete Freund's adjuvant for primary immunizations. Secondary injections were administered in incomplete adjuvant and subsequent boosts in dH20. Immunized and nonimmunized mice (groups of 2 to 5 animals) were challenged with S. pneumoniae strains A66.3, BG7322, DBL6A, WU2, DBL5, BG9739, and L81905 intravenously (tail vein) to induce pneumococcal sepsis. Infected animals were monitored for 21 days and mice that survived the 3-week evaluation period were designated protected against death and scored as surviving 22 days for statistical analysis. Protection that resulted in extension of life was calculated as a comparison between mean number of days to death for immunized versus pooled control mice (nonimmunized and RCT125 sham-immunized; total of 6–7 animals).

Determination of PsPA Serum Levels.

Mice were bled retro-orbitally following the secondary boost and again prior to challenge. Representative mouse titers were evaluated by enzyme-linked immunorsorbent assay (ELISA) using native, parental PspAs isolated from pneumococcal strains DBL5, BG9739, and L81905. PspAs were immobilized on microtiter plates by incubating in 0.5 $NaHCO_3$, 0.5 M $Na_2CO_3$ pH9.5 at 4° C. overnight. Alkaline phosphataselabeled goat anti-mouse immunoglobulin (Southern Biotechnology Associates, Inc.) was used to detect mouse serum antibodies. Color development was with p-nitrophenyl phosphate (Sigma, 1 mg/ml) in 0.5 m $MgCL_2$ pH 9.8 with 10% diethanolamine and absorbance was read at 405 nm after a 30 min incubation. Reciprocal titers were calculated as the last dilution of antibody that registered an optical density value of 0.1. Sera from individual mice within a particular immunogen group were evaluated separately and then the respective titers from four mice per group were combined to obtain titer range (Table 3).

Statistics.

The one-tailed Fisher exact and two sample rank tests [28] were used to evaluate protection against death and extension of life in the mouse model.

Cloning of Truncated pspA Genes.

Using primers N192 and C588, truncated pspA genes from fifteen diverse pneumococcal strains representing eight different capsular types (Table 1) were amplified by PCR. Even though variability exists in pspA genes from different strains [18], this result demonstrates that sufficient conversation exists between variant pspA genes to allow sequence amplification in all strains examined to date. Successful pspA PCR-amplification extended to all capsule types evaluated.

Fourteen of the amplified pspA genes were cloned and three clones containing truncated PspA molecules from pneumococcal strains DBL5, BG9739, and L81905 were further studies (Table 2). To verify the constructions, plasmids from recombinant E. coli strains (RCT105, RCT113, RCT117, and RCT125 (Table 2) were isolated, digested with NdeI and BAMHI restriction endonucleases, and electrophoresed in 1% agarose side-by-side with the PCR products used in their respective constructions (FIG. 1A). The digestion reaction was complete for pRCT105, while pRCT113 and pRCT117 digestions were incomplete (lanes 5 and 7, respectively). This gel was denatured and DNA transferred to nylon for Southern analysis. FIG. 1B depicts the corresponding Southern blot probed with full-length Rx1pspA DNA. Lane 1 contains pRCT125, digested vector alone, which does not react with the pneumococcal DNA-specific probe, as expected. The pspA-specific probe hybridized with the PCT products and the digested plasmid inserts (see arrow, FIG. 1B) as well as the partially undigested pRCT113 and pRCT117 (lane 5 and 7), confirming successful cloning of DBL5, BG9739, and L81905 pspA DNA. Constructions were similarly confirmed with the eleven additional recombinant strains containing truncated pspA genes from S. pneumoniae strains of different capsular and PspA types.

Expression of Recombinant PsPA in E. coli B121(De3).

Transformed E. coli strains RCT105, RCT113, RCT117, and RCT125 were cultured to mid-exponential phase prior to the addition of IPTG to induce expression of the cloned, truncated pspA gene in each strain. A cell fractionation experiment was performed to identify the location of recombinant PspA proteins in transformed E. coli strains. Samples representing uninduced cells, included cells (1 hr, 2 hr, and 3 hr time intervals), the periplasmic fraction, the cytoplasmic fraction, and insoluble cell wall/membrane material were resolved by SDS-PAGE. Proteins were then transformed to introcellulose and Western analysis was performed using monoclonal antibodies specific for PspA epitopes.

FIG. 2 reveals that both the cytoplasmic (lane 8) and the insoluble matter fractions (lane 9), from recombinant strain RCT 105, contain a protein of approximately 53.7 kDa that is recognized by MAb XiR278 that is not seen in the uninduced cell sample (lane 3). This protein increases in quantity in direct correlation with the length of IPTG induction (lanes 4–6; 1 hr, 2 hr, and 3 hr respectively). No truncated RCT105 PspA was found in the periplasmics fraction (lane 7), which was expected since the pET-9a vector lacks a signal sequence that would be necessary for directing proteins to the periplasm. The observed molecular weight (ca. 53.5 kDa) is larger than the predicted molecular weight for the 1.2 kb DBL5pspA gene product (43.6 kDa; FIG. 1A, lane 4). Like full-length Rx1 PspA (Yother, 1992), the observed and predicted molecular weights for truncated PspAs do not agree precisely. In addition, immunoblot analysis was performed for recombinant E. coli strains RCT113, and RCT117 (using MAbs 1A4 and P50-92D, respectively) and similar results were obtained, while no cell fractions from control strain RCT125 were recognized by MAb XiR278.

Evaluating the Protective Capacity of Recombinant, Truncated PsPAs.

The truncated PspA proteins from strains RCT113, RCT117, and RCT105 were expressed and analyzed for their ability to generate cross-protection against a battery of seven S. pneumoniae strains. Control mice (non-immunized and RCT125 sham-immunized) and recombinant PspA-immunized mice were challenged with mouse-virulent strains A66.3, BG7322, DBL6A, WU2, DBL5, BG9739, and L81905. Table 3 presents the day of death for each infected mouse.

Immunization with truncated PcpA from RCT113, RCT117, and RCT105 conferred protection against death for all mice challenged with capsular type 3 strains (A66.3 and WU2 (Table 3)). The three truncated PSpAs also provided significant protection against death with DBL6A, and BG7322 pneumococci (capsular types 6A and 6B, respectively). In addition, immunization with recombinant RCT113 PspA extended days to death in mice challenged with strains DBL5, BG9739, and L81905, while RCT117 PspA prolonged the lives of mice inoculated with BG9739 pneumococci (Table 3). Truncated BG9739 PspA elicited protection against all challenge strains (100%) evaluated in this study, while recombinant L81905 and DBL5 truncated PspAs conferred protection against death with 71% and 57% of S. pneumoniae challenge strains, respectively.

Anti-PspA antibody titers elicited by the three immunogens vary over approximately a 10-fold range (Table 3).

The lowest antibody levels were elicited by RCT105 and this truncated PspA also elicited protection against the fewest number of challenge strains. RCT113 and RCT117 elicited three and nine time as much anti-PspA antibody, respectively. As expected, no antibody to PspA was detected in nonimmunized mice nor was specific-PspA antibody measured in mice immunized with the vector-only control strain (RCT125).

In summary, immunization with RCT113 and RCT117 PspAs protected mice against fatal challenge with capsular type 3 and 6A strains and extended life for mice inoculated with type 4, 5, and 6B pneumococci. RCT105 PspA immunization protected against fatal infection with capsular type 3 and 6B strains and prolonged time to death for type 6A S. pneumoniae but offered not protection against type 4 and 5 strains. These data demonstrate that truncated PspAs from capsular type 4 and 5 pneumococci collectively protect mice and ergo other hosts, such as humans, against or delay death caused by each of the seven challenge strains. In general, however, more complete protection was observed against strains of capsular type 3, 6A, and 6B than against type 4 and 5 S. pneumoniae.

PspA has been shown to be a protection-eliciting molecule of S. pneumoniae [10, 7, 29]. Immunization with PspA has also been shown to be cross-protective, although eliciting more complete protection against certain strains than others [7]. Thus, it is possible that a broadly protective PspA vaccine might need to contain PspAs of more than one pneumococcal strain. The distal third of the a-helical region of PspA has been identified as a major protective region of PspA [15]. Moreover, this region is presented in a very antigenic form when expressed with the intact C-terminal half of the molecule [15]. In this Example, the ability to use truncated PspA proteins homologous to the region of Rx1 PspA extending from amino acid residue 192 to the C-terminus at residue 588 is demonstrated.

The C-terminal two-thirds of PspA was cloned from fourteen strains by PCR amplification of a gene fragment of the appropriate size (1.2 kb) which hybridized with full-length Rx1 pspA. Successful PCR amplification extended to all capsule types analyzed. Thus, the C-terminal two-third of PspA may be amplified from many, if not all, pneumococcal capsule types with Rx1 pspA-specific primers. This technique is thus applicable to the development of antigenic immunological or vaccine compositions containing multiple PspA or fragments thereof.

Of these clones, three truncated PspA proteins were expressed and evaluated in mouse immunization studies to determine their ability to cross-protect against challenge with a variety of pneumococcal capsular types. All three recombinant PspAs elicited antibody reactive with their respective donor PspA and all three elicited protection against pneumococcal infection. Of the two truncated PspA proteins that elicited the highest antibody responses, 100% and 71% of the challenge strains were protected. RCT105 PspA, which elicited the lowest titers of PspA-specific antibody, yielded protection against 57% of *S. pneumoniae* strains evaluated. With all truncated PspAs, significant levels of protection were observed in four of the seven challenge strains. In fact, in all instances except for on (RCT105-immunized mice challenged with strain BG9739) the trend was for truncated PspA-immunization to elicit protection against pneumococcal challenge. These results demonstrate that truncated Rx1 PspA (amino acids 192–588) cross-protects mice against fatal *S. pneumoniae* WU2 challenge. More importantly, these data show that the homologous regions of diverse PspAs demonstrate comparable cross-protective abilities.

Strains of capsular type 4 and 5 were more difficult to protect against than were type 3, 6A and 6B pneumococcal strains. Serological differences in PspAs might affect cross-protection in some cases. Yet the difficulty in protecting against the type 4 and 5 strains used herein could not be explained on this basis, since the truncated PspA immunogens were cloned from the same three type 4 and 5 strains used for challenge. Both PspAs from the type 4 strains delayed death caused by one or both type 4 challenge strains but neither could prevent death caused by either type 4 pneumococcal strain. Moreover, the truncated PspA from the type 5 strain DBL5 elicited protection against death or delayed death with strains of capsular types 3, 6A and 6B but failed to protect against infection with its donor strain or either type 4 challenge strain.

There may be several reasons why the truncated PspAs from capsular type 4 and type 5 strains failed to protect against death even with their homologous donor *S. pneumoniae* strains. One possibility is that the type 4 and 5 strains chosen for study are especially virulent in the XID mouse model. XID mice fail to make antibodies to polysaccharides [26, 27] and are therefore extremely susceptible to pneumococcal infection with less than 100 CFU of most strains, including those of capsular type 3, 4, 5, 6A, and 6B. The increased mouse virulence of types 4 and 5 is apparent from the fact that in immunologically normal mice these strains have lower $LD_{50}$s and/or are more consistently fatal than strains of capsular types 3, 6A, or 6B [17].

Another possibility is that epitopes critical to protection-eliciting capacity with capsular type 4 and 5 strains are not present in the C-terminal two-thirds of PspA (amino acids 192–588), the truncated fragments used for immunization. The critical epitopes for these strains may be located in the N-terminal two thirds of the a-helical region of their PspA molecules. Finally, it is also possible that PspA may be less exposed on some *S. pneumoniae* strains than others. Strain Rx1 PspA amino acid sequence does not contain the cell wall attachment motif LPXTGX described by Schneewind et al [30] found in many gram-positive bacteria. Rather, PspA has a novel anchoring mechanism that is mediated by choline interactions between pneumococcal membrane-associated lipoteichoic acid and the repeat region in the C-terminus of the molecule [31]. Electron micrographic examination has confirmed the localization of PspA on the pneumococcal surface [32] and PspA-specific MAb data supports the accessibility of surface-exposed PspA. However, it is not known whether *S. pneumoniae* strain differ substantially in the degree to which different PspA regions are exposed to the surounding environment. Nor is it known if the quantity of PspA expressed on the bacterial cell surface differs widely between strains.

TABLE 1 pspA recombinant strains categorized by pneumococcal capsular type.

| Capsular Type | Parent Strains | Respective Recombinant Strains |
|---|---|---|
| 3 | WU2, EF10197 | RCT111, RCT137 |
| 4 | BG9739, EF5668 | RCT113, RCT115 |
| | L81905, EF3296 | RCT117, RCT133 |
| 5 | DBL5 | RCT105 |
| 6A | DBL6A, EF6796 | RCT109, RCT135 |
| 6B | BC9163, DBL1 | RCT129, RCT131 |
| 14 | TJ0893 | none* |
| 19 | BG8090 | RCT121 |
| 23 | 0922134, BG8743 | RCT119, RCT123 |

*Truncated pspA amplified recently, not yet cloned

TABLE 2

Description of recombinant strains used in evaluating the protection-eliciting capacity of truncated PspAs in mice.

| Recombinant Strain | Description | Capsule of Type Parent PspA |
|---|---|---|
| RCT 105 | BL21(DE3) *E. coli* with pET-9a:DBLS | 5 |
| RCT 113 | BL21(DE3) *E. coli* with pET-9a:BG9739 | 4 |
| RCT 117 | BL21(DE3) *E. coli* with pET-9a:L81905 | 4 |
| RCT 125 | BL21(DE3) *E. coli* with pET-9a (vector only) | |

TABLE 3

Evaluation of the protection elicited by truncated *S. pneumoniae* PspA molecules in mice by days to death post-challenge*.

| Immunizing recombinant PspA/ PspA donor strain | Reciprocal anti-PspA titer† | Challenge Strain [capsular type] ($\log_{10}$ dose in CFU) | | | | | | |
|---|---|---|---|---|---|---|---|---|
| | | A66.3 [type 3] (2.78) | WU2 [type 3] (3.57) | DBL6A [type 6A] (3.24) | BG7322 [type 6B] (3.11) | DBL5 [type 5] (3.81) | BG9739 [type 4] (3.56) | L81905 [type 4] (3.62) |
| RCT113/BG9739 | 5590–50,300 | 4x > 21‡ | 4x > 21§ | 15, 3x > 21‡ | 12, 13, 16, >21‡ | 3, 3, 4, 5§ | 5, 5, 5, 7§ | 5, 6, 8, 8‡ |
| RCT117/L81905 | 5590–150,900 | 4x > 21‡ | 4x > 21§ | 7, 16, 2x > 21‡ | 10, 12, 13, >21§ | 3, 3, 4, 4¶ | 4, 5, 13, >21§ | 3, 4, 6, 8 |
| RCT105/DBL5 | 1860–16,770 | 4x > 21‡ | 4x > 21§ | 8, 10, 13, 21‡ | 4x > 21‡ | 2, 2, 2, >21 | 2, 2, 2, 4 | 4, 5, 5, 5 |
| RCT125/vector only | 20–620 | 3, 6, 6, >21 | 2, 3, 3, >21 | 3, 6, 6, 6 | 7, 8, 8, 14 | 2, 2, 2, 2 | 2, 2, 3, 4, 5 | 2, 3, 5, 5 |
| none | 0 | 2, 2, 2 | 2, 3 | 3, 3, 4 | 6, 7, 9 | 2, 5 | 3, 5 | 2, 5 |
| RCT113/BG9739 | 5590–50,300 | 4x > 21‡ | 4x > 21§ | 15, 3x > 21‡ | 12, 13, 16, >21‡ | 3, 3, 4, 5§ | 5, 5, 5, 7§ | 5, 6, 8, 8‡ |
| RCT117/L81905 | 5590–150,900 | 4x > 21‡ | 4x > 21§ | 7, 16, 2x > 21‡ | 10, 12, 13, >21§ | 3, 3, 4, 4¶ | 4, 5, 13, >21§ | 3, 4, 6, 8 |
| RCT105/DBL5 | 1860–16,770 | 4x > 21‡ | 4x > 21§ | 8, 10, 13, 21‡ | 4x > 21‡ | 2, 2, 2, >21 | 2, 2, 2, 4 | 4, 5, 5, 5 |
| RCT125/vector only | 20–620 | 3, 6, 6, >21 | 2, 3, 3, >21 | 3, 6, 6, 6 | 7, 8, 8, 14 | 2, 2, 2, 2 | 2, 2, 3, 4, 5 | 2, 3, 5, 5 |
| none | 0 | 2, 2, 2 | 2, 3 | 3, 3, 4 | 6, 7, 9 | 2, 5 | 3, 5 | 2, 5 |

*Animals surviving the 3-week evaluation period were sacrificed and days to death recorded as >21 days. For statistical analysis, P values were calculated at 22 days for these fully protected mice.
†Range of four sera per group of mice; titers measured against native donor PspAs
‡P ≤ 0.012
§P ≤ 0.035
¶P ≤ 0.057
Note:
One-tailed Fisher exact and two sample rank tests were used for statistical analysis.

REFERENCES

1. Mufson M A. *Streptococcus pneumoniae*. In: Principles and Practice of Infectious Diseases. New York: John Wiley and Sons, Inc., 1990: 1539–1550.
2. Cohen C, Parry D A D. a-helical coiled coils: more facts and better predictions. Science 1994; 236: 488–289.
3. Shapiro E D, Berg A T, Austrian R, et al. Protective efficacy of polyvalent pneumococcal polysaccharide vaccine. N. Engl. J. Med 1991; 325: 1453–1460.
4. Feldman C, Munro N C, Jeffery P K, et al. Pneumolysin induces the salient histologic features of penumococcal infection in the rat lung in vivo. Am. J. Respir. Cell Mol. Biol. 1992; 5: 416–423.
5. Lock R A, Paton J C, Hansman D. Comparative efficacy of pneumococcal neuraminidase and pneumolysin as immunogens protective against *Streptococcus pneumoniae*. Microb. Pathog. 1988; 5: 461–467.
6. Sampson J S, O'connor S P, Stinson A R, Tharpe J A, Russell H. Cloning and nucleotide sequence analysis of psaA, the *Streptococcus pneumoniae* gene encoding a 37-kilodalton protein homologus to previously reported Streptococcus sp. adhesins. 1994;
7. McDaniel L S, Sheffield J S, Delucchi P, Briles D E. PspA, a surface protein of *Streptococcus pneumoniae*, is capable of eliciting protection against pneumococci of more than one capsular type. Infect. Immun. 1991; 59: 222–228.
8. Berry A M, Lock R A, Hansman D, Paton J C. Contribution of autolysin to virulence of *streptococcus pneumoniae*. Infect. Immun. 1989; 57: 2324–2330.
9. Berry A M, Yother J, Briles D E, Hansman D, Paton J C. Reduced virulence of a defined pneumolysin-negative mutant of *Streptococcus pneumoniae*. Infect. Immun. 1989; 57: 2037–2042.
10. McDaniel L S, Yother J, Vijayakumar. M, McGarry L, Guild W R, Briles D E. Use of insertional inactivation to facilitate studies of biological properties of pneumococcal surface protein A (PspA). J. Exp. Med. 1987; 165: 381–394.
11. Waltman W D II, McDaniel L S, Gray B M, Briles D E. Variation in the molecular weight of PspA (Pneumococcal Surface Protein A) among *Streptococcus pneumoniae*. Microb. Pathog. 1990; 8: 61–69.
12. Crain M J, Waltman W D II, Turner J S, et al. Pneumococcal surface protein A (PspA) is serologically highly variable and is expressed by all clinically important capsular serotypes of *Streptococcus pneumoniae*. Infect. Immun. 1990; 58: 3293–3299.
13. Yother J, Briles D E. Structural properties and evolutionary relationships of PspA, a surface protein of *Streptococcus pneumoniae*, as revealed by sequence analysis. J. Bact. 1992.
14. McDaniel L S, Scott G, Kearney J F, Briles D E. Monoclonal antibodies against protease sensitive pneumococcal antigens can protect mice from fatal infection with *Streptococcus pneumoniae*. J. Exp. Med. 1984; 160: 386–397.
15. Localization of protection-eliciting epitopes on PspA of *streptococcus pneumoniae*: Example 2, infra.
16. Yother J, Forman C, Gray B M, Briles D E. Protection of mice from infection with *Streptococcus pneumoniae* by anti-phosphocholine antibody. Infect. and Immun. 1982; 36:184–188.
17. Briles D E, Crain M J, Gray B M, Forman C, Yother J. Strong association between capsular type and virulence for mice among human isolates of *Streptococcus pneumoniae*. Infect. Immun. 1992; 60: 111–116.
18. McDaniel L S, Sheffield J S, Swiatlo E, Yother J, Crain M J, Briles D E. Molecular localization of variable and conserved regions of pspA, and identification of additional pspA homologous sequences in *Streptococcus pneumoniae*. Microbial Pathogenesis 1992; 13: 261–269.
19. McDaniel L S, McDaniel D O. Analysis of the gene encoding type 12 PspA of *S. pneumoniae* EF5668. In: Ferretti J J, Gilmore M S, Klaenhammer T R, Brown F ed. Genetics of Streptococci, Enterococci and Lactococci. Basal: Karger, 1995: 283–286.
20. Briles D E, Forman C, Crain M. Mouse antibody to phosphocholine can protect mice from infection with mouse-virulent human isolates of Streptococcus pneumoniae. Infect. Immun. 1992; 60: 1957–1962.
21. Davis R W, Boststein D, Roth J R. A manual for genetic engineering: advanced bacterial genetics. Cold Spring Harbor, N.Y.: Cold Spring Harbor Laboratory Press, 1980:

22. Studier F W, Moffatt B A. Use of baceriophage T7 RNA polymerase to direct selective high-level expression of cloned genes. J. Mol. Biol. 1986; 189:113–130.
23. Hanahan D. Studies on transformation of *Escherichia coli* with plasmids. J. Mol. Biol. 1983; 166: 557–580.
24. Laemmli U K. Cleavage of structural proteins during the assembly of the head of bacteriophage T4. Nature 1970; 227: 680–685.
25. Towbin H, Staehelin T, Gordon J. Electrophoretic transfer of proteins from polyacrylamide gels to nitrocellulose sheets: Procedure and some applications. Proc. Natl. Acad. Sci. USA 1979; 76: 4350–4354.
26. Amsbaugh D F, Hansen C T, Prescott B, Stashak P W, Barthold D R, Baker P J., Genetic control of the antibody response to type III pneumococcal polysaccharide in mice. I. Evidence that an X-linked gene plays a decisive role in determining responsiveness. J. Exp. Med 1972; 136: 931–949.
27. Briles D E, Nahm. M, Schroer K, et al. Antiphosphocholine antibodies found in normal mouse serum are protective against intravenous infection with type 3 *Streptococcus pneumoniae*. J. Exp. Med. 1981; 153: 694–705.
28. Zar J H. Biostatistical Analysis. (second ed.). Englewood Cliffs, N.J.: Prentice-Hall, Inc., 1984: 718.
29. Talkington D F, Crimmins D L, Voellinger D C, Jother J, Briles D E. A 43-kilodalton pneumococcal surface protein, PspA: isolation, protective abilities, and structural analysis of the amino-terminal sequence. Infect. Immun. 1991; 59:: 1285–1289.
30. Schneewind 0, Model P, Fischetti V A. Sorting of protein A to the staphylococcal cell wall. Cell 1992; 70: 267–281.
31. Yother J, White J M. Novel surface attachment mechanism for the *streptococcus pneumoniae* protein PspA. J. Bact. 1994; 176: 2976–2985.
32. Gray B M. Pneumococcal infection in an era of multiple antibiotic resistance. Adv. Ped. Inf. Dis. 1995; 11: In press:

Example 2

Localization of Protection-eliciting Epitopes and PspA of *S. pneumoniae*

This Example, the ability of PspA epitopes on two PspA fragments (amino acids 192–588 and 192–299) to elicit cross-protection against a panel of diverse pneumococci is demonstrated. Also, this Example identifies regions homologous to amino acids 192–299 of Rx1 in 15 other diverse pneumococcal strains. The DNA encoding these regions was then amplified and cloned. The recombinant PspA fragments expressed were evaluated for their ability to elicit cross-protection against a panel of virulent pneumococci.

Bacterial Strains and Media Conditions.

*S. pneumoniae* strains were grown in Todd Hewitt broth with 0.5% yeast extract (THY) (both from Difco Laboratories, Detroit, Mich.) at 37° C. or on blood agar plates containing 3% sheep blood at 37° C. under reduced oxygen tension. *E. coli* strains were grown in Luria-Bertani medium or minimal E medium (Davis, 1980 #143]. Bacteria were stored at −8° C. in growth medium supplemented with 10% glycerol. *E. Coli* were transformed by the methods of Hanahan [Hanahan, 1983]. Ampicillin (Ap) was used at a concentration of 100 μg/ml for *E. Coli*.

Construction of pIN-III-ompA3 and pMAL-based *E. Coli* strains. Recombinant plasmids pBC100 and pBAR416 that express and secrete pspA fragments from *E. Coli* were constructed with pIN-III-ompA3 as previously described [McDaniel, 1994].

The pMAL-p2 vector (New England Biolabs, Protein Fusion & Purification System, catalog #800) was used for cloning pspA gene fragments to amino acids 192–299 from strain Rx1 and from 7 other S. pneumoniae strains: R36A, D39, A66, BF9739, DBL5, DBL6A, and LM100. Amplification of the pspA gene fragments was done by the polymerase chain reaction (PCR) as described previously [McDaniel, 1994] using primers 5'CCGGATCCGCT-CAAAGAGATTGATGAGTCTG3' [LSM4] and 5'CTGAGTCGACTGAGTTTCTGGAGCTGGAGC3' [LMS6] made with BamHI and SalI restriction endonuclease sites, respectively. Primers were based on the sequence of Rx1 PspA [Yother, 1992]. PCR products and the pMAL vector were digested with BAMHI and SalI, and ligated together. Clones were transformed into *E. Coli* DH5α by the methods of Hanahan (Hanahan, 1983]. Stable transformants were selected on LB plates containing 100 μg/ml Ap. These clones were screened on LB plates containing 0.1 mM IPTG, 80 μg/ml X-gal and 100 μg/ml Ap and replica LB plates with 100 μg/ml Ap as per manufacturer's instructions. The strain designations for these constructs are listed in Table 6. Positive clones were evaluated for the correct pspA gene fragment by agarose gel electrophoresis following plasmid isolation by the methods of Birnboim and Doly [Birnboim, 1979]. Southern analysis was done as previously described [McDaniel, 1994] using a full-length pspA probe randomly primed labeled with digoxigenin-11-dUTP (Genius System, Boehringer Mannheim, Indianapolis, Ind.) and detected by chemiluminescence.

Expression of Recombinant PspA Protein Fragments.

For induction of expression of strains BC100 and BAR416, bacteria were grown to an optical density of approximately 0.6 at 660 nm at 37° C. in minimal media, and IPTG was added to a final concentration of 2 mM. The cells were incubated for an additional 2 hours at 37° C., harvested, and the periplasmic contents released by osmotic shock [Osborn, 1974 #100]. For strains BAR36A, BAR39, BAR66, BAR5668, BAR9739, BARL5, BAR6A and BAR100, bacteria were grown and induced as above except LB media +10 mM. Glucose was the culture medium. Proteins from these strains were purified over an amylose resin column as per manufacturer's instructions (New England Biolabs, Protein Fusion & Purification System, Catalog #800). Briefly, amylose resin was poured into a 10 mL column and washed with column buffer. The diluted osmotic shock extract was loaded at a flow rate of approximately 1 mL/minute. The column was then washed again with column buffer and the fusion protein eluted off the column with column buffer +10 mM maltose. Lysates were stored at −20° C. until further use.

Characterization of Truncated PspA Proteins used for Immunization.

Immunoblot analysis was carried out as described previously (McDaniel, 1991 #14). Briefly, the truncated PspA molecules, controls and molecular weight markers (Bio-Rad, Richmond, Calif.) were electrophoresed in a 10% sodium dodecyl (SDS)-polyacrylamide gel and electroblotted onto nitrocellulose. Rabbit polyclonal anti-PspA serum and rabbit antimaltose binding protein were used as the primary antibodies to probe the blots.

A direct binding ELISA procedure was used to quantitatively confirm reactivities observed by immunoblotting. For all protein extracts, osmotic shock preparations were diluted to a concentration of 3 μg/ml in phosphate buffered saline (PBS), and 100 μl was added to the wells of Immulon 4 microtitration plates (Dynatech Laboratories, Inc., Chantilly, Va.). After blocking with 1.5% bovine serum albumin in PBS, unfactionated tissue culture supernates of individual MAbs were titered in duplicated by three-fold serial dilution through seven wells and developed using an alkaline phosphatase-labeled goat anti-mouse immunoglobulin secondary antibody (Southern Biotech Associates, Birmingham, Ala.) and alkalinephosphatase substrate (Sigma, St. Louis, Mo.) as previously described (McDaniel, 1994). The plates were read at 405 nm in a Dynatech plate reader after 25 minutes, and the 30% end point was calculated for each antibody with each preparation.

Immunization and Protection Assays.

Six to nine week old CBA/CAHN-XID/J (CBA/N) mice were obtained from the Jackson Laboratory, Bar Harbor, Me. CBA/N mice carry an X-linked immunodeficiency trait, which renders them relatively unable to respond to prolysaccharide antigens, but they do respond with normal levels of antibodies against protein antigens (Amsbaugh, 1972; Wicker, 1986). Because of the absence of antibodies reactive with the phosphocholine determinant of C-polysaccharide in their serum, the mice are highly susceptible to pneumococcal infection (Briles, 1981). Mice immunized with the BC100 fragment were injected inguinally with antigen emulsified in CFA, giving an approximate dose of 3 µl of protein per mouse. Fourteen days later the mice were boosted intraperitoneally with 3 µl of antigen diluted in Ringer's lactate without adjuvant. Control mice were immunized following the same protocol with diluent and adjuvant, but no antigen. Mice immunized with the BAR416 fragment were injected with 0.2 ml at two sites in the subinguinal area with antigen emulsified in CFA. The mice were boosted inguinally fourteen days later with antigen emulsified in IFA and were boosted a second time fourteen days later intraperioneally with 0.2 ml of antigen diluted in Ringer's lactate without adjuvant.

Mice that were immunized with the homologues of Rx1 BAR416 were immunized as described above. The control animals followed the same immunization protocol but received maltose binding protein (MBP) diluted 1:1 in CFA for their immunization and were also boosted with MBP.

Serum Analysis.

Mice were retro-orbitally bled with a 75 µl heparinized microhematocrit capillary tube (Fisher Scientific) before the first immunization and then once approximately 2 hours before challenge with virulent pneumococci. The serum was analyzed for the presence of antibodies to PspA by an enzyme-linked immunosorbent assay (ELISA) using native full-length R36A PspA as coating antigen as previously described (McDaniel, 1994).

Intravenous Infection of Mice.

Pneumococcal cultures were grown to late log phase in THY. Pneumococci were diluted to 104 CFU based on the optical density at 420 nm into lactated Ringer's solution. Seven days following the last boost injection for each group, diluted pneumococci were injected intravenously (tail vein) in a volume of 0.2 ml and plated on blood agar plates to confirm the numbers of CFU per milliliter. The final challenge dose was approximately 50–100 times the $LD_{50}$ of each pneumococcal strain listed in Tables 4–6. The survival of the mice was followed for 21 days. Animals remaining alive after 21 days were considered to have survived the challenge.

Statistical Analysis.

Statistical significance of differences in days to death was calculated with the Wilcoxon two-sample rank test. Statistical significance of survival versus death was made using the Fisher exact test. In each case, groups of mice immunized with PspA containing preparations were compared to unimmunized controls, or controls immunized with preparations lacking PspA. One-tailed, rather than two-tailed, calculations were used since immunization with PspA or fragments of PspA has never been observed to cause a statistically significant decrease in resistance to infection.

Cloning into PMAL Vector.

Using primers based on the sequence of RxI PspA, LSM4 and LSM6, pspA gene fragments were amplified by PCR from fifteen out of fifteen pneumococcal strains examined. Seven of the eleven gene fragments were cloned into pMAL-p2 and transformed into E. coli (Table 6). The correct insert for each new clone was verified by agarose gel electrophoresis and Southern hybridization analysis. Plasmids from recombinant E. coli strains BAR36A, BAR39, BAR66, BAR9739, BARL5, BAR6A and BARlOO were isolated, digested with BamHI and SalI restriction endonucleases and electrophoresed on a 0.7% TBE agarose gel. The gel was then denatured and the DNA transferred to a nylon membrane for southern hybridization. The blot was probed with full-length Rx1 pspA DNA at high stringency conditions. The cloning of R36A, D39, A66, BG9739, DBL5, DBL6A and LM100 pspA DNA into pMal-p2 was confirmed by the recognition of all BamHI and SalI digested DNA inserts by the Rx1 probe.

Expression and Conformation of Truncated Recombinant Proteins.

The transformed E. coli strains BAR36A, BAR39, BAR66, BAR9739, BARL5, BAR6A and BAR100 were grown in LB media supplemented with 10 mM glucose and induced with 2 mM IPTG for expression of the truncated PspA protein fused with maltose binding protein. Transformed E. coli strains BC100 and BAR416, which express PspA fragments fused to the OmpA leader sequence in the pIN-III-ompA3 vector, were grown in minimal medium and induced with 2 mM IPTG for expression. Both vectors, pIN-IIIompA3 and pMal-p2, are vectors in which fusion proteins are exported to the periplasmic space. Therefore, an osmotic shock extract from the pMal-p2 containing bacteria was then run over an amylose column for purification and resolved by SDS-PAGE western blotting. The western blot of the protein extracts from BAR36A, BAR39, BAR66, BAR9739, BARL5, BAR6A and BAR100 were recognized by a rabbit polyclonal antibody made to strain BC100 PspA. The apparent $M_r$ of full-length PspA from WU2 is 91.5 kD. The $M_r$ of maltose binding protein is 42 kD and the expected $M_r$ for the PspA portion of the fusion is 12 kD. All extracts exhibited molecular weights that ranged from 54 to 80 kD. This range of molecular weights can be attributed to the variability of pspA among different pneumococcal strains. An ELISA, with plates coated with the various cloned fragments quantitatively confirmed the reactivities that were observed in the western blots with all protein extracts.

Protection and Cross-protection Against Fatal Pneumococcal Infection Elicited by Cloned PsPA Fragments.

CBA/N mice were immunized with the truncated PspA fragment encoded by pBC1o0, which is composed of amino acids 192 to 588 of Rx1 PspA, and challenged with 13 different S. pneumoniae strains representing 7 different capsular types (Table 4). With all 13 strains, the immunization resulted in protection from death or an extended time to death. With 10 of the strains the difference was statistically significant. With strains of capsular types 3, 6A, and 6B, all immunized mice were protected against death. Although there were fewer survivors in the case of capsular types 2, 4, and 5, the immunization with BC100 resulted in significant increases in times to death.

The BC100 immunization studies made it clear that epitopes C-terminal to residue 192 could elicit cross-protection. The BAR416 fragment, which includes amino acids 192–299, could elicit protection from fatal infection with a single challenge strain WU2. This Example shows the ability of BAR416 immunization to protect against the 6 strains that had been best protected against by immunization with BC100. Immunization with the BAR416 construct resulted in increased time to death for all 6 challenge strains examined (Table 5). BAR416 provided significant protection against death with WU2, A66, BG7322 and EF6796 pneumococci (capsular types 3, 3, 6B and 6A respectively). It also prolonged the lives of mice challenged with ATCC6303 and DBL6A pneumococci (capsular types 3 and 6A respectively). Serum from mice immunized with the BAR416 fragment yielded a geometric mean reciprocal anti-PspA ELISA titer to full-length Rx1 PspA of 750. Mice immunized with BC100 had geometric mean reciprocal titers of close to 2000, while non-immunized mice had anti-PspA titers of <10.

The above data indicates that the BAR416 fragment from Rx1 elicits adequate cross-reactive immunity to protect against diverse pneumococci and suggests that this region must be serologically conserved among PspAs. This hypothesis was confirmed by immunized with recombinant BAR416 homologous regions from the 7 different clones and then challenging with strain WU2 (Table 6). All 7 immunogens elicited significant protection. PspA fragments from capsular types 2 and 22 and the rough R36A strain elicited complete protection against death with all challenged mice. All of the other immunogens were able to extend the time to death of all the mice with the median days to death being 21 days or >21 days. Serum from mice immunized with the BAR416 homologous fragments had anti-PspA reciprocal titers that ranged from 260 to 75,800 with an average of 5700 while control animals immunized with only maltose binding protein had anti-PspA reciprocal titers of <10.

Antibody Reactives.

All of the above immunization studies attest to the cross-reactivity of epitopes encoded by amino acids from position 192–299. This region includes the C-terminal third of the α-helical region and the first amino acids of the proline rich region. Other evidence that epitopes within this region are cross-reactive among different PspAs comes form the cross-reactivity of a panel of nine MAbs all of which were made by immunization with Rx1 PspA. The epitopes of four of the antibodies in the panel reacted with epitopes mapping between amino acids 192–260. The epitopes of the other five MAbs in the panel map between amino acids 1 and 115 (McDaniel, 1994). Each of these 9 MAbs were tested for its ability to react with 8 different PspAs in addition to Rx1. The 5 MAbs whose epitopes were located within the first 115 amino acids, reacted on average with only 1 other PspA. Three of the 5 in fact, did not react with any of the other 8 PspAs. In contrast the MAbs whose epitopes map between 192 and 260 amino acids each cross-reacted with an average of 4 of the 8 non-Rx1 PspAs, and all of them reacted with at least two non-Rx1 PspAs. Thus, based on this limited section of individual epitopes, it would appear that epitopes in the region from 192–260 amino acids are generally much more cross-reactive than epitopes in the region from 1–115 amino acids.

The BC100 fragment of Rx1 PspaA can elicit protection against the encapsulated type 3 strain WU2. Although the PspAs of the two strains can be distinguished serologically they are also cross-reactive (Crain, 1990). The earlier finding made it clear that epitopes cross-protective between Rx1 and WU2 PspAs exist. The importance of cross-reactions in the region C-terminal to residue 192 is demonstrated in this Example where 13 mouse virulent challenge strains have been used to elicit detectable protection against all of them. The first indication that epitopes C-terminal to position 192 might be able to elicit cross-protection came from our earlier study where we showed the MAbs Xi64, XiR278, XiR1323, and XiR1325, whose epitopes mapped between amino acids 192 and 260 of strain Rx1 PspA, could protect against infection with WU2. Moreover, immunization with PspA fragments from 192–588 and 192–299 were able to elicit protection against infection against WU2. This Example shows that the BC100 Rx1 fragment (192–588) elicits significant protection against each of 13 different mouse virulent pneumococci, thereby firmly establishing the ability of epitopes C-terminal to position 192 to elicit a protective response. The observation that a fusion protein containing amino acids 192–299 fused C-terminal to maltose binding protein could also elicit cross-protection, permits the conclusion that epitopes in this 107 amino acid region of PspA are sufficient to elicit significant cross-protection against a number of different strains.

Evidence that a comparable region of other PspAs is also able to elicit cross-protection cam from the studies where sequences homologous to the 192–299 region of Rx1 PspA were made from 5 other PspAs. All 5 of these fragments elicited significant protection against challenge with strain WU2. These data provide some suggestion for serologic differences in cross-protection elicited by the 192–299 region.

Based on present evidence, without wishing to be bound by any one particular theory, it is submitted that the PspAs in strains D39, Rx1 and R36A are identical. All of the 9 mice immunized with the 192–299 fragments from R36A and D39 survived challenge with WU2. Only LM100, one of the non-R36A/D39 PspAs, protected as high a percentage of mice from WU2. The difference in survival elicited by the R36A/D39 PspAs and the non-Rx1 related PspAs was statistically significant.

The data do indicate however, that all of the differences in protection against different strains are not due to differences in serologic cross-reactivity. BC100, which is made from Rx1, protected against death in 100% of the mice challenged with 7 different strains of *S. pneumonia*, but only delayed death with strain D39, which is thought to have the same PspA as strain Rx1. Thus, some of the differences in cross-protection are undoubtedly related to factors other than PspA cross-reactivity. Whether such factors are related to differences in virulence of the different strains in the hypersuceptible Xid mouse, or differences in requirements for epitopes N-terminal to amino acid 192, or difference in the role of PspA in different strains is not yet known.

These results suggest that a vaccine containing only the recombinant PspA fragments homologous with Rx1 amino acids 192–299 is effective against pneumococcal infection. Moreover, the results demonstrate that utility of PspA a.a. 192–299, a.a. 192–260 and DNA coding therefor, e.g. primers N192 or 588 (variants of LSM4 and LSM2) as useful for detecting the presence of pneumococciae by detecting presence of that which binds to the amino acid or to the DNA, or which is amplified by the DNA, e.g., by using that DNA as a hybridization probe, or as a PCR primer, or by using the amino acids in antibody-binding kits, assays or tests; and, the results demonstrate that a.a. 192–299 and a.a. 192–260 can be used to elicit antibodies for use in antibody-binding kits assays or tests.

TABLE 4

Protection of mice by immunization with BC100 from Rx1 PspA

| Challenge Strain* | Capsule type | PspA type | BC100 Immunogen | | | Controls | | | P Value§ |
| --- | --- | --- | --- | --- | --- | --- | --- | --- | --- |
| | | | # alive/ # dead | % Survival | Median days alive | # alive/ # dead | % Survival | Median days alive | |
| D39 | 2 | 25 | 0/5 | 0% | 5 | 0/3 | 0% | 2 | 0.02 |
| WU2 | 3 | 1 | 4/0 | 100% | >21 | 0/3 | 0% | 3 | 0.002 |
| ATCC6303 | 3 | 7 | 5/0 | 100% | >21 | 0/5 | 0% | 7 | 0.004 |
| A66 | 3 | 13 | 4/0 | 100% | >21 | 0/3 | 0% | 1 | 0.03 |
| EF10197 | 3 | 18 | 5/0 | 100% | >21 | 0/3 | 0% | 2 | 0.02 |
| EF5668 | 4 | 12 | 1/3 | 25% | 9 | 0/3 | 0% | 4 | N.S. |
| EF3296 | 4 | 20 | 1/3 | 25% | 5 | 0/3 | 0% | 3 | N.S. |
| L81905 | 4 | 23 | 1/4 | 20% | 4 | 0/6 | 0% | 2 | 0.02 |
| BG9739 | 4 | 26 | 0/4 | 0% | 6.5 | 0/3 | 0% | 2 | N.S. |
| DBL5 | 5 | 33 | 0/5 | 0% | 5 | 0/3 | 0% | 2 | 0.02 |
| BG7322 | 6 | 24 | 4/0 | 100% | >21 | 1/2 | 33.3% | 6 | 0.03 |
| EF6796 | 6A | 1 | 4/0 | 100% | >21 | 0/3 | 0% | 1 | 0.03 |
| DBL6A | 6A | 19 | 5/0 | 100% | >21 | 0/3 | 0% | 7 | 0.03 |

*Mice were challenged with approximately $10^3$ CFU/mL of each strain
§P values were based on comparison of days alive by a one-tailed Wilcoxon 2 sample-rank test

TABLE 5

Protection of mice by immunization with BAR416 from Rx1 PspA

| Challenge Strain* | Capsule type | PspA type | BAR416 Immunogen | | | Controls | | | P Value§ |
| --- | --- | --- | --- | --- | --- | --- | --- | --- | --- |
| | | | # alive/ # dead | % Survival | Median days alive | # alive/ # dead | % Survival | Median days alive | |
| WU2 | 3 | 1 | 4/1 | 80% | >21 | 0/3 | 0% | 1 | 0.002 |
| ATCC6303 | 3 | 7 | 2/3 | 40% | 13 | 1/5 | 20% | 4 | 0.048 |
| A66 | 3 | 13 | 5/0 | 100% | >21 | 0/5 | 0% | 2 | 0.004 |
| BG7322 | 6 | 24 | 3/2 | 60% | >21 | 0/4 | 0% | 7 | 0.02 |
| EF6796 | 6A | 1 | 3/2 | 60% | >21 | 0/5 | 0% | 5 | 0.004 |
| DBL6A | 6A | 19 | 0/5 | 0% | 7 | 0/5 | 0% | 2 | 0.008 |

Note,
mice were challenged with about $10^3$ CFU of each strain
§P values were based on comparison of days alive by a one-tailed Wilcoxon 2 sample-rank test

TABLE 6

Protection of mice against *S. pneumoniae* WU2 by immunization with BAR416 Analogs of 7PspAs

| Immunogen | Parent Strain | Capsule type | PspA type | # alive/ total # | % Survival | Median days alive | P value* vs. MBP |
| --- | --- | --- | --- | --- | --- | --- | --- |
| BAR36A | R36A | — | 25 | 4/4 | 100% | >21 | 0.002 |
| BAR39 | D39 | 2 | 25 | 5/5 | 100% | >21 | 0.0008 |
| BAR66 | A66 | 3 | 13 | 7/8 | 88% | >21 | <0.0001 |
| BAR9739 | BG9739 | 4 | 26 | 5/8 | 63% | >21 | 0.0002 |
| BARL5 | DBL5 | 5 | 33 | 4/8 | 50% | 21 | 0.03 |
| BAR6A | DBL6A | 6A | 19 | 3/5 | 60% | >21 | 0.05 |
| BAR100 | LM100 | 22 | ND | 5/5 | 100% | >21 | 0.008 |
| MBP | — | — | — | 0/8 | 0% | 2 | — |

*P values were based on comparison of days alive by a one-tailed Wilcoxon 2 sample-rank test
Note,
the PspA fragments used for immunization were cloned from products amplified with primers LSM4 and LSM6. In addition to the strains listed above, PCR reactions with LSM4 and LSM6 amplified products of the appropriate size from strains BG9163, WU2, L81905, EF6796, EF5668, BG7376, BG7322, and BG5-8A.

TABLE 7

Reactivity of MAbs with PspAs of Different Pneumococci

| Donor of test PspA | | | MAb mapping to 1–115 amino acids | | | | | MAb mapping to 192–260 amino acids | | | |
|---|---|---|---|---|---|---|---|---|---|---|---|
| Strain | Capsule Type | PspA Type | Xi126 IgG2b | XiR1224 IgM | XiR1526 IgG2b | XiR35 IgG2a | XiR16 IgG2a | XiR1323 IgM | Xi64 IgM | XiR278 IgG1 | XiR1325 IgG2a |
| Rx1 | rough | 25 | ++ | ++ | ++ | ++ | ++ | ++ | ++ | ++ | ++ |
| ATCC101813 | 3 | 3 | ++ | – | – | – | – | ++ | ++ | ++ | ++ |
| EF10197 | 3 | 18 | – | – | – | – | – | – | – | ++ | +/– |
| BG9739 | 4 | 26 | – | – | – | – | – | ++ | – | + | ++ |
| L81905 | 4 | 23 | – | – | – | – | – | – | – | – | – |
| BG-5-8A | 6A | 0 | +/– | + | – | – | – | + | – | + | – |
| BG9163 | B | 21 | – | – | – | – | – | – | – | + | – |
| LM100 | 22 | N.D. | +/– | – | – | – | – | – | – | – | – |
| WU2 | 3 | 1 | ++ | – | – | – | – | ++ | ++ | ++ | ++ |

Note,
immunoblot analysis was carried out with the nine MAbs from this study against a panel of nine different pneumococcal strains. Rx1 served as a positive control. The results are presented as ++ (strong reaction), + (weak, but clearly positive reaction), +/– (difficult to detect), and – (no reaction). The PspA of all strains gave a positive reaction with rabbit antiserum against PspA. N.D. means not determined. Mapping of epitopes was to fragments of strain Rx1 PspA Example 3

Isolation of PspA and Truncated Forms Thereof, and Immunization Thereby

PspA is attached to the pneumococcal surface through a choline binding site on PspA. This allows for successful procedures for the isolation of FL-PspA. PspA can be released from the surface of pneumococci by elution with 2 percent choline chloride (CC), or by growth in a chemically defined medium (CDM) containing 1.2 percent CC (CDM-CC) or medium in which the choline had been replaced by ethanolamine (CDM-ET). Since CDM-ET supernatants lack high concentrations of choline, the PspA released into them can be adsorbed to a choline (or choline analog) column and isolated by elution from the column with 2 percent choline chloride (CC).

This Example describes the ability to obtain PspA by these procedures, and the ability of PspA obtained by these procedures to elicit protection in mice against otherwise fatal pneumococcal sepsis. Native PspA from strains R36A, RX1, and WU2 was used because these strains have been used previously in studies of the ability of PspA to elicit protective immunity (See, e.g., Examples infra and supra). The first MAbs to PspA were made against PspA from strain R36A and the first cloned fragments of PspA and PspA mutants came from strain Rx1. Strain Rx1 was derived from strain R36A, which was in turn derived from the encapsulated type 2 strain, D39. PspAs from these three strains appears to be indentical based on serologic and molecular weight analysis. Molecular studies have shown no differences in the pspA genes of strains D39, Rx1, and R36A. The third strain that provided PspA in this Example is the mouse virulent capsular type 3 strain WU2. Its PspA is highly cross-reactive with that from R36A and Rx1, and immunization with Rx1 and D39 PspA can protect against otherwise fatal infections with strain WU2.

S. Pneumoniae

Strains of S. pneumoniae used in this study have been described previously (Table 8). Bacteria were grown in either Todd-Hewitt broth with 0.5 percent yeast extract (THY), or a chemically defined medium (CDM) described previously 32, 43. Serial passage of stock cultures was avoided. Strains were maintained frozen in THY+20 percent glycerol and cultured from a scraping of the frozen culture.

Recovery of PspA from Pneumococci

PspA is not found in the medium of growing pneumococci unless they have reached stationary phase and autolysis has commenced[36]. To release PspA from pneumococci three procedures were used. In one approach were grow pneumococci in 100 ml of THY and collect the cells by centrifugation at mid-log phase. The pellet was washed three times in lactated Ringer's solution (Abbot Lab. North Chicago, Ill.), suspended in a small volume of 2 percent choline chloride in phosphate buffered saline (PBS) (pH 7.0), incubated for 10 minutes at room temperature, and centrifuged to remove the whole pneumococci. From immunoblots with anti-PspA MAb Xi126[48] at serial dilutions of the original culture, the suspended pellet, and the supernatant, it was evident that this procedure released about half of the PspA originally present on the pneumococci. Analysis of silver stained polyacrylamide gels showed this supernatant to contain proteins in addition to PspA[36].

The CDM used in the remaining two procedures was modified from that of Van der Rijn[43]. For normal growth it contained 0.03% CC. To cause PspA to be released during bacterial growth, the pneumococci were grown in CDM containing 1.2 percent choline chloride (CDM-CC), or in CDM containing 0.03 percent ethanolamine and only 0.000, 001 percent choline (CDM-ET). In media lacking a normal concentration of choline the F-antigen and C-polysaccharide contain phosphoethanolamine rather than phosphocholine[49]. In CDM-CC and CDM-ET, PspA is released from the pneumococcal surface because of its inability to bind to the cholines in the lipoteichoic acids[36]. In addition to releasing PspA from the pneumococcal surface, growth in CDM-CC or CDM-ET facilitates PspA isolation by its other effects on the cell wall. In these media pneumococci do not autolyse[49], thus permitting them to be grown into stationary phase to maximize the yield of PspA. In these media septation does not occur and the pneumococci grow in long chains[36, 49]. As the pneumococci reach stationary phase they die, cease making PspA, and rapidly settle out. Preliminary studies, using serial dilution dot blots to quantitate PspA, indicated that the production of PspA ceases at about the time the pneumococci begin to settle out, with the formation of visible strands of the condensed pneumococcal chains. When the pneumococci began to settle out, the medium was recovered by centrifugation at 2900×g for 20 minutes, and filtered with a low protein-binding filler (0.45 g Nalgene Tissue Culture Filter #158–0045).

For growth in CDM-CC or CDM-ET, the pneumococci were first adapted to the defined medium and then, in the case of CDM-ET, to very low choline concentrations. To do this, strains were first inoculated into 1 part of THY and 9 parts of CDM medium containing 0.03 percent choline and 0.03 percent ethanolamine. After two subsequent subcultures in CDM containing 0.03 percent choline and 0.03 percent ethanolamine (0.1 ml of culture+0.9 ml of prewarmed fresh medium), the culture was used to inoculate CDM with only 0.003 percent choline (and 0.03 percent ethanolamine). These steps were repeated until the strain would grow in CDM-ET containing 0.000,001 percent choline arid 0.03 percent ethanolamine. It was critical that cultures be passed while in exponential growth phase (at about 107 CFU/ml). Even trace contamination of the medium by exogenous choline resulted in the failure of the PspA to be released from the pneumococcal surface[36]. Thus, disposable plastic ware was used for the preparation of CDM-ET media and for growth of cultures. Once a strain was adapted to CDM-ET it was frozen in 80 percent CDM-ET and 20 percent glycerol at −80° C. When grown subsequently the strain was inoculated directly into the CDM-ET.

Isolation of Native (Full-length) PspA

PspA was isolated from the medium of cells grown in CDM-ET using choline-Sepharose prepared by conjugating choline to epoxy-activated Sepharose[50]. A separate column was used for media from different strains to avoid cross-contamination of their different PspAs. For isolation of PspA from clarified CDM-ET, we used a 0.6ml bed volume of choline-Sepharose. The column bed was about 0.5 cm high and 1.4 cm in diameter. The flow rate during loading and washing was approximately 3 Ml/min. After loading 300 ml CDM-ET supernatant, the column was washed 10 times with 3 ml volumes of 50 mM Tris acetate buffer, pH 6.9 containing 0.25 M NaCl (TAB). The washed column was eluted with sequential 3 ml volumes of 2 percent CC in TAB. Protein eluted from the column was measured (Bio-Rad protein assay, Bio-Rad, Hercules, Calif.). The column was monitored by quantitative dot blot. The loading material, washes, and the eluted material were dot blotted (1 µl) as undiluted, ¼, ¹⁄₁₆, ¹⁄₆₄, ¹⁄₂₅₆, and ¹⁄₁₀₂₄ on nitrocellulose. The membranes were then blocked with 1 percent BSA in PBS, incubated for 1 hr with PspA-specific MAbs Xi126 or XiR278, and developed with biotinylated goat-anti-mouse Ig, alkaline phosphatase conjugated streptavidin (Southern Biotechnology Associates Inc. Birmingham, Ala.), and nitrobluetetrazolium substrate with 5-bromo 4-chloro-3-indoyl phosphate p-toluidine salt (Fisher Scientific, Norcross Ga.)[17]. The purity of eluted PspA was assessed by silver-stained (silver stain kit, Bio Rad, Hercules, Calif.) SDS-PAGE gels run as described previously[32]. Immunoblots of SDS-PAGE gels were developed with MAbs Xi126 and XiR278[17].

Isolation of 29 kDa PspA

The 29 kDa fragment comprising the N-terminal 260 amino acids of PspA was produced in DH1 *E. coli* from pJY4306[31, 37]. An overnight culture of JY4306 was grown in 100 ml of Luria Broth (LB) containing 50 µg/ml ampicillin. The culture was grown at 37° C. in a shaker at 225 rpm. This culture was used to inoculate 6 one liter cultures that were grown under the same conditions. When the culture O.D. at 600 nm reached 0.7, 12 grams of cells, as a wet paste, were harvested at 4° C. at 12,000×g. The pellet was washed in 10 volumes of 25 mM Tris pH 7.7 at 0° C. and suspended in 600 ml of 20% sucrose, 25 MM Tris pH 7.7 with 10 mM ethylenediamine tetraacetic acid (EDTA) for 10 minutes. The cells were pelleted by centrifugation (8000×g) and rapidly suspended in 900 ml of 1 percent sucrose with 1 mM Pefabloc SC hydrochloride (Boehringer Mannheim Corp., Indianapolis, Ind.) at 0° C. The suspension was pelleted at 8000×g at 4° C. for 15 minutes and the PspA-containing supernatant (periplasmic extract)[51] recovered. The recombinant PspA was precipitated from the periplasmic extract by 70 percent saturated ammonium sulfate overnight at 4° C. The precipitated material was collected by centrifugation at 12,000×g at 4° C. for 30 minutes. The precipitated protein was resuspended in 35 ml of 20 mM histidine 1 percent sucrose at pH 6.6 (HSB). Insoluble materials were removed at 1,000×g at 4° C. for 10 minutes. The clarified material was dialyzed versus HSB, passed through a 0.2 µm filter and further purified on a 1 ml MonoQ HR 5/5 column (Pharmacia Biotech, Inc., Piscataway, N.J.) equilibrated with HSB. The clarified material was loaded on the column at 1 Ml/min and the column was washed with 10 column volumes of HSB. The column was then eluted with a gradient change to 5 mM NaCl per minute at a flow rate of 1 ml/min. As detected by immuno blot with Xi126, SDS-PAGE and absorbance, PspA eluted as a single peak at approximately 0.27 to 0.30 M NaCl. By SDS-PAGE the material was approximately 90 percent pure. The yield from 6 liters of culture was 2 mg (Bio-Rad protein assay) of recombinant PspA.

Growth of Pneumococci for Challenge

Mice were challenged with log-phase pneumococci grown in THY. For challenge, the pneumococci were diluted directly into lactated Ringer's without prior washing or centrifugation. To inject the desired numbers of pneumococci, their concentration in lactated Ringer's solution was adjusted to an O.D. of about 0.2 at 420 nM (LKB Ultrospec III spectrophotometer). The number of pneumococci present was calculated at $5 \times 10^8$ CFU per ml/O.D. and confirmed by colony counts (on blood agar) of serial dilutions of the inoculum.

Immunization, Challenge, and Bleeding of Mice

CBA/CAHN/XID/J (CBA/N) and BALB/cByJ (BALB/c) mice were purchased from Jackson Laboratory Bar Harbor, Me. Mice were given two injections two weeks apart and challenged i.v. two weeks later. Injections without CFA were given intrapertioneally in a 0.1 ml of Ringers. Where indicated, the first injection was given in complete Freund's adjuvant (CFA) consisting of approximately a 1:1 emulsion of antigen solution and CFA oil (Difco, Detroit Mich.). Antigen in CFA was injected inguinally in 0.2 ml divided between the two hind legs. All mice were boosted i.p. without adjuvant. When mice were injected with media supernatants or 2 percent choline chloride eluates of whole bacteria, the amounts of material injected were expressed as the volume of media from which the injected material was derived. For example, if the clarified medium from pneumococci grown in CDM-CC or CDM-ET was used for immunization without dilution or concentration, the dose was described as 100 µl. If the material was first diluted ¹⁄₁₀, or concentrated 10 fold, the dose was referred to as 10 or 1000 µl respectively.

ELISA for Antibodies to PspA

Specific modifications of previously reported ELISA conditions are described. Microtitration plates (Nunc Maxisorp, P.G.C. Scientific, Gaithersburg Md.) were coated with undiluted supernatants of Rx1 and WG44.1 pneumococci grown in CDM-ET or 1 percent BSA in PBS. Mice were bled retro-orbitally (75 μl) in a heparanized capillary tube (Fisher Scientific, Fair Lawn, N.J.) The blood was immediately diluted in 0.5 ml of one percent bovine serum albumin in PBS. The dilution of the resultant sera was 1/15 based on an average hematocrit of 47 percent. The sera were diluted in 7 three fold dilution in microtitration wells starting at 1/45. Mab Xi126 was used as a positive control. The maximum reproducible O.D. observed with Xil 126 was defined as "maximum O.D." The O.D. observed in the absence of immune sera or MAb was defined as "minimum O.D." Antibody titers were defined as the dilution that gives 33 percent of maximum O.D. The binding to the Rx1 CDM-ET coated plates was shown to be PspA-specific, since in no case did we observe ≧33 percent of maximum binding of immune sera or Xi 126 on plates coated with WG44.1 CDM-ET or BSA.

Statistical Analysis.

Unless otherwise indicated P values refer to comparisons using the Wilcoxin two-sample rank test to compare the numbers of days to death in different groups. Mice alive at 21 days were assigned a value of 22 for the sake of calculation. P values of >0.05 have been regarded as not significant. Since we have never observed immunization with PspA or other antigens to make pneumococci more susceptible to infection the P values have been calculated as single tailed tests. To determine what the P value would have been if a two tailed test had been used the values given should be multiplied by two. In some cases P values were given for comparisons of alive versus dead. These were always calculated using the Fisher exact test. All statistical calculations were carried out on a Macintosh computer using InStat (San Diego, Calif.).

PspA is the major protection-eliciting component released from pneumococci grown in CDM-ET or CDM-CC, or released from conventionally grown pneumococci by elution with 2% CC.

PspA-containing preparations from pneumococci were able to protect mice from fatal sepsis following i.v. challenge with $3 \times 10^3$ ($100 \times LD_{50}$) capsular type 3 *S. pneumoniae* (Table 9). Comparable preparations from the strains unable to make PspA (WG44.1 and JY1119), or unable to make full length PspA (LM 134 and JY2141) were unable to elicit protection. Regardless of the method of isolation the minimum protective dose was derived from pneumococci grown in from 10–30 μl of medium. We also observed 9 that supernatants of log phase pneumococci grown in normal THY or CDM media could not elicit protection (data not shown). This finding is consistent with earlier studies[36, 37] indicating the PspA is not normally released in quantity into the medium of growing pneumococci.

Isolated PspA can Elicit Protection Against Fatal Infection

Although PspA was necessary for these preparations to elicit protection it was possible that it did not act alone. Mice were thus, immunized with purified FL-PspA to address this question.

Isolation of FL-PspA from CDM-ET growth medium. We isolated the FL-PspA from CDM-ET rather than from CDM-CC medium or a 2 percent choline chloride elution of live cells, because the high levels of choline present in the latter solutions prevents adsorption of the PspA to the choline residues on the choline-Sepharose column. PspA for immunization was isolated from strain R36A, as the strain is non-encapsulated and the isolated PspA could not be contaminated with capsular polysaccharide. As a control we have conducted mock isolations from WG44.1 since this strain has an inactivated pspA gene and produces no PspA. The results shown in Table 10 are typical of isolations from 300 ml of CDM-ET medium from R36A grown pneumococci. We isolated 84 μg of PspA from 300 ml of medium, or about 280 μg/liter. Based on the dot blot results this appears to be about 75% of the PspA in the original medium, and that CDM-ET from R36A cultures contains about 400 μg/liter of PspA, or about 0.4 μg/ml.

Figure 3:
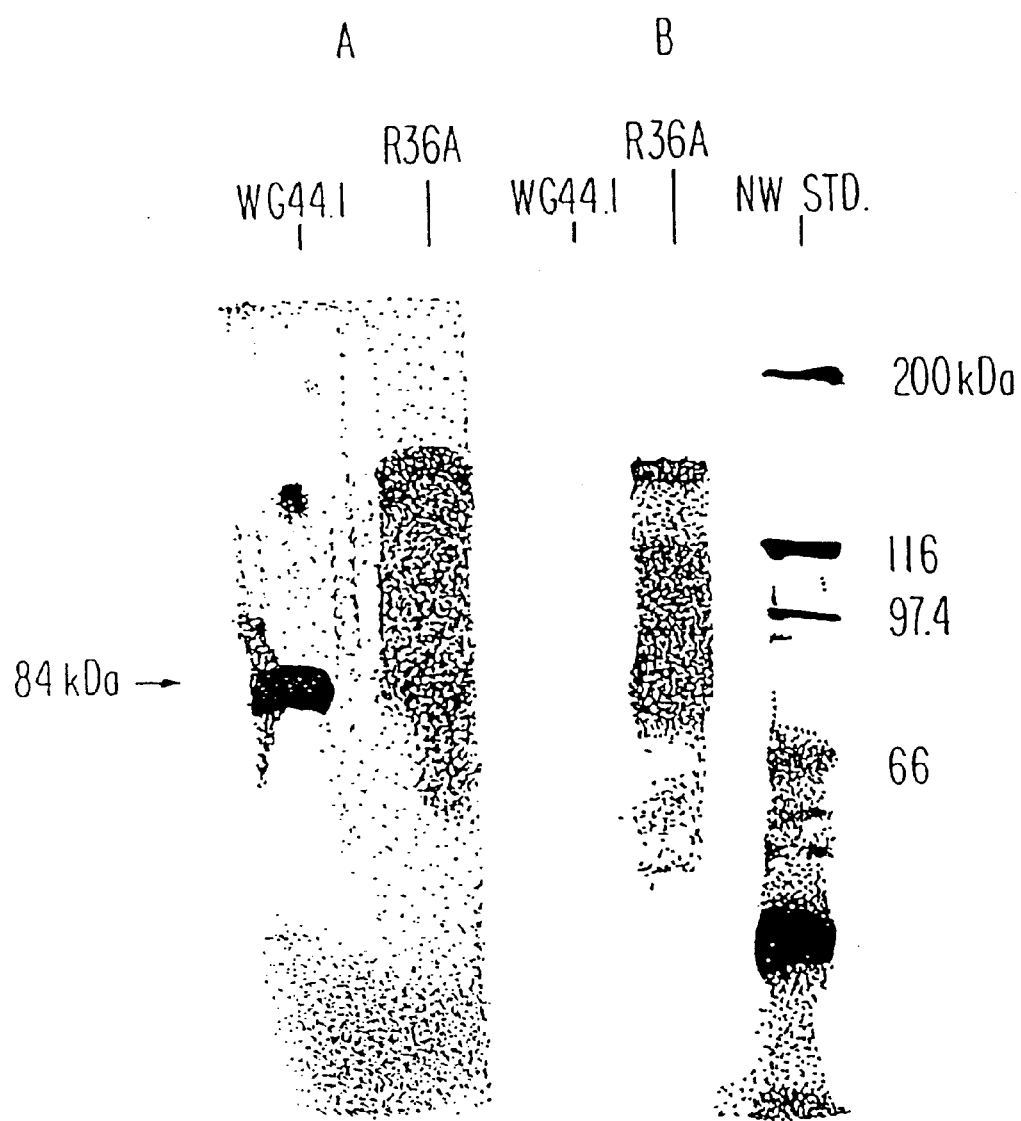
FIG. 3 shows: SDS-PAGE of R36A PspA (80 ng) column isolated from CDM-ET and an equal volume of an equivalent WG44.1 prep. Identical gels are shown stained with Bio-Rad silver kit(A) or immunoblotted with PspA MAb XiR278(B). The PspA isolated from R36A shows the characteristic monomer (84 kDa) and dimer bands.

No serologically detectable PspA was seen in the CDM-ET from WG44.1 cultures. More significantly there was undetectable protein recovered from the choline-Sepharose column after adsorption of CDM-ET from a WG44.1 culture, indicating that PspA is the only protein that could be isolated by this procedure. Moreover by silver stained SDS PAGE gel the PspA isolated from R36A appeared to be homogenous (FIG. 3). Although autolysin can also be isolated on choline-Sepharose 20, 50, we did not expect it to be isolated by this procedure since autolysin is not released from pneumococci grown in choline deficient medium [36]. The immunologic purity of the isolated PspA was emphasized by the fact that immunization with it did not elicit any antibodies detectable on plates coated with CDM-ET supernatants of WG44.1.

Loading more than 300 ml on the 0.6 ml bed volume column did not result in an increased yield, which suggested that the column capacity had been reached. However, increasing the depth of the choline-Sepharose bed to greater than 0.5 cm, decreased the amount of PspA eluted from the column, presumably because of non-specific trapping of aggregates in the column matrix. The elution buffer contains 50 mM Tris acetate 0.25 M NaCl and 2% choline chloride. Elution without added NaCl or with 1M NaCl resulted in lower yields. Elution with less than 1% CC also reduced yields.

Immunization of mice with purified R36A PspA. For immunization we used only the first 3 ml fraction of the R36A column. Mice were immunized with two injections of 1, 0.1, or 0.0 1 μg of R36A PspA, spaced two weeks apart. As controls, some mice were inoculated with a comparable dilutions of the first 3 ml fraction from the WG44.1 column. Purified FL-PspA elicited antibody to PspA at all doses regardless of whether CFA was used as an adjuvant (Table 11). In the absence of CFA the highest levels of antibody were seen with the 1 μg dose of PspA. In the presence of CFA, however, the 0.1 μg dose was as inunuogenic as the 1 μg dose.

To test the ability of the different doses of PspA to elicit protection against challenge we infected the immunized mice with two capsular type 3 strains, WU2 and A66. Although both of these strains are able to kill highly susceptible CBA/N X1D Mice at challenge doses of less than $10^2$, the A66 strain is several logs more virulent when BALB/c mice are used 47, 52. The difference in virulence of A66 and WU2, was partially compensated for by challenging the immunized CBA/N mice with lower doses of strain A66 than WU2.

After immunization of CBA/N Mice with 1 and 0.1 μg doses of PspA we observed protection against WU2 challenge regardless of whether or not CFA was used as an adjuvant (Table 4). At the lowest dose, 0.01 μg PspA, most of the mice immunized with PspA+CFA lived whereas most immunized with PspA alone did not; however, the difference was not statistically significant. When immunized mice were challenged with the more virulent strain A66[47, 53], survivors were only observed among mice immunized with the 1 and 0.1 μg doses. There was slightly, more protection against fatal A66 infection among mice immunized with CFA than without, but the difference was not statistically significant.

When the two sample rank test was used to analyze the time to death of mice infected with A66 we observed a statistically significant delay in the time to death in each immunized group as compared to the pooled controls.

The 29 kDa N-terminal Fragment of PspA Can Elicit Protection Against Infection when Injected with CFA We have compared the immunogenicity, with and without CFA, of an isolated 29 kDa fragment composed of the first 260 amino acids of PspA. Unlike the case with FL-PspA, adjuvant was required for the 29 kDa fragment to elicit a protective response. This was observed even though the immunizing doses of the 29 kDa antigen used were 10 and 30 μg/mouse, or about 100 and 300 times the minimum dose of FL-PspA that can elicit protection in the absence of adjuvant.

Injection with CFA Revealed the Presence of Additional Protection Eliciting Antigen(s) in CDM-CC, and CDM-ET Growth Medium but not in the 2 Percent Choline Chloride Eluates of Live Cells The observation that Freund's adjuvant could have such a major effect on the immunogenicity of the 29 kDa fragment (Table 12), prompted us to reexamine the immunogens described in Table 2 to determine if immunization with adjuvant might enhance protection elicited by PspA-containing preparations or provide evidence for protection eliciting antigens in addition to PspA. By using CFA with the primary injection, the dose of PspA-containing growth medium (CDM-CC and CDM-ET) required to elicit protection was reduced from 10–30 μl (Table 9) down to 1 to 3 μl (Table 13). When CFA was used as an adjuvant with CDM-CC and CDM-ET from PspA- strains WG44.1 and JY 1119 we were able to elicit protective immune responses if material from $\geq 100$ μl or more of media were injected. Thus, although there were apparently some protection eliciting components other than PspA in CDC-CC and CDM-ET growth media, PspA remained the major protection eliciting component even in the presence of adjuvant.

One of the media used for injection was CDM-ET in which JY2141 had been grown. This medium elicited protection against WU2 challenge even when injected at doses as low as 1 μl. It should be noted that although this strain does not make full-length PspA, it secretes a truncated molecule comprising the first 115 amino acids of PspA into the growth medium. Thus, unlike CDM-ET from WG44.1 and JY 1119, CDM-ET from JY2141 has the potential to elicit PspA-specific immunity. In contrast to these results, the material eluted from JY2141 with 2 percent CC was relatively non-immunogenic even when emulsified with CFA. This result is consistent with the fact that the 115 amino acid N-terminal PspA fragment of JY2141 is not surface attached[37], and would be expected to be washed away prior to the elution with 2 percent CC.

Extension of Studies to BALB/c Mice and i.p. Challenge Route

The studies above all involve i.v. challenge of CBA/N mice expressing with the XID genetic defect. The i.v. route, used in the present studies provides a relevant model for bacteremia and sepsis, but pneumococci have higher $LD_{50s}$ when injected i.v. than i.p. CBA/N mice are hypersusceptible to pneumococcal infection because of the XID defect. This genctic defect prevents them from having circulating naturally occurring antibody to phosphocholine. The absence of these antibodies has been shown to make XID mice several logs more susceptible to pneumococci than isogenic mice lacking the immune defect. From the data in Table 14 it is clear, however, that immunization with PspA can protect against infection in mice lacking the XID defect even when the challenge is by the i.p. route. Thus, there is no reason to suspect that the results presented are necessarily dependent on the use of the CBA/N XID mouse or the i.v. route.

PspA is Highly Immunogenic

These studies provide the first quantitative data on the amount of purified FL-PspA that is required to elicit protective immunity in mice. The isolated PspA for these studies was obtained by taking advantage of the fact that the C-terminal half of PspA binds to cell surface choline 36. The isolated FL-PspA was found to be highly immunogenic in the mouse. Only two injections of 100 ng of PspA in the absence of adjuvant were required to elicit protection against otherwise fatal sepsis with greater than 100 $LD_{50}$ of capsular type 3 S. pneumoniae. When the first injection was given with adjuvant, doses as small as 10 ng could elicit protective response. The potent immunogenicity of PspA, and the ability to isolate it on choline-Sepharose columns provides a demonstration for the possible use of PspA as a vaccine in humans.

A large body of published [17, 29, 37] as well as unpublished evidence indicates that the major protection eliciting epitopes of PspA are located in the α-helical (N-terminal) half of the molecule. From the present studies, it is clear that immunization with N-terminal fragments containing the first 115 or 260 of the 288 amino acid a-helical region are able to elicit protection when given with CFA. However, these fragments were not able to elicit protective responses without CFA. In the case of the both the 115 and 260 amino acid fragments, even immunization at 100 times the minimum dose that is immunogenic for FL-PspA failed to elicit a protective response. This result is consistent with previous results showing that a fragment composed of the N-terminal 245 amino acids[31, 37] could elicit protection against otherwise fatal pneumococcal infection of mice when the immunization was given with CFA[32]. In that study no immunization without CFA was attempted. Even though the C-terminal half of PspA may not contain major protection-eliciting epitopes it appears to contain sequence important in the immunogenicity of the molecule as a whole, since the full length molecule elicited much greater protection than the N-terminal fragments. The effect of the C terminal half on antigenicity may be in part that it doubles the size of the immunogen. Molecules containing the C-terminal half of PspA may also be especially immunogenic because they exhibit more extensive aggregation than is seen with fragments expressing only the α-helical region[38]. Protein aggregates are known to generally be more antigenic and less tolerogenic than individual free molecules[54].

PspA is the Major Protection Eliciting Component of our Pneumococcal Extracts

Evidence that PspA is the major protection eliciting component of the CDM-ET, CDM-CC growth media and the two percent CC eluates was dependent on the use of mutant pneumococci that lacked the ability to produce FL-PspA. More than one pspA mutant strain was used to insure that the failure to elicit protection in the absence of FL-PspA was not a spurious result of non-PspA mutation blocking the production of some other antigen. Strains WG44.1 and JY1119 contain identical deletions that include the 5' end of the pspA genes and extend about 3 kb upstream of pspA[37]. WG44.1 is a mutant of the non-encapsulated strain Rx1 and JY1119 was made by transforming capsular type 3 strain WU2 with the WG44.1 pspA mutation. In no case were preparations from WG44.1 and JY1119 as efficient at eliciting protection as those from the PspA⁺ strains. To rule out the possibility that protection elicited by preparations from the PspA⁺ strains was elicited by some non-PspA molecule also encoded by a 3 kb deletion linked to the mutant pspA genes of WG44.1 and JY1119, we also used strains JY2141 and LM34[26, 37]. In these strains the Rx1 pspA gene has been insertionally inactivated causing the production of N-terminal fragments of 115 and 245 amino acids respectively. These strains have no other known mutations. Although Rx1 and R36A are closely related non-encapsulated strains, some of the studies included Rx1 as the PspA+ control since it is the isogenic partner to WG44.1, LM34, and JY2141. The N terminal fragments produced by JY2141 and LM34 lack the surface anchor and are secreted into the medium[36]. Two percent CC eluates of JY2141 were non-protection eliciting even in the presence of adjuvant. In the absence of adjuvant, CDM-ET from JY2141 was not protection-eliciting. LM34 was tested without CFA in only 3 mice, but gave results consistent with those obtained with JY2141.

Anticapsular antibodies are known to be protective against pneumococcal infection[5, 19]. However, in these studies it is unlikely that they account for any of the protection we attributed to PspA. Our challenge strain bore the type 3 capsular polysaccharide and our primary source of PspA was strain R36A, which is a spontaneous non-encapsulated mutant of a capsular type 2 strain[39, 41]. The R36A strain has been recently demonstrated to lack detectable type 3 capsule on the surface or in its cytoplasm[55]. Furthermore, the CBA/N mice used in most of the studies are unable to make antibody responses to capsular type 3 polysaccharide[56].

Non-PspA Protection Eliciting Components

The observation that CDM-CC and CDM-ET supernatants of WG44.1 could elicit protection when injected in large amounts with adjuvant, suggested that these supernatants contained at least trace amounts of non-PspA protection eliciting molecules. In the case of preparations containing PspA eluted from the surface of live washed pneumococci with 2 percent CC, there was no evidence for any protection eliciting components other than PspA, presumably because the protection-eliciting non-PspA proteins released into the media were removed by the previous washing step. The identity of the protection eliciting molecules in the WG44.1 supernatant are unknown. In this regard, it is of interest that unlike R36A, strain Rx1 has been shown to contain a very small amount of cytoplasmic type 3 polysaccharide (but totally lacks surface type 3 polysaccharide[55]). This difference from Rx1 apparently came about through genetic manipulations in the construction of Rx1 from R36A[39, 41], Thus, preparations made from Rx1 or from its daughter strains WG44.1, LM34, or JY2141 could potentially contain small amounts of capsular polysaccharide. For a number of reasons however, it seems very unlikely that the non-PspA protection-eliciting material identified in these studies was type 3 capsular polysaccharide (expressed by the WU2 challenge strain: 1) growth of these strains was either in CDM-CC or CDM-ET, each of which prevent autolysin activity and lysis[57] that would be required to release the small amount of type 3 polysaccha ride from the cytoplasm of the Rx1 family of strains; 2) CBA/N mice made protective responses to the non-PspA antigens, but express the XID immune response deficiency which permits responses to proteins, but blocks antibody to most polysaccharides[46], including type 3 capsular polysaccharide[56]; and 3) immunogenicity of the non-PspA component required CFA, an adjuvant known to stimulate T-dependent (protein) rather than T-independent (polysaccharide) antibody responses.

A number of non-PspA protection eliciting pneumococcal proteins have been identified: pneumolysin, autolysin, neuraminidase, and PsaA which are 52, 36.5, 107 and 37 kDa respectively[21, 58, 59, 60]. The non-PspA protection eliciting components reported here could be composed of a mixture of these and/or other non-identified proteins. Attempts to identify lambda clones producing non-PspA protection eliciting proteins as efficacious as PspA have not been successful[25].

Isolation of PspA

The protective capacity of the CDM-CC, CDM-ET and material eluted from live cells with 2% CC were similar in terms of the volume of the original culture from which the injected dose was derived. The major advantage of eluting the PspA from the surface of pneumococci with 2 percent CC is that the pneumococci may be grown in any standard growth medium, and do not have to be first adapted to a defined medium. Moreover, concentration of PspA can be accomplished by centrifugation of the pneumococci prior to the elution of the PspA. An advantage of using either CDM-CC and CDM-ET media was that these media prevented lysis and pneumococci could be grown into stationary phase without contaminating the preparations with cytoplasmic contents and membrane and wall components. A particular advantage of CDM-ET growth medium is that since it lacks high concentrations of choline the PspA contained in it can be adsorbed directly to a choline-Sepharose column for affinity purification.

One liter of CDM-ET growth medium contains about 400 μg of PspA, and we were able to isolate about ¾ of it to very high purity. At 0.1 μg/dose, a liter of CDM-ET contains enough PspA to immunize about 4,000 mice; or possibly 40–400 humans. Our present batch size for a single column run is only 300 ml of CDM-ET. This could presumably be increased by increasing the amount of the adsorbent surface by increasing the diameter of the column. Using our present running buffer we have found that a choline-Sepharose resin depth of 0.5 cm was optimal; increases beyond 0.5 cm caused the overall yield to decrease rather than increase, even in the presence of larger loading volumes of R36A CDM-ET

TABLE 8

Pneumococcal Strains

| Strain | Capsule type | PspA expressed | Parent strain | Construction technique | References |
|---|---|---|---|---|---|
| D39 | 2 | full length | — | clinical isolate | 26, 44 |
| R36A | non-encapsulated | full length | D39 | non-encapsulated mutant | 23, 44, 45 |
| Rx1 | non-encapsulated | full length | R36A | derived from R36A | 26, 39, 41 |
| WG-44.1 | non-encapsulated | none | Rx1 | aberrant insertion inactivation with pKSD300 | 26, 37 |

TABLE 8-continued

Pneumococcal Strains

| Strain | Capsule type | PspA expressed | Parent strain | Construction technique | References |
|---|---|---|---|---|---|
| LM34 | non-encapsulated | aa 1–245 of Rx1[a] | Rx1 | insertional inactivation with pKSD300 | 26, 37, 42 |
| JY2141 | non-encapsulated | aa 1–115 of Rx1[a] | Rx1 | insertional inactivation with pJY4208 | 37 |
| WU2 | 3 | full length | — | clinical isolate | 25, 46 |
| JY1119 | 3 | none | WU2 | transformation with WG44.1 DNA | 37 |
| A66 | 3 | full length | — | clinical isolate | 44, 47 |

[a]LM35 and LY2141 express fragments containing the first 245 and first 115 amino acids of Rx1 PspA respectively.

TABLE 9

PspA is the major protection-eliciting component in antigen preparations made by three different methods

| Preparation | Strain (PspA status) | Dose as volume of media in μl[a] | Median Days Alive | Alive: Dead | P versus controls[b] |
|---|---|---|---|---|---|
| 2% CC eluate from live cells | R36A (PspA+) | 1000 | >21 | 2:0 | |
| | | 200 | >21 | 2:0 | |
| | | 20 | >21 | 2:0 | |
| | | 2 | 1.5 | 0:2 | |
| | all R36A | >21 | | 6:2 | 0.03 |
| | JY2141 (aa 1-115) | 1000 | 3, >21 | 1:1 | |
| | | 200 | 1 | 0:2 | |
| | | 20 | 1 | 0:2 | |
| CDM-CC | Rx1 | 100 | >21 | 9:0 | <0.0001 |
| clarified medium | (PspA+) | 30 | >21 | 2:1 | |
| | | 10 | 2 | 1:2 | |
| | | 3 | 2 | 0:3 | |
| | | ALL | 2, >21 | 12:6 | 0.0004 |
| | LM34 | 100 | 2, 2, >21 | 1:2 | |
| | WG44.1 (PspA−) | 100 | 2 | 0:9 | |
| | | 30 | 2 | 0:3 | |
| | | 10 | 2 | 0:3 | |
| | | 4 | 2 | 0:3 | |
| | WU2 (PspA+) | 1000 | >21 | 3:0 | 0.05 |
| | | 100 | >21 | 1:0 | |
| | | ALL | >21 | 4:0 | 0.03 |
| | JY1119 (PspA−) | 1000 | 4 | 0:3 | |
| | CDM-CC | 100 | 2 | 0:2 | |
| CDM-ET clarified medium | R36A (PspA+) | 100 | >21 | 8:0 | <0.0001 |
| | | 10 | 3, >21 | 5:5 | 0.004 |
| | | 1 | 1.5 | 3:5 | |
| | | 0.1 | 2 | 0:2 | |
| | | ALL | >21 | 16:12 | 0.006 |
| | JY2141 (aa 1-115) | 100 | 1.5 | 0:2 | |
| | | 10 | 1.5 | 0:2 | |
| | WG44.1 (PspA−) | 100 | 3 | 0:2 | |
| | | 10 | 1.5 | 0:2 | |
| None | — | | 2 | 0:14 | — |

[a]Antigen dose is given as the volume of growth media from which the 0.1 ml of injected material was derived. Each mouse was injected twice i.p. with the indicated dose diluted as necessary in lactated Ringer's injection solution.
[b]Controls used for statistical comparisons: 2% CC, all JY2141; CDM-CC Rx1, all WG44.1; CDM-CC WU2, JY1119; CDM-ET, all WG44.1 + all JY2141.

TABLE 10

Isolation of PspA from 300 ml of CDM-ET media after the growth of R36A or WG44.1 pneumococci[a]

| | R36A | | | | WG44.1 | | |
|---|---|---|---|---|---|---|---|
| fraction | μg protein/ml | total μg protein[b] | max. reciprocal dot blot[c] | total dot blot units[b,d] | μg protein per/ml | total μg protein[b] | max. reciprocal dot blot[c] |
| growth media | 13.3 | 3,990 | 4 | 1200 | 13.7 | 4,110 | <1 |
| fall-through | 13.6 | 4,080 | 1 | 300 | 13.5 | 4,050 | <1 |
| 1st wash | | | <1 | | | | <1 |
| 10th wash | | | <1 | | | | <1 |
| elution #1 | 26 | 78 | 256 | 770 | <1 | — | <1 |
| elution #2 | 2 | 6 | 16 | 48 | <1 | — | <1 |
| elution #3 | <1 | — | 4 | 12 | <1 | — | <1 |
| total eluted | | 84 | | 830 | | — | <1 |

[a]The columns were loaded with 300 ml of clarified CDM-ET medium after the growth of R36A or WG44.1. The column was washed with 10 sequential 3 ml fractions of TBA. Elution was with TBA plus 2 percent CC.
[b]Total μg protein or total dot blot units reflect the total protein in the 300 ml of the loading material or the 3 ml size of the eluted fractions.
[c]MAb XiR278 was used in the immunoblots to detect PspA in the dot blots.
[d]Dot blot units were calculated as the reciprocal dot blot titer times the volume in ml.

TABLE 11

Purified full-length PspA is able to elicit protection against fatal sepsis in mice.

| Antigen | Dose[a] | Adjuvant or Diluent | Anti-PspA titer[b] (Log mean ± S.E.) | Challenge with $10^{5.1}$ WU2 | | | Challenge with $10^{4.2}$ A66 | | |
|---|---|---|---|---|---|---|---|---|---|
| | | | | Alive: Dead | Median Days Alive | P vs. pooled control[c] | Alive: Dead | Median Days Alive | P vs. pooled controls[c] |
| R36A | 1 μg | Ringer's | 3.3 ± 0.2 | 5:0 | >21 | 0.015 | 2:3 | 4 | 0.002 |
| (PspA+) | 0.1 | Ringer's | 2.6 ± 0.2 | 4:0 | >21 | 0.041 | 1:4 | 4 | 0.0032 |
| | 0.01 | Ringer's | 2.7 ± 0.2 | 1:4 | 4 | n.s. | 0:5 | 3 | 0.0058 |
| | 1 μg | CFA | 3.5 ± 0.2 | 5:0 | >21 | 0.027 | 3:2 | >21 | 0.0012 |
| | 0.1 | CFA | 3.6 ± 0.1 | 4:1 | >21 | 0.015 | 0:5 | 3 | 0.0058 |
| | 0.01 | CFA | 3.1 ± 0.2 | 4:1 | >21 | 0.015 | 0:5 | 3 | 0.0058 |
| WG44.1 | 3600 μml | Ringer's | <1.6 | n.d. | n.d. | | 1:4 | 3 | n.s. |
| (PspA−) | 360 | Ringer's | <1.6 | n.d. | n.d. | | 0:5 | 2 | n.s. |
| | 36 | Ringer's | <1.6 | n.d. | n.d. | | 0:5 | 2 | n.s. |
| | 3600 μl | CFA | <1.6 | n.d. | n.d. | | 0:5 | 2 | n.s. |
| | 360 | CFA | <1.6 | n.d. | n.d. | | 1:4 | 2 | n.s. |
| | 36 | CFA | <1.6 | n.d. | n.d. | | 0:5 | 2 | n.s. |
| saline | — | CFA | <1.6 | 1:5 | 4 | — | n.d. | n.d. | — |
| pooled controls | | | <1.6 | 1:5 | 4 | | 2:28 | 2 | — |

[a]For comparison with the data in Table 2, it should be noted that the 1, 0.1, and 0.01 μg doses were derived from 3600, 360 and 36 μl of R36A growth media. Equivalent dilutions of the PspA− eluate from strain WG44.1 were injected as controls. The amount of the WG44.1 preparation injected is listed as 3600, 360, and 36 μl and corresponds to the volume original growth medium from which the doses of WG44.1 was prepared.
[b]Antibody values were expressed as reciprocal ELISA titer.
[c]P values calculated by the Wilcoxon two sample rank test. By Kruskal-Wallis nonparametric ANOVA for the WU2 challenge was significant at P = 0.01, for A66 significance was at P < 0.0001.

TABLE 12

The 29 kDa N-terminal fragment of Rx1 PspA must be injected with adjuvant to elicit protection agaist WU2[a]

| μg 29 kDa PspA | Adjuvant or diluent | Median Days Alive | Alive:Dead | P versus none[b] |
|---|---|---|---|---|
| 30 | CFA | >21 | 3:0 | 0.0006 |
| 3 | CFA | >21 | 3:0 | |
| 30 | Ringer's | 2 | 0:3 | |
| 3 | Ringer's | 2 | 1:2 | |
| none | CFA | 2 | 0:7 | |
| none | Ringer's | 2 | 0:7 | |

[a]The 29 kDa fragment comprises the first 260 amino acids of PspA.
[b]For the calculation of P values the 30 μg and 3 μg data were pooled; mice immunized with PspA + CFA were compared to CFA controls; mice immunized with PspA + Ringer's were compared to controls immunized with Ringer's. Only the statistically significant P values are shown. The calculated P value of PspA + CFA versus CFA alone, was 0.0006 by both the Wilcoxon two sample rank test and the Fisher exact test.

TABLE 13

PspA is not the only protection elicting molecule released from pneumococci by interference with binding to choline on the surface of pneumococci

| Preparation | Strain (PspA status) | Dose (as volume in μl) | Median Day Alive | Alive: Dead | P values[a] |
|---|---|---|---|---|---|
| 2% CC eluate from live cells | R36A (PspA+) | 1000 | >21 | 2:0 | P vs. all JY2141 |
| | | 200 | >21 | 5:0 | 0.02 |
| | | 20 | >21 | 5:0 | 0.02 |
| | | 2 | >21 | 5:0 | 0.02 |
| | all R36A | | >21 | 17:0 | 0.001 |
| | JY2141 (aa 1–115) | 1000 | >21 | 2:0 | |
| | | 200 | 1 | 0:2 | |
| | | 20 | 1 | 0:2 | |
| | | 2 | 1 | 0:2 | |
| | all JY2141 | | 1 | 2:6 | |
| | | | | | P versus pooled cont. |
| CDM-CC clarified medium + CFA | Rx1 (PspA+) | 1000 | >21 | 3:0 | 0.002 |
| | | 100 | >21 | 3:0 | 0.002 |
| | WU2 (PspA+) | 1000 | >21 | 3:0 | 0.002 |
| | | 100 | >21 | 3:0 | 0.002 |
| | | 3 | >21 | 3:0 | 0.002 |
| | WG44.1 (PspA−) | 1000 | >21 | 5:1 | <0.0001 |
| | | 100 | 2.5 | 2:4 | 0.002 |
| | JY1119 (PspA−) | 1000 | >21 | 3:0 | 0.002 |
| | | 100 | >21 | 3:0 | 0.002 |
| CDM-ET clarified medium + CFA | R36A (PspA+) | 1000 | >21 | 3:1 | 0.004 |
| | | 10 | >21 | 4:0 | 0.004 |
| | | 1 | >21 | 3:1 | 0.004 |
| | | 0.2 | 2 | 0:4 | |
| | JY2141 (aa 1–115) | 10 | >21 | 2:0 | |
| | | 1 | >21 | 2:0 | |
| | all JY2141 | — | >21 | 4:0 | 0.004 |
| | WG44.1 (PspA−) | 100 | >21 | 2:0 | |
| | | 10 | 2 | 0:2 | |
| CDM-ET only | + CFA | | 2 | 0:9 | |
| None | none | | 1.5 | 0:4 | |
| Pooled Controls[b] | | | 2 | 0:13 | |

TABLE 13-continued

PspA is not the only protection eliciting molecule released
from pneumococci by interference with binding to choline on the
surface of pneumococci

| Preparation | Strain (PspA status) | Dose (as volume in μl) | Median Day Alive | Alive: Dead | P values[a] |
|---|---|---|---|---|---|

[a]In cases where there were not statistically significant results no P value was shown.
[b]"Pooled Controls" refers to "CDM-ET only" Data and "None" data.

TABLE 14

Immunization of BALB/c mice with isolated PspA elicits
protection against WU2 S. pneumoniae

| Antigen Source | Dose[a] | Adjuvant or diluent | Challenge Log CFU | Route | Days to Death | P vs. controls TSR/FE[b] |
|---|---|---|---|---|---|---|
| R36A (PspA+) | 1 μg | CFA | 4 | i.p. | 2, >21, >21, >21 | 0.06/0.03 |
| WG44.1 (PspA−) | 100 μl | CFA | 4 | i.p. | 2, 3 | |
| None | — | CFA | 4 | i.p. | 2, 2, 2, 4 | |
| R36A (PspA+) | 1 μg | none | 6 | i.v. | 2, >21, >21, >21 | 0.06/0.03 |
| WG44.1 (PspA−) | 100 μl | none | 6 | i.v. | 5, 7 | |
| none | — | none | 6 | i.v. | 2, 2, 2, 3 | |
| Pooled i.v. and i.p. results | | | | i.v. or i.p. | | 0.008/0.0007 |

[a]The 1 μg dose of R36A PspA was isolated from 100 μl of CDM-ET medium. As a control mice were injected with a corresponding volume of choline-column effluent from a mock isolation of PspA from the PspA-strain WG44.1. The dose of WG44.1 material is expressed as 100 μl since this is the volume CDM-ET from which the injected column effluent was derived.
[b]P values calculated by Wilcoxon two-sample rank test, TSR, or Fisher exact, FE versus pooled controls for each group. "Pooled controls" include data obtained with by injection of "WG44.1" and "none". The i.p. and i.v. studies gave comparable results. When the data from the two studies were pooled the P values by both tests were <0.008. In cases where there were not statistically significant results no P value was shown.

REFERENCES

1. Anonymous. Pneumococcal polysaccharide vaccine. MMWR 1981, 30, 410–419
2. Farley, J. J., King, J. C., Nair, P., al., e. Infasive pneumococcal disease among infected and uninfected children of mothers with immunodeficiency virus infection. *J. Pediatr.* 1994, 124, 853–858
3. Schwartz, B., Gove, S., Lob-Lovit, J., Kirkwood, B. R. Potential interactions for the prevention of childhood pneumonia in developing countries: etiology of acute lower respiratory infections among young children in developing countries. *Ped. Infect. Dis.* in Press,
4. Avery, O. T., Goebel, W. F. Chemoimmunological studies of the soluable specific substance of pneumococcus. I. The isolation and properties of the acetyl polysaccharide of pneumococcus type 1. *J. Exp. Med.* 1933, 58, 731–755
5. Austrian, R. Pneumococcal Vaccine: Development and Prospects. *Am. J. Med* 1979, 67, 547–549
6. Shapiro, E. D., Berg, A. T., Austrian, R., Schroeder, D., Parcells, V., Margolis, A., Adair, R. K., Clemmens, J. D. Protective efficacy of polyvalent pneumococcal polysaccharide vaccine. *N. Engl. J. Med* 1991, 325, 1453–1460
7. Fedson, D. S. Pneumococcal vaccination in the prevention of community-acquired pneumonia: an optimistic view of cost-effectiveness. *Sem. Resp. Infect.* 1993, 8, 285–293
8. Robbins, J. B., Austrian, R., Lee, C.-J., Rastogi, S. C., Schiffman, G., Henrichsen, J., Makela, P. H., Broome, C. V., Facklam, R. R., Tiesjema, R. H., Parke, J. C., Jr. Considerations for formulating the second-generation pneumococcal capsular polysaccharide vaccine with emphasis on the cross-reactive types within groups. *J Infect Dis* 1983, 148, 1136–1159
9. Gotschlich, E. C., Goldschneider, I., Lepow, M. L., Gold, R., *The immune response to bacterial polysaccharides in man*. Antibodies in human diagnosis and therapy, . New York, Raven, 1977, 391–402.
10. Cowan, M. J., Amman, A. J., Wara, D. W., Howie, V. M., Schultz, L., Doyle, N., Kaplan, M. Pneumococcal polysaccharide immunization in infants and children. *Pediatrics* 1978, 62, 721–727
11. Mond, J. J., Lees, A., Snapper, C. M. T cell-independent antigens type 2. *Ann. Rev. Immunol.* 1995, 13, 655–692
12. Chu, S. S., Greenberg, P. D., Marcy, S. M., Wong, V. K., Chang, S. J., Chiu, C. Y., Ward, J. I. Mucosal antibody responses in infants following immunization with *Haemophilus influenzae*. *Pediatric Res. Abstracts* 1994, 35, 10A
13. Kauppi, M., Eskola, J., Kathty, H. H. influenzae type b (Hib) conjugate vaccines induce mucosal IgA1 and IgA2 antibody responses in infants and children. *ICAAC Abstracts* 1993, 33, 174
14. Dagen, R., Melamed, R., Abramson, O., Piglansky, L., Greenberg, D., Mendelman, P. M., Bohidar, N., Ter-Minassian, D., Cvanovich, N., Lov, D., Rusk, C., Donnelly, J., Yagupsky, P. Effect of heptavalent pneumococcal-OMPC conjugate vaccine on nasopharyngeal carriage when administered during the 2nd year of life. *Pediat. Res.* 1995, 37, 172A
15. Fattom, A., Vann, W. F., Szu, S. C., Sutton, A., Bryla, D., Shiffman, G., Robbins, J. B., Schneerson, R. Synthesis and physiochemical and immunological characterization of pneumomcoccus type 12F polysaccharide-diptheria toxoid conjugates. *Infect. Immun.* 1988, 56, 2292–2298
16. Kennedy, D., Derousse, C., E., A. Immunologic response of 12–18 month children to licensed pneumococcal polysaccharide vaccine primed with *Streptococcus pneumoniae* 19F conjugate faccine. ICAAC 1994 Abstract, G89
17. McDaniel, L. S., Ralph, B. A., McDaniel, D. O., Briles, D. E.
  Localization of protection-eliciting epitopes on PspA of *Streptococcus pneumoniae* between amino acid residues 192 and 260. *Microbial Pathogenesis* 1994, 17, 323–337

18. Langermann, S., Palaszynski, S. R., Burlein, J. E., Koenig, S., Hanson, M. S., Briles, D. E., Stover, C. K. Protective humoral response against pneumococcal infection in mice elicited by recombinant Bacille Calmette-Guerin vaccines expressing PspA. *J. Exp. Med.* 1994, 180, 2277–2286

19. Siber, G. R. Pneumococcal Disease: Prospects for a New Generation of Vaccines. *Science* 1994, 265, 1385–1387

20. Lock, R. A., Hansman, D., Paton, J. C. Comparative efficacy of autolysin and pneumolysin as immunogens protecting mice against infection by *Streptococcus pneumoniae. Microbial Pathogenesis* 1992, 12, 137–143

21. Sampson, J. S., O'connor, S. P., Stinson, A. R., Tharpe, J. A., Russell, H. Cloning and nucleotide sequence analysis of psaA, the *Streptococcus pneumoniae* gene encoding a 37-kilodalton protein homologus to previously reported Streptococcus sp. adhesins. *Infect. Immun.* 1994, 62, 319

22. Paton, J. C., Lock, R. A., Lee, C.-J., Li, J. P., Berry, A. M., Mitchell. Purification and immunogenicity of genetically obtained pneumolysin toxoids and their conjugation to *Streptococcus pneumoniae* type 19F polysaccharide. *Infect. Immun.* 1991, 59, 23. McDaniel, L. S., Scott, G., Kearney, J. F., Briles, D. E. Monoclonal antibodies against protease sensitive pneumococcal antigens can protect mice from fatal infection with *Streptococcus pneumoniae. J. Exp. Med.* 1984, 160, 386–397

24. Briles, D. E., Forman, C., Horowitz, J. C., Volanakis, J. E., Benjamin, W. H., Jr., McDaniel, L. S., Eldridge, J., Brooks, J. Antipneumococcal effects of C-reactive protein and monoclonal antibodies to pneumococcal cell wall and capsular antigens. *Infect. Immun.* 1989, 57, 1457–1464

25. McDaniel, L. S., Sheffield, J. S., Delucchi, P., Briles, D. E. PspA, a surface protein of *Streptococcus pneumoniae*, is capable of eliciting protection against pneumococci of more than one capsular type. *Infect. Immun.* 1991, 59, 222–228

26. McDaniel, L. S., Yother, J., Vijayakumar, M., McGarry, L., Guild, W. R., Briles, D. E. Use of insertional inactivation to facilitate studies of biological properties of pneumococcal surface protein A (PspA). *J. Exp. Med.* 1987,165,381–394

27. Yother, J., McDaniel, L. S., Crain, M. J., Talkington, D. F., Briles, D. E. *Pneumococcal surface protein A: Structural analysis and biological significance* In: Durnny, G. M., Cleary, P. P., McKay, L. L. ed. Genetics and Molecular Biology of Streptococci, Lactococci, and Enterococci. Washington, D.C.: American Society for Microbiology, 1991, 88–91

28. Waltman, W. D., II, McDaniel, L. S., Gray, B. M., Briles, D. E. Variation in the molecular weight of PspA (Pneumococcal Surface Protein A) among *Streptococcus pneumoniae. Microb. Pathog.* 1990, 8, 61–69

29. Crain, M J., Waltman, W. D., II, Turner, J. S., Yother, J., Talkington, D. E., McDaniel, L. M., Gray, B. M., Briles, D. E. Pneumococcal surface protein A (PspA) is serologically highly variable and is expressed by all clinically important capsular serotypes of *Streptococcus pneumoniae*. Infect. Immun. 1990, 58, 3293–3299

30. McDaniel, L. S., Scott, G., Widenhofer, K., Carroll, Briles, D. E. Analysis of a surface protein of *Streptococcus pneumoniae* recognized by protective monoclonal antibodies. *Microb. Pathog.* 1986, 1, 519–531

31. Yother, J., Briles, D. E. Structural properties and evolutionary relationships of PspA, a surface protein of *Streptococcus pneumoniae*, as revealed by sequence analysis. *J. Bact.* 1992, 174, 601–609

32. Talkington, D. F., Crimmins, D. L., Voellinger, D. C., Jother, J., Briles, D. E. A 43-kilodalton pneumococcal surface protein, PspA: isolation, protective abilities, and structural analysis of the amino-terminal sequence. *Infect. Immun.* 1991, 59:, 1285–1289

33. McDaniel, L. S., McEdaniel, D. O. Genetic analysis of the gene encoding type 12 PspA of Streptococcus pneumoniae strain EF5668 In: Feretti, J. J., Gilmore, M. S., Khenhammer, T. R., Brown, F. ed. Genetics of the streptococci, enterococci, and lactococci. Basel: Dev. Biol. Stand. Basel Krager, 1995, 283–286

34. Fischetti, V. A., Pancholi, V., Schneewind, O. Conservation of a hexapeptide sequence in the anchor region of surface proteins from gram-positive cocci. *Molec. Microbiol.* 1990, 4, 1603–1605

35. Schneewind, O., Fowler, A., Faull, K. F. Structure of cell wall anchor of cell surface proteins in *Staphylococcus aureus. Science* 1995, 268, 103–106

36. Yother, J., White, J. M. Novel surface attachment mechanism for the *streptococcus pneumoniae* protein PspA. J. Bact. 1994, 176, 2976–2985

37. Yother, J., Handsome, G. L., Briles, D. E. Truncated forms of PspA that are secreted from *Streptococcus pneumoniae* and their use in functional studies and cloning of the pspA gene. *J. Bact.* 1992, 174, 610–618

38. Talkington, D. F., Voellinger, D. C., McDaniel, L. S., Briles, D. E. Analysis of pneumococcal PspA microheterogeneity in SDS polyacrylamide gels and the association of PspA with the cell membrane. *Microbial Pathogenesis* 1992, 13, 343–355

39. Smith, M. D., Guild, W. R. A plasmid in *Streptococcus pneumoniae. J. Bacteriol.* 1979, 137, 735–739

40. Shoemaker, N. B., Guild, W. R. Destruction of low efficiency markers is a slow process occurring at a heteroduplex stage of transformation. Mol. Gen. Genet. 1974, 128, 283–290

41. Raven, A. W. Recriprocal capsular transformations of pneumococci *J. Bact.* 1959, 77, 296–309

42. McDaniel, L. S., Sheffield, J. S., Swiatlo, E., Yother, J., Crain, M. J., Briles, D. E. Molecular localization of variable and conserved regions of pspA,and identification of additional pspA homologous sequences in *Streptococcus pneumoniae. Microbial Pathogenesis* 1992, 13, 261–269

43. Rijn, V. D., Kessler, R. E. Growth characteristics of Group A Streptococci in a new chemically defined medium. *Infec. Immun.* 1980, 27,444–448

44. Avery, O. T., MacLeod, C. M., McCarty, M. Studies on the chemical nature of the substance inducing transformation of pneumococcal types. Induction of transformation by a desoxyribonucleic acid fraction isolated from pneumococcus type III. *J. Exp. Med* 1944, 79, 137–158

45. McCarty, M. The transforming principle. New York, Norton, 1985, 252.

46. Briles, D. E., Nahm, M., Schroer, K., Davie, J., Baker, P., Kearney, J., Barletta, R. Antiphosphocholine antibodies found in normal mouse serum are protective against intravenous infection with type 3 *Streptococcus pneumoniae. J. Exp. Med.* 1981, 153, 694–705

47. Briles, D. E., Crain, M. J., Gray, B. M., Forman, C., Yother, J. A strong association between capsular type and mouse virulence among human isolates of *Streptococcus pneumoniae. Infect. Immun.* 1992, 60, 111–116

48. Waltman, W. D., II, McDaniel, L. S., Andersson, B., Bland, L., Gray, B. M., Svanborg-Eden, C., Briles, D. E, Protein serotyping of *Streptococcus pneumoniae* based on reactivity to six monoclonal antibodies. *Microb. Pathog.* 1988, 5, 159–167

49. Tomasz, A. Surface components of *Streptococcus pneumoniae*. *Rev. Infect. Dis* 1981, 3, 190–211
50. Garcia, J. L., Garcia, E., Lopez, R. Overproduction and rapid purifcation of the amidase of *Streptococcus pneumoniae*. *Arch. Microbiol.* 1987,149,52–56
51. Osborn, M. J., Munson, J. Separation of the inner (cytoplasmic) and outer membranes of gram negative bacteria. *Methods Enzymol.* 1974, 31A, 642–653
52. Briles, D. E., Horowitz, J., McDaniel, L. S., Benjamin, W. H., Jr., Claflin, J. L., Booker, C. L., Scott, G., Forman, C. Genetic control of susceptibility to pneumococcal infection. *Curr. Top. Microbiol. Immunol.* 1986, 124, 103–120
53. Briles, D. E., Forman, C., Crain, M. Mouse antibody to phosphocholine can protect mice from infection with mouse-virulent human isolates of *Streptococcus pneumoniae*. *Infect. Immun.* 1992, 60, 1957–1962
54. Weigle, W. O. *Immunological unresponsiveness*. Academic Press, New York, N.Y., 1973
55. Dillard, J. P., Yother, J. Genetic and molecular characterization of capsular polysaccharide biosynthesis in *Streptococcus pneumoniae* type 3. *Molec. Microbiol.* 1994, 12, 959–972
56. Amsbaugh, D. F., Hansen, C. T., Prescott, B., Stashak, P. W., Barthold, D. R., Baker, P. J. Genetic control of the antibody response to type III pneumococcal polysaccharide in mice. I Evidence that an X-linked gene plays a decisive role in determining responsiveness. *J. Exp. Med* 1972, 136, 931–949
57. Tomasz, A. Biolobical consequences of the replacement of choline by ethanolamine in the cell wall of pneumococcus: chain formation, loss of transformability and loss of autolysis. *Proc. Natl. Acad. Sci. USA* 1968, 59, 86–93.
58. Paton. J. C., Lock, R. A., Hansman, D. C. Effect of immunization with pneumolysin on survival time of mice challenged with *Streptococcus pneumoniae*. *Infect. Immun.* 1983, 40, 548–552
59. Berry, A. M., Lock, R. A., Hansman, D., Paton, J. C. Contribution of autolysin to virulence of *streptococcus pneumoniae*. *Infect. Immun.* 1989, 57, 2324–2330
60. Lock, R. A., Paton, J. C., Hansman, D. Purification and immunologic characterization of neuraminidase produced by *Streptococcus pneumoniae*. *Microbial Pathogenesis* 1988, 4, 33–43
61. Tuomanen, E., Liu, H., Hengstler, B., Zak, O. , Tomasz, A. The Induction of meningeal inflammation by components of the pneumococcal cell wall. 1985, 151, 859–868
62. Tuomanen, E., Tomasz, A., Hengstler, B., Zak, O. The relative role of bacterial cell wall and capsule in the induction of inflammation in pneumococcal meningitis. *J. Infect. Dis.* 1985, 151, 535–540
63. Paton, J. C. *Pathogenesis of pneumococcal disease*. 1993, 363–368
64. T., Hakenbeck, R. Interaction of the pneumococcal amidase with lipoteichoic acid and choline. 1985, 146, 417–427

Example 4

Evidence For Simultaneous Expression of Two PsPAs

From Southern blot analysis there has been an issue as to whether most isolates of *S. pneumoniae* has two DNA sequences that hybridize with both 5' and 3' halves of Rx1 pspA, or whether this is an artifact of Southern blot (9). When bacterial lysates have been examined by Western blot, the results have always been consistent with the production of a single PspA by each isolate (1, 10). This Examiner provides evidence for the first time that two PspAs of different apparent molecular weights and different serotypes can be simultaneously expressed by the same isolate.

Different PspAs frequently share cross-reactive epitopes, and an immune serum to one PspA was able to recognize PspAs on all pneumococci (1). In spite of these similarities, PspAs of different strains can generally be distinguished by their molecular weights and by their reactivity with a panel of PspA-specific monoclonal antibodies (MAbs) (1).

A serotyping system for PspA has been developed which uses a panel of seven MAbs. PspA serotypes are designated based on the pattern of positive or negative reactivity in immunoblots with this panel of MAbs. Among a panel of 57 independent isolates of 9 capsular groups/types, we observed 31 PspA serotypes (1). The large diversity of PspA was substantiated in a subsequent study of 51 capsular serotype 6B isolates from Alaska, provided by Alan Parkinson at the Arctic Investigations Laboratory of the Centers for Disease Control and Prevention.

Among these 51 capsular type 6B isolates we observed 22 different PspAs based on PspA serotype and molecular weight variations of Pspa (4, 11).

While most pneumococcal strains appear to have two DNA sequences homologous with both the 5' and 3' halves of pspA (9), site-specific truncation mutations of Rx1 have revealed that one these, pspA, encodes PspA (8, 9). The other sequence has been provisionally designated as the pspA-like sequence. At present whether the pspA-like sequence makes a gene product is unknown. Evidence that the pspA and pspA-like genes are homologous but distinct groups of alleles comes from Southern blot analysis at high stringencies (9). Additional evidence that pspA and the pspA-like loci are distinct comes from studies using PCR primers that permit amplification of a single product approximately 2 Kb in size from 70% of pneumococci. For the remaining 30% of pneumococci no amplification was observed with the primers used (12).

Figure 4:
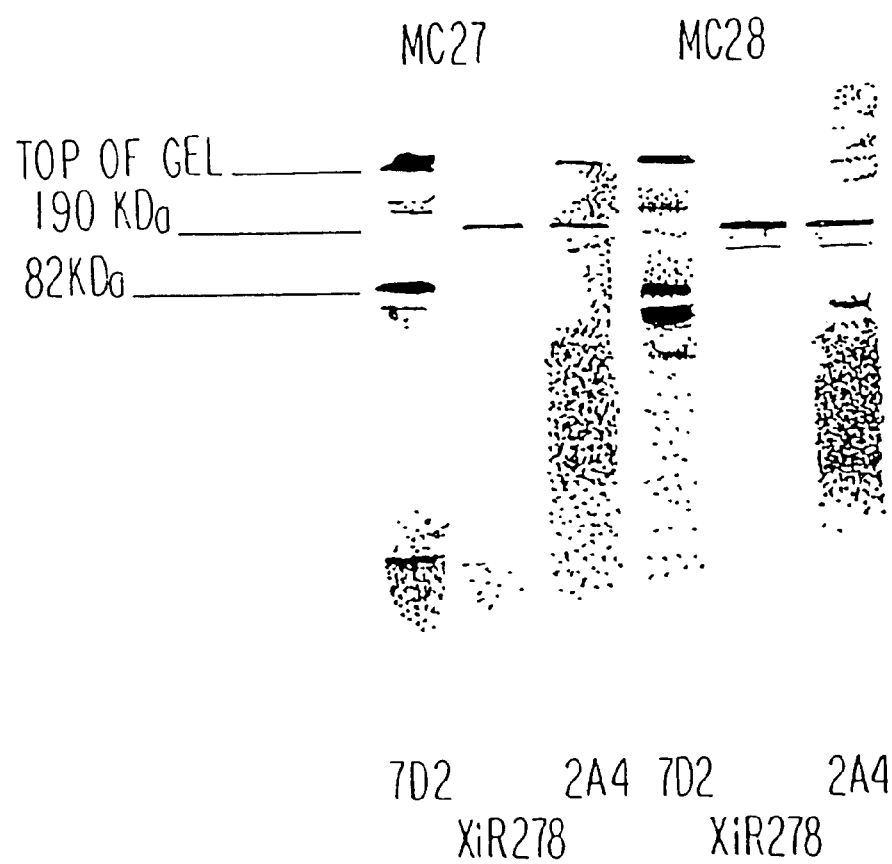
FIG. 4 shows: Cell lysates of pneumococcal isolates MC27 and MC28 were subjected to SDS-PAGE and transferred to nitrocellulose for Western blotting with seven MAb to PspA. 7D2 detected a protein of 82 kDa in each isolate and XiR278 and 2A4 detected a protein of 190 kDa in each isolate. MAb Xi64, Xi126, 1A4 and SR4W4 were not reactive. Strains MC25 and MC26 yielded identical results.

Evidence for Two PspAs:

When the strains of MC25–28 were examined with the panel of seven MAbs specific for different PspA epitopes, all four demonstrated the same patterns of reactivity (FIG. 4). The MAbs XiR278 and 2A4 detected a PspA molecule with an apparent molecular weight of 190 KDa in each isolate. In accordance with our previous PspA serotyping system, the 190 KDa molecule was designated as PspA type 6 because of its reactivity with XiR278 and 2A4, but none of the five other MAbs in the typing system. Each isolate also produced a second PspA molecule with an apparent molecular weight 82 KDa. The 82 KDs PspA is each isolate was detected only with the MAb 7D2 and was designated as type 34. No reactivity was detected with MAbs Xi126, Xi64, 1A4, or SR4W4. The fact that all four capsular 6B strains exhibit two PspAs, based on both molecular weights and PspA serotypes, suggested that they might be members of the same clone.

Simultaneous Production of Both PspAs:

Results from the colony immunobloting showed that both PspAs were present simultaneously in each colony of these isolates when grown in vitro. All colonies on each plate of the original culture, as well as all of the progeny colonies from a single colony, reacted with MAbs XiR278, 2A4, and 7D2 as previously described.

Figure 5A:
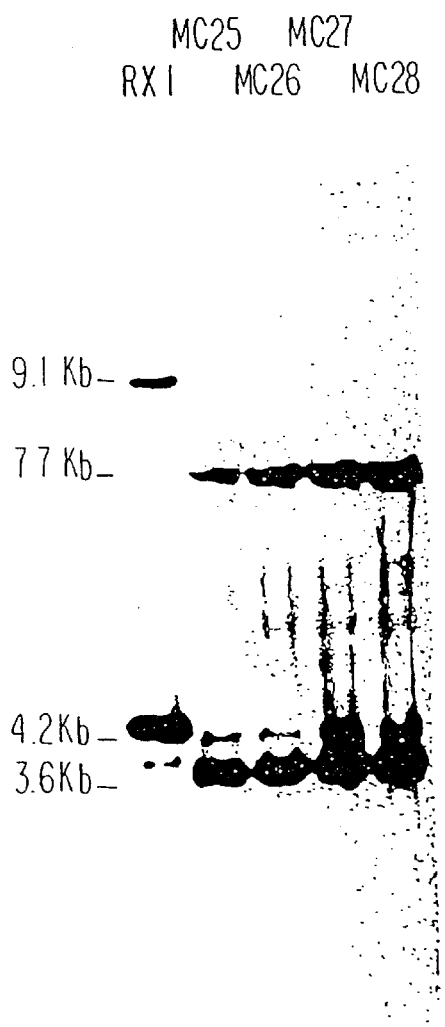
FIG. 5 (FIGS. 5A and 5B) shows: Southern blot of Hind III digest of MC25–MC28 chromosomal DNA developed at a stringency greater than 95 percent. A digest of Rx1 DNA was used as a comparison. The blot was probed with LSMpspA13/2, a full length Rx1 probe (FIG. 5) and LSMpspA12/6 a 5' probe of Rx1 pspA (FIG. 5). The same concentration of Rx1 DNA was used in both panels, but the concentrations of MC25–MC28 DNA in FIG. 5B were half that used in FIG. 5A to avoid detection of partial digests.

Number of pspA Genes:

One explanation for the second PspA molecule was that these strains contained an extra pspA gene. Since most strains contain a pspA gene and a pspA-like gene (9) we expected that if an extra gene were present we might observe at least three pspA homologous loci in isolates MC25–28. In Hind III digests of MC25–28 each strain revealed a 7.7 and 3.6 Kb band when probed with plSMpspA13/2 (FIG. 5A). In comparison, when Rx1 DNA was digested with Hind III and hybridized with plSMpspA13/2, homologous sequences were detected on 9.1 and 4.2 Kb fragments as expected from previous studies (9) (FIG. 5A). Results consistent with only two pspA-homologous genes in MC25–28 were also obtained with digestion using four additional enzymes (Table 15).

Figure 5B:
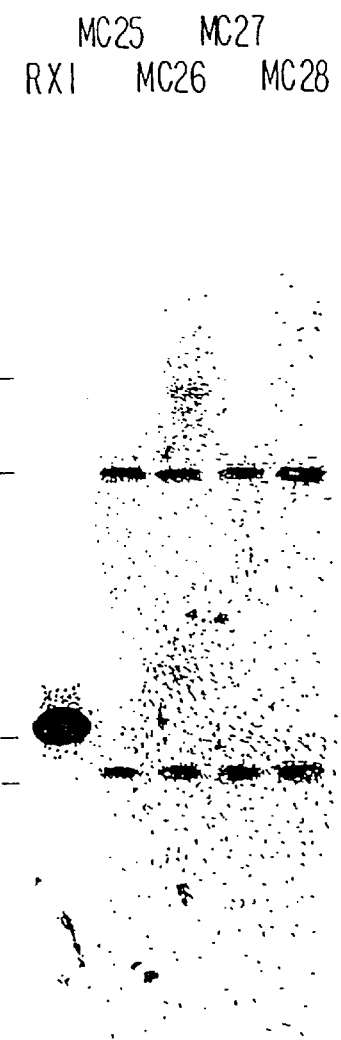

In previous studies it has been reported that probes for the 5' half of pspA (encoding the a-helical half of the protein) bind the pspA-like sequence of most strains only at a stringency of around 90% (9). With chromosomal digests of MC25–28 we observed that the 5' Rx1 probe of pLSMpspA12/6 bound both pspA homologous bands at a stringency of greater than 95 percent. The same probe bound only the pspA containing fragment Rx1 at a stringency above 95 percent (FIG. 5B).

Figure 6:
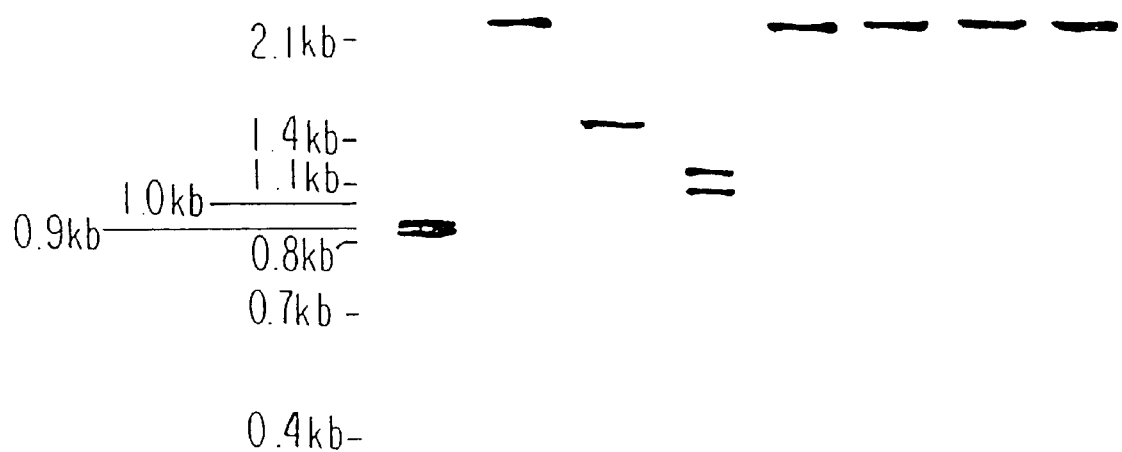
FIG. 6 shows: RFLP of amplified pspA. PspA from MC25 was amplified by PCR using 5' and 3' primers for pspA (LSM13 and LSM, respectively). The amplified DNA was digested with individual restriction endonucleases prior to electrophoresis and staining with ethidium bromide. Lane 1 BclI, Lane 2 BAMHI, Lane 3 BstNI, Lane 4 PstI, Lane 5 SacI, Lane 6 EcoRI, Lane 7 SmaI, Lane 8 KpnI.

Further characterization of the pspA gene was done by RFLP analysis of PCR amplified pspA from each strain. Since previous studies indicated that individual strains yielded only one product, and since the amplification is carried out with primers based on a known pspA sequence, it seems likely that in each case the amplified products represent the pspA rather than the pspA-like gene (12). When MC25–28 were subjected to this procedure, an amplified pspA product of 2.1 Kb was produced in each case. When digested with Hha 1 digest the sum of the fragments obtained with each enzyme was approximately equal to the size of the 2.1 Kb amplified product (FIG. 6). These results suggest that the 2.1 Kb amplified DNA represents the amplified product of only a single DNA sequence. Rx1, by comparison, produced an amplified product of 2.0 Kb and five fragments of 0.76, 0.468, 0390, 0.349 and 0.120, when digested with Hha 1 as expected from its known pspA sequence (5).

The four isolates examined in this Example are the first in which two PspAs have unambiguously been observed. The interpretation that two PspAs are simultaneously expressed by a single pneumococcal isolate is based on the observation that bands of different molecular weights were detected by different MAbs to PspA. Isolates used in this study were from a group originally selected for study by Brian Spratt because of their resistance to penicillin. It is very likely that all four of the isolates making two PspAs are related since they share PspA serotypes, amplified pspA RFLPs, chromosomal pspA RFLPs, capsule type, and resistance to penicillin.

The interpretation of studies presented her, showing the existence of two PspAs in the four strains MC25–28, must be set in the context of what is know about the serology PspA as detected by Western blots. PspAs of different strains have been shown previously to exhibit apparent molecular weight sizes ranging from 60 to 200 KDa as detected by Western blots (1, 10). At least part of this difference in size is attributable to secondary structure (8, 10). Even for the PspA of a single isolate, band of several sizes are generally observed. Mutation and immunochemistry studies have demonstrated, however, that all of the different sized PspA band from Rx1 are made by a single gene capable of encoding a 69 KDa protein (1). The heterogeneity of band size on Western blots of PspA made by a single strain appears to be due to both degradation and polymerization (13).

PspA was originally defined by reciprocal absorption studies demonstrating that a panel of MAbs to Rx1 surface proteins each reacted with some protein (14) and later by studies using Rx1 and WU2 derivatives expressing various truncated forms of PspA (8). In both cases it was clear that each of our MAbs to the PspA of a given strain reacted with the same protein. Such detailed studies have not been done with each of the several hundred human isolates. It is possible that with some isolates, reactivity of the MAbs with two PspAs may have gone unnoticed. This could have happened if all reactive antibodies detected both PspAs of the same isolate, or if the most prominent migration bands from each of the two PspAs co-migrated. With isolates MC25–28 the observation of two PspAs was possible because clearly distinguishable bands of different molecular weights reacted preferentially with different MAbs.

Applicants favor the interpretation that isolates MC25–28 each make two PspAs, because an alternative possibility, namely, that the 190 KDa PspA detected by MAbs XiR278 and 2A4 might be a dimer of the 84 KDa monomer detected by MAb 7D2, if the epitopes recognized by the different MAbs were dependent on either the dimeric or monomeric status of the protein, seems unlikely since whenever MAbs react with the PspA of a strain, they usually detect both the monomeric and the dimeric forms. No other isolates have been observed where some MAbs detected only the apparent dimeric form of PspA while others detected only the monomeric form.

There could be several possible explanations for the failure to observe two PspAs produced by most strains. 1) All pneumococci might make two pspAs in culture, but MAbs generally recognize only one of them (perhaps in this isolate there has been a recombination between pspa DNA and the pspA-like locus, thus allowing that locus to make a product detected by MAb to PspA). 2) All pneumococci can have two pspAs but the expression of one of them generally does not occur under in vitro growth conditions. 3) The pspA-like locus is normally a nonfunctional pseudogene sequence that for an unexplained reason has become functional in these isolates.

It seems unlikely that the expression of only a single PspA by most strains is the result of a phase shift that permits the expression of only the pspA or pspA-like gene at any one time, since many of the strains examined repeatedly and consistently product the same PspA (10, and unpublished data). In the case of strains MC25–28, the appearance of two PspAs is apparently not the result of a phase switch, since individual colonies produced both the type 6 and the type 34 PspAs.

Presumably in these four strains, the second PspA protein is produced by the pspA-like DNA sequence. At high stringency, the probe comprising the coding region of the a-helical half of PspA recognized both pspA homologous sequences of MC25–28 but not the pspA-like sequence of Rx1. This finding indicates that the pspA-like sequence of MC25–28 is more similar to the Rx1 pspA sequence than is the Rx1 pspA-like sequence. If the pspA-like sequence of these strains is more similar to pspA than most pspA-like sequences, it could explain why we were able to see the products of pspA-like genes of these strains with our MAbs. The finding of two families of PspAs made in vivo by pneumococci, allows for use of the second PspA in compositions, as well as the use of DNA primers or probes for the second gene for more conclusive detecting, determining or isolating of pneumococci.

Isolates and Bacterial Cell Culture:

Pneumococcal isolates described in these studies were cultured from patients in Barcelona, Spain (one adult at Bellvitge Hospital, and three children at San Juan de Dios)

between 1986 and 1988 (Table 2). These penicillin resistant pneumococci originally in the collection of Dr. Brian Spratt were shared with applicants by Dr. Alexander Tomasz at the Rockefeller Institute. Rx1 is a rough pneumococcus used in previous studies, and it is the first isolate in which pspA was sequenced (3, 8, 15). Bacteria were grown in Todd-Hewitt broth with 0.5% yeast extract or on blood agar plates overnight in a candle jar. Capsular serotype was confirmed by cell agglutination using Danish antisera (Statens Seruminstitut, Copenhagen, Denmark) as previously described (13). The isolates were subsequently typed as 6B by Quellung reaction, utilizing rabbit antisera against 6A or 6B capsule antigen prepared by Dr. Barry Gray (16).

Bacterial Lysates:

Cell lysates were prepared by incubating the bacterial cell pellet with 0.1% sodium deoxycholate, 0.01% sodium dedecylsulfate (SDS), and 0.15 M sodium citrate, and then diluting the lysate in 0.5M Tris hydrochloride (pH 6.8) as previously described (1). Total pneumococcal protein in the lysates was quantitated by the bicinchonic acid method (BCA Protein Assay Reagent; Pierce Chemical Company, Rockford, Ill.) (17).

PsPA Serotyping:

Serotyping of PspA was performed according to previously published methods (1). Briefly, pneumococcal cell lysates were subjected to SDS-PAGE, transferred to nitrocellulose membranes, and developed as Western blots using a panel of seven MAbs to PspA. PspA serotypes were assigned based on the particular combination of MAbs with which each PspA was reactive.

Colony Immunoblotting:

A ten ml. tube of Todd-Hewitt broth with 0.5% yeast extract was inoculated with overnight growth of MC23 from a blood agar plate. The isolate was allowed to grow to a concentration of $10^7$ cells/ml as determined by an O.D. of 0.07 at 590nm. MC23 was serially diluted and spread-plated on blood agar plates to give approximately 100 cells per plate. The plates were allowed to grow overnight in a candle jar, and a single block agar plate with well-defined colonies was selected. Four nitrocellulose membranes were consecutively placed on the plate. Each membrane was lightly weighted and left in place for 5 minutes. In order to investigate the possibility of phase-variation between the two proteins detected on Western blots a single colony was picked from the plate, resuspended in ringers, and spread-plated onto a blood agar plate. The membranes were developed as Western blots according to PspA serotyping methods (1).

Chromosomal DNA Preparation:

Pneumococcal chromosomal DNA was prepared as previously described (15). The cells were harvested, washed, lysed, and digested with 0.5% (wt/vol) SDS and 100 [Mg/ml proteinase K at 37° C. for 1 hour (18, 19). The cell wall debris, proteins, and polysccharides were complexed with 1% hexadecyl trimethyl ammonium bromide (CTAB) and 0.7M sodium chloride at 65° C. for 20 minutes, then extracted with chloroform/isoamyl alcohol. DNA was precipitated with 0.6 volumes isopropanol, washed, and resuspended in 10 mM Tris-HCL, 1 mM EDTA, pH 8.0 (20). DNA concentration was determined by spectrophotometric analysis at 260 nm.

Probe Preparation:

5' and 3' oligonucleotide primers homologous with nucleotides 1 to 26 and 1967 to 1990 of Rx1 pspA (LSM 13 and LSM2, respectively) were used to amplify the full length pspA and construct probe LSMpspA13/2 from Rx1 genomic DNA (21). 5' and 3' oligonucleotide primers homologous to nucleotides 161 to 187 and nucleotides 1093 to 1117 (LSM 12 and LSM 6, respectively) were used to amplify the variable a-helical region to construct probe LSMpspA12/6 (21). PCR generated DNA was purified by Gene Clean (Bio101 Inc., Vista, Calif.) and random prime-labeled with digoxigenin-11-dUTP using the Genius 1 Nonradioactive DNA Labeling and Detection Kit as described by the manufacturer (Boehringer Mannheim, Indianapolis, Ind.).

DNA Electrophoresis:

For Southern blot analysis, approximately 10 µg of chromosomal DNA was digested to completion with a single restriction endonuclease, (Hind III, Kpn 1, EcoR 1, Dra 1, or Pst 1) then electrophoresed on a 0.7% agarose gel for 16–18 hours at 35 volts. For PCR analysis, 5 µl of product were incubated with a single restriction endonuclease, (Bcl 1, BamH 1, Pst 1, Sac 1, EcoR 1 Sma 1, and Kpn 1) then electrophoresed on a 1.3% agrose gel for 2–3 hours at 90 volts. In both cases, 1 Kb DNA ladder was used for molecular weight makers (BRL, Gaithersburg, Md.) and gels were stained with ethidium bromide for 10 minutes and photographed with a ruler.

Southern Blot Hybridization

The DNA in the gel was depurinated in 0.25N HCL for 10 minutes, denatured in 0.5M NaOH and 1.5M NsCl for 30 minutes, and neutralized in 0.5M Tric-HCl (pH 7.2), 1.5M NaCl and 1 mM disodium EDTA for 30 minutes. DNA was transferred to a nylon membrane (Micron Separations INC, MA) using a POSIBLOT pressure blotter (Strategene, La Jolla, Calif. for 45 minutes and fixed by UV irradiation. The membranes were prehybridized for 3 hours at 42° C. in 50% formamide, 5×SSC, 5×Denhardt solution, 25mM sodium phosphate (pH 6.5), 0.5% SDS 3% (wt/vol) dextran sulfate and 500 µg/ml of denatured salmon containing 45% formamide, 5×SSC, 1×Denhardt solution, 20 mM sodium phosphate (pH 6.5), 0.5% SDS, 3% dextran sulfate, 250 µg/ml denatured sheared salmon sperm DNA and about 20 ng of heat-denatured diogoxigenin-labeled probe DNA. After hybridization, the membranes were washed twice in 0.1% SDS and 2×SSC for 3 minutes at room temperature. The membranes were washed twice to a final stringency of 0.1% SDS in 0.3×SSC at 65° C. for 15 minutes. This procedure yields a stringency greater than 95 percent (9, 15, 22). The membranes were developed using the Genius 1 Nonradioactive DNA Labeling and Detection Kit as described by the manufacturer (Boehringer Mannheim, Indianapolis, Ind.). To perform additional hybridization with other probes, the membranes were stripped in 0.2N NaOH/ 0.1% SDS at 40° C. for 30 minutes and then washed twice in 2×SSC (23).

Polymerase Chain Reaction (PCR):

5' and 3' primers homologous with the DNA encoding the N- and C-terminal ends of PspA (LSM13 and LSM2, respectively) were used in these experiments (21). Amplifications were made using Taq DNA polymerase, $MgCl_2$ and 10X reaction buffer obtained from Promega (Madison, Wis.). DNA used for PCR was prepared using the method previously described in this paper. Reactions were conducted in 50ml volumes containing 0.2 mM of each dNTP, and 1 ml of each primer at a working concentration of 50 mM. $MgCl_2$ was used at an optimal concentration of 1.75 mM with 0.25 units of Taq DNA polymerase. Ten to thirty ng of genomic DNA was added to each reaction tube. The amplification reactions were performed in a thermal cycler (M.J. Research, Inc.) using the following three step program. Step 1 consisted of a denaturing temperature of 94° C. for 2 minutes. Step 2 consisted of 9 complete cycles of a denaturing temperature of 94° C. for 1 minute, an annealing temperature of 50° C. for 2 minutes, and an extension temperature of 72° C. for 3 minutes. Step 3 cycled for 19 times with a denaturing temperature of 94° C. for 1 minute, an annealing temperature of 60° C. for 2 minutes, and an extension temperature of 72° C. for 3 minutes. At the end of the last cycle, the samples were held at 72° C. for 5 minutes to ensure complete extension.

Band Size Estimation:

Fragment sizes in the molecular weight standard and in the Southern blot hybridization patterns calculated from migration distances. The standard molecular sizes were fitted to a logarithmic regression model using Cricket Graph (Cricket Software, Malvern, Pa.). The molecular weight of the detected bands were estimated by entering the logarithmic line equation obtained by Cricket Graph into Microsoft Excel (Microsoft Corporation, Redmond, Wash.) in order to calculate molecular weight based in migration distances observed in the Southern blot.

TABLE 15

| Restriction Enzyme | Strains Examined | | | | | Restriction Fragments (sizes in kilobases) | |
|---|---|---|---|---|---|---|---|
| | MC25 | MC26 | MC27 | MC28 | RX1 | MC25–MC28 | RX1 |
| Hind III | + | + | + | + | + | 7.7, 3.6 | 9.1, 4.2 |
| Kpn I | + | + | + | + | + | 11.6, 10.6 | 10.6, 9.8 |
| EcoR I | + | | | | + | 8.4, 7.6 | 7.85, 6.6 |
| Dra I | + | | | | + | 2.1, 1.1 | 1.9, 0.9 |
| Pst I | + | | | | + | >14, 6.1 | 10.0, 4.0 |

TABLE 16

Penicillin Resistant Capsular Serogroup 6 Strains from Spain

| Isolate | Penicillin MIC (µg/ml) | Year | Site | Hospital |
|---|---|---|---|---|
| MC25 | 1 | 1986 | sputum | Bellvitge |
| MC2G | 4 | 1988 | ear | San Juan de Dios |
| MC27 | 1 | 1988 | ear | San Juan de Dios |
| MC28 | 2 | 1988 | ? | San Juan de Dios |

REFERENCES

1. Crain M. J., W. D. Waltman II, J. S. Turner, J. Yother, D. E. Talkington, L. S. McDaniel, B. M. Gray and D. E. Briles. Pneumococcal surface protein A (PspA) is serologically highly variable and is expressed by all clinically important capsular serotypes of Streptococcus pneumoniae. Infect Immun 1990; 58:3293–3299.
2. Briles D. E., J. Yother and L. S. McDaniel. Role of pneumococcal surface protein A in the virulence of Streptococcus pneumoniae. Rev Infect Dis 1988; 10:S372–374.
3. McDaniel L. S., J. Yother, M. Vijayakumar, L. McGarry, W. R. Guild and D. E. Briles. Use of insertional inactivation to facilitate studies of biological properties of pneumococcal surface protein A (PspA). J Exp Med 1987; 165:381–394.
4. Crain M. J. Unpublished data.
5. Yother J. and D. E. Briles. Structural properties and evolutionary relationships of PspA, a surface protein of Streptococcus pneumoniae, as revealed by sequences analysis. J Bact 1992; 174:601–609.
6. Talkington D. F., D. L. Crimmins, D. C. Voellinger, J. Yother and D. E. Briles. A 43-kilodalton pneumococcal surface protein, PspA: isolation, protective abilities, and structural analysis of the amino-terminal sequence. Infect Immun 1991; 59:1285–1289.
7. McDaniel L. S., B. A. Ralph, D. O. McDaniel and D. E. Briles. Localization of protection-eliciting epitopes on PspA of Streptococcus pneumoniae between amino acid residues 192 and 260. Microb Pathogen 1994; 17:323–337.
8. Yother J., G. L. Handsome and D. E. Briles. Truncated forms of PspA that are secreted from Streptococcus pneumoniae and their use in functional studies and cloning of the PspA gene. J Bact 1992; 174:610–618.
9. McDaniel L. S., J. S. Sheffield, E. Swiatlo, J. Yother, M. J.
   Crain and D. E. Briles. Molecular localization of variable and conserved regions of pspA, and identification of additional pspA homologous sequences in Streptococcus pneumoniae. Microb Pathogen 1992; 13:261–269.
10. Waltman W. D. II, L. S. McDaniel, B. M. Gray and D. E. Briles. Variation in the molecular weight of PspA (Pneumococcal Surface Protein A) among Streptococcus pneumoniae. Microb Pathogen 1990; 8:61–69.
11. Munoz R., J. M. Musser, M. Crain, D. E. Briles, A. Marton, A. J. Parkinson, U. Sorensen and A. Tomasz. Geographic distribution of penicillin-resistant clones of Streptococcus pneumoniae: characterization by penicillin-binding protein profile, surface protein A typing, and multilocus enzyme analysis. Clinic Infect Dis 1992; 15:112–118.
12. Brooks-Walter A. and L. S. McDaniel. 1994. Unpublished data.
13. Talkington D. F., D. C. Voellinger, L. S. McDaniel and D. E. Briles. Analysis of pneumococcal PspA microheterogeneity in SDS polyacrylamide gels and the association of PspA with the cell membrane. Microb Pathogen 1992; 13:343–355.
14. McDaniel L. S., G. Scott, K. Widenhofer, Carroll and D. E. Briles. Analysis of a surface protein of Streptococcus pneumoniae recognized by protective monoclonal antibodies. Microb Pathogen 1986; 1:519–531.
15. Sheffield J. S., W. H. Benjamin and L. S. McDaniel. Detection of DNA in Southern Blots by Chemiluminescence is a sensitive and rapid technique. Biotechniques 1992; 12:836–839.
16. Briles D. E., M. J. Crain, B. M. Gray, C. Forman and J. Yother. A strong association between capsular type and mouse virulence among human isolates of Streptococcus pneumoniae. Infect Immun 1992; 60:111–116.
17. Smith P. K., R. I. Krohn , G. T, Hermanson, A. K. Mallia, F. H.
   Gartner, M. D. Provenzano, E. K. Fujimoto, N. M. Goeke, B. J. Olson and D. C. Klenk. Measurement of Protein using Bicinchoninic Acid. Anal Biochem 1985; 150:76–85.
18. Meade H. M., S. R. Long, C. B. Ruvkin, S. E. Brown and F. M. Ausubel. Physical and genetic characterization of symbiotic and auxotrophic mutants of Rhizobium melioti induced by transposon Tn5 mutagenesis. J Bacteriol 1982; 149:114–122.
19. Silhavy T. J., M. L. Berman and L. W. Enquist. Experiments with gene fusions. Cold Springs Harbor: Cold Springs Harbor Laboratory. 1984.
20. Murray M. G. and W. F. Thompson. Rapid isolation of high molecular weight plant DNA. Nucl Acids Res 1980; 8:4321–4325.
21. Use of PCR to amplify pspAs and fragments of pspAs: Example 5, infra.
22. Southern E. M. Detection of specific sequences among DNA fragments separated by gel electrophoresis. J Mol Biol 1975; 98:503–517.
23. Badenes M. J., and Dan E. Parfitt. Reducing background and interference on Southern Blots probed with nonradioactive chemiluminescent probes. BioTechniques 1994; 17:622–624.

Example 5

Use of PCR To Amplify pspAs and Fragments of pspa

In this example, Applicants used oligonucleotides derived from the DNA sequence of pspA of *S. pneumoniae* Rx1 both as hybridization probes and as primers in the polymerase chain reaction to investigate the genetic variation and conservation of the different regions of pspA and pspA-like sequences. The probes used ranged in size from 17 to 33 bases and included sequences representing the minus 35, the leader, the α-helical region, the proline-rich regions, the repeat regions, and the C-terminus. Applicants examined 18 different isolates representing 12 capsular and 9 PspA serotypes. The proline-rich, repeat, and leader, regions were highly conserved among pspA and pspA-like sequence.

In the previous Example, it was shown that strain Rx1 and most other strains of *S. pneumoniae* had two homologous sequences that could hybridize with probes encoding the N terminal and C terminal halves of PspA. This conclusion that these were separate sequences was supported by the fact that no matter which restriction enzymes was used there were always at least two (generally two sometimes three or four) restriction fragments of Rx1 and most other strains hybridized with the pspA probes. When the genome of Rx1 was digested with HindIII and hybridized with these, two pspA-homologous sequences were found to be in 4.0 and 9.1 kb fragments. Using derivative of Rx1 which had insertion mutations in pspA, it was possible to determine that the 4.0 kb fragment contained the functional pspA sequence. The pspA-homologous sequence included within the 9.1 kb band was referred to as the pspA-like sequence. Whether or not the pspA-like sequences makes a product is not know, and none has been identified in vitro. Since pspA-specific mutants can be difficult to produce in most strains, and exist for only a limited number of pneumococcal isolates, this Example identifies oligonucleotide probes that could distinguish between the pspA and pspA-like sequences.

The purpose of this Example was to further define both the conserved and variable regions of pspA, and to determine whether the central proline-rich region is variable or conserved, and identify those domains of pspA that are most highly conserved in the pspA-like sequence (and ergo, provide oligonucleotides that can distinguish between the two). Oligonucleotides were used and are therefore useful as both hybridization probes and as primers for polymerase chain reaction (PCR) analysis.

Hybridization with Oligonucleotide Probes.

Figure 7:
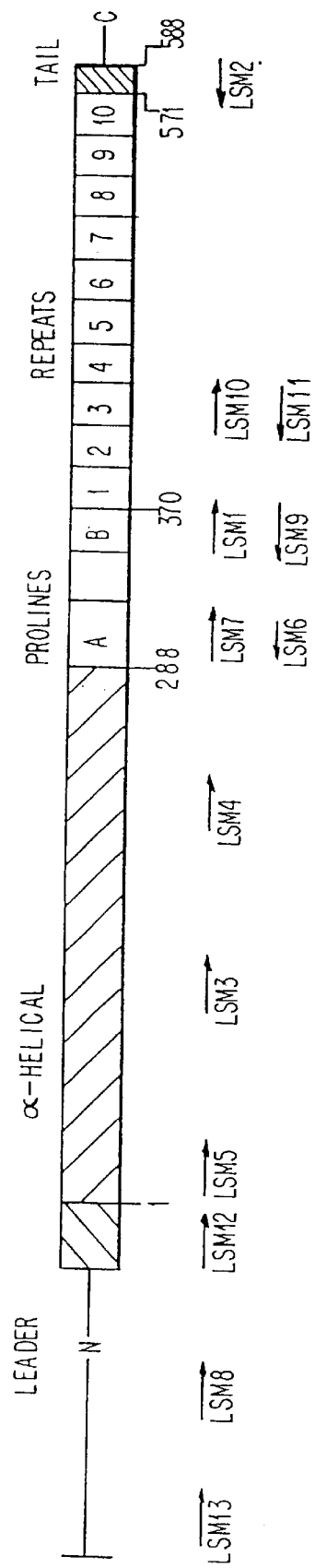
FIG. 7 shows: A depiction of PspA showing the relative location and orientation of the oligonucleotides.

The oligonucleotides used in this study were based on the previously determined sequence [Yother, 1992] of Rx1 PspA. Their position and orientation relative to the structural domains of Rx1 PspA are shown in FIG. 7. The reactivity of these oligonucleotide probes with the pspA and pspA-like sequences was examined by hybridization with a HindIII digest of Rx1 genomic DNA (Table 17). As expected, each of the eight probes recognized the pspA-containing 4.0 kb fragment of the HindIII digested Rx1 DNA. Five of the 8 probes (LSM1, 2, 3, 7, and 12) could also recognize the pspA-like sequence of the 9.1 kb band at least at low stringency. At high stringency four of the probes (LSM2, 3, 4 and 5) were specific for the 4.0 kb.

These 8 probes were used to screen HindIII digest of the DAN from 18 strains of *S. pneumoniae* at low and high stringency. For comparison to earlier studies each of the strains was also screened using a full-length pspA probe. Table 23 illustrates the results obtained with each strain at high stringency. Table 18 summarizes the reactivities of the probes with the strains at high and low stringency. Strain Rx1 is a laboratory derivative of the clinical isolate, D39. The results obtained with both strains were identical. They are listed under a single heading in Table 23 and are counted as a single strain in Table 28. Although AC17 and AC94 are related clinical isolates (Swiatlo et al. unpublished), they have distinguishable pspAs and are listed separately. All of the other strains represent independent isolates.

The only strain not giving at least two pspA-homologous HindIII fragments was WU2. This observation was expected since WU2 was previously shown to have only one pspA-homologous sequence and to give only a single HindIII fragment that hybridizes with Rx1 pspA. Even at high stringency 6 of the 8 probes detected more than one fragment in at least one of the 18 strains Tables 18 and 23. Probes LSM7, 10 and 12 reacted with DNA from a majority of the strains and detected two fragments in over 59% of the strains they reacted with. In almost every case the fragments detected by the oligonucleotide probes were identical in size to those detected by the full-length pspA probe. Moreover, the same pairs of fragments were frequently detected by probes from the 3' as well as the 5' half Rx1 pspA. These results are consistent with earlier findings [McDaniel, 1992] that the pairs of HindIII fragments from individual isolated generally include two separate but homologous sequences, rather than fragments of a single pspA gene.

The differences in the frequency with which the oligonucleotides reacted with (at least one fragment) of the strains in the panel was significant at P<0.0001 by 2×8 chi square). When the oligonucleotides were compared in terms of their ability to react with both fragments of each strain the P value was also <0.0001. Table 18 gives the percentage of strains reactive with each probe, the percentage in which only one fragment was reactive, and the percentage in which two (or more) fragments were reactive.

The last column in Table 18 give the ratio of strains that showed one reactive HindIII fragment at high stringency divided by the total number of reactive strains. In this column values of 1 were obtained with probes that only reacted with one band in each reactive strain. Such probes are assumed to be those that are most specific for pspA. The lowest values were obtained with probes that generally see two bands in each strain. Such probes are assumed to be those that represent regions relatively conserved between the pspA and pspA-like sequences. At high stringency, probes LSM3 and LSM4 detected only a single HindIII fragment in the DAN of strains they reacted with. These findings suggested probes LSM3 and LSM4 were generally detecting alleles of pspA rather than the pspA-like sequence. The observation that the fragments detected by LSM3 or LSM4 were also detected by all of the other reactive probes, strengthened the conclusion that these probes generally detected the pspA rather than the pspA-like sequence. WU2 has only one pspA-homologous DNA sequence and secretes a serologically detectable PspA. The fact that LSM3 reacts with the single HindIII fragment of WU2 is consistent with the interpretation that LSM3 detects the pspA sequences. Sequences representing the second proline region (LSM1) and the C-terminus (LSM2) appeared to also be relatively specific for the pspA sequences since they were generally detected in only one of the HindIII fragments of each strain.

Oligonucleotides, LSM12, and LSM10 detected the most conserved epitopes of pspA and generally reacted with both pspA-homologous fragments of each strain (Table 18). LSM7 was not quite as broadly cross-reactive but detected two PspAs in 41% of strains including almost 60% of the strains it reacted with. Thus, sequences representing the leader, first proline region, and the repeat region appear to be relatively conserved not only within pspA but between the pspA and pspA-like sequences. LSM3, 4, and 5 reacted with the DNA from the smallest fraction of strains of any oligonucleotide (29–35 percent), suggesting that the portion of pspA encoding the a-helical region is the least conserved region of pspA.

With two strains BG85C and L81905, the oligonucleotides detected more than two HindIII fragments containing pspA-homologous sequences. Because of the small size of the oligonucleotide probes and the absence of HindIII restriction sites within any of them, it is very unlikely that these multiple fragments were the results of fragmentation of the target DNA within the probed regions. In almost every case the extra oligonucleotides were detected at high stringency by more than one oligonucleotide. These data strongly suggest that at least in these two strains there are 3 or 4 sequences homologous to at least portions of the pspA. The probes most reactive with these additional sequences are those for the leader, the a-helical region and the proline rich region. The evidence for the existence of these additional pspA-related sequences was strengthened by results with BG58C and L81905 at low stringency where the LSM3 (α-helical) primer picked up the extra 1.2 kb band of L81905 (in addition to the 3.6 kb band) and the LSM7 (proline-rich) primer picked up the extra 3.2 and 1.4 kb bands (in addition to the 3.6 kb band) of BG58C.

Amplification of pspa

The utility of these oligonucleotides as PCR primers was examined by determining if they could amplify fragments of pspA from the genomic DNA of different pneumococcal isolates. Applicants attempted to amplify pspAs from 14 diverse strains of *S. pneumoniae* comprising 12 different capsular types using primers based on the Rx1 pspA sequence. Applicants observed that the 3' primer LSM2, which is located at the 3' end of pspA, would amplify an apparent pspA sequence from each of the 14 pneumococcal strains when used in combination with LSM1 located in the region of pspA encoding the proline-rich region (Table 19). LSM2 was also used in combination with four other 5' primers LSM1, 3, 7, 8 and 12. LSM8 is located 5' of the pspA start site (near the −35 region).

If a predominant sequence of the expected length was amplified that could be detected on a Southern blot with a full-length pspA probe, we assumed that pspA gene of the amplified DNA had homologous sequences similar to those of the pspA primers used. Based on these criteria the primer representing the α-helical sequence was found to be less conserved than the primers representing the leader, proline, and C-terminal sequences. These results were consistent with those observed for hybridization. The lowest frequency of amplification was observed with LSM8 which is from the Rx1 sequence 5' of the pspA start site. This oligonucleotide was not used in the hybridization studies.

Further evidence for variability comes from differences in the sizes of the amplified pspA gene. The Example showed that when PCR primers LSM12 and LSM2 were used to amplify the entire coding region of PspA, PCR products from different pneumococcal isolates ranged in size from 1.9 and 2.3 kb (Table 20). The regions within pspA encoding the a-helical, proline-rich, and repeats were also amplified from the same isolates. As seen in Table 20, the variation in size of pspA appeared to come largely from variation in the size of pspA encoding encodes the α-helical region.

Using probes that consisted of approximately the 5' and 3' halves of pspA it has been determined that the portion of pspA that encodes the a-helical regions is less conserved than the portion of pspA that encodes the C-terminal half of the molecule. This Example show using 4 oligonucleotide probes from within each half of the DNA encoding PspA. Since a larger number of smaller probes were used, Applicants have been able to obtain a higher resolution picture of conserved and variable sequences within pspA and have also been able to identify regions of likely differences and similarities between pspA and the pspA-like sequences.

The only strains in which the pspA gene has been identified by molecular mutations are Rx1, D39 and WU2 [McDaniel, 1992; Yother, 1992]. Rx1 and D39 apparently have identical pspA molecules [Crain, 1990; McDaniel, 1992] that are the result of the common laboratory origin of these two strains. WU2 lacks the pspA-like gene. Thus, when most pneumococci are examined by Southern blotting using full length-pspA as a probe, it is not possible to distinguish between the pspA and pspA-like loco, since both are readily detected. A major aim of these studies was to attempt to identify conserved and variable regions within the pspA and pspA-like loci. A related aim was to determine whether probes based on the Rx1 pspA could be identified that would permit one to differentiate pspA from the pspA-like sequence. Ideally such probes would be based on relatively conserved portion of the pspA sequence that was quite different in the pspA-like sequence. A useful pspA specific probe would be expected to identify the known Rx1 and WU2 pspA genes and identify only a single HindIII fragment in most other strains. Two probes (LSM3 and LSM4) never reacted with more than one pspA-homologous sequence in any particular strain. Both of reacted with Rx1 pspA and LSM3 reacted with WU2 pspA. Each of these probes reacted with 4 of the other 15 strains. When these probes identified a band, however, the band was generally also detected by all other Rx1 probes reactive with that strain's DNA. Additional evidence that the LSM3 and LSM4 were restricted to reactivity with pspA was that they reacted with the same bands in all three non-Rxi strains. Each probe identifies pspA in certain strains and even when used in combination they recognized pspA in over 40 percent of strains. Probes for the second proline-rich region (LSM1) and the C-terminus of pspA (LSM2) generally, but not always, identified only one pspA-homologous sequence at high stringency. Collectively LSM1, 2, 3, and 4 reacted with 16 of the 17 isolates and in each case revealed a consensus band recognized by most to all of the reactive probes.

By making the assumption that in different strains the Rx1 pspA probes are more likely to recognize pspA than the pspA-like sequences, it is possible to make some predictions about areas of conservation and variability within the pspA and pspA-like sequences. When a probe detected only a single pspA-homologous sequence in an isolate, it was assumed that it was pspA. If the probe detected two pspA-homologous sequences, it was assumed that it was reacting with both the pspA and pspA-like sequence. Thus, the approximate frequency with which a probe detects pspA can be read from Table 18 as the percent of strains where it detects at least one pspA-homologous band. The approximate frequency with which the probes detect the pspA-like sequence is the percent of strains in which two or more pspA-homologous band are detected.

Using these assumptions the most variable portion of portion of the pspA gene was observed to be the −35 region and the portion encoding α-helical region. The most conserved portion of pspA was found to be the repeat region, the leader and the proline rich region. Although only one probe from the region was used, the high degree of conservation among the 10 repeats in the Rx1 sequence [Yother, 1992] makes it likely that other probes for the repeat regions give similar results.

The portion of the pspA-like sequence most similar to Rx1 pspA was that encoding the leader sequence, the 5' portion of the proline rich region, and the repeat region, and those portions encoding the N-terminal end of the proline-rich and repeat regions. The repeat region of PspA has been shown to be involved in the attachment to PspA to the pneumococcal surface. The conservation of the repeat region among both pspA and pspA-like genes suggests that if is PspA-like protein is produced, that it may have a surface attachment mechanism similar to that of PspA. The need for a functional attachment site may explain the conservation of the repeat region. Moreover, the conservation in DNA encoding the repeat regions of the pspA and pspA-like genes suggests that the repeat regions may serve as a potential anti-pneumococcal drug target. The conservation in the leader sequence between pspA and the pspA-like sequence was also not surprising since similar conservation has been reported for the leader sequence of other gram positive proteins, such as M protein of group A streptococci [Haanes-Fritz, 1988]. It is noteworthy, however, that there is little evidence at the DNA level that the PspA lead is shared by many genes other than PspA and the possible gene product of the pspA-like locus.

Although the region encoding the C-terminus of pspA (LSM12) or the 3' portion of the proline-rich sequence (LSM1) appear to be highly conserved within pspA genes, corresponding regions in the pspA-like sequences are either lacking, or very distinct from those in pspA. The reason for conservation at these sites is not apparent. In the case of the PspA, its C-terminus does not appear to be necessary for attachment, since mutants lacking the C-terminal 49 amino acids are apparently as tightly attached to the cell surface as those with the complete sequence. Whether these difference from pspA portends a subtle difference in the mechanism of attachment of proteins produced by these two sequences in unknown. If the C-terminal end of the pspA-like sequence, or the 3' portion of the proline-rich sequence in the pspA-like sequence are as conserved within the pspA-like family of genes as it is within pspA, then this region of pspA and the pspA-like sequence serve as targets for the development of probes to distinguish between all pspA and pspA-like genes.

With two strains, some of the oligonucleotide probes identified more than two pspA-homologous sequences. In the case of each of these strains, there was a predominant sequence recognized by almost all of the probes, and two or three additional sequences that were each recognized by at least two of the probes. One interpretation of the data is that there may be more than two pspA-homologous genes in some strains. The significance of such sequences is far from established. It is of interest however, that although the additional sequences is far from established. It is of interest however, that although the additional sequences share areas of homology with the leader, α-helical, and proline region, they exhibited no homology with the repeat region of the C-terminus of pspA. These sequences, thus, might serve as elements that can recombine with pspA and/or the pspA-like sequences to generate sequence diversity. Alternatively the sequences might produce molecules with very different C-terminal regions, and might not be surface attached. If these pspA-like sequences make products, however, they, like PspA, may be valuable as a component of a pneumococcal antigenic, immunological vaccine compositions.

Bacterial Strains, Growth Conditions and Isolation of Chromosomal DNA.

S. pneumoniae strains used in this study are listed in Table 5. Strains were grown in 100 ml of Todd-Hewitt broth with 0.5% yeast extract at 37° C. to an approximate density of $5 \times 10^8$ cells/ml. Following harvesting of the cells by centrifugation (2900×g, 10 minutes), the DNA was isolated as previously described [McDaniel, 1992 #536] and stored at 4° C. in TE (10 mM Tris, 1mM EDTA, pH 8.0).

Amplification of pspA Sequences.

Polymerase chain reaction (PCR) primers, which were also used as oligonucleotide probes in Southern hybridizations, were designed based on the sequence of pspA from pneumococcal strain Rx1 (Yother, 1992]. These oligonucleotides were obtained from Oligos Etc. (Wilsonville, Oreg.) and are listed in Table 22.

PCRs were done with a MJ Research, Inc., Programmable Thermal Cycler (Watertown, Mass.) as previously described using approximately 10 ng of genomic pneumococcal DAN with appropriate 5' and 3' primer pair. The sample was brought to a total volume of 50 μl containing a final concentration of 50 mM KCl, 10 mM Tris-HCl (PH 8.3), 1.5 mM $MgCl_2$ 0.001% gelatin, 0.5 mM each primer, 200 mM of each deoxynucleotide triphosphate, and 2.5 U of Taq DNA polymerase. Following overlaying of the samples with 50 μl of mineral oil, the samples were denatured at 94° C. for 2 minutes. Then the samples were subjected to 10 cycles consisting of 1 minute at 94° C., 2 minutes at 50° C., and 3 minutes at 72° C. followed by another 20 cycles of 1 minute at 94° C., 2 minutes at 50° C., and 3 minutes at 72° C. followed by another 20 cycles of 1 minute at 94° C., 2 minutes at 60° C., and 3 minutes at 72° C. After all 30 cycles, the samples were held at 72° C. for an additional 5 minutes prior to cooling to 4° C. The PCR products were analyzed by agarose gel electrophoresis.

DNA Hybridization Analysis.

Approximately 5 μg of chromosomal DNA was digested with HindIII as per the manufacturer's instructions (Promega, Inc., Madison, Wis.). The digested DNA was electrophoresesed at 35 mV overnight in a 0.8% agarose gels and then vacuum-blotted onto Nytran membranes (Schleicher & Schuell, Keene, N.H.).

Labeling of oligonucleotide with and detection of probe-target hybrids were both performed with the Genius System according to the manufacturer's instructions (Mannheim, Indianapolis, Ind.). All hybridization were done for 18 hours at 42° C. without formamide. By assuming that 1% base-pair mismatching results in a 1° C. decrease in Tm designations of "high" and "low" stringency were defined by salt concentration and temperature of post-hybridization washes.

Homology between probe and target sequences was derived using calculated Tm the established method. High sringency is defined as 90% or greater homology, and low stringency is 80–85% sequence homology.

TABLE 17

Hybridization of oligonucleotides with HindIII restriction fragments of Rx1 DNA.

| Oligonucleotide | Region | Stringency Low | Stringency High |
|---|---|---|---|
| LSM12 | Leader | N.D. | 4.0, 9.1 |
| LSM5 | α-helix | N.D. | 4.0 |
| LSM3 | α-helix | 4.0, 9.1 | 4.0 |
| LSM4 | α-helix | 4.0 | 4.0 |
| LSM7 | Proline | 4.0, 9.1 | 4.0, 9.1 |
| LSM1 | Proline | 4.0, 9.1 | 4.0, 9.1 |
| LSM10 | Repeats | N.D. | 4.0, 9.1 |
| LSM2 | C-terminus | 4.0, 9.1 | 4.0 |

Note.
Values indicated are the sizes of restriction fragments expressed as kb.

TABLE 18

Summary of Hybridization at High and Low Stringency of 8 Oligonucleotides with HindIII Restriction Fragments of the 17 Pneumococcal Isolates Listed in FIG. 2

| Oligonu-cleotide | Percent with ≥1 band Low | Percent with ≥1 band High | Percent with ≥2 bands Low | Percent with ≥2 bands High | Percent with 1 band Low | Percent with 1 band High | 1 band/ ≥1 band Low | 1 band/ ≥1 band High |
|---|---|---|---|---|---|---|---|---|
| LSM12 |  | 82 |  | 59 |  | 24 |  | 0.29 |
| LSM5 |  | 29 |  | 18 |  | 12 |  | 0.40 |
| LSM3 | 65 | 35 | 41 | 0 | 24 | 35 | 0.36 | 1.00 |
| LSM4 | 35 | 29 | 0 | 0 | 35 | 29 | 1.00 | 1.00 |
| LSM7 | 94 | 71 | 71 | 41 | 24 | 29 | 0.25 | 0.42 |
| LSM1 | 100 | 65 | 53 | 12 | 47 | 53 | 0.47 | 0.82 |
| LSM10 |  | 94 |  | 59 |  | 35 |  | 0.37 |
| LSM2 | 88 | 53 | 41 | 12 | 47 | 41 | 0.53 | 0.78 |

Note,
for all values listed all 17 strains were examined. If no value is listed, then no strains were examined.

TABLE 19

Amplification of Pneumococcal Isolates using the Indicated 5' Primer Combination with the 3' Primer LSM2 at the 3' end of pspA

| 5' Primer | Region | Nucleotide Position | Amplified/ Tested | Percent Amplified |
|---|---|---|---|---|
| LSM8 | −35 | 47 to 70 | 2/14 | 14 |
| LSM12 | leader | 162 to 188 | 8/14 | 57 |
| LSM3 | α-helical | 576 to 598 | 3/14 | 21 |
| LSM7 | proline | 1093 to 1117 | 12/14 | 86 |
| LSM1 | proline | 1312 to 1331 | 14/14 | 100 |

Note,
by 2 × 5 chi square analysis the differnet primers amplified different frequencies of pspAs (P < 0.0001). The tendency for there to be more amplification with the 3' most primers was significant at P < 0.0001.

TABLE 20

Size of amplified pspA fragments in kilobases

| pspA Region | Primer Pairs | number pspAs examined | Size | Range | S.D. |
|---|---|---|---|---|---|
| Full length | LSM12 + LSM2 | 9 | 1.9–2.3 | 0.4 | 0.17 |
| α-helical | LSM12 + LSM6 | 6 | 1.1–1.5 | 0.4 | 0.17 |
| Proline | LSM7 + LSM9 | 3 | 0.23 | 0 | 0 |
| Repeats | LSM1 + LSM2 | 19 | 0.6–0.65 | 0.05 | 0.01 |

Note:
amplification was attempted with each set of primers on a panel of 19 different pspAs. Data is shown only for pspAs that could be amplified with the indicated primer pairs.

TABLE 21

| Strain | Pneumococcal strains Relevant characteristics |
|---|---|
| WU2 | Capsular type 3, PspA type 1 |
| D39 | Capsular type 2, PspA type 25 |
| R36A | Nonencapsulated mutant of D39, PspA type 25 |
| Rx1 | Nonencapsulated variant of R36A, PspA type 25 |
| DBL5 | Capsular type 5, PspA type 33 |
| DBL6A | Capsular type 6A, PspA type 19 |
| A66 | Capsular type 3, PspA type 13 |
| AC94 | Capsular type 9L, PspA type 0 |
| AC17 | Capsular type 9L, PspA type 0 |
| AC40 | Capsular type 9L, PspA type 0 |
| AC107 | Capsular type 9V, PspA type 0 |
| AC100 | Capsular type 9V, PspA type 0 |
| AC140 | Capsular type 9N, PspA type 18 |
| D109-1B | Capsular type 23, PspA type 12 |
| BG9709 | Capsular type 9, PspA type 0 |
| BG58C | Capsular type 6A, PspA type ND |
| L81905 | Capsular type 4, PspA type 25 |
| L82233 | Capsular type 14, PspA type 0 |
| L82006 | Capsular type 1, PspA type 0 |

TABLE 22

PCR primers

| Primer | Sequence (5' to 3') (Sequence ID Nos. 1–13) |
|---|---|
| LSM1 | CCGGATCCAGCTCCTGCACCAAAAAC |
| LSM2 | GCGCGTCGACGGCTTAAACCCATTCACCATTGG |
| LSM3 | CCGGATCCTGAGCCAGAGCAGTTGGCTG |
| LSM4 | CCGGATCCGCTCAAAGAGATTGATGAGTCTG |
| LSM5 | GCGGATCCCGTAGCCAGTCAGTCTAAAGCTG |
| LSM6 | CTGAGTCGACTGGAGTTTCTGGAGCTGGAGC |
| LSM7 | CCGGATCCAGCTCCAGCTCCAGAAACTCCAG |
| LSM8 | GCGGATCCTTGACCAATATTTACGGAGGAGGC |
| LSM9 | GTTTTTGGTGCAGGAGCTGG |
| LSM10 | GCTATGGCTACAGGTTG |
| LSM11 | CCACCTGTAGCCATAGC |
| LSM12 | CCGGATCCAGCGTGCCTATCTTAGGGGCTGGTT |
| LSM13 | GCAAGCTTATGATATAGAAATTTGTAAC |

TABLE 23

Hybridization at high stringencyh of eight different PspA probes with HindIII digests of 18 strains of Streptococcus pneumoniae

| Probe | Rx1/D39 | WU2 | DBL 5 | DBL 6A | A66 | AC94 | AC17 | AC40 | AC107 | AC100 | AC140 | DC109 | BG9709 | BG58C | L81905 | L82233 | L82006 |
|---|---|---|---|---|---|---|---|---|---|---|---|---|---|---|---|---|---|
| FL-Rx1 | 4.0, 9.1 | 3.8 | 3.7, 5.8 | 3.0, 3.4 | 3.6, 4.3 | 3.6, 6.3 | 3.6, 6.3 | 3.2, 3.6 | 3.6, 6.3 | 4.0, 8.0 | 3.0, 4.0 | 3.3, 4.7 | 2.2, 9.6 | 1.4, 3.2, 3.6 | 3.6, 5.2 | 3.7, 8.2 | 4.3, 6.4 |
| LSM 12 | 4.0, 9.1 | 3.8 | 3.7, 5.8 | 3.0, 3.4 | 4.3 | | 3.6, 6.3 | 3.2, 3.6 | | 4.0, 8.0 | 4.0 | 3.3, 4.7 | 2.2, 9.6 | 1.4, 3.2, 3.6 | 3.6 | 1.3, 3.7 | |
| LSM 5 | 4.0 | | | | | 3.6, 6.3 | | | | | | | 2.2, 9.6 | 3.6 | 1.2, 2.3, 3.6 | | |
| LSM 3 | 4.0 | 3.8 | | | | 6.3 | | | | | | | 2.2 | 3.6 | 3.6 | | |
| LSM 4 | 4.0 | | | | | | | | | | | | 2.2 | 3.6 | 3.6 | 3.7 | |
| LSM 7 | 4.0, 9.1 | 3.8 | 3.7 | 3.0, 3.4 | 3.6 | | | 3.2, 3.6 | | | 3.0, 4.0 | 3.3, 4.7 | 2.2, 9.6 | 3.6 | 2.3, 3.6 | 3.7 | |
| LSM 1 | 4.0, 9.1 | 3.8 | 3.7, 5.8 | 3.4 | | 6.3 | | 3.2 | 3.6 | 4.0 | 4.0 | | 2.2 | | 5.2 | | |
| LSM 10 | 4.0, 9.1 | 3.8 | 3.7 | 3.4 | 3.6, 4.3 | | 3.6, 6.3 | 3.2 | 3.6, 6.3 | 4.0 | 4.0 | 3.3, 4.7 | 2.2, 9.6 | 3.2, 3.6 | 3.6, 5.2 | 1.3, 3.7 | 4.3, 6.4 |
| LSM 2 | 4.0 | | 3.7 | | | 3.6 | 3.6 | | 3.6, 6.3 | 4.0 | 3.0, 4.0 | 4.7 | | | | | 4.3 |

Note:
All probes were tested versus HindIII digests of all strains. If no bands are listed none were detected. Strains Rx1 and D39 gave identical results and are shown in a single column. The full name of strain AC109 is AC109-1B

Example 6

Restriction Fragment Length Polymorphisms of pspA Reveals Grouping

Pneumococcal surface A (PspA) is a protection eliciting protein of Streptococcus pneumoniae. The deduced amino acid sequence of PspA predicts three distinct domains; an α-helical coiled-coil region, followed by two adjacent proline-rich regions, and ten 20 amino acid repeats. Almost all PspA molecules are cross-reactive with each other in variable degrees. However, using a panel of monoclonal antibodies specific for individual epitopes, this protein has been shown to exhibit considerable variability even within strains of the same capsular type. Oligonucleotide primers based on the sequence of pspA from S. pneumoniae Rx1 were used to amplify the full-length pspA gene and the 5' portion of the gene including the a-helical and the proline-rich region. PCR-amplified product were digested with Hha I or Sau3A I to visualize restriction fragment length polymorphism of pspA. Although strains were collected from around the world and represented 21 different capsular types, isolates could be grouped into 17 families or subfamilies based on their RFLP pattern. The validity of this approach was confirmed by demonstrating that pspA of individual strains which are known to be clonally related were always found within a single pspA family.

Numerous techniques have been employed in epidemiological surveillance of pneumococci which include serotyping, ribotyping, pulsed field electrophoresis, multilocus enzyme electrophoresis, penicillin-binding protein patterns, and DNA fingerprinting [Lefever, 1993] [Viering, 1989] [Markiewic, 19891. Previous studies have also utilized the variability of pneumococcal surface protein A (PspA) to differentiate pneumococci [Crain, 1990]. This protein, which can elicit protective antipneumococcal antibodies, is a virulence factor found on all pneumococcal isolates (McDaniel, 1991]. Although PspA molecules are commonly cross-reactive, they are seldom antigenically identical (Crain, 1990]. This surface protein is the most serologically diverse protein know on pneumococci; therefore, it is an excellent market to be used to follow individual strains. Variations in PspA and the DNA surrounding its structural gene have proven useful for differentiation of S. pneumoniae [McDaniel, 1992].

When polyclonal sera are used to identify PspA, cross-reaction is observed between virtually all isolates [Crain, 1990]. Conversely, when panels of monoclonal antibodies are used to compare PspA of independent isolation they are almost always observed to express different combinations of PspA epitopes. A typing system based on this approach has limitations because it does not easily account for differences in monoclonal binding strength to different PspA molecules. Moreover, some strains are weakly reactive with individual monoclonal antibodies and may not always give consistent results.

A less ambiguous typing system that takes advantage of the diversity of PspA was therefore necessary to develop and was used to examine the clonality of strains. This method involves examination of the DNA within and adjacent to the pspA locus. Southern hybridizations of pneumococcal chromosomal DNA digested with various endonucleases, such as Hind III, Dra I, or Kpn I, and probed with labeled pspA provided a means to study the variability of the chromosome surrounding pspA. When genomic DNA is probed, the pspA and the pspA-like loci are revealed. In most digests the pspA probe hybridizes to 2–3 fragments and, digests of independent isolates were generally dissimilar.

Like the monoclonal typing system, the Southern hybridization procedure permitted the detection of clones of pneumococci. However, it did not provide a molecular approach for following pspA diversity. Many of the restriction sites defining the restriction fragment length polymorphism (RFLP) were outside of the pspA gene, and it was difficult to differentiate the pspA gene from the pspA-like locus. In an effort to develop a system to follow pspA diversity Applicants examined the RFLP of PCR-amplified pspA. Amplified pspA was digested with Sau3A I and Hha I, restriction enzymes with four base recognition sites. To evaluate the utility of this approach pspA from clinical and laboratory strains known to be clonally related as well as random isolates were examined.

Bacterial Strains.

Figure 8:
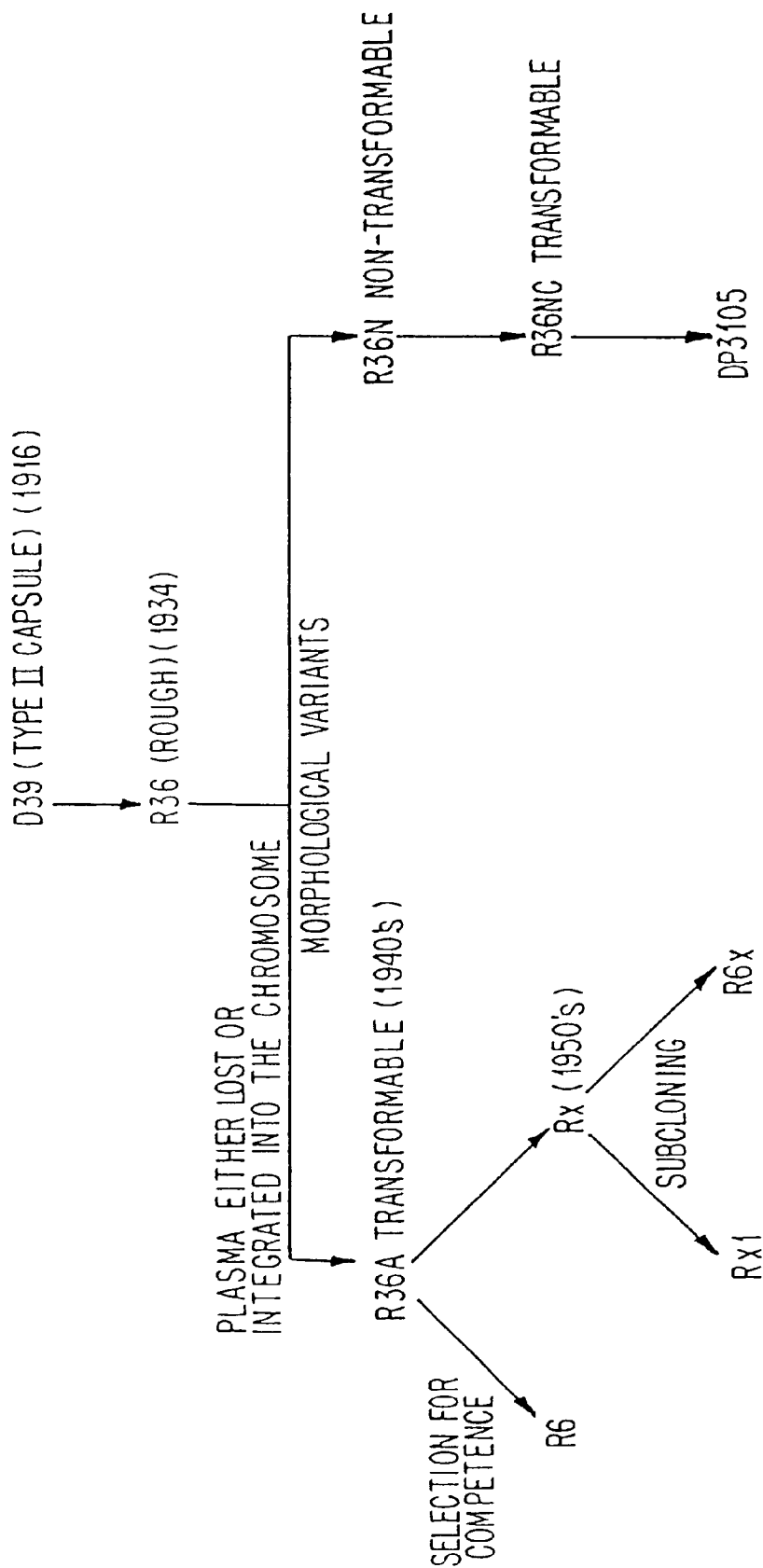
FIG. 8 shows: Derivatives of the S. pneumoniae D39-Rx1 family.

Derivatives of the *S pneumoniae* D39-Rx1 family were kindly provided by Rob Massure and Sanford Lacks (FIG. 8). Eight clinical isolates from Spain and four isolates from Hungary, a gift from Alexander Tomasz. Seventy-five random clinical isolates from Alabams, Sweden, Alaska, and Canada were also studied (Crain 1990, Tomaz and Crain, Waltamn).

PCR Amplifications.

The oligonucleotide primers used in this study are listed in Table 24. Chromosomal DNA, which was isolated according to procedures described by Dillard et al., was used as template for the PCR reactions. Amplification was accomplished in a 50 $\mu$l reaction containing approximately 50 ng template DNA, 0.25 U Taq, 50 $\mu$M of each primer, 175 $\mu$M MgCl 2, and 200 $\mu$M dNTP in a reaction buffer containing 10 $\mu$M Tris-HCl, pH 9.0, 50 $\mu$M KCl, 0.1% Triton X-100, 0.01% wt/vol. gelatin. The mixture was overlaid with mineral oil, and placed in a DNA thermal cycler. The amplification program consisted of an initial denaturation step at 94° C., followed by 29 cycles opf 94° C. for 1 min, 55° C. for 2 min, and 72° C. for 3 min. The final cycle included an incubation at 72° C. for 5 min.

Restriction Fragment Analysis of PCR-amplified Product.

Aliquots of the PCR mixtures were digested with Hha I or Sau3A I in a final volume of 20 $\mu$l according to manufacturer's protocols. After digestion the DNA fragments were electrophoresed on a 1.3% TBE agarose gel and stained with ethidium bromide. Fragment sizes were estimated by comparison to a 1 kb DNA ladder (Gibco BRL).

Because of the variability of pspA, and the fact that the entire pspA sequence is known for only one gene, it has not been possible to design primers which amplify pspA from 100% of pneumococcal strains. However, oligonucleotide primers, LSM2 and LSM1, can amplify an 800 bp region of the C-terminal end in 72 of the 72 stains tested. Based on hybridizations at different stringencies, this region was found to be relatively conserved in pneumococcal strains, and thus would not be expected to be optimal for following restriction polymorphisms within the pspA molecule. LSM13 and LSM2, primers which amplify the full length pspA gene, can amplify pspA from approximately 79% 55/75 of the strains tested (Table 25).

Stability of Amplified RFLP Pattern within Clonally Related Pneumococci

Figure 9:
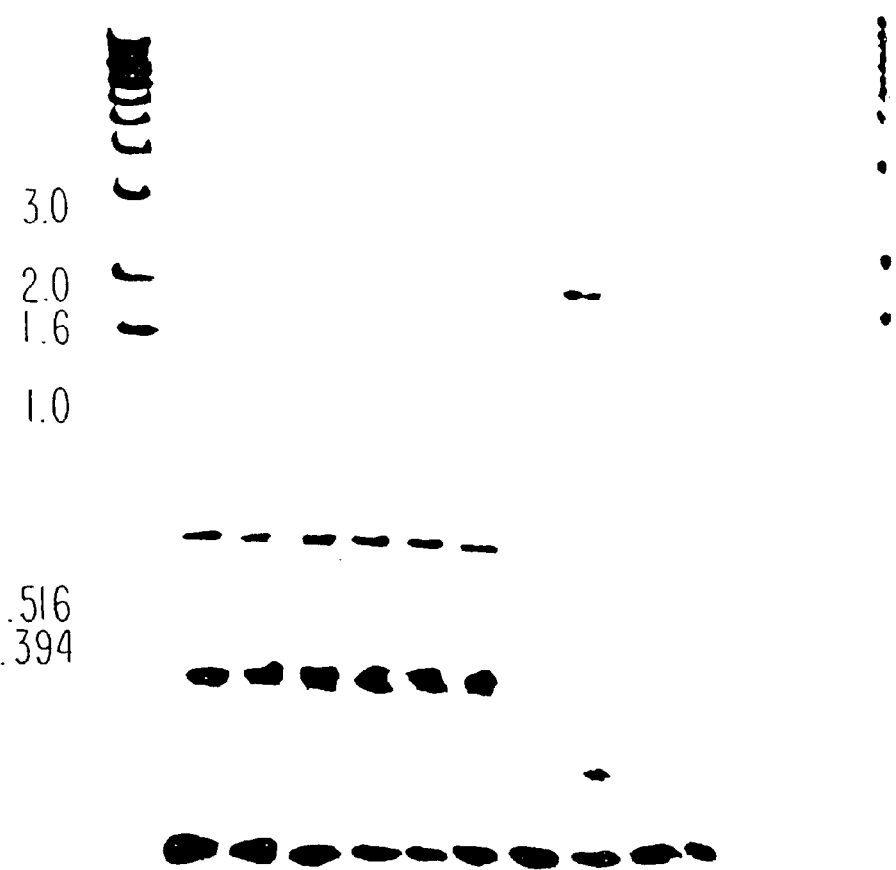
FIGS. 9 to 10 show: Electrophoresis of pspA or amplified pspA product with HhaI (FIG. 9), Sau3AI (FIG. 10).

To determine the stability of pspA during long passages in vitro, we examined the RFLP pattern of the pspA gene of the derivatives of the *S. pneumoniae* D39-Rx1 family. Rx1 is an acapsular derivative of *S. pneumoniae* D39, the prototypical pneumococcal laboratory strain isolated by Avery in 1914. Throughout the 1900's spontaneous and chemical mutations have been introduced into D39 by different laboratories (FIG. 8) [Smith, 1979]. During this period unencapsulated strains were maintained in vitro, and D39 was passed both in vivo and in vitro passage. All the derivatives of D39, including Rx1, R6, RNC, and R36A, produced a 1.9 kb fragment upon PCR amplification of full length pspA. All members of the family exhibited the RFLP pattern. Digestion with Sau3A I of PCR amplified full length pspA revealed a 0.83, 0.58, 0.36 and a 0.27 kb fragment in all of the D39-rX1 derivatives of the family. Digesting the full length pspA with Hha I resulted in bands which were 0.76. 0.47, 0.39, 0.35, and 0.12 kb (FIG. 9 or Table 26).

Figure 10:
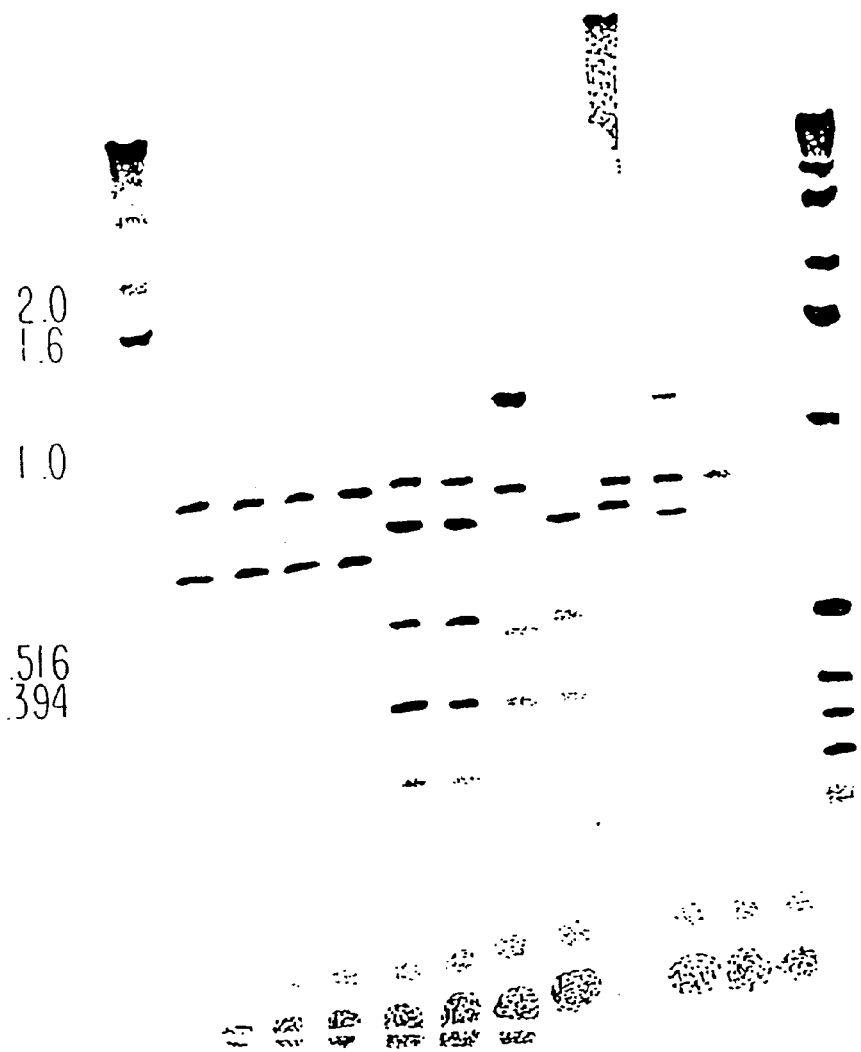

The stability of pspA polymorphism was also investigated using pneumococcal isolates which had previously been shown to be clonally related by other criteria, including capsule type, antibiotic resistance, enzyme electromorph, and PspA serotype. Three sets of isolates, all of which were highly penicillin resistant, were collected from patients during an outbreak in Hungary and two separate outbreaks in Spain. PCR amplified full length pspA from the capsular type 19A pneumococcal strains from the outbreak in Hungary, DB18, DB19, DB20, and DB21, resulted in a band approximately 2.0 kb. After digesting full length pspA with Hha I, four fragments were visualized., 89, 0.48, and 0.28 kb. Digestion with Sau3A I yielded five fragments 0.880, 0.75, 0.35, 0.34, and 0.10 kb. Capsule type 6B pneumococcal strains, DB1, DB2, DB3, and DB4, were obtained from an outbreak in Spain. Full length pspA from these strains were approximately 1.9 kb. Digestion of the PCR-amplified fragment with Hhs I resulted in four fragments which were 0.83, 0.43, 0.33, and 0.28 kb. Sau3A I digestion yield a 0.88, 0.75, 0.34, and 0.10 kg fragments. DB6, DB8, and DB9, which are capsular serotype 23F strains, were isolated from a second outbreak in Spain. DB6, DB8, and DB9 had an amplified pspA product which was 2.0 kb. Hha I digested fragments were 0.90, 0.52, 0.34, and 0.30 kb and Sau3A I fragments were 0.75, 0.52, 0.39, 0.22, 0.20, and 0.10 kb in size (FIG. 10). DB7 had a 19A capsular serotype and was not identical to DB6, DB8, and DB9. In the D39/Rx1 family and in each of the three outbreak families the size of the fragments obtained from the Hha I and the Sau3A I digests totaled approximately 2.0 kb which is expected if the amplified product represents a single pspA sequence.

Diversity of RFLP Pattern of Amplified pspA from Random Pneumococcal Isolates

PCR amplification of the pspA gene from 70 random clinical pneumococcal isolates yielded full-length pspA ranging in size from 1.8 kb to 2.3 kb. RFLP analysis of PCR-derived pspA revealed two to six DNA fragments ranging in size from 100 bp to 1.9 kb depending on the strain. The calculated sum of the fragments never exceeded the size of the original amplified fragment. Not all pneumococcal strains had a unique pspA, and some seemingly unrelated isolates from different geographical regions and different capsular types exhibited similar RFLP patterns. Isolates were grouped into families based on the number of fragments produced by Hha I and Sau3A I digests and the relative size of these fragments.

Based on the RFLP patterns it was possible to identify 17 families with four of the families containing pairs of subfamilies. Within families all of the restriction fragments were essentially the same regardless which restriction enzyme was used. The subfamilies represent situations where two families share most but not all the restriction fragments. With certain strains an FRLP pattern was observed where detectable fragment size differed from the pattern of the established family by less than 100 bp. Since the differences were considered small compared to the differences in the fragment size and the number of fragments between families, they were not considered in family designation. The RFLP pattern of two isolates from six of the families is pictured in FIG. 11, Table 27. These families were completely independent of the capsular type or the protein type as identified by monoclonal antibodies (Table 28 and 29).

Previous DNA hybridization studies have demonstrated that the pspA gene of different isolates are the most conserved in their 3' region of the gene and more variable in the 5' region of the gene. Thus, if seemed likely that the differences in the pspA families reflected primarily differences in the 5' end of the gene. To confirm this theory, the a helical and proline region of pspA was examined without the amino acid repeats. Nucleotide primers LSM13 and KSH2 were used to amplify this fragment which is approximately 1.6 kb. Examination of this region of pspA afforded two things.

This primer pair permitted amplification of 90% of the strains which is greater than the 75% of the strains which can be amplified with oligonucleotides which amplify the full length gene. Second, it allowed Applicants to examine if the original groupings which were based on the full length gene coincide with the fingerprint patterns obtained by looking at the 5' half of the gene.

Figure 11:
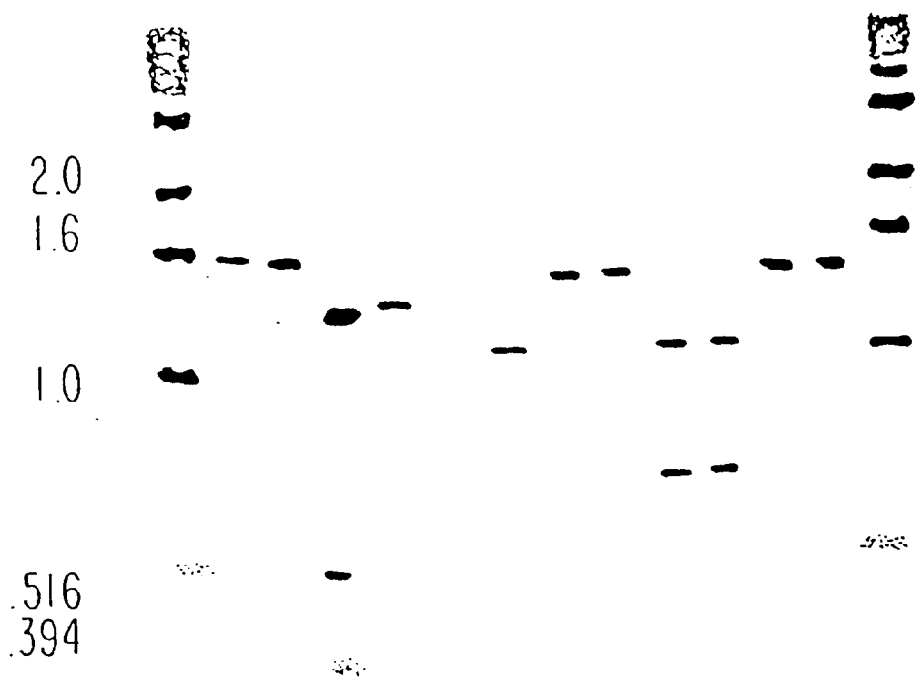
FIG. 11 shows: RFLP pattern of two isolates from six families.

FIG. 12 contains the same strains which were examined in FIG. 11 but the PCR products were amplified with SKH2 and LSM13. The RFLP patterns obtained from digestion of the amplified a helical and proline rich region confirms the original designated families. However, these primers amplify a smaller portion of the psaA and therefore the difference is the families is not as dramatic as the RFLP patterns obtained from the RFLP pattern of the full length gene.

The polymerase chain reaction has simplified the process of analyzing pspA gene and have provided a means of using pspA diversity to examine the epidemiology of S. pneumoniae. Because not all strains contained a unique fingerprint of pspA, RFLP patterns of pspA cannot be used alone to identify the clonality of a strain. Our results indicate the RFLP of PCR-amplified pspA from pneumococcal strains in conjunction with other techniques may be useful for identifying the clonal relatedness among pneumococcal isolates, and that this pattern is stable over long passages in vitro.

These finding suggests that the population of pspA is not as diverse as originally believed. PCR-RFLP of pspA may perhaps represent a relatively simplistic technique to quickly access the variability of the gene within a population. Further, these findings enable techniques to diagnose. S. pneumoniae via PCR or hybridization by primers on probes to regions of pspA common within groupings.

The sequence studies divide the known strains into several families based on sequence homologies. Sequence data demonstrates that there have been extensive recombinations occurring in nature within pspA genes. The net effect of the recombination is that the "families" identified by specific sequences differ depending upon which part of the pspA molecule is used for analysis. "Families" or "grouping identified by the 5' half of the alpha-helical region, the 3' half of the α-helical regions and the proline rich region are each distinct and differ slightly from each other. In addition there is considerable evidence of other diversity (including base substitutions and deletions and insertions in the sequences) among othenvise closely related molecules.

This result indicates that it is expected that there will be a continuum of overlapping sequences of PspAs, rather than a discrete set of sequences.

The findings indicate that there is the greatest conservation of sequence in the 3' half of the α-helical region and in the immediate 5' tip. Because the diversity in the mid half of the α-helical region is greater, this region is of little use in predicting cross-reactivity among vaccine components and challenge strains. Thus, the sequence of 3' half of the alpha-helical region and the 5' tip of the coding sequence are likely to the critical sequences for predicting PspA cross-reactions and vaccine composition.

The sequence of the proline-rich region may not be particularly important to composition of a vaccine because this region has not been shown to be able to elicit cross-protection even though it is highly conserved. The reason for this is presumably because antibodies to epitopes in this region are not surface exposed.

Figure 13H:
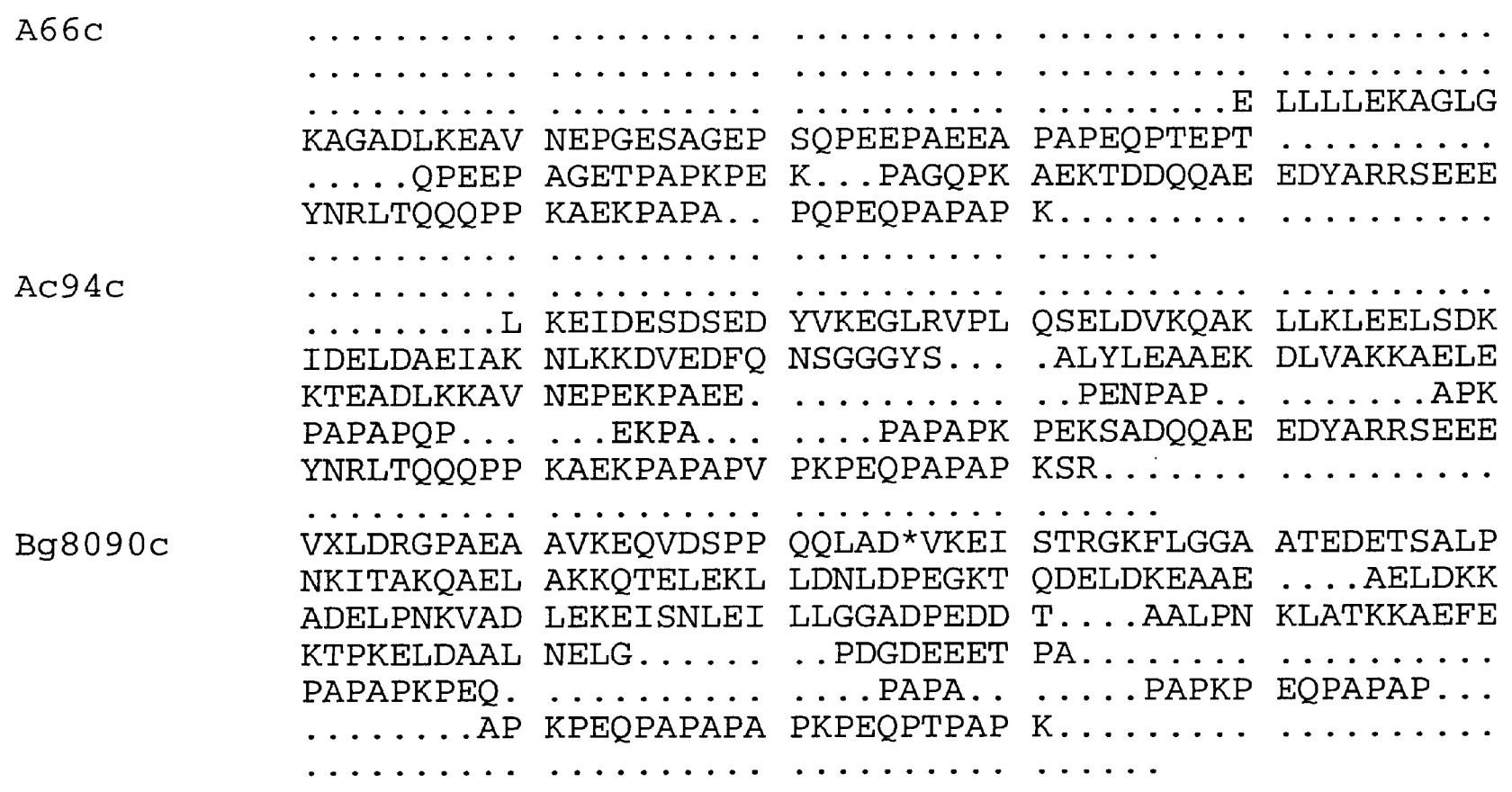

Based on our present sequences of 27 diverse pspAs we have found that there are 4 families of the 3' half of the α-helical region and 2–3 families of the very 5' tip the α-helical region. Together these form 6 combinations of the 3' and 5' families. This approach therefore should permit us to identify a panel of pspAs with 3' and 5' helical sequences representative of the greatest number of different pspas. See FIG. 13.

TABLE 24

Oligonucleotides used in this study.

| Designation | Sequence 5'-3' | Nucleotide position |
|---|---|---|
| LSM2 | GCG CGT CGA CGG CTT AAA CCC ATT CAC CAT TGG | 1990 to 1967 |
| LSM1 | CCG GAT CCA GCT CCT GCA CCA AAA AC | 1312 to 1331 |
| LSM13 | GCA AGC TTA TGA TAT AgA AAT TTG TAA C | 1 to 26 |
| SKH2 (Sequence ID No. 16) | CCA CAT ACC GTT TTC TTG TTT CCA GCC | 1333 to 1355 |

TABLE 25

Amplification of pspA from a panel of 72 independent isolates* of S. pneumoniae.

| CAPSULE TYPE | NUMBER OF STRAINS EXAMINED | LSM13 AND LSM2 % OF STRAINS AMPLIFIED | LSM13 AND SKH2 % OF STRAINS AMPLIFIED |
|---|---|---|---|
| 1 | 3 | 100 | 100 |
| 2 | 1 | 100 | 100 |
| 3 | 8 | 50 | 87 |
| 4 | 6 | 67 | 100 |
| 5 | 1 | 100 | 100 |
| 6 | 7 | 29 | 86 |
| 6A | 2 | 100 | 100 |
| 6B | 6 | 100 | 100 |
| 7 | 2 | 50 | 100 |
| 8 | 1 | 100 | 100 |
| 9V | 3 | 100 | 100 |
| 9A | 2 | 100 | 100 |
| 9L | 1 | 100 | 100 |
| 9N | 3 | 100 | 100 |
| 10 | 1 | 100 | 100 |
| 11 | 2 | 50 | 100 |
| 12 | 2 | 0 | 100 |
| 13 | 1 | 100 | 100 |
| 14 | 4 | 0 | 75 |
| 15 | 2 | 50 | 50 |
| 19 | 5 | 100 | 100 |
| 22 | 3 | 33 | 100 |
| 23 | 1 | 100 | 100 |
| 33 | 1 | 0 | 100 |
| 35 | 1 | 0 | 100 |
| nd | 3 | 100 | 100 |

TABLE 25-continued

Amplification of pspA from a panel of 72 independent isolates* of *S. pneumoniae*.

| CAPSULE TYPE | NUMBER OF STRAINS EXAMINED | LSM13 AND LSM2 % OF STRAINS AMPLIFIED | LSM13 AND SKH2 % OF STRAINS AMPLIFIED |
|---|---|---|---|

*Our strain collection contains several groups of isolates known to be previously to be clonal and collected for that purpose. The data reported in the table includes only one representative isolate from such clonal groups.

TABLE 26

Rx1-D39 derivatives

| ISOLATE | SIZE OF Hha I DIGEST (Kb) | SIZE OF Sau3A I DIGESTS (Kb) |
|---|---|---|
| D39 | .76, .47, .39, .35, .12 | .83, .58, .36, .27 |
| Rx1 | .76, .47, .39, .35, .12 | .83, .58, .36, .27 |
| R800 | 76, .47, .39, .35, .12 | .83, .58, .36, .27 |
| R6 | 76, .47, .39, .35, .12 | .83, .58, .36, .27 |
| R61 | 76, .47, .39, .35, .12 | .83, .58, .36, .27 |
| R6X | .76, .47, .39, .35, .12 | .83, .58, .36, .27 |

TABLE 26-continued

Rx1-D39 derivatives

| ISOLATE | SIZE OF Hha I DIGEST (Kb) | SIZE OF Sau3A I DIGESTS (Kb) |
|---|---|---|
| R36NC | .76, .47, .39, .35, .12 | .83, .58, .36, .27 |
| R36A | .76, .47, .39, .35, .12 | .83, .58, .36, .27 |

TABLE 27

Strain information and family designation of independent isolates.

| STRAIN | CAPSULE TYPE | PspA TYPE | FAMILY | SIZE OF Hha I FRAGMENTS | SIZE OF Sau3A I FRAGMENTS |
|---|---|---|---|---|---|
| BG9163 | 6B | 21 | C | 1.55, .35 | 1.05, .35, .22 |
| EF6796 | 6A | 1 | C | 1.5, .35 | 1.05, .35, .22 |
| EF5668 | 4 | 12 | DD | 1.25, .49, .32 | 1.0, .80, .35 |
| EF8616A | 4 | ND | DD | 1.25, .49, .32 | 1.0, .80, .35 |
| EF3296 | 4 | 20 | E | 1.0, .40, .33 | 1.15, .50, .34 |
| EF4135 | 4 | ND | E | 1.0, .40, .33 | 1.15, .50, .34 |
| BG7619 | 10 | ND | F | 1.3, .40, .29, .10 | .82, .76, .35 |
| BG7941 | 11 | ND | F | 1.3, .40, .29, .10 | .82, .76, .35 |
| BG7813 | 14 | 8 | H | 1.05, .70, .36 | .90, .77, .35 |
| BG7736 | 8 | ND | H | 1.05, .70, .36 | .90, .77, .35 |
| AC113 | 9A | ND | I | 1.4, .34, .28 | 1.2, .80 |
| AC99 | 9V | 5 | I | 1.4, .34, .28 | 1.2, .80 |

TABLE 28

Relationship of RFLP family and PspA type.
RELATIONSHIP BETWEEN PSPA TYPE AND RFLP FAMILY

| pspA FAMILY | \multicolumn{20}{c}{PspA Type} |
|---|---|

| pspA FAMILY | 0 | 1 | 3 | 5 | 8 | 12 | 13 | 16 | 18 | 19 | 20 | 21 | 24 | 25 | 26 | 30 | 33 | 34 | 36 | 37 | ND |
|---|---|---|---|---|---|---|---|---|---|---|---|---|---|---|---|---|---|---|---|---|---|
| A |  | 1 |  |  | 1 |  |  |  |  |  |  |  |  |  |  |  |  |  |  |  |  |
| B |  |  |  |  |  |  |  |  |  |  |  |  |  | 1 | 1 |  |  |  |  |  | 1 |
| C |  | 2 |  |  |  |  |  |  |  |  |  | 1 | 1 |  |  |  |  |  |  |  | 4 |
| D |  |  |  |  |  |  | 1 |  | 1 |  |  |  |  |  |  |  |  |  |  |  |  |
| DD |  |  |  |  |  | 2 |  |  |  |  |  |  |  |  |  |  |  |  |  |  |  |
| E |  |  | 1 |  |  |  |  |  |  |  | 1 |  |  |  | 1 |  |  |  |  |  |  |
| F |  |  |  |  |  | 1 |  |  |  |  |  |  |  |  |  |  | 1 |  |  |  | 4 |
| FF |  |  |  |  |  |  |  |  |  |  |  |  |  |  | 1 |  |  |  |  |  | 3 |
| G |  |  |  |  |  |  | 1 |  |  |  |  |  |  |  |  |  |  | 1 |  |  |  |
| H | 1 |  |  |  | 1 |  | 1 |  |  | 1 |  |  |  |  |  |  |  |  |  |  | 5 |
| I | 3 |  |  | 1 |  |  | 2 | 2 |  |  |  |  |  |  |  |  |  |  |  |  | 1 |
| II |  |  |  |  |  |  |  |  |  |  |  |  |  |  |  | 1 |  |  |  |  |  |
| J | 4 |  |  |  |  |  |  |  | 1 | 1 |  |  |  |  |  |  |  |  |  | 1 | 3 |
| K | 1 |  |  |  |  |  |  |  |  | 1 |  |  |  | 1 |  |  |  |  |  |  |  |
| KK | 1 |  |  |  |  |  |  |  |  |  |  |  |  |  |  |  |  |  |  | 1 | 3 |
| L |  |  |  |  |  | 1 |  |  |  |  |  |  |  |  |  |  |  |  |  |  | 1 |
| M |  |  |  |  |  |  | 1 | 1 |  |  |  |  |  |  |  |  |  |  | 1 |  | 1 |
| MM |  |  |  |  |  | 1 |  |  |  |  |  |  |  |  |  |  |  |  |  |  |  |

TABLE 29

Relationship of Capsular type and RFLP family.
RELATIONSHIP BETWEEN CAPSULAR TYPE AND RFLP FAMILY Capsule Type

| pspA Family | 1 | 2 | 3 | 4 | 5 | 6 | 6A | 6B | 7 | 8 | 9A | 9L | 9N | 9V | 10 | 11 | 12 | 13 | 14 | 15 | 19 | 22 | 23 | 31 | 33 | 35 | ND |
|---|---|---|---|---|---|---|---|---|---|---|---|---|---|---|---|---|---|---|---|---|---|---|---|---|---|---|---|
| A |   |   | 3 |   |   |   |   |   |   |   |   |   |   |   |   |   |   |   |   |   |   |   |   |   |   |   |   |
| B |   |   | 1 | 1 |   |   |   |   |   |   |   |   |   |   |   |   |   |   |   |   |   |   |   |   |   |   |   |
| C |   |   |   |   |   | 2 | 1 | 2 |   |   |   |   |   |   |   |   |   |   |   |   | 2 |   |   |   |   |   | 1 |
| D |   |   | 1 |   |   |   |   | 1 |   |   |   |   |   |   |   |   |   |   |   |   |   |   |   |   |   |   |   |
| DD |   |   |   |   | 2 |   |   |   |   |   |   |   |   |   |   |   |   |   |   |   |   |   |   |   |   |   |   |
| E |   |   | 1 | 2 |   |   | 1 |   |   |   |   |   |   |   |   |   |   |   |   |   |   |   |   |   |   |   |   |
| F |   |   |   |   |   |   | 1 |   |   |   |   |   |   |   |   |   |   | 1 |   |   |   |   | 3 |   |   |   | 1 |
| FF |   |   | 1 |   |   |   | 1 |   |   |   |   |   |   |   | 1 | 1 |   |   |   |   |   |   |   |   |   |   |   |
| G |   |   |   |   |   |   |   |   |   |   |   |   |   |   |   |   |   | 1 |   |   |   | 1 |   |   |   |   |   |
| H |   |   | 1 |   |   |   | 1 |   | 2 | 1 |   |   |   |   |   |   |   | 1 |   | 1 | 1 | 1 |   |   |   |   |   |
| I |   |   |   |   |   |   |   |   |   |   | 2 |   | 2 | 4 |   |   |   |   |   |   |   |   |   |   |   |   |   |
| II |   |   |   |   | 1 |   |   |   |   |   |   |   |   |   |   |   |   |   |   |   |   |   |   |   |   |   |   |
| J | 2 |   |   |   |   |   | 2 |   |   |   |   | 1 | 1 |   |   |   |   | 1 | 2 |   | 2 |   |   |   |   |   | 1 |
| K |   | 1 |   |   |   |   |   |   |   |   |   |   |   |   |   |   |   |   |   |   |   | 1 |   | 1 |   |   |   |
| KK | 1 |   |   |   |   |   | 1 |   |   | 1 |   |   |   |   |   |   |   | 1 |   |   | 1 |   |   |   |   |   |   |
| L |   |   |   |   |   |   |   |   |   |   |   |   |   |   |   |   |   |   |   |   |   | 1 |   |   |   |   | 1 |
| M |   |   |   |   |   |   |   |   |   | 1 |   |   |   |   |   |   |   |   |   |   |   |   |   | 1 |   |   |   |
| MM |   |   |   |   |   |   |   |   |   |   |   |   |   |   |   |   |   |   | 1 |   |   |   |   |   |   |   |   |

Example 7

Ability of PspA Immunogens to Protect Against Individual Challenge Strains

Protocol: CBA/N or BALB cJ mice were given 1 injection of 0.5 μg PspA in CFA, followed 2 weeks later by a boost in saline, and challenged between 7 and 14 (average 10) days post boost. Control mice were administered a similar immunization regimen, except that the immunization came from an isogeneic strain unable to make PspA. The PspA was either full length, isolated from pneumococci or cloned full length or BC100 PspA, as little statistical significance has been seen in immunogenicity between full length PspA and BC100. The challenge doses ranged from about $10^3$ to $10^4$ pneunocci in inoculum, but in all cases the challenge was at least 100 times $LD_{50}$.

Result: The results are shown in the following Tables 30 to 60, and the conclusions set forth therein. From the data, it appears that an antigenic, immunological or vaccine composition can contain any two to seven, preferably three to five PspA, e.g., PspAs from R36A and BG9739, alone, or combined with any or all of PspAs from Wu2, Ef5668, and DB15. Note that surprisingly Wus PspA provided better protection against D39 that did R36a/Rx1/D39, and that also surprisingly PspA from Wu2 protected better against BG9739 than did PspA from BG9739. Combinations containing R36A, BG9739 and WU2 PspAs were most widely protective; and therefore, a preferred composition can contain any three PspA, preferably R36A, BG9739 and WU2. The data in this Example shows that PspA from varying strains is protective, and that it is possible to formulate protective compositions using any PspA or any combination of the PspAs from the eight different PspAs employed in the tests. Similarly, one can select PspaS on the basis of the groupings in the previous Example. Note additionally that each of PspA from R36A, BG9739, EF5668 and DBL5 are, from the data, good for use in compositions.

A Note About use of Medians Rather Than Averages.

Applicants have chosen to express data as median (a nonparametric parameter) rather than averages because the times to death do not follow a normal distribution. In fact there are generally two peaks. One is around day 3 or 6 when most of the mice die and the other is at >21 for mice that live. Thus, it becomes nonsensical to average values like 21 or 22 with values like 3 or 6. One mouse that lives out of 5 has a tremendous effect on such an average but very little effect on the median. Thus, the median becomes the most robust estimate of time to death of most of the mice.

Having thus described in detail certain preferred embodiments of the present invention, it is to be understood that the invention defined by the appended claims is not to be limited by particular details set forth in the above description, as many apparent variations thereof are possible without departing from the spirit or scope thereof.

TABLE 30

Relative ability of different PspAs to Protect against each challenge strains of *S. pneumoniae*
(Summary of statistically significant protection)

| | | | | Vaccine PspA | | | | | | | | |
|---|---|---|---|---|---|---|---|---|---|---|---|---|
| Challenge Strain | Caps type | PspA type | pspA family | R36A, Rx1, D39 K | JD908/ WU2 a | JS1020/ BG9739 b | EF3296 E | EF5668 DD | L81905 b | JS5010.3 DBL5 II | JS3020 DBL6A D | All immune — | best protect — |
| D39 | 2 | 25 | K | ++ | +++ | | + | | | | ++ | +++ |
| WU2 | 3 | 1 | a | +++ | +++ | +++ | +++ | +++ | +++ | +++ | +++ | +++ |

TABLE 30-continued

Relative ability of different PspAs to Protect against each challenge strains of *S. pneumoniae*
(Summary of statistically significant protection)

| Challenge Strain | Caps type | PspA type | pspA family | R36A, Rx1, D39 K | JD908/ WU2 a | JS1020/ BG9739 b | EF3296 E | EF5668 DD | L81905 b | JS5010.3 DBL5 II | JS3020 DBL6A D | All immune — | best protect — |
|---|---|---|---|---|---|---|---|---|---|---|---|---|---|
| A66 | 3 | 13 | a | +++ | +++ | +++ | | +++ | +++ | +++ | +± | +++ | +++ |
| EF10197 | 3 | 18 | M | +++ | | +++ | | | | | | +++ | +++ |
| ATCC6303 | 3 | 7 | a | +++ | | | | | | | | +++ | +++ |
| BG9739 | 4 | 26 | b | + | +++ | + | 0+ | 0 | +± | 0 | 0 | ++ | +++ |
| EF3296 | 4 | 20 | E | +± | +± | 0+ | | | | 0 | 0 | 0 | +± |
| EF5668 | 4 | 12 | DD | + | 0 | +++ | 0+ | +++ | 0+ | + | 0+ | ++ | +++ |
| L81905 | 4 | 23 | b | + | + | ++ | ++ | 0 | + | +± | +± | ++ | ++ |
| DBL5 | 5 | 33 | II | + | | + | | + | + | ++ | 0 | ++ | ++ |
| EF6796 | 6A | 11 | C | +++ | | | | | | | | +++ | +++ |
| DBL6A | 6A | 19 | D | +++ | +± | ++ | +± | +++ | +± | +± | +++ | ++ | +++ |
| BG9163 | 6B | 21 | C | +++ | | +++ | | | | | | +++ | +++ |
| BG7322 | 6B | 24 | C | +++ | +++ | +± | 0 | +++ | +± | +++ | +± | +++ | +++ |

Note:
Empty cells indicate that no experiment has been done. Bold means significant at P < 0.05, Small font bold (+) means $0.02 \leq P < 0.05$. Large font bold means P < 0.02. For this table statistical significance refers to delay in time to death except as indicate in the (+) footnote below. When "all immune" showed significant protection against death but individual data cells did not, the result for "all immune" is presented under best protection on the assumption that if more mice were done in each data cell one or more of them would have exhibited significant protection against death.
+++ = statistically significant protection against death; $\geq 50\%$ protection from death
++ = statistically significant protection against death; <50% protection from death
+± = statistically significant delay in death; $\geq 20$ protection from death
+ = statistically significant delay in death; <20 protection from death, (or significant protection against death but not a significant delay in death)
0++ = Not statistically delay in time to death; but $\geq 50\%$ protection from death
0+ = Not statistically delay in time to death; but <1.5 day extension in median time to death or $\geq 20\%$ protection from death.
0 = No apparent extension in time to death or protection from death.

TABLE 31

Relative ability of different PspAs to Protect against each challenge strains of *S. pneumoniae*
(Expressed as Median days Alive post challenge)

| Challenge Strain | Caps type | PspA type | pspA family | R36A, Rx1,D39 K | JD908 WU2 a | JS1020/ BG9739 b | EF3296 E | EF5668 DD | L81905 b | JS5010.3 DBL5 II | JS3020 DBL6A D | All immune — | All control — |
|---|---|---|---|---|---|---|---|---|---|---|---|---|---|
| D39 | 2 | 25 | K | 4.5 | >21 | | 4 | | | | | 5 | 2 |
| WU2 | 3 | 1 | a | >21 | >21 | >21 | | >21 | >21 | >21 | >21 | >21 | 2 |
| A66 | 3 | 13 | a | >21 | >21 | >21 | | >21 | >21 | >21 | 4 | >21 | 2 |
| EF10197 | 3 | 18 | M | >21 | | >21 | | | | | | >21 | 2 |
| ATCC6303 | 3 | 7 | a | >21 | | | | | | | | >21 | 5 |
| BG9739 | 4 | 26 | b | 3 | >21 | 6 | 3 | 3 | 5, 13 | 2 | 2 | 3 | 2 |
| EF3296 | 4 | 20 | E | 5 | 5 | 4.5 | | | | 2 | 2 | 3 | 2 |
| EF5668 | 4 | 12 | DD | 6 | 2 | >21 | 13 | >21 | 4 | >21 | 5 | 8 | 3 |
| L81905 | 4 | 23 | b | 5 | 5 | 8 | 6 | 3 | 5 | 3 | 3.5 | 5 | 2 |
| DBL5 | 5 | 33 | II | 4 | | 3 | | 3 | 3.5 | 6 | 2 | 3.5 | 2 |
| EF6796 | 6A | 1 | C | >21 | | | | | | | | >21 | 1 |
| DBL6A | 6A | 19 | D | >21 | 8.5 | 13 | 9 | >21 | 8 | 12 | >21 | 12.5 | 5.5 |
| BG9163 | 6B | 21 | C | >21 | | >21 | | | | | | >21 | 8.5 |
| BG7322 | 6B | 24 | C | >21 | >21 | 14.5 | 6 | >21 | 12.5 | >21 | 11 | >21 | 7 |

Note:
Bold denotes statistically significant extension of life at P < 0.05. Small font denotes $0.02 \leq P < 0.05$; large font denotes P > 0.02. Median times to death indicated as 8, >21, are situations where the medium as not within a continuum of values. In those cases the numbers shown are those closest to the median. In these cases the values give are those closest to the calculated median. Fractional values such as 3.5, indicate that the median is halfway between two numbers, in this case 3 and 4. As indicated in the original data (S103B), some experiments were terminated prior to 21 days post infection. There is little reason to assume, however, that results would have been significantly effected by the early termination's since very few mice infected with the strains used in those studies, have ever been observed to die later than 10 or 15 days post challenge. For statistical purposes all mice alive at the end of experiments were assumed to have been completely protected, and for the sake of calculations all surviving mice were assigned values of >21.

TABLE 32

Ability of different PspAs to Protect Against Each Challenge strain of *S. pneumoniae*
(Expressed as increase in survival time in days)
(A denotes ≥ 50% immune mice alive)

| Challenge Strain | Caps type | PspA type | pspA family | R36A, Rx1,D39 K | JD908 WU2 a | JS1020/ BG9739 b | EF3296 E | EF5668 DD | L81905 b | JS5010.3 DBL5 II | JS3020 DBL6A D | All immune | Best Result |
|---|---|---|---|---|---|---|---|---|---|---|---|---|---|
| D39 | 2 | 25 | K | 2.5 | A | | | 2 | | | | 3 | A |
| WU2 | 3 | 1 | a | A | A | A | | A | A | A | A | A | A |
| A66 | 3 | 13 | a | A | A | A | | A | A | A | 2 | A | A |
| EF10197 | 3 | 18 | M | A | | A | | | | | | A | A |
| ATCC6303 | 3 | 7 | a | A | | | | | | | | A | A |
| BG9739 | 4 | 26 | b | 1 | A | 4 | 1 | 1 | 3, 11 | 0 | 0 | 1 | A |
| EF3296 | 4 | 20 | E | 3 | 3 | 2.5 | | | | 0 | 0 | 1 | 3 |
| EF5668 | 4 | 12 | DD | 3 | −1 | A | 10 | A | 1 | A | 2 | 5 | A |
| L81905 | 4 | 23 | b | 3 | 3 | 6 | 4 | 1 | 3 | 1 | 1.5 | 3 | 6 |
| DBL5 | 5 | 33 | II | 2 | | 1 | | 1 | 1.5 | 4 | 0 | 1.5 | 4 |
| EF6796 | 6A | 1 | C | A | | | | | | | | A | A |
| DBL6A | 6A | 19 | D | A | 3 | 7.5 | 3.5 | A | 2.5 | 6.5 | A | 7 | A |
| BG9163 | 6B | 21 | C | A | | A | | | | | | A | A |
| BG7322 | 6B | 24 | C | A | A | 7.5 | −1 | A | 5.5 | A | 4 | A | A |
| | | | | R36A | WU2 | BG9739 | EF3296 | EF5668 | L81905 | DBL5 | DBL6A | All | Best |

Note:
Bold denotes statistically significant extension of life at P < 0.05. Small font denotes 0.02 ≤ P ≤ 0.05; large font denotes P < 0.02. Median increases in survival listed as 3, 9 or 1,A denote groups where the median does not fall within a continuum of values. In these cases the values give are those closest to the calculated median. Fractional values such as 3.5, indicate that the median is halfway between two numbers, in this case 3 and 4.

TABLE 33

Relative ability of different PspAs to Protect against each challenge strains of *S. pneumoniae*
(expressed % alive at 21 days post challenge)

| Challenge Strain | Caps type | PspA type | pspA family | R36A, Rx1,D39 K | JD908 WU2 a | JS1020/ BG9739 b | EF3296 E | EF5668 DD | L81905 b | JS5010.3 DBL5 II | JS3020 DBL6A D | All immune | Best Result |
|---|---|---|---|---|---|---|---|---|---|---|---|---|---|
| D39 | 2 | 25 | K | 38 | 60 | | | 30 | | | | 38 | 3 |
| WU2 | 3 | 1 | a | 100 | 100 | 100 | | 100 | 100 | 100 | 100 | 100 | 1.5 |
| A66 | 3 | 13 | a | 75 | 100 | 80 | | 75 | 100 | 60 | 20 | 76 | 5 |
| EF10197 | 3 | 18 | M | 100 | | 80 | | | | | | 90 | 0 |
| ATCC6303 | 3 | 7 | a | 100 | | | | | | | | 100 | 0 |
| BG9739 | 4 | 26 | b | 11 | 60 | 13 | 25 | 0 | 25 | 0 | 0 | 12 | 0 |
| EF3296 | 4 | 20 | E | 25 | 20 | 10 | | | | 0 | 0 | 8 | 0 |
| EF5668 | 4 | 12 | DD | 22 | 25 | 60 | 40 | 100 | 40 | 60 | 0 | 41 | 9 |
| L81905 | 4 | 23 | b | 10 | 0 | 31 | 40 | 0 | 0 | 14 | 0 | 14 | 0 |
| DBL5 | 5 | 33 | II | 10 | | 14 | | 0 | 0 | 29 | 0 | 4 | 0 |
| EF6796 | 6A | 1 | C | 100 | | | | | | | | 100 | 0 |
| DBL6A | 6A | 19 | D | 67 | 25 | 33 | 0 | 60 | 25 | 0 | 80 | 35 | 4 |
| BG9163 | 6B | 21 | C | 89 | | | | 80 | | | | 86 | 20 |
| BG7322 | 6B | 24 | C | 100 | 60 | 25 | 0 | 89 | 25 | 80 | 25 | 55 | 6 |

Bold, denotes statistically significant protection against death at P < 0.05. Bold small font, indicates significant protection against death at 0.02 ≤ P ≤ 0.05. Bold large font, indicates significant protection against death at P < 0.02.

TABLE 34

Relative ability of different PspAs to Protect against each challenge strain of *S. pneumoniae*
(% protected from death at 21 days post challenge)

| Challenge Strain | Caps type | PspA type | pspA family | R36A, Rx1,D39 K | JD908 WU2 a | JS1020/ BG9739 b | EF3296 E | EF5668 DD | L81905 b | JS5010.3 DBL5 II | JS3020 DBL6A D | All immune | Best Result |
|---|---|---|---|---|---|---|---|---|---|---|---|---|---|
| D39 | 2 | 25 | K | 36 | 59 | | | 28 | | | | 36 | 59 |
| WU2 | 3 | 1 | a | 100 | 100 | 100 | | 100 | 100 | 100 | 100 | 100 | 100 |
| A66 | 3 | 13 | a | 71 | 100 | 79 | | 74 | 100 | 58 | 16 | 75 | 100 |
| EF10197 | 3 | 18 | M | 100 | | 80 | | | | | | 90 | 100 |

TABLE 34-continued

Relative ability of different PspAs to Protect against each challenge strain of *S. pneumoniae*

(% protected from death at 21 days post challenge)

| | | | | Vaccine PspA | | | | | | | | | |
|---|---|---|---|---|---|---|---|---|---|---|---|---|---|
| Challenge Strain | Caps type | PspA type | pspA family | R36A, Rx1,D39 K | JD908 WU2 a | JS1020/ BG9739 b | EF3296 E | EF5668 DD | L81905 b | JS5010.3 DBL5 II | JS3020 DBL6A D | All immune | Best Result |
| ATCC6303 | 3 | 7 | a | 100 | | | | | | | | 100 | 100 |
| BG9739 | 4 | 26 | b | 11 | 60 | 13 | 25 | 0 | 25 | 0 | 0 | 12 | 60 |
| EF3296 | 4 | 20 | E | 25 | 20 | 10 | | | | 0 | 0 | 8 | 25 |
| EF5668 | 4 | 12 | DD | 14 | 18 | 56 | 34 | 100 | 34 | 56 | −10 | 35 | 100 |
| L81905 | 4 | 23 | b | 10 | 0 | 31 | 40 | 0 | 0 | 14 | 0 | 14 | 40 |
| DBL5 | 5 | 33 | II | 10 | | 14 | | 0 | 0 | 29 | 0 | 4 | 29 |
| EF6796 | 6A | 1 | C | 100 | | | | | | | | 100 | 100 |
| DBL6A | 6A | 19 | D | 66 | 22 | 30 | −4 | 58 | 22 | −4 | 79 | 33 | 79 |
| BG9163 | 6B | 21 | C | 86 | | 75 | | | | | | 83 | 86 |
| BG7322 | 6B | 24 | C | 100 | 57 | 22 | 0 | 88 | 22 | 79 | 22 | 52 | 100 |

Bold, denotes statistically significant protection against death at P < 0.05. Bold small font, indicates significant protection against death at 0.02 ≦ P ≦ 0.05. Bold large font, indicates significant protection against death at P < 0.02.

% protected has been corrected for any survivors in the control mice.

% protected = 100 × (% alive in immune − % alive in control)/(100 − % alive in control). Thus if there were any mice alive in the control animals, the calculated "% protected" is less than the observed "% alive" listed in the previous table. The only exceptions to this are if 100% of immunized mice lived. Negative numbers mean that less immunized mice lived than did control mice. Please note that none of these negative numbers are significant even though we are using a one tailed test.

TABLE 35

Recommended Immunogens to Protection against the indicated challenge strains of *S. pneumoniae* Based on Protection Score
Based on median days alive and percent protected
(numbers refer to preference as a vaccine strain with respect to the indicated challenge strain, 1 = best)

| | | | | Vaccine PspA | | | | | | | |
|---|---|---|---|---|---|---|---|---|---|---|---|
| Challenge Strain | Caps type | PspA type | pspA family | R36A, Rx1,D39 K | JD908 WU2 a | JS1020/ BG9739 b | EF3296 E | EF5668 DD | L81905 b | JS5010.3 DBL5 II | JS3020 DBL6A D |
| D39 | 2 | 25 | K | 2 | 1 | | | 3 | | | |
| WU2 | 3 | 1 | a | 1 | 1 | 1 | | 1 | 1 | 1 | 1 |
| A66 | 3 | 13 | a | 2 | 1 | 2 | | 2 | 1 | 3 | 0 |
| EF10197 | 3 | 18 | M | 1 | | 2 | | | | | |
| ATCC6303 | 3 | 7 | a | 1 | | | | | | | |
| BG9739 | 4 | 26 | b | 3 | 1 | 2 | 3 | 3 | 2 | 0 | 0 |
| EF3296 | 4 | 20 | E | 1 | 1 | 2 | | | | 0 | 0 |
| EF5668 | 4 | 12 | DD | 0 | 0 | 2 | 3 | 1 | 0 | 2 | 0 |
| L81905 | 4 | 23 | b | 2 | 0 | 1 | 1 | 0 | 0 | 0 | 0 |
| DBL5 | 5 | 33 | II | 2 | | 3 | | 0 | 3 | 1 | 0 |
| EF6796 | 6A | 1 | C | 1 | | | | | | | |
| DBL6A | 6A | 19 | D | 2 | 0 | 3 | 0 | 2 | 0 | 0 | 1 |
| BG9163 | 6B | 21 | C | 1 | | 1 | | | | | |
| BG7322 | 6B | 24 | C | 1 | 2 | 3 | | 1 | 3 | 1 | 3 |
| Number of #1's | | | | 7 | 5 | 3 | 1 | 3 | 2 | 3 | 2 |

Bold, denotes statistically significant protection against death at P < 0.05. Where more than one PspA were equally protective, the same values were given to each. Recommendations are based on days to death with % protection dividing ties, especially among those where greater than 50% of mice lived to 21 days. "0" indicates test were conducted but compared to the other PspAs this one is not recommended.

Conclusions:
Statistically significant protection against death with >50% protection; 11/14 of the strains = 79%
Statistically significant protection against death; 13/14 strains = 93%
Statistically significant extension of life in 14/14 or 100% of strains.

TABLE 36

Best Choice for Vaccine Components as of Aug. 27, 1995

Vaccine Component
(cumulative strains protected)
% maximally protected

| Criterion | 1 | 2 | 3 | 4 | 5 | 6 |
|---|---|---|---|---|---|---|
| ≧#1 PspA for each challenge strain | R36A (7) 50% | WU2 (10) 71% | BG9739* (11) 79% | EF5668 (12) 86% | DBL5 (13) 93% | DBL6A (14) 100% |
| ≧#2 PspA for each challenge strain | R36A (12) 86% | BG9739 (12) 100% | | | | |
| Max score (+) type score | R36A (9) 64% | WU2 (11) 79% | BG9739 (13) 92% | DBL5 (14) 100% | | |
| Max Increase in Days alive | R36A (9) 64% | WU2 (11) 79% | BG9739 (13) 92% | DBL5 (14) 100% | | |

TABLE 36-continued

Best Choice for Vaccine Components as of Aug. 27, 1995

Vaccine Component
(cumulative strains protected)
% maximally protected

| Criterion | 1 | 2 | 3 | 4 | 5 | 6 |
|---|---|---|---|---|---|---|
| % protected | R36A (7) 50% | WU2 (10) 64% | DBL5 (11) 79% | EF5668 (12) 86% | DBL6A (13) 92% | EF3296 (14) 100% |
| Theoretical mixture based on a few testable assumptions (see below) | R36A (10) 64% | BG9739 (12) 86% | DBL5 (13) 92% | EF3296 (14) 100% | | |

*This is not a unique combination. See table below.

TABLE 37

Combinations where all Challenge Strains have a Vaccine strain with a score of ≧#2

| Number of PspAs in Combination | Combination | Number of #1 strains | Total #1s | Total #1s and #2s |
|---|---|---|---|---|
| 2 | R36A + BG9739 | 8 | 10 | 20 |
| 3 | R36A + BG9739 + WU2 | 11 | 15 | 25 |
| 3 | R36A + WU2 + DBL5 | 11 | 15 | 21 |
| 3 | R36A + WU2 + EF5668 | 11 | 15 | 23 |
| 3 | R36A + WU2 + DBL5 | 11 | 15 | 22 |

TABLE 38

Pooled Data for Protection against D39 by various PspAs;
Days alive for each mouse

| | | | Days to Death/immunogen | | | |
|---|---|---|---|---|---|---|
| Exp. | Log CFU D39 | Mice | Rx1/R36A D39 | JD908 (WU2) | EF5668 | All Immune | control |
| 143 | 4.5 | CBA/N | | 1, 1, 2, 2, 2 | | | 1, 1, 2, 2, 3 |
| E145 | 4.0 | CBA/N | 2, 3, 3, 3, 4 | | | | 1, 1, 2, 3, 4 |
| E028 BCG | 5.93 | BALB/c | 3, 3x < 21 | | | | 2, 2, 2, 4 |
| E143 | 3.0 | CBA/N | | 2, 6, 3x < 10 | | | 3, 3, 3, 5, 5 |
| E140 BC100 | 2.81 | CBA/N | 4, 4, 5, 7, 15 | | | | 2, 2, 2 |
| E169 | 2.7 | CBA/N | 2, 4x < 21 | 2, 5, 3x < 21 | | | 1, 2, 2, 2, 3 |
| E154 | 2.6 | CBA/N | 2, 2, 3, 2x < 21 | | | | 4x 2, 5, < 21 |
| All ≦3.0 | | | 2, 3, 3, 3, 4, 4, 4, 5, 7, 15 | | 1, 1, 2, 2, 2 | | 4x 1, 6x 2, 3, 3, 4 |
| All | | | 4x 2, 5x 3, 3x 4, 5, 7 15, 9x < 21 | 2, 5, 3x < 21 | 1, 1, 2, 2, 2, 2, 6 3x < 21 | 1, 1, 9x 2 5x 3, 3x 4, 5, 5, 6, 7, 15 15x < 21 | 5x 1, 16x 2 6x 3, 4, 4 5, 5, 5, < 21 |

TABLE 39

Pooled Data for Protection against D39 by various PspAs
Median Days Alive & alive:dead with corresponding P values.

| Exp. | Log CFU D39 | Mice | Rx1/R36A D39 med | a:d | JD908 (WU2) med | a:d | EF5668 med | a:d | All Immune med | a:d | Control med | a:d |
|---|---|---|---|---|---|---|---|---|---|---|---|---|
| 143 | 4.5 | CBA/N | | | | | 2 | 0:5 n.s. | | | 2 | 0:5 |
| E145 | 4.0 | CBA/N | 3 n.s. | 0:5 | | | | | | | 2 | 0:5 |
| E028 BCG | 5.93 | BALB/c | >21 .029 | 3:1 n.s. | | | | | | | 2 | 0:4 |
| E143 | 3.0 | CBA/N | | | | | >21 n.s. | 3:2 n.s. | | | 3 | 0:5 |
| E140 BC100 | 2.81 | CBA/N | 5 0.018 | 0:5 | | | | | | | 2 | 0:3 |
| E169 | 2.7 | CBA/N | >21 .016 | 4:1 .024 | >21 .016 | 3:2 n.s. | | | | | 2 | 0:5 |
| E154 | 2.6 | CBA/N | 3 n.s. | 2:3 n.s. | | | | | | | 2 | 1:5 |
| All ≦3.0 | | | 4 .0008 | 0:10 | | | 2 n.s. | 0:5 | | | 2 | 0:13 |
| All | | | 4.5 .0057 | 9:15 .001 ++ | >21 .006 | 3:2 .0045 +++ | 4(2.6) n.s. | 3:7 .034 + | 5 .0001 | 15:24 .0002 ++ | 2 | 1:32 |
| % alive | | | | 38 36 Rx1/D39 | | 60 59 WU2 | | 30 28 EF5668 | | 38 36 All immune | | 3 controls |

TABLE 40

Pooled Data for Protection against WU2 by various PspAs

Days to Death/immunogen

| Exp. | CFU WU2 | Mice | FL-R36A | Rx1 BC100 | JD108 (WU2) | JS1020 (BG9739) | BG9739 bc100 | EF5668 | L81905 bc100 | DBL5 bc100 | JS3020 (DBL6A) | control |
|---|---|---|---|---|---|---|---|---|---|---|---|---|
| Dr. Ed, expt. lots of prior expts. | | | +++ | | | | | | | | +++ | |
| E012 | 3.0 | CBA/N | 15x < 21 | | | | | | | | | 1, 1, 11x 2, 7x 3, 4 |
| E028 | 6.01 | BALB/c | 4x < 21 0.05/n.s. | | | | | | | | | 4, 6, 6, < 21 |
| E084 | 3.75[1] | CBA/N | | | | 3x < 15 | | | | | | 1, 2, 2, 2, 3, 3, <15 |
| E125 bc100 | 3.57 | CBA/N | | | | | 4x < 21 | | 4x < 21 | 4x < 21 | | 2, 2, 3, 3, 3, <21 |
| E129 | 3.18 | CBA/N | | | | 5x < 23 | | | | | | 2, 2, 2, 2, 3 |
| E140 BC100 | 3.43 | CBA/N | | 4x < 21 | | | | | | | | 1, 5x 2, 3, 4 |
| E143 | 3.0 | CBA/N | | | | | | 8x < 10 | | | | 1, 1, 2, 2, 2, 3 |
| E144 | 3.9 | CBA/N | | | | | | | | | 5x < 21 | 5x 2 |
| E172 | 3.98 | CBA/N | | | 5x < 21 | | | | | | | 5x 3 |
| All | | | 19x < 21 | 4x < 21 | 5x < 21 | 8x < 21 | 4x < 21 | 8x < 21 | 4x < 21 | 4x < 21 | 5x < 21 | 6x 1, 33x 2, 20x 3, 4, 4, 4, 6, 6, <21 |
| All Immune | | | 61x < 21 | | | | | | | | | |

TABLE 41

Pooled Data for Protection against WU2 by various PspAs

Median days Alive
Alive:Dead
P value based on Alive:Dead
P value calculated compared to pooled controls (in this case 65 control mice)
Score

| Exp. | CFU WU2 | Mice | FL-R36A | Rx1 BC100 | JD108 (WU2) | JS1020 (BG9739) | BG9739 bc100 | EF5668 | L81905 bc100 | DBL5 bc100 | JS3020 (DBL6A) | control |
|---|---|---|---|---|---|---|---|---|---|---|---|---|
| Dr. Ed, expt. lots of prior expts. | | | +++ | | | | | | | | +++ | |

TABLE 41-continued

Pooled Data for Protection against WU2 by various PspAs

| Exp. | | Mice | | | | | | | | | | control |
|---|---|---|---|---|---|---|---|---|---|---|---|---|
| E012 | −3.0 | CBA/N | >21 15:0 | | | | | | | | | 1, 1, 11x 2, 7x 3, 4 |
| E028 | 6.01 | BALB/c | 4x > 21 | | | | | | | | | 4, 6, 6, >21 |
| E084 | 3.75[1] | CBA/N | | | | 3x > 15 | | | | | | 1, 2, 2, 2, 3, 3, >15 |
| E125 bc100 | 3.57 | CBA/N | | | | | 4x > 21 | | 4x > 21 | 4x > 21 | | 2, 2, 3, 3, 3, >21 |
| E129 | 3.18 | CBA/N | | | | 5x > 23 | | | | | | 2, 2, 2, 2, 3 |
| E140 BC100 | 3.43 | CBA/N | | 4x > 21 | | | | | | | | 1, 5x 2, 3, 4 |
| E143 | 3.0 | CBA/N | | | | | | 8x > 10 | | | | 1, 1, 2, 2, 2, 3 |
| E144 | 3.9 | CBA/N | | | | | | | | 5x > 21 | | 5x 2 |
| E172 | 3.98 | CBA/N | | | 5x > 21 | | | | | | | 5x 3 |
| All | | | >21 19:0 <.0001 +++ | >21 4:0 <.0001 +++ | >21 5:0 <.0001 +++ | >21 8:0 <.0001 +++ | >21 4:0 <.0001 +++ | >21 8:0 <.0001 +++ | >21 4:0 <.0001 +++ | >21 4:0 <.0001 +++ | >21 4:0 <.0001 +++ | 2 1:64 |
| | % alive | | 100 FL-R36A | 100 Rx1 BC100 | 100 JD108 (WU2) | 100 JS1020 (BG9739) | 100 BG9739 bc100 | 100 EF5668 | 100 L81905 bc100 | 100 DBL5 bc100 | 100 JS3020 (DBL6A) | 2 control |

| WU2 Challenge | days of death | median days of death | alive: dead | P value based on days to death | P value based on alive:dead | Score | % alive | % prot. |
|---|---|---|---|---|---|---|---|---|
| All immune | 61x > 21 | >21 | 61:0 | <.0001 | <.0001 | +++ | 100 | 100 |
| All controls | 6x 1, 33x 2, 20x 3, 4, 4, 4, 6, 6, >21 | 2 | 1:64 | | | | 2 | 2 |

TABLE 42

Pooled Data for Protection against A66. by various PspAs

Days to Death/immunogen

| Exp. | CFU A66 | Mice | FL-R36A/ D39 | Rx1 BC100 | JD908 (WU2) | JS1020 (BG9739) | BG9739 bc100 | EF5668 | L81905 FL | L81905 bc100 | JS5010.3 FL (DBL5) | DBL5 bc100 | JS3020 (DBL6A) | control |
|---|---|---|---|---|---|---|---|---|---|---|---|---|---|---|
| E169 | 2.60 | CBA/N | 5x > 21 | | 5x > 21 | | | | | | | | | 1, 1, 2, 2, 6 |
| E152 bc100 | 2.78 | CBA/N | | | | | 4x > 21 | | 4x > 21 | | 4x > 21 | | | 3x 2, 3, 6, 6, >21 |
| E104 | 3.0 | CBA/N | | | | 2, 8, 3x >22 | | | | | 3, 4, 4, 2x >22 | | 2, 5, 4, 5, >22 | 2, 2, 2, 2, 3 |
| E143 | 3.0 | CBA/N | | | | | | 4, 4x > 10 | | | | | | 2, 2, 3, 3 |
| E140 | 3.43 | CBA/N | | 4x > 21 | | | | | | | | | | 1, 1, 1 |
| E172 | 3.94 | CBA/N | | | | | | | 5x > 21 | | | | | 1, 2, 2, 2, 4 |
| E145 | 3.97 | CBA/N | 13, 4x > 21 | | | | | | | | | | | |
| E121 | 4.16 | CBA/N | 3x 3, 2x 4, 5x > 21 | | | | | | | | | | | 1, 8x 2, >21 |
| All | | | 3x 3, 2x 4, 13, 14x > 21 | 4x > 21 | 5x > 21 | 2, 8, 3x > 21 | 4x > 21 | 4, 4x > 21 | 5x > 21 | 4x > 21 | 3, 4, 4, 2x > 21 | 4x > 21 | 2, 4, 4, 5, >21 | 7x 1, 22x 2, 3x 3, 4, 3x 6, 2x > 21 |
| | median; A:D P values | | >21 14:6 <0.0001 <0.0001 | >21 4:0 0.0002 0.0001 | >21 5:0 <0.0001 <0.0001 | >21 3:2 0.004 0.0075 | >21 5:0 0.0002 <0.0001 | >21 4:1 0.0006 0.006 | >21 5:0 <0.0001 <0.0001 | >21 4:0 0.0002 0.0001 | 4 2:3 0.0025 n.s. | >21 4:0 0.0002 0.0001 | 4 1:4 0.015 n.s. | 2 2:36 |

| Mini Pools | R36A/Rx1/WG44.1 | JD908 | BG9739 | EF5668 | L81905 | DBL5 3, 4, 4, 4, 6x > 21 | DBL6A | Control |
|---|---|---|---|---|---|---|---|---|
| | >21 | >21 | >21 | >21 | >21 | >21 | 4 | 2 |

TABLE 42-continued

Pooled Data for Protection against A66. by various PspAs

|  | 18:6 | 5:0 | 8:2 | 4:1 | 9:0 | 6:4 | 1:4 | 2:36 |
|---|---|---|---|---|---|---|---|---|
| P values |  | <0.0001 |  | 0.0006 |  |  | 0.015 |  |
| rank/a:d | <0.0001 | <0.0001 | <0.0001 | 0.006 | <0.0001 | 0.0004 | n.s. |  |
| Score | +++ | +++ | +++ | +++ | +++ | +++ | +± |  |
| % alive | 72 | 100 | 80 | 75 | 100 | 60 | 20 | 5 |
|  | 71 | 100 | 79 | 74 | 100 | 58 | 16 | 0 |
| A66 challenge | R36A/Rx1/WG44.1 | JD908 | BG9739 | EF5668 | L81905 | DBL5 | DBL6A |  |

| A66 challenge | days of death | median days alive | alive: dead | P - days to death | P - alive: dead | Score | % alive | % protected |
|---|---|---|---|---|---|---|---|---|
| All immune | 2, 2, 4x 3, 7x 4, 5, 8, 13, 50x > 21 | >21 | 50:16 | <0.0001 | <0.0001 | +++ | 76 | 75 |
| All controls | 7x 1, 22x 2, 3x 3, 4, 3x 6, 2x > 21 | 2 | 2:36 |  |  |  | 5 | 0 |

TABLE 43

Pooled Data for Protection against EF10197. by various PspAs

Days to Death/immunogen

| Exp. | CFU EF10197 | Mice | Rx1 BC100 | JS1020 (BG9739) | L81905 | JS3020 (DBL6A) | EF5668 | JS5010.3FL (DBL5)0 | control |
|---|---|---|---|---|---|---|---|---|---|
| E140 | 3.00 | CBA/N | 5x < 21 |  |  |  |  |  | 2, 2, 2 |
| MI BCG | 2.70 | CBA/N | * |  |  |  |  |  | 2, 2, 2, 2, 2 |
| E129 | 3.34 | CBA/N |  | 8, 4x < 23 |  |  |  |  | 2, 2, 2, 2, 9 |

*This was a passive protection study. Its controls have been included to increase the number of control mice.

TABLE 44

Pool of Pools for protection agaisnt EF10197

| Group | | Delay in death and/or survival | | Survival | |
|---|---|---|---|---|---|
| line | Description | days to death (median) | P values etc. | alive:dead | P values etc. |
| 1a | Rx1 (E140) | 5x > 21 | 0.017 vs 1b<br>0.0013 vs 4b | 5.0 | 0.0018 vs 1b<br>0.008 vs 4b |
| 3a | JS1020 (E129) | 8, 4x > 23 | 0.0007 vs 3b | 4:1 | 0.024 vs 3b |
| 4a | all immune | 8, 9x > 21 | <0.0001 vs 4b | 9:1 | 0.0002 vs 4b |
| 1b | Rx1 controls (E140) | 2,2,2 |  | 0:3 |  |
| 2b | MI BCG | 2,2,2,2,2 |  | 0:5 |  |
| 3b | JS1020 cont. (E129) | 2,2,2,9 |  | 0:5 |  |
| 4b | all controls (without MI BCG) | 2,2,2,2,2,2,2,9 |  | 0:8 |  |

TABLE 45

Summary of protection against EF10197

| Immunogen | alive:dead | % alive | % protected | median DOD | P time alive | P alive:dead | Score* |
|---|---|---|---|---|---|---|---|
| Rx1 | 5:0 | 100 | 100 | <21 | 0.017 | 0.018 | +++ |
| JS1020 | 4:1 | 80 | 80 | <21 | 0.0007 | 0.024 | +++ |
| all immune | 9:1 | 90 | 90 | <21 | >0.0001 | 0.0002 | +++ |
| all controls | 0:8 | 0 | 0 | 2 | — | — | — |

*+++ = statistically significant protection against death with ≥50% protected.

TABLE 46

Pooled Data for Protection against ATCC6303, by various PspAs

| | | | | | Days to Death/immunogen | | | | |
|---|---|---|---|---|---|---|---|---|---|
| Exp. | CFU ATCC6303 | Mice | Rx1 BC100 | JS1020 (BG9739) | L81905 | JS3020 (DBL6A) | EF5668 | JS5010.3 FL (DBL5)0 | control |
| E140 | 2.30 | CBA/N | 5x < 21 | | | | | | 4, 4x 5 |
| E129 | 3.80 | CBA/N | | | n.v. | | | | |

TABLE 47

Pool of Pools for protection agaisnt ATCC6303

| Group | | Delay in death and/or survival | | | Survival | |
|---|---|---|---|---|---|---|
| line | Description | days to death (median) | | P values etc. | alive:dead | P values etc. |
| 1a | Rx1 (E140) | 5x > 21 | (>21) | 0.0040 | 5:0 | 0.004 |
| 1b | RX1 controls (E140) | 4, 4x 5 | 5 | — | 0:5 | — |

TABLE 48

Summary of protection against ATCC6303

| Immunogen | alive:dead | % alive | % protected | median DOD | P time alive | P alive:dead | Score* |
|---|---|---|---|---|---|---|---|
| Rx1 | 5:0 | 100 | 100 | <21 | 0.004 | 0.004 | +++ |
| Rx1 controls | 0:5 | 0 | 0 | 5 | — | — | — |

*+++ = statistically significant protection against death with ≧50% protected.

TABLE 49

Pooled Data for Protection against BG9739, by various FL PspAs

| | | | | | | | Days to Death/immunogen | | | | | | |
|---|---|---|---|---|---|---|---|---|---|---|---|---|---|
| Exp. | CFU BG9739 | Mice | R36A FL | BC100 (Rx1) | JD908 (WU2) | JS1020 (BG9739) | bc100 (BG9739) | EF3296 FL | EF5668 FL | bc100 (L81905) | JS5010.3 FL (DBL5) | bc100 (DBL5) | JS3020 (DBL6A) | control |
| E140 | 2.76 | CBA/N | 3, 3, 10, 11 | | | | | | | | | | | 2, 2, 3 |
| E104 | 2.89 | Xid | | | | 6, 6, 7, 8, 8 | | | | | 2, 2, 2, 3, 4 | | 2, 2, 2, 2, 3 | 2, 2, 3, 5, 5 |
| E125 | 3.56 | CBA/N | | | | 5, 5, 5, 7 | | | | 4, 5, 13, >21 | | 2, 2, 2, 4 | | 3, 3, 4, 4, 5, 6 |
| E172 | 3.71 | CBA/N | | | 6, 7, 3x > 21 | | | | | | | | | 3, 4, 6, 6, 7 |
| E124 | 3.76 | Xid | | | | | | | | | 2, 2, 2, 2, 3 | | 2, 2, 2, 2, 9 | 2, 2, 2 |
| E084 | 4.05 | BALB/c | | | | 4x2, 2x > 14 | | | | | | | | 9x 2 |
| E144 | 4.09 | Xid | 2, 3, 3, 6, >21 | | | | | 2, 3, 3, 7, >10 | 2, 3, 3, 3, 4 | | | | | 2, 2, 2, 3, 3 |
| All | | | 2, 3, 3, 6, >21 | 3, 3, 10, 11 | 6, 7, 3x > 21 | 4x2, 6, 6, 7, 8, 8, 2x > 21 | 5, 5, 5, 7 | 2, 3, 3, 7, >21 | 2, 3, 3, 3, 4 | | 7x 2, 3, 3 4 | 8x 2, 3, 9 | | 21x 2, 7x 3, 3x 4, 3x 5, 3x 6, 7 |
| median | | | 3 | 3, 10 | >21 | 6 | 5 | 3 | 3 | 5, 13 | 2 | 2 | 2 | 2 |
| a:d | | | 1:4 | 0:4 | 3:2 | 2:9 | 0:4 | 1:4 | 0:5 | 1:3 | 0:10 | 0:4 | 0:10 | 0:38 |
| P rank | | | | | | | | | | | | | | |
| P a:d | | | | | | | | | | | | | | |

TABLE 50

Pooled Data for Protection against BG9739. by bc100s and FL PspAs

| Exp. | CFU BG9739 | Mice | R36A FL | BC100 (Rx1) | JD908 (WU2) | JS1020 (BG9739) | bc100 (BG9739) | EF3296 FL | EF5668 FL | bc100 (L81905) | JS5010.3 FL (DBL5) | bc100 (DBL5) | JS3020 (DBL6A) | control |
|---|---|---|---|---|---|---|---|---|---|---|---|---|---|---|
| E140 | 2.76 | CBA/N | | 3, 3, 10, 11 | | | | | | | | | | 2, 2, 3 |
| E104 | 2.89 | Xid | | | | 6, 6, 7, 8, 8 | | | | | 2, 2, 2, 3, 4 | | 2, 2, 3 | 2, 2, 3, 5, 5 |
| E125 | 3.56 | CBA/N | | | | | 5, 5, 5, 7 | | | 4, 5, 13, >21 | | 2, 2, 2, 4 | | 3, 3, 4, 4, 5, 6 |
| E172 | 3.71 | CBA/N | | | 6, 7, 3x > 21 | | | | | | | | | 3, 4, 6, 6, 7 |
| E124 | 3.76 | Xid | | | | | | | | | 2, 2, 2, 2, 3 | | 2, 2, 2, 2, 9 | 2, 2, 2 |
| E084 | 4.05 | BALB/c | | | | 4x2, 2x > 14 | | | | | | | | 9x 2 |
| E144 | 4.09 | Xid | 2, 3, 3, 6, >21 | | | | | 2, 3, 3, 7, >10 | 2, 3, 3, 3, 4 | | | | | 2, 2, 2, 3, 3 |

| FL + bc100 BG9739 | R36A/Rx1/D39 | WU2 | BG9739 | EF3296 | EF5668 | L81905 | DBL5 | DBL6A | Cont. |
|---|---|---|---|---|---|---|---|---|---|
| All | 2, 4x 3, 6, 10, 11, >21 | 6, 7 3x > 21 | 4x2, 3x 5, 2x 6, 2x 7, 2x 8, 2x > 21 | 2, 3, 3, 7, >21 | 2, 3x 3, 4 | 4, 5, 13, >21 | 10x 2, 3, 3, 4, 4 | 8x 2, 3, 9 | 21x 2, 7x 3, 3x 4, 3x 5, 3x 6, 7 |
| median days alive | 3 | >21 | 6 | 3 | 3 | 5, 13 | 2 | 2 | 2 |
| alive:dead | 1:8 | 3:2 | 2:13 | 1:4 | 0:5 | 1:3 | 0:14 | 0:10 | 0:38 |
| P - days alive | 0.0096 | <0.0001 | 0.0013 | n.s. | n.s. | 0.0022 | n.s. | n.s. | |
| P - alive:dead | n.s. | 0.0008 | n.s. | n.s. | n.s. | n.s. | n.s. | n.s. | |
| Score | + | +++ | + | 0+ | 0 | +± | 0 | 0 | |
| % alive | 11 | 60 | 13 | 25 | 0 | 25 | 0 | 0 | 0 |
| % protected | 11 | 60 | 13 | 25 | 0 | 25 | 0 | 0 | 0 |
| BG9739 challenge | R36A/Rx1/D39 | WU2 | BG9739 | EF3296 | EF5668 | L81905 | DBL5 | DBL6A | Cont. |

| BG9739 | days of death | median days of death | alive: dead | P value based on days to death | P value based on alive: dead | Score | % Alive | % |
|---|---|---|---|---|---|---|---|---|
| All immune | | 3 | 8:59 | 0.009 | 0.023 | ++ | 12 | 12 |
| All controls | | 2 | 0:38 | | | | | |

TABLE 51

Pooled Data for Protection against EF3296. by various PspAs

| Exp. | CFU EF3296 | Mice | Rx1 BC100 | JD908 WU2 | JS1020 (BG9739) | JS5010.3 FL (DBL5) | JS3020 (DBL6A) | control |
|---|---|---|---|---|---|---|---|---|
| E84[1] | 3.99 | BALB/c | | | 4x 2, >14 | | | 9x 2 |
| E140 | 2.92 | CBA/N | 3, 4, 6, >21 | | | | | 3, 3, 3 |
| E104 | 3.11 | CBA/N | | | 4, 5, 5, 5, 6 | 2, 2, 2, 3, 3 | 2, 2, 3, 4, 5 | 2, 2, 2, 3, 4 |
| E124 | 3.94 | CBA/N | | | | 1, 1, 2, 2, 2 | 1, 1, 2, 2, 2 | 1, 1, 2, 2, 2 |
| E172 | 4.06 | CBA/N | | 3, 3, 5, 5, >21 | | | | 3, 4x 6 |
| All | | | 3, 4, 6, >21 | 3, 3, 5, 5, >21 | 4x 2, 3x 5, 6, >21 | 1, 1, 5x 2, 3, 3 | 1, 1, 5x 2, 4, 5 | 1, 1, 15x 2, 5x 3, 4, 4x 6 |
| median days to death | | | 5 | 5 | 4.5 | 2 | 2 | 2 |
| alive:dead | | | 1:3 | 1:4 | 1:9 | 0:9 | 0:10 | 0:27 |
| P - days to death | | | 0.0077 | 0.0094 | n.s. | n.s. | n.s. | |
| P - alive:dead | | | n.s. | n.s. | n.s. | n.s. | n.s. | |

TABLE 51-continued

Pooled Data for Protection against EF3296. by various PspAs

| Score | ±+ | ±+ | 0+ | 0 | 0 | |
|---|---|---|---|---|---|---|
| % alive | 25 | 20 | 10 | 0 | 0 | 0 |
| % prot. | 25 | 20 | 10 | 0 | 0 | 0 |
| Best EF3296 challenge | Rx1 BC100 | JD908 WU2 | JS1020 (BG9739) | JS5010.3 FL (DBL5) | JS3020 (DBL6A) | control |

| EF3296 challenge | median days alive | alive: dead | P - days to death | P - alive: dead | Score | % alive | % prot |
|---|---|---|---|---|---|---|---|
| All immune | 3 | 3:35 | n.s. | n.s. | 0 | 8 | 8 |
| All control | 2 | 0:27 | | | | | |

TABLE 52

Pooled Data for Protection against EF5668. by various FL-PspAs and bc100s

| | | | | | Days to Death/immunogen | | | | | | |
|---|---|---|---|---|---|---|---|---|---|---|---|
| Exp. | CFU EF5668 | Mice | R36A | Rx1 BC100 | JD908 (WU2) | JS1020 (BG9739) | EF3296 | EF5668 | L81905 | JS5010.3 FL DBL5 | JS3020 DBL6A | control |
| E143 | 3.0 | CBA/N | | | | | | 5x > 10 | | | | 1, 1, 2, 2, >10 |
| E140 | 3.59 | CBA/N | | 4, 6, 12, >21 | | | | | | | | 2, 4, 6 |
| E171 | 3.69 | CBA/N | | | 2, 2, 2, 3, >21 | | | | 3, 3, 4, 2x > 21 | | | 1, 3, 6, 6, 7 |
| E124 | 3.90 | CBA/N | | | | | | | | 3, 3, 3x > 15 | 3, 4, 5, 6, 6 | 3, 3, 3, 4, 9 |
| E145 | 3.94 | CBA/N | 3, 4, 4, 16, >19 | | | 2, 10, 3x > 19 | 2, 4, 13, 2x > 19 | | | | | 2, 3, 3, 4, >21 |
| Pool | | | 3, 3x 4, 6, 12, 16, 2x > 21 | 2, 2, 2, 3, >21 | 2, 10, 3x > 21 | 2, 4, 13, 2x > 21 | 5x > 21 | 3, 3, 4, 2x > 21 | 3, 3, 3x > 21 | 3, 4, 5, 6, 6 | 3x 1, 4x 2, 6x 3, 3x 4, 3x 6, 7, 9, 2x > 21 | |
| median days alive | | | 6 | 2 | >21 | 13 | >21 | 4 | >21 | 5 | 3 | |
| alive:dead | | | 2:7 | 1:4 | 3:2 | 2:3 | 5:0 | 2:3 | 3:2 | 0:5 | 2:21 | |
| P - days alive | | | 0.013 | n.s. | 0.0187 | n.s. | 0.001 | n.s. | n.s. | n.s. | | |
| P - alive:dead | | | n.s. | n.s. | 0.027 | n.s. | 0.0002 | n.s. | 0.027 | n.s. | | |
| Score | | | + | 0 | +++ | 0+ | +++ | 0+ | + | 0+ | | |
| % alive | | | 22 | 25 | 60 | 40 | 100 | 40 | 60 | 0 | 9 | |
| % prot | | | 14 | 18 | 56 | 34 | 100 | 34 | 56 | −10 | 9 | |
| EF5668 | | | R36A/Rx1/D39 | WU2 | BG9739 | EF3296 | EF5668 | L81905 | DBL5 | DBL6A | control | |

Summary of protection against EF6796

| Immunogen | alive:dead | % alive | % protected | median DOD | P - time alive | P alive vs dead |
|---|---|---|---|---|---|---|
| Rx1 | 4:0 | 100 | 100 | >21 | 0.029 | 0.029 |
| controls | 0:3 | 0 | 0 | 1 | — | — |

+++ = statistically significant protection from death with ≧50% protected;

TABLE 53

Pooled Data for Protection against DBL6A. by various FL PspAs and bc100 PspAs

| | CFU | | | | | | Days to Death/immunogen | | | | | | | |
|---|---|---|---|---|---|---|---|---|---|---|---|---|---|---|
| Exp. | DBL6A | Mice | BC100 Rx1 | R36A | JD908 WU2 | JS1020 BG9739 | bc100 BG9739 | EF3296 | EF5668 | L81905 FL | bc100 L81905 | JS5010.3 DBL5 | bc100 DBL5 | JS3020 DBL6A | control |
| E171 | 2.69 | CBA/N | | | 6, 7, 8, 9, | | | | | 3, 3, 7, 9, | | | | | 2, 3, 4, 6, |

TABLE 53-continued

Pooled Data for Protection against DBL6A. by various FL PspAs and bc100 PspAs

| | | | | | | | | | | |
|---|---|---|---|---|---|---|---|---|---|---|
| E152 | 3.24 | CBA/N | | >21<br>15,<br>3x<br>>21 | | >21 | 7, 16,<br>2x > 21 | 8, 10,<br>13,<br>21 | | 6<br>3x 3,<br>4,<br>3x 6 |
| E140 | 3.25 | CBA/N | 4x > 21 | | | | | | | 4, 7, 7 |
| E146 | 3.57 | CBA/N | | 7, 8,<br>10,<br>2x > 21 | | 6, 8,<br>9,<br>10, 10 | 10, 13,<br>3x > 21 | | 7, 8,<br>12,<br>13, 13 | 9,<br>4x > 21 | 4, 4,<br>5, 5,<br>18 |
| E129 | 4.14 | CBA/N | | 3, 6,<br>8, 10,<br>13 | | | | | | | 4, 5,<br>6, 8,<br>>23 |

| Total Name of Pools | R36A/Rx1/D39 | WU2 | BG9739 | EF3296 | EF5668 | L81905 | DBL5 | DBL6A | controls |
|---|---|---|---|---|---|---|---|---|---|
| Pooled data | 7, 8, 10, 6x > 21 | 6, 8, 9<br>>21 | 3, 6, 8, 10, 13,<br>15, 3x > 21 | 6, 8, 9,<br>10, 10 | 10, 13,<br>3x > 21 | 3, 3, 7, 7, 9, 16,<br>2x > 21 | 7, 8, 8, 10, 12,<br>3x 13, 21 | 9,<br>4x > 21 | 2,<br>4x 3,<br>6x 4,<br>3x 5,<br>6x 6,<br>7, 7,<br>8, 18,<br>>21 |
| median days alive | >21 | 8.5 | 13 | 9 | >21 | 8 | 12 | >21 | 5 |
| alive:dead | 6:3 | 1:3 | 3:6 | 0:5 | 3:2 | 2:6 | 0:9 | 4:1 | 1:24 |
| P - days alive | <0.0001 | 0.0082 | 0.0025 | 0.0036 | 0.0001 | 0.037 | 0.002 | <0.0001 | |
| P - alive:dead | 0.0019 | n.s. | 0.048 | n.s. | 0.0093 | n.s. | n.s. | 0.0009 | |
| Score | +++ | +± | ++ | +± | +++ | +± | +± | +++ | |
| | 67 | 25 | 33 | 0 | 60 | 25 | 0 | 80 | 4 |
| | 66 | 22 | 30 | −4 | 58 | 22 | −4 | 79 | 0 |
| DBL6A challenge | R36A/Rx1/D39 | WU2 | BG9739 | EF3296 | EF5668 | L81905 | DBL5 | DBL6A | controls |

| DBL6A challenge | days of death | median days of death | alive:dead | P value based on days to death | P value based on alive:dead | Score | % alive | % prot. |
|---|---|---|---|---|---|---|---|---|
| All immune | | 12.5 | 19:35 | <0.0001 | 0.0019 | ++ | 35 | 33 |
| All control | | 5 | 1:24 | | | | | |

TABLE 54

Pooled Data for Protection against BG9163 by various PspAs

| | | | Days to Death/immunogen | | | | |
|---|---|---|---|---|---|---|---|
| Exp. | CFU BG9163 | Mice | Rx1 | Rx1.BCG | JS1020 (BG9739) | all immune | control |
| E169 | 2.67 | CBA/N | 5x > 24 | | | | 4, 5, 8, 8, >24 |
| E140 | 3.14 | CBA/N | n.v. | | | | |
| E129 | 4.0 | CBA/N | | | 12, 4x > 23 | | 7, 9, 9, 13,<br>>23 |
| E028 | 6.217 | CBA/N | | 6. 3x > 21 | | | 5, 6, 8, 10 |

| Immunogens | Rx1/R36A/D39 | BG9739 | all immune | control |
|---|---|---|---|---|
| Pooled Data | 6, 8x > 21 | 12, 4x > 21 | 6, 12,<br>12x > 21 | 4, 5, 7, 8, 8, 9,<br>9, 12, 2x > 21 |
| median days alive | >21 | >21 | >21 | 8.5 |
| alive:dead | 8:1 | 4:1 | 12:2 | 2:8 |
| P - days alive | 0.0086 | 0.0097 | 0.0027 | |
| P - alive:dead | 0.0045 | 0.047 | 0.0022 | |
| % alive | 89 | 80 | 86 | 20 |
| % prot. | 86 | 75 | 83 | 0 |
| score | +++ | +++ | +++ | |
| BG9163 Challenge | Rx1/R36A/D39 | BG9739 | all immune | control |

| EF5668 | days of death | median days of death | alive:dead | P value based on days to death | P value based on alive:dead | Score | % alive | % prot. |
|---|---|---|---|---|---|---|---|---|

TABLE 54-continued

Pooled Data for Protection against BG9163 by various PspAs

| All immune | 8 | 18:26 | <0.0015 | 0.005 | ++ | 41 | 35 |
|---|---|---|---|---|---|---|---|
| All control | 3 | 2:21 | | | | | |

TABLE 55

Pooled Data for Protection against L81905. by various FL-PspAs

| | | | | | | Days to Death/immunogen | | | | | | | |
|---|---|---|---|---|---|---|---|---|---|---|---|---|---|
| Exp. | CFU L81905 | Mice | R36A | BC100 (Rx1) | JD908 (WU2) | JS1020 (BG9739) | bc100 BG9739 | EF3296 | EF5668 | bc100 L81905 | JS5010.3 (DBL5) | bc100 (DBL5) | JS3020 (DBL6A) | control |
| E172 | 2.45 | CBA/N | | | 3, 4, 5, 6, 6 | | | | | | | | | 3, 3, 4, 4, 4 |
| E140 | 3.11 | CBA/N | | 2, 5, 5, 6, 8 | | | | | | | | | | 2, 2, 2, 3, 3 |
| E084 | 3.86 | BALB | | | | 2, 2, 5x >14 | | | | | | | | 1, 8x 2 |
| E104 | −3.5 | CBA/N | | | | 3, 7, 8, 8, 11 | | | | | 3, 3, 3, 2x >22 | | 3, 4, 5, 5, 6 | 2, 4, 4, 4, 5 |
| E124 | −3.5 | CBA/N | | | | | | | | | 2, 2, 2, 2, 3 | | 2, 2, 2, 3, 5 | 1, 2, 2, 2, 2 |
| E125 | 3.6 | CBA/N | | | | | 5, 6, 8, 8 | | | | 3, 4, 6, 8 | 4, 5, 5, 5 | | 2, 2, 3, 5, 5, 5 |
| E144 | 4.11 | CBA/N | 3, 3, 5, 6, >10 | | | | | 6, 6, 6, 2x >10 | 2, 2, 3, 3, 3 | | | | | 2, 2, 3x 3 |
| All | | | 3, 3, 5, 6, >21 | | 3, 4, 5, 6, 6 | 2, 2, 3, 7, 8, 8, 11, 5x > 21 | 5, 6, 8, 8 | 6, 6, 6, 2x >10 | 2, 2, 3, 3, 3 | 3, 4, 6, 8 | 4x 2, 4x 3, 2x > 21 | 4, 5, 5, 5 | 3x 2, 3, 3, 4, 3x 5, 6 | 1, 1, 20x 2, 8x 3, 6x 4, 4x 5 |
| median alive: dead P rank P a:d score | | | 5 1:4 | 5 0:5 | 5 0:5 | >21 5:7 | 7 0:4 | 6 2:3 | 3 0:5 | 5 0:4 | 3 2:8 | 5 0:4 | 3.5 0:10 | 2 0:40 |

| L81905 challenge | days of death | median days of death | alive: dead | P value based on days to death | P value based on alive:dead | Score | % alive | % prot. |
|---|---|---|---|---|---|---|---|---|
| All immune | | 5 | 10:59 | <0.0001 | 0.008 | ++ | 14 | 14 |
| All control | | 2 | 0:40 | | | | | |

TABLE 56

Protection against L81905 by various bc100s & FL-PspAs pooled together

| | | | | | | Days to Death/immunogen | | | | | | | |
|---|---|---|---|---|---|---|---|---|---|---|---|---|---|
| Exp. | CFU L81905 | Mice | R36A | BC100 (Rx1) | JD908 (WU2) | JS1020 (BG9739) | bc100 BG9739 | EF3296 | EF5668 | bc100 L81905 | JS5010.3 (DBL5) | bc100 (DBL5) | JS3020 (DBL6A) | control |
| E172 | 2.45 | CBA/N | | | 3, 4, 5, 6, 6 | | | | | | | | | 3, 3, 4, 4, 4 |
| E140 | 3.11 | CBA/N | | 2, 5, 5, 6, 8 | | | | | | | | | | 2, 2, 2, 3, 3 |
| E084 | 3.86 | BALB | | | | 2, 2, 5x >14 | | | | | | | | 1, 8x 2 |

TABLE 56-continued

Protection against L81905 by various bc100s & FL-PspAs pooled together

| | | | | | | | Days to Death/immunogen | | | | | | |
|---|---|---|---|---|---|---|---|---|---|---|---|---|---|
| Exp. | CFU L81905 | Mice | R36A | BC100 (Rx1) | JD908 (WU2) | JS1020 (BG9739) | bc100 BG9739 | EF3296 | EF5668 | bc100 L81905 | JS5010.3 (DBL5) | bc100 (DBL5) | JS3020 (DBL6A) | control |
| E104 | −3.5 | CBA/N | | | | 3, 7, 8, 8, 11 | | | | | 3, 3, 3, 2x >22 | | 3, 4, 5, 5, 6 | 2, 4, 4, 4, 5 |
| E124 | −3.5 | CBA/N | | | | | | | | | 2, 2, 2, 2, 3 | | 2, 2, 2, 3, 5 | 1, 2, 2, 2, 2 |
| E125 | 3.6 | CBA/N | | | | | | 5, 6, 8, 8 | | | 3, 4, 6, 8 | 4, 5, 5, 5 | | 2, 2, 3, 5, 5, 5 |
| E144 | 4.11 | CBA/N | 3, 3, 5, 6, >10 | | | | | 6, 6, 6, 2x >10 | 2, 2, 3, 3, 3 | | | | | 2, 2, 3x 3 |
| | Pooled | | 2, 3, 3, 3x 5, 6, 6, 8, >21 | 3, 4, 5, 6, 6 | | 2, 2, 3, 5, 6, 7, 4x 8, 11, 5x > 21 | 6, 6, 6, 2x >10 | 2, 2, 3, 3, 3 | | 3, 4, 6, 8 | 4x 2, 4x 3, 4, 5, 5, 5, 2x > 21 | 3x 2, 3, 3, 4, 3x 5, 6 | 1, 1, 20x 2, 8x 3, 6x 4, 4x 5 |
| | median days alive | | 5 | 5 | | 8 | 6 | 3 | 5 | 3 | 3.5 | 2 |
| | alive:dead | | 1:9 | 0:5 | | 5:11 | 2:3 | 0:5 | 0:4 | 2:12 | 0:10 | 0:40 |
| | P - days alive | | 0.0005 | 0.0035 | | <0.0001 | 0.0002 | n.s. | 0.01 | 0.035 | 0.044 | |
| | P - alive:dead | | n.s. | n.s. | | 0.0001 | 0.01 | n.s. | n.s. | n.s. | n.s. | |
| | score | | + | + | | ++ | ++ | 0 | + | + | + | |
| | % alive | | 10 | 0 | | 31 | 40 | 0 | 0 | 14 | 0 | 0 |
| | % protected challenge with L81905 | | R36A/Rx1/D39 | WU2 | | BG9739 | EF3296 | EF5668 | L81905 | DBL5 | DBL6A | controls |

TABLE 57

Pooled Data for Protection against DBL5 by various FL-PspAs & bc100s

| | | | | | | | Days to Death/immunogen | | | | | |
|---|---|---|---|---|---|---|---|---|---|---|---|---|
| Exp. | CFU DBL5 | Mice | R36A | BC100 Rx1 | JS1020 BG9739 | bc100 JS1020 | EF5668 | bc100 L81905 | JS5010.3 DBL5 | bc100 DBL5 | JS3020 DBL6A | control |
| E84[1] | 3.90 | BALB/c | | | 6x 2 | | | | | | | 9x 2 |
| E140 | 3.27 | CBA/N | | 4, 4, 5, 5, 5 | | | | | | | | 2, 2, 2 |
| E104 | 3.39 | Xid | | | 3, 3, 6, >22, >22 | | | | 7, 7, 15, >22, >22 | | 2, 2, 4, 5, 5 | 2, 4x 3 |
| E124 | 3.76 | Xid | | | | | | | 2, 2, 2, 5, >15 | | 5x 2 | 1, 1, 2, 2, 2 |
| E125 | 3.81 | CBA/N | | | | 3, 3, 4, 5 | | 3, 3, 4, 4 | | 2, 2, 2, >21 | | 5x 2, 5 |
| E144 | 4.13 | XID | 3, 3, 3, 3, >10 | | | | 2, 2, 3, 4, 4 | | | | | 5x 2 |
| | total name of pool | | R36A/Rx1/D39 | | BG9739 | | EF5668 | L81905 | DBL5 | | DBL6A | controls |
| | pooled data | | 4x 3, 2x 4, 3x 5, >21 | | 6x 2, 4x 3, 4, 5, >21, >21 | | 2, 2, 3, 4, 4 | 3, 3, 4, 4 | 6x2, 5, 7, 7, 15, 4x > 21 | | 7x 2, 4, 5 | 1, 1, 26x 2, 4x 3, 5 |
| | median days alive | | 4 | | 3 | | 3 | 3.5 | 6 | | 2 | 2 |
| | alive:dead | | 1:9 | | 2:12 | | 0:4 | 0:4 | 4:10 | | 0:10 | 0:32 |
| | P - days alive | | <0.0001 | | 0.0063 | | .041 | 0.001 | 0.0025 | | n.s. | |
| | P - alive:dead | | n.s. | | n.s. | | n.s. | n.s. | 0.0056 | | n.s. | |
| | Score | | + | | + | | +* | + | ++ | | 0 | |
| | % alive | | 10 | | 14 | | 0 | 0 | 29 | | 0 | 0 |

TABLE 57-continued

Pooled Data for Protection against DBL5 by various FL-PspAs & bc100s

| % protected DBL5 challenge | 10 R36A/Rx1/D39 | 14 BG9739 | Days to Death/immunogen 0 EF5668 | 0 L81905 | 29 DBL5 | 0 DBL6A | 0 controls |
|---|---|---|---|---|---|---|---|
| DBL5 challenge | days of death | median days of death | alive: dead | P value based on days to death | P value based on alive:dead | Score | % alive | % prot. |
| All immune | | 3.5 | 7:49 | <0.0001 | 0.034 | ++ | 3.6 | 3.6 |
| All control | | 2 | 0:33 | | | | | |

[1]This immunization was with cell eluted PspA. Note BALB/cJ mice were used. Also note $10^4$ Challenge CFU

TABLE 58

Pooled Data for Protection against EF6796 by various PspAs

| | | | | | Days to Death/immunogen | | | | |
|---|---|---|---|---|---|---|---|---|---|
| Exp. | CFU WU2 | Mice | Rx1 BC100 | JS1020 (BG9739) | L81905 | JS3020 (DBL6A) | JS5010.3 FL (DBL5) | DBL5 bc100 | control |
| E140 | 3.75 | CBA/N | 4x > 21 | | | | | | 1, 1, 1 |
| E28 | 7 | BALB | n.v. | | | | | | |

TABLE 59

Pool of Pools for protection against EF6796

| line | Group Description | Delay in time to death and/or survival | | Protection against death | |
|---|---|---|---|---|---|
| | | days to death (median DOD) | P values etc. | alive:dead | P values etc. |
| 1a | Rx1 | 4x > 21 (>21) | 0.029 | 4:0 | 0.029 |
| 1b | Rx1 controls | 1, 1, 1 (1) | — | 0:3 | — |

TABLE 60

Pooled Data for Protection against BG7322. by various FL-PspAs and bc100s

| | CFU | | | | | Days to Death/immunogen | | | | | | | |
|---|---|---|---|---|---|---|---|---|---|---|---|---|---|
| Exp. | BG 7322 | Mice | D39/ R36A | Rx1 BC100 | JD908 (WU2) | bc100 BG9739 | EF3296 | EF5668 | bv100 L81905 | JS5010.3 DBL5 | bc100 DBL5 | JS3020 DBL6A | control |
| E171 | 2.78 | CBA/N | | | 10, 15, 3x > 21 | | | | | | | | 1, 3, 6, 6, 7 |
| S143 | 3.0 | CBA/N | | | | | | 7, 8x > 10 | | | | | 2, 2, 4, 5, 7, 7, 8, 8 |
| E140 BC100 | 3.14 | CBA/N | | 4x > 21 | | | | | | | | | 3, 6, 6, >21 |
| E152 | 3.11 | CBA/N | | | | 12, 13, 16, >21 | | | 10, 12, 13, >21 | >21, >21, >21, >21 | | | 6, 7, 7, 8, 8, 9, 14 |
| E146 | 3.57 | CBA/N | 18, 20, 3x > 21 | | | 5, 3x 6, 10 | | | 6, 10, 11, 11, 19 | | 4, 8, 11, 18, >21 | | 4, 5, 5, 6, >21 |

TABLE 60-continued

Pooled Data for Protection against BG7322. by various FL-PspAs and bc100s

| E169 | 3.94 | CBA/N | 5x > 21 | | | | | | | 2, 5, 5, 6, 7 |
|---|---|---|---|---|---|---|---|---|---|---|
| Immunogens | R36A/Rx1/D39 | JD908 | BG9739 | EF3296 | EF5668 | L81905 | | DBL5 | DBL6A | Cont. |
| Pools | 18, 20, 12x > 21 | 10, 15, 3x > 21 | 12, 13, 16, >21 | 5, 3x 6, 10 | 7, 8x > 21 | 10, 12, 13, >21 | | 6, 10, 11, 11, 19 >21, >21, >21, >21 | 4, 8, 11, 18, >21 | 1, 3x 2, 3, 3, 4, 4, 5x 5, 7x 6, 6x 7, 4x 8, 9, 14, 2x >21 |
| median day alive | >21 | >21 | 14.5 | 6 | >21 | 12.5 | | >21 | 11 | 6 |
| alive:dead | 9:0 | 3:2 | 1:3 | 0:5 | 8:1 | 1:3 | | 4:5 | 1:3 | 2:32 |
| P - days alive | <0.0001 | 0.0007 | 0.001 | n.s. | <0.0001 | 0.0013 | | 0.0002 | 0.028 | |
| P - alive:dead | <0.0001 | 0.004 | n.s. | n.s. | <0.0001 | n.s. | | 0.0076 | n.s. | |
| % alive | 100 | 60 | 25 | 0 | 89 | 25 | | 80 | 25 | 6 |
| % protected | 100 | 57 | 22 | 0 | 88 | 22 | | 79 | 22 | 6 |
| Score | +++ | +++ | +± | 0 | +++ | +± | | +++ | +± | |
| BG7322 Challenge | R36A/Rx1/D39 | JD908 | BG9739 | EF3296 | EF5668 | L81905 | | DBL5 | DBL6A | Cont. |

| BG7322 Challenge | median days of death | alive: dead | P value based on days to death | P value based on alive:dead | Score | % alive | % prot. |
|---|---|---|---|---|---|---|---|
| All immune | >21 | 30:25 | <0.0001 | <0.0001 | +++ | 55 | 52 |
| All controls | 6 | 2:32 | | | | | |

---

What is claimed is:

1. An immunological composition comprising at least two different full length isolated PspAs.

2. An immunological composition comprising at least two different isolated PspAs.

3. The immunological composition of claim 2 wherein the two PspAs are from different groups based on restriction fragment polymorphism analysis.

* * * * *